(12) United States Patent
Winslow et al.

(10) Patent No.: US 8,083,775 B2
(45) Date of Patent: *Dec. 27, 2011

(54) LOAD-SHARING BONE ANCHOR HAVING A NATURAL CENTER OF ROTATION AND METHOD FOR DYNAMIC STABILIZATION OF THE SPINE

(75) Inventors: Charles J. Winslow, Walnut Creek, CA (US); Steven T. Mitchell, Pleasant Hill, CA (US); John J. Flynn, Walnut Creek, CA (US); James F. Zucherman, San Francisco, CA (US); Ken Y. Hsu, San Francisco, CA (US); Henry A. Klyce, Piedmont, CA (US); H. Adam R. Klyce, Berkeley, CA (US)

(73) Assignee: Spartek Medical, Inc., Concord, CA (US)

(*) Notice: Subject to any disclaimer, the term of this patent is extended or adjusted under 35 U.S.C. 154(b) by 100 days.

This patent is subject to a terminal disclaimer.

(21) Appl. No.: 12/566,516

(22) Filed: Sep. 24, 2009

(65) Prior Publication Data

US 2010/0168795 A1    Jul. 1, 2010

Related U.S. Application Data

(63) Continuation-in-part of application No. 12/130,395, filed on May 30, 2008, and a continuation-in-part of application No. 12/130,095, filed on May 30, 2008.

(60) Provisional application No. 61/100,625, filed on Sep. 26, 2008, provisional application No. 61/100,593, filed on Sep. 26, 2008, provisional application No. 61/119,651, filed on Dec. 3, 2008, provisional application No. 61/122,658, filed on Dec. 15, 2008, provisional application No. 61/144,426, filed on Jan. 13, 2009, provisional application No. 61/167,789, filed on Apr. 8, 2009, provisional application No. 61/217,556, filed on Jun. 1, 2009, provisional application No. 61/225,478, filed on Jul. 14, 2009, provisional application No. 61/031,598, filed on Feb. 26, 2008, provisional application No. 61/057,340, filed on May 30, 2008.

(51) Int. Cl.
*A61B 17/70* (2006.01)
*A61B 17/86* (2006.01)

(52) U.S. Cl. ........................................ 606/264; 606/305

(58) Field of Classification Search .................. 606/246, 606/264, 305, 301, 308, 302, 257, 260, 254, 606/279, 266, 255

See application file for complete search history.

(56) References Cited

U.S. PATENT DOCUMENTS 4,041,939 A    8/1977  Hall ................................ 128/69

(Continued)

FOREIGN PATENT DOCUMENTS

DE         2649042 B1    10/1976

(Continued)

OTHER PUBLICATIONS

Mekanika, Inc. Website, 2003; Mekanika—The Spinal Stabilization Company, product description for Modulus System, 2 pages, <http://mekanika.com/htm/modsystem.htm>.

(Continued)

*Primary Examiner* — Pedro Philogene
(74) *Attorney, Agent, or Firm* — Fliesler Meyer LLP

(57) ABSTRACT

A dynamic bone anchor for anchoring a spine stabilization assembly which supports the spine while providing for the preservation of spinal motion. The dynamic bone anchor provides load sharing while preserving range of motion and reducing stress exerted upon the bone anchors and spinal anatomy. The dynamic bone anchor includes a deflectable post connected by a ball joint to a threaded anchor. Deflection of the deflectable post is controlled by a compliant sleeve. The force/deflection properties of the dynamic bone anchor may be adapted to the anatomy and functional requirements of the patient. When implanted the pivot point for the deflectable post is placed close to the instantaneous center of rotation of the spine. The dynamic bone anchor may be used as a component of a dynamic stabilization system which supports the spine while providing for the preservation of spinal motion.

25 Claims, 57 Drawing Sheets

U.S. PATENT DOCUMENTS

| | | | |
|---|---|---|---|
| 4,065,817 A | 1/1978 | Branemark et al. | 3/1.91 |
| 4,274,401 A | 6/1981 | Miskew | |
| 4,347,845 A | 9/1982 | Mayfield | 128/303 |
| 4,369,770 A | 1/1983 | Bacal et al. | 128/69 |
| 4,382,438 A | 5/1983 | Jacobs | 128/69 |
| 4,409,968 A | 10/1983 | Drummond | 128/69 |
| 4,411,259 A | 10/1983 | Drummond | 128/69 |
| 4,422,451 A | 12/1983 | Kalamchi | 128/69 |
| 4,479,491 A | 10/1984 | Martin | 128/92 |
| 4,567,885 A | 2/1986 | Androphy | 128/92 |
| 4,573,454 A | 3/1986 | Hoffman | 128/69 |
| 4,604,995 A | 8/1986 | Stephens et al. | 128/69 |
| 4,611,580 A | 9/1986 | Wu | 128/69 |
| 4,611,581 A | 9/1986 | Steffee | 128/69 |
| 4,611,582 A | 9/1986 | Duff | 128/69 |
| 4,641,636 A | 2/1987 | Cotrel | 128/69 |
| 4,648,388 A | 3/1987 | Steffee | 128/69 |
| 4,653,481 A | 3/1987 | Howland et al. | 128/69 |
| 4,653,489 A | 3/1987 | Tronzo | 128/92 |
| 4,655,199 A | 4/1987 | Steffee | 128/69 |
| 4,658,809 A | 4/1987 | Ulrich et al. | 128/92 |
| 4,696,290 A | 9/1987 | Steffee | 128/69 |
| 4,719,905 A | 1/1988 | Steffee | 128/69 |
| 4,763,644 A | 8/1988 | Webb | 128/69 |
| 4,773,402 A | 9/1988 | Asher et al. | 128/69 |
| 4,805,602 A | 2/1989 | Puno et al. | 128/69 |
| 4,815,453 A | 3/1989 | Cotrel | 128/69 |
| 4,887,595 A | 12/1989 | Heinig et al. | 606/61 |
| 4,913,134 A | 4/1990 | Luque | 128/69 |
| 4,946,458 A | 8/1990 | Harms et al. | 606/61 |
| 4,950,269 A | 8/1990 | Gaines, Jr. | 606/61 |
| 4,955,885 A | 9/1990 | Meyers | 606/53 |
| 4,987,892 A | 1/1991 | Krag et al. | 606/61 |
| 5,005,562 A | 4/1991 | Cotrel | 128/69 |
| 5,024,213 A | 6/1991 | Asher et al. | 128/69 |
| 5,030,220 A | 7/1991 | Howland | 606/61 |
| 5,042,982 A | 8/1991 | Harms et al. | 606/61 |
| 5,047,029 A | 9/1991 | Aebi et al. | 606/61 |
| 5,067,955 A | 11/1991 | Cotrel | 606/61 |
| 5,074,864 A | 12/1991 | Cozad et al. | 606/54 |
| 5,084,049 A | 1/1992 | Asher et al. | 606/61 |
| 5,092,866 A | 3/1992 | Breard et al. | 606/61 |
| 5,102,412 A | 4/1992 | Rogozinski | 606/61 |
| 5,112,332 A | 5/1992 | Cozad et al. | 606/61 |
| 5,113,685 A | 5/1992 | Asher et al. | 72/458 |
| 5,116,334 A | 5/1992 | Cozad et al. | |
| 5,127,912 A | 7/1992 | Ray et al. | 606/61 |
| 5,129,388 A | 7/1992 | Vignaud et al. | 606/61 |
| 5,129,900 A | 7/1992 | Asher et al. | 606/61 |
| 5,147,359 A | 9/1992 | Cozad et al. | 606/61 |
| 5,154,718 A | 10/1992 | Cozad et al. | 606/61 |
| 5,176,680 A | 1/1993 | Vignaud et al. | 606/61 |
| 5,180,393 A | 1/1993 | Commarmond | 623/13 |
| 5,190,543 A | 3/1993 | Schläpfer | 606/61 |
| 5,201,734 A | 4/1993 | Cozad et al. | 606/62 |
| 5,207,678 A | 5/1993 | Harms et al. | 606/61 |
| 5,261,911 A | 11/1993 | Carl | 606/61 |
| 5,261,912 A | 11/1993 | Frigg | 606/61 |
| 5,261,913 A | 11/1993 | Marnay | 606/61 |
| 5,281,222 A | 1/1994 | Allard et al. | 606/54 |
| 5,282,801 A | 2/1994 | Sherman | 606/61 |
| 5,282,863 A | 2/1994 | Burton | 623/17 |
| 5,290,289 A | 3/1994 | Sanders et al. | 606/61 |
| 5,312,402 A | 5/1994 | Schläpfer et al. | 606/53 |
| 5,312,404 A | 5/1994 | Asher et al. | 606/61 |
| 5,344,422 A | 9/1994 | Frigg | 606/61 |
| 5,346,493 A | 9/1994 | Stahurski et al. | 606/61 |
| 5,360,429 A | 11/1994 | Jeanson et al. | 606/61 |
| 5,360,431 A | 11/1994 | Puno et al. | 606/72 |
| 5,374,267 A | 12/1994 | Siegal | |
| 5,380,325 A | 1/1995 | Lahille et al. | 606/61 |
| 5,380,326 A | 1/1995 | Lin | 606/61 |
| 5,382,248 A | 1/1995 | Jacobson et al. | 606/60 |
| 5,385,583 A | 1/1995 | Cotrel | 623/17 |
| 5,387,213 A | 2/1995 | Breard et al. | 606/61 |
| 5,415,661 A | 5/1995 | Holmes | 606/69 |
| 5,429,639 A | 7/1995 | Judet | 606/61 |
| 5,437,672 A | 8/1995 | Alleyne | |
| 5,443,467 A | 8/1995 | Biedermann et al. | 606/65 |
| 5,466,237 A | 11/1995 | Byrd, III et al. | 606/61 |
| 5,474,555 A | 12/1995 | Puno et al. | 606/73 |
| 5,480,442 A | 1/1996 | Bertanoli | |
| 5,487,742 A | 1/1996 | Cotrel | 606/61 |
| 5,496,321 A | 3/1996 | Puno et al. | 606/61 |
| 5,498,264 A | 3/1996 | Schläpfer et al. | 606/72 |
| 5,520,689 A | 5/1996 | Schläpfer et al. | 606/61 |
| 5,534,001 A | 7/1996 | Schläpfer et al. | 606/61 |
| 5,536,268 A | 7/1996 | Griss | 606/61 |
| 5,540,688 A | 7/1996 | Navas | 606/61 |
| 5,545,167 A | 8/1996 | Lin | 606/61 |
| 5,549,607 A | 8/1996 | Olson et al. | 606/61 |
| 5,562,737 A * | 10/1996 | Graf | 623/17.14 |
| 5,569,248 A | 10/1996 | Mathews | 606/61 |
| 5,591,166 A | 1/1997 | Bernhardt et al. | |
| 5,601,552 A | 2/1997 | Cotrel | |
| 5,609,592 A | 3/1997 | Brumfield et al. | 606/61 |
| 5,609,593 A | 3/1997 | Errico et al. | 606/61 |
| 5,611,800 A | 3/1997 | Davis et al. | 606/61 |
| 5,624,441 A | 4/1997 | Sherman et al. | 606/61 |
| 5,628,740 A | 5/1997 | Mullane | 606/61 |
| 5,630,816 A | 5/1997 | Kambin | 606/61 |
| 5,643,260 A | 7/1997 | Doherty | 606/61 |
| 5,645,599 A | 7/1997 | Samani | 623/17 |
| 5,651,789 A | 7/1997 | Cotrel | 606/61 |
| 5,653,708 A | 8/1997 | Howland | 606/61 |
| 5,658,284 A | 8/1997 | Sebastian et al. | 606/61 |
| 5,658,285 A * | 8/1997 | Marnay et al. | 606/264 |
| 5,667,506 A | 9/1997 | Sutterlin | 606/61 |
| 5,667,507 A | 9/1997 | Corin et al. | 606/61 |
| 5,669,910 A | 9/1997 | Korhonen et al. | 606/61 |
| 5,672,175 A | 9/1997 | Martin | 606/61 |
| 5,672,176 A | 9/1997 | Biedermann et al. | 606/61 |
| 5,676,665 A | 10/1997 | Bryan | 606/61 |
| 5,676,703 A | 10/1997 | Gelbard | 623/17 |
| 5,681,310 A | 10/1997 | Yuan et al. | |
| 5,681,311 A | 10/1997 | Foley et al. | 606/61 |
| 5,681,319 A | 10/1997 | Biedermann et al. | 606/104 |
| 5,683,391 A | 11/1997 | Boyd | 606/61 |
| 5,683,392 A | 11/1997 | Richelsoph et al. | 606/61 |
| 5,683,393 A | 11/1997 | Ralph | 606/61 |
| 5,688,272 A | 11/1997 | Montague et al. | 606/61 |
| 5,688,273 A | 11/1997 | Errico et al. | 606/61 |
| 5,690,629 A | 11/1997 | Asher et al. | 606/61 |
| 5,690,632 A | 11/1997 | Schwartz et al. | 606/73 |
| 5,690,633 A | 11/1997 | Taylor et al. | 606/73 |
| 5,693,053 A | 12/1997 | Estes | 606/61 |
| 5,697,929 A | 12/1997 | Mellinger | 606/61 |
| 5,700,292 A | 12/1997 | Margulies | 623/17 |
| 5,702,392 A | 12/1997 | Wu et al. | 606/61 |
| 5,702,394 A | 12/1997 | Henry et al. | 606/61 |
| 5,702,395 A | 12/1997 | Hopf | 606/61 |
| 5,702,396 A | 12/1997 | Hoenig et al. | 606/69 |
| 5,702,399 A | 12/1997 | Kilpela et al. | 606/72 |
| 5,702,452 A | 12/1997 | Argenson et al. | 623/17 |
| 5,713,900 A | 2/1998 | Benzel et al. | 606/61 |
| 5,713,904 A | 2/1998 | Errico et al. | 606/73 |
| 5,716,355 A | 2/1998 | Jackson et al. | 606/61 |
| 5,716,356 A | 2/1998 | Biedermann et al. | 606/61 |
| 5,716,357 A | 2/1998 | Rogozinski | 606/61 |
| 5,716,358 A | 2/1998 | Ochoa et al. | 606/62 |
| 5,716,359 A | 2/1998 | Ojima et al. | 606/76 |
| 5,720,751 A | 2/1998 | Jackson | 606/86 |
| 5,725,528 A | 3/1998 | Errico et al. | 606/61 |
| 5,725,582 A | 3/1998 | Bevan et al. | 623/17 |
| 5,728,098 A | 3/1998 | Sherman et al. | 606/61 |
| 5,733,286 A | 3/1998 | Errico et al. | 606/61 |
| 5,735,851 A | 4/1998 | Errico et al. | 606/61 |
| 5,741,254 A | 4/1998 | Henry et al. | 606/61 |
| 5,743,907 A | 4/1998 | Asher et al. | 606/61 |
| 5,743,911 A | 4/1998 | Cotrel | 606/61 |
| 5,752,957 A | 5/1998 | Ralph et al. | 606/61 |
| 5,766,254 A | 6/1998 | Gelbard | 623/17 |
| 5,776,135 A | 7/1998 | Errico et al. | |
| 5,782,833 A | 7/1998 | Haider | 606/61 |
| 5,785,711 A | 7/1998 | Errico et al. | 606/61 |
| 5,797,911 A | 8/1998 | Sherman et al. | 606/61 |
| 5,800,435 A | 9/1998 | Errico et al. | 606/61 |

| Patent | Date | Inventor | Class |
|---|---|---|---|
| 5,810,819 A | 9/1998 | Errico et al. ............... 606/61 |
| 5,863,293 A | 1/1999 | Richelsoph ............... 606/61 |
| 5,868,745 A | 2/1999 | Alleyne |
| 5,879,350 A | 3/1999 | Sherman et al. ........... 606/61 |
| 5,885,286 A | 3/1999 | Sherman et al. ........... 606/61 |
| 5,891,145 A | 4/1999 | Morrison et al. ........... 606/61 |
| 5,899,904 A | 5/1999 | Errico et al. ............... 606/61 |
| RE36,221 E | 6/1999 | Breard et al. ............... 606/61 |
| 5,910,142 A | 6/1999 | Tatar ........................ 606/61 |
| 5,925,047 A | 7/1999 | Errico et al. ............... 606/65 |
| 5,928,231 A | 7/1999 | Klein et al. ............... 606/60 |
| 5,928,232 A | 7/1999 | Howland et al. ........... 606/61 |
| 5,928,233 A | 7/1999 | Apfelbaum et al. ........ 606/61 |
| 5,947,965 A | 9/1999 | Bryan ........................ 606/61 |
| 5,947,969 A | 9/1999 | Errico et al. ............... 606/61 |
| 5,954,725 A | 9/1999 | Sherman et al. ........... 606/78 |
| 5,961,517 A | 10/1999 | Biedermann et al. ........ 606/61 |
| 5,964,760 A | 10/1999 | Richelsoph ............... 606/61 |
| 5,980,521 A | 11/1999 | Montague et al. ........... 606/61 |
| 5,980,523 A | 11/1999 | Jackson ..................... 606/61 |
| 5,984,922 A | 11/1999 | McKay ..................... 606/61 |
| 5,989,251 A | 11/1999 | Nichols ..................... 606/61 |
| 5,989,254 A | 11/1999 | Katz ........................ 606/73 |
| 6,001,098 A | 12/1999 | Metz-Stavenhagen et al. 606/61 |
| 6,004,322 A | 12/1999 | Bernstein ................... 606/61 |
| 6,010,503 A | 1/2000 | Richelsoph et al. ........ 606/61 |
| 6,015,409 A | 1/2000 | Jackson ..................... 606/61 |
| 6,033,410 A | 3/2000 | McLean et al. |
| 6,036,693 A | 3/2000 | Yuan et al. ............... 606/61 |
| 6,050,997 A * | 4/2000 | Mullane .................. 606/250 |
| 6,053,917 A | 4/2000 | Sherman et al. ........... 606/61 |
| 6,063,089 A | 5/2000 | Errico et al. ............... 606/61 |
| 6,077,262 A | 6/2000 | Schläpfer et al. ........... 606/61 |
| 6,086,588 A | 7/2000 | Ameil et al. ............... 606/61 |
| 6,090,111 A | 7/2000 | Nichols ..................... 606/61 |
| 6,096,039 A | 8/2000 | Stoltenberg et al. ........ 606/61 |
| 6,113,600 A | 9/2000 | Drummond et al. ........ 606/61 |
| 6,113,601 A | 9/2000 | Tatar ........................ 606/61 |
| 6,127,597 A | 10/2000 | Beyar et al. ............... 623/16 |
| 6,132,430 A | 10/2000 | Wagner ..................... 606/61 |
| 6,132,434 A | 10/2000 | Sherman et al. ........... 606/78 |
| 6,132,464 A | 10/2000 | Martin |
| 6,136,000 A | 10/2000 | Louis et al. ............... 606/61 |
| 6,146,383 A | 11/2000 | Studer et al. ............... 606/61 |
| 6,171,311 B1 | 1/2001 | Richelsoph ............... 606/61 |
| 6,193,720 B1 | 2/2001 | Yuan et al. ............... 606/61 |
| 6,197,028 B1 | 3/2001 | Ray et al. ................. 606/61 |
| 6,210,413 B1 | 4/2001 | Justis et al. ............... 606/61 |
| 6,217,578 B1 | 4/2001 | Crozet et al. ............... 606/61 |
| 6,248,106 B1 | 6/2001 | Ferree ..................... 606/61 |
| 6,254,602 B1 | 7/2001 | Justis ........................ 606/61 |
| 6,261,287 B1 | 7/2001 | Metz-Stavenhagen ...... 606/61 |
| 6,267,765 B1 | 7/2001 | Taylor et al. |
| 6,273,888 B1 | 8/2001 | Justis ........................ 606/61 |
| 6,273,914 B1 | 8/2001 | Papas ..................... 623/17.11 |
| 6,280,442 B1 | 8/2001 | Barker et al. |
| 6,280,443 B1 | 8/2001 | Gu et al. ................... 606/61 |
| 6,287,311 B1 | 9/2001 | Sherman et al. ........... 606/78 |
| 6,293,949 B1 | 9/2001 | Justis et al. ............... 606/61 |
| 6,302,882 B1 | 10/2001 | Lin et al. |
| 6,302,888 B1 | 10/2001 | Mellinger et al. ........... 606/73 |
| 6,309,391 B1 | 10/2001 | Crandall et al. ........... 606/61 |
| 6,325,802 B1 | 12/2001 | Frigg ........................ 606/61 |
| 6,328,740 B1 | 12/2001 | Richelsoph ............... 606/61 |
| 6,344,057 B1 | 2/2002 | Rabbe et al. ............... 623/17 |
| 6,355,040 B1 | 3/2002 | Richelsoph et al. ........ 606/61 |
| 6,379,354 B1 | 4/2002 | Rogozinski ............... 606/61 |
| 6,402,749 B1 | 6/2002 | Ashman ................... 606/61 |
| 6,402,751 B1 | 6/2002 | Hoeck et al. ............... 606/61 |
| 6,402,752 B2 | 6/2002 | Schäffler-Wachter et al. . 606/61 |
| 6,413,257 B1 | 7/2002 | Lin et al. ................... 606/61 |
| 6,416,515 B1 | 7/2002 | Wagner ..................... 606/61 |
| 6,423,064 B1 | 7/2002 | Kluger ..................... 606/61 |
| 6,440,169 B1 | 8/2002 | Elberg et al. ............... 623/17.16 |
| 6,451,021 B1 | 9/2002 | Ralph et al. ............... 606/61 |
| 6,454,773 B1 | 9/2002 | Sherman et al. ........... 606/78 |
| 6,458,131 B1 | 10/2002 | Ray ........................ 606/61 |
| 6,458,132 B2 | 10/2002 | Choi ........................ 606/61 |
| 6,468,276 B1 | 10/2002 | McKay ..................... 606/61 |
| 6,471,705 B1 | 10/2002 | Biedermann et al. ........ 606/61 |
| 6,475,219 B1 | 11/2002 | Shelokov |
| 6,478,797 B1 | 11/2002 | Paul ........................ 606/61 |
| 6,482,207 B1 | 11/2002 | Errico ..................... 606/61 |
| 6,485,491 B1 | 11/2002 | Farris et al. ............... 606/61 |
| 6,488,681 B2 | 12/2002 | Martin et al. ............... 606/61 |
| 6,520,962 B1 | 2/2003 | Taylor et al. ............... 606/61 |
| 6,520,990 B1 | 2/2003 | Ray ........................ 623/17.11 |
| 6,537,276 B2 | 3/2003 | Metz-Stavenhagen ...... 606/61 |
| 6,540,748 B2 | 4/2003 | Lombardo ............... 606/61 |
| 6,540,749 B2 | 4/2003 | Schäfer et al. ............. 606/61 |
| 6,547,789 B1 | 4/2003 | Ventre et al. ............... 606/61 |
| 6,554,831 B1 * | 4/2003 | Rivard et al. ............... 606/253 |
| 6,554,832 B2 | 4/2003 | Shluzas ..................... 606/61 |
| 6,554,834 B1 | 4/2003 | Crozet et al. ............... 606/65 |
| 6,565,565 B1 | 5/2003 | Yuan et al. ............... 606/61 |
| 6,565,566 B1 | 5/2003 | Wagner et al. ............. 606/61 |
| 6,565,567 B1 | 5/2003 | Haider ..................... 606/61 |
| 6,565,605 B2 | 5/2003 | Goble et al. ............... 623/17.11 |
| 6,572,617 B1 | 6/2003 | Senegas ................... 606/61 |
| 6,572,653 B1 | 6/2003 | Simonson ............... 623/17.13 |
| 6,579,290 B1 | 6/2003 | Hardcastle et al. ........ 606/61 |
| 6,585,737 B1 | 7/2003 | Baccelli et al. ............. 606/61 |
| 6,589,243 B1 | 7/2003 | Viart et al. |
| 6,616,669 B2 | 9/2003 | Ogilvie et al. ............. 606/61 |
| 6,623,485 B2 | 9/2003 | Doubler et al. ............. 606/61 |
| 6,626,905 B1 | 9/2003 | Schmiel et al. ............. 606/61 |
| 6,626,908 B2 | 9/2003 | Cooper et al. ............. 606/61 |
| 6,645,207 B2 | 11/2003 | Dixon et al. ............... 606/61 |
| 6,652,526 B1 | 11/2003 | Arafiles ..................... 606/61 |
| 6,656,181 B2 | 12/2003 | Dixon et al. ............... 606/69 |
| 6,660,004 B2 | 12/2003 | Barker et al. ............... 606/61 |
| 6,660,005 B2 | 12/2003 | Toyama et al. ............. 606/61 |
| 6,676,661 B1 | 1/2004 | Antonio et al. |
| 6,695,845 B2 | 2/2004 | Dixon et al. ............... 606/70 |
| 6,706,045 B2 | 3/2004 | Lin et al. ................... 606/61 |
| 6,709,434 B1 | 3/2004 | Gournay et al. ............. 606/61 |
| 6,716,213 B2 | 4/2004 | Shitoto ..................... 606/61 |
| 6,716,214 B1 | 4/2004 | Jackson ..................... 606/61 |
| 6,726,689 B2 | 4/2004 | Jackson ..................... 606/73 |
| 6,736,820 B2 | 5/2004 | Biedermann et al. ........ 606/73 |
| 6,740,086 B2 | 5/2004 | Richelsoph |
| 6,749,614 B2 | 6/2004 | Teitelbaum et al. ......... 606/61 |
| 6,752,807 B2 | 6/2004 | Lin et al. ................... 606/61 |
| 6,755,829 B1 | 6/2004 | Bono et al. ............... 606/61 |
| 6,755,835 B2 | 6/2004 | Schultheiss et al. ........ 606/73 |
| 6,761,719 B2 | 7/2004 | Justis et al. ............... 606/61 |
| 6,783,526 B1 | 8/2004 | Lin et al. ................... 606/61 |
| 6,783,527 B2 | 8/2004 | Drewry et al. ............. 606/61 |
| 6,786,907 B2 | 9/2004 | Lange ..................... 606/61 |
| 6,793,656 B1 | 9/2004 | Mathews ................... 606/61 |
| 6,805,695 B2 | 10/2004 | Keith et al. ............... 606/61 |
| 6,805,714 B2 | 10/2004 | Sutcliffe ................... 623/17.11 |
| 6,811,567 B2 | 11/2004 | Reiley ..................... 623/17.11 |
| 6,827,743 B2 | 12/2004 | Eisermann et al. |
| 6,832,999 B2 | 12/2004 | Ueyama et al. ............. 606/61 |
| 6,840,940 B2 | 1/2005 | Ralph et al. ............... 606/61 |
| 6,843,791 B2 | 1/2005 | Serhan ..................... 606/61 |
| 6,852,128 B2 | 2/2005 | Lange ..................... 623/17.11 |
| 6,858,029 B2 | 2/2005 | Yeh |
| 6,858,030 B2 | 2/2005 | Martin et al. ............... 606/61 |
| 6,869,433 B2 | 3/2005 | Glascott ................... 606/73 |
| 6,875,211 B2 | 4/2005 | Nichols et al. ............. 606/61 |
| 6,881,215 B2 | 4/2005 | Assaker et al. ............. 606/61 |
| 6,883,520 B2 | 4/2005 | Lambrecht et al. ........ 128/898 |
| 6,887,242 B2 * | 5/2005 | Doubler et al. ............. 606/274 |
| 6,899,714 B2 | 5/2005 | Vaughan ................... 606/61 |
| 6,918,911 B2 | 7/2005 | Biedermann et al. ........ 606/61 |
| 6,932,817 B2 | 8/2005 | Baynham et al. ........... 606/61 |
| 6,945,974 B2 | 9/2005 | Dalton ..................... 606/70 |
| 6,951,561 B2 | 10/2005 | Warren et al. ............. 606/73 |
| 6,964,666 B2 | 11/2005 | Jackson ..................... 606/61 |
| 6,966,910 B2 | 11/2005 | Ritland ..................... 606/61 |
| 6,986,771 B2 | 1/2006 | Paul et al. ................. 606/61 |
| 6,991,632 B2 | 1/2006 | Ritland ..................... 606/61 |
| 7,008,423 B2 | 3/2006 | Assaker et al. ............. 606/61 |
| 7,011,685 B2 | 3/2006 | Arnin et al. ............... 623/17.16 |
| 7,018,378 B2 | 3/2006 | Biedermann et al. ........ 606/61 |
| 7,018,379 B2 | 3/2006 | Drewry et al. ............. 606/61 |

| Patent No. | Date | Inventor | Class |
|---|---|---|---|
| 7,022,122 B2 | 4/2006 | Amrein et al. | 606/61 |
| 7,029,475 B2 | 4/2006 | Panjabi | 606/61 |
| 7,033,392 B2 | 4/2006 | Schmiel | |
| 7,048,736 B2 | 5/2006 | Robinson et al. | 606/61 |
| 7,051,451 B2 | 5/2006 | Augostino et al. | 33/512 |
| 7,060,066 B2 | 6/2006 | Zhao et al. | 606/61 |
| 7,074,237 B2 | 7/2006 | Goble et al. | 623/17.11 |
| 7,081,117 B2 | 7/2006 | Bono et al. | 606/61 |
| 7,083,621 B2 | 8/2006 | Shaolian et al. | 606/61 |
| 7,083,622 B2 | 8/2006 | Simonson | 606/61 |
| 7,087,056 B2 | 8/2006 | Vaughan | 606/61 |
| 7,087,057 B2 | 8/2006 | Konieczynski et al. | 606/73 |
| 7,087,084 B2 | 8/2006 | Reiley | 623/17.11 |
| 7,090,698 B2 | 8/2006 | Goble et al. | 623/17.11 |
| 7,101,398 B2 | 9/2006 | Dooris et al. | 623/13.11 |
| 7,104,991 B2 | 9/2006 | Dixon | |
| 7,104,992 B2 | 9/2006 | Bailey | 606/61 |
| 7,107,091 B2 | 9/2006 | Jutras et al. | 600/429 |
| 7,125,410 B2 | 10/2006 | Freudiger | 606/61 |
| 7,125,426 B2 | 10/2006 | Moumene et al. | 623/23.42 |
| 7,137,985 B2 | 11/2006 | Jahng | |
| 7,163,538 B2 | 1/2007 | Altarac et al. | |
| 7,189,235 B2 | 3/2007 | Cauthen | |
| 7,214,227 B2 | 5/2007 | Colleran et al. | 606/61 |
| 7,250,052 B2 | 7/2007 | Landry et al. | 606/61 |
| 7,270,665 B2 | 9/2007 | Morrison et al. | |
| 7,282,064 B2 | 10/2007 | Chin | 623/17.15 |
| 7,294,128 B2 | 11/2007 | Alleyne et al. | |
| 7,294,129 B2 | 11/2007 | Hawkins et al. | 606/61 |
| 7,306,603 B2 | 12/2007 | Boehm, Jr. et al. | 606/61 |
| 7,306,606 B2 | 12/2007 | Sasing | 606/61 |
| 7,309,355 B2 | 12/2007 | Donnelly et al. | |
| 7,326,210 B2 | 2/2008 | Jahng et al. | 606/61 |
| 7,335,201 B2 | 2/2008 | Doubler et al. | 606/61 |
| 7,338,490 B2 | 3/2008 | Ogilvie et al. | |
| 7,338,491 B2 | 3/2008 | Baker et al. | |
| 7,344,539 B2 | 3/2008 | Serhan et al. | |
| 7,361,196 B2 | 4/2008 | Fallin et al. | |
| 7,377,923 B2 | 5/2008 | Purcell et al. | |
| 7,445,627 B2 | 11/2008 | Hawkes et al. | |
| 7,455,684 B2 | 11/2008 | Gradel et al. | |
| 7,476,238 B2 | 1/2009 | Panjabi | |
| 7,479,156 B2 | 1/2009 | Lourdel et al. | |
| 7,481,828 B2 | 1/2009 | Mazda et al. | |
| 7,491,218 B2 | 2/2009 | Landry et al. | |
| 7,503,924 B2 | 3/2009 | Lee et al. | |
| 7,513,905 B2 | 4/2009 | Jackson | |
| 7,513,911 B2 | 4/2009 | Lambrecht et al. | |
| 7,520,879 B2 | 4/2009 | Justis | |
| 7,530,992 B2 | 5/2009 | Biedermann et al. | |
| 7,533,672 B2 | 5/2009 | Morgan et al. | |
| 7,553,320 B2 | 6/2009 | Molz, IV et al. | |
| 7,553,329 B2 | 6/2009 | Lambrecht et al. | |
| 7,559,943 B2 | 7/2009 | Mujwid | |
| 7,563,274 B2 | 7/2009 | Justis et al. | |
| 7,572,279 B2 | 8/2009 | Jackson | |
| 7,578,833 B2 | 8/2009 | Bray | |
| 7,585,312 B2 | 9/2009 | Rawlins et al. | |
| 7,588,575 B2 | 9/2009 | Colleran et al. | |
| 7,588,588 B2 | 9/2009 | Spitler et al. | |
| 7,594,924 B2 | 9/2009 | Albert et al. | |
| 7,597,707 B2 | 10/2009 | Freudiger | |
| 7,601,166 B2 | 10/2009 | Biedermann et al. | |
| 7,608,095 B2 | 10/2009 | Yuan et al. | |
| 7,611,526 B2 | 11/2009 | Carl et al. | |
| 7,615,068 B2 | 11/2009 | Timm et al. | |
| 7,625,394 B2 | 12/2009 | Molz, IV et al. | |
| 7,625,396 B2 | 12/2009 | Jackson | |
| 7,635,379 B2 | 12/2009 | Callahan et al. | |
| 7,648,520 B2 | 1/2010 | Markworth | |
| 7,648,522 B2 | 1/2010 | David | |
| 7,662,172 B2 | 2/2010 | Warnick | |
| 7,662,173 B2 | 2/2010 | Cragg et al. | |
| 7,662,175 B2 | 2/2010 | Jackson | |
| 7,674,293 B2 | 3/2010 | Kuiper et al. | |
| 7,678,136 B2 | 3/2010 | Doubler et al. | |
| 7,678,137 B2 | 3/2010 | Butler et al. | |
| 7,682,377 B2 | 3/2010 | Konieczynski et al. | |
| 7,691,129 B2 | 4/2010 | Felix | |
| 7,691,132 B2 | 4/2010 | Landry et al. | |
| 7,699,873 B2 | 4/2010 | Stevenson et al. | |
| 7,699,875 B2 | 4/2010 | Timm et al. | |
| 7,704,270 B2 | 4/2010 | De Coninck | |
| 7,708,762 B2 | 5/2010 | McCarthy et al. | |
| 7,713,287 B2 | 5/2010 | Timm et al. | |
| 7,713,288 B2 | 5/2010 | Timm et al. | |
| 7,717,939 B2 | 5/2010 | Ludwig et al. | |
| 7,722,646 B2 | 5/2010 | Ralph et al. | |
| 7,722,649 B2 | 5/2010 | Biedermann et al. | |
| 7,722,654 B2 | 5/2010 | Taylor et al. | |
| 7,727,259 B2 | 6/2010 | Park | |
| 7,727,261 B2 | 6/2010 | Barker et al. | |
| 7,731,734 B2 | 6/2010 | Clement et al. | |
| 7,731,736 B2 | 6/2010 | Guenther et al. | |
| 7,763,051 B2 | 7/2010 | Labrom et al. | |
| 7,763,052 B2 | 7/2010 | Jahng | |
| 7,766,944 B2 | 8/2010 | Metz-Stavenhagen | |
| 7,766,945 B2 | 8/2010 | Nilsson et al. | |
| 7,776,071 B2 | 8/2010 | Fortin et al. | |
| 7,785,350 B2 | 8/2010 | Eckhardt et al. | |
| 7,785,354 B2 | 8/2010 | Biedermann et al. | |
| 7,789,896 B2 | 9/2010 | Jackson | |
| 7,794,477 B2 | 9/2010 | Melkent et al. | |
| 7,794,481 B2 | 9/2010 | Molz, IV et al. | |
| 7,799,060 B2 | 9/2010 | Lange et al. | |
| 7,803,189 B2 | 9/2010 | Koske | |
| 7,806,913 B2 | 10/2010 | Fanger et al. | |
| 7,806,914 B2 | 10/2010 | Boyd et al. | |
| 7,811,288 B2 | 10/2010 | Jones et al. | |
| 7,811,309 B2 | 10/2010 | Timm et al. | |
| 7,811,311 B2 | 10/2010 | Markworth et al. | |
| 7,815,664 B2 | 10/2010 | Sherman et al. | |
| 7,815,665 B2 | 10/2010 | Jahng et al. | |
| 7,819,899 B2 | 10/2010 | Lancial | |
| 7,819,901 B2 | 10/2010 | Yuan et al. | |
| 7,819,902 B2 * | 10/2010 | Abdelgany et al. | 606/267 |
| 7,828,824 B2 | 11/2010 | Kwak et al. | |
| 7,828,825 B2 | 11/2010 | Bruneau et al. | |
| 7,828,826 B2 | 11/2010 | Drewry et al. | |
| 7,828,830 B2 | 11/2010 | Thramann et al. | |
| 7,833,250 B2 | 11/2010 | Jackson | |
| 7,833,256 B2 | 11/2010 | Biedermann et al. | |
| 7,842,072 B2 | 11/2010 | Dawson | |
| 7,850,715 B2 | 12/2010 | Bonouskou et al. | |
| 7,854,752 B2 | 12/2010 | Colleran et al. | |
| 7,857,833 B2 | 12/2010 | Abdou | |
| 7,857,834 B2 | 12/2010 | Boschert | |
| 7,862,586 B2 | 1/2011 | Malek | |
| 7,862,587 B2 | 1/2011 | Jackson | |
| 7,862,588 B2 | 1/2011 | Abdou | |
| 7,862,591 B2 | 1/2011 | Dewey et al. | |
| 7,862,594 B2 | 1/2011 | Abdelgany et al. | |
| 7,871,413 B2 | 1/2011 | Park et al. | |
| 7,875,059 B2 | 1/2011 | Patterson et al. | |
| 7,875,060 B2 | 1/2011 | Chin | |
| 7,879,074 B2 | 2/2011 | Kwak et al. | |
| 7,892,266 B2 | 2/2011 | Carli | |
| 7,909,856 B2 | 3/2011 | Yuan et al. | |
| 7,914,558 B2 | 3/2011 | Landry et al. | |
| 7,918,792 B2 | 4/2011 | Drzyzga et al. | |
| 7,927,359 B2 * | 4/2011 | Trautwein et al. | 606/264 |
| 7,942,910 B2 | 5/2011 | Doubler et al. | |
| 2003/0004511 A1 | 1/2003 | Ferree | |
| 2003/0171749 A1 | 9/2003 | Le Couedic et al. | |
| 2004/0015166 A1 | 1/2004 | Gorek | |
| 2004/0034374 A1 | 2/2004 | Zatzsch et al. | |
| 2004/0049285 A1 | 3/2004 | Haas | |
| 2004/0097925 A1 | 5/2004 | Boehm, Jr. et al. | |
| 2004/0111088 A1 | 6/2004 | Picetti et al. | |
| 2004/0122425 A1 | 6/2004 | Suzuki et al. | |
| 2004/0147928 A1 | 7/2004 | Landry et al. | |
| 2004/0153077 A1 | 8/2004 | Biedermann et al. | |
| 2004/0158247 A1 | 8/2004 | Sitiso et al. | |
| 2004/0162560 A1 | 8/2004 | Raynor et al. | |
| 2004/0172022 A1 | 9/2004 | Landry et al. | |
| 2004/0172024 A1 | 9/2004 | Gorek | |
| 2004/0215192 A1 | 10/2004 | Justis et al. | |
| 2004/0225289 A1 | 11/2004 | Biedermann et al. | |

| | | |
|---|---|---|
| 2004/0230192 A1 | 11/2004 | Graf |
| 2004/0230304 A1 | 11/2004 | Yuan et al. |
| 2005/0049589 A1 | 3/2005 | Jackson |
| 2005/0080415 A1 | 4/2005 | Keyer et al. |
| 2005/0090822 A1 | 4/2005 | DiPoto |
| 2005/0096652 A1 | 5/2005 | Burton |
| 2005/0107788 A1 | 5/2005 | Beaurain et al. |
| 2005/0113923 A1 | 5/2005 | Acker et al. |
| 2005/0131404 A1 | 6/2005 | Mazda et al. |
| 2005/0131406 A1 | 6/2005 | Reiley et al. |
| 2005/0143737 A1 | 6/2005 | Pafford et al. |
| 2005/0171537 A1 | 8/2005 | Mazel et al. |
| 2005/0171543 A1 | 8/2005 | Timm et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0182400 A1 | 8/2005 | White |
| 2005/0182401 A1 | 8/2005 | Timm et al. |
| 2005/0192569 A1 | 9/2005 | Nichols et al. |
| 2005/0228382 A1 | 10/2005 | Richelsoph et al. |
| 2005/0228385 A1 | 10/2005 | Iott et al. |
| 2005/0240180 A1 | 10/2005 | Vienney et al. |
| 2005/0240265 A1 | 10/2005 | Kuiper et al. |
| 2005/0261770 A1 | 11/2005 | Kuiper et al. |
| 2005/0267470 A1 | 12/2005 | McBride |
| 2005/0277922 A1 | 12/2005 | Trieu et al. |
| 2005/0288670 A1 | 12/2005 | Panjabi et al. |
| 2006/0025771 A1 | 2/2006 | Jackson |
| 2006/0036324 A1 | 2/2006 | Sachs et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058787 A1 | 3/2006 | David |
| 2006/0058788 A1 | 3/2006 | Hammer et al. |
| 2006/0079894 A1 | 4/2006 | Colleran et al. |
| 2006/0079896 A1 | 4/2006 | Kwak et al. |
| 2006/0084978 A1 | 4/2006 | Mokhtar |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084990 A1 | 4/2006 | Gournay et al. |
| 2006/0085069 A1 | 4/2006 | Kim |
| 2006/0085070 A1 | 4/2006 | Kim |
| 2006/0089643 A1 | 4/2006 | Mujwid |
| 2006/0095035 A1 | 5/2006 | Jones et al. |
| 2006/0106383 A1 | 5/2006 | Biedermann et al. |
| 2006/0111712 A1 | 5/2006 | Jackson |
| 2006/0122620 A1 | 6/2006 | Kim |
| 2006/0129148 A1 | 6/2006 | Simmons et al. |
| 2006/0129149 A1 | 6/2006 | Iott et al. |
| 2006/0142761 A1 | 6/2006 | Landry et al. |
| 2006/0149242 A1 | 7/2006 | Kraus et al. |
| 2006/0149244 A1 | 7/2006 | Amrein et al. |
| 2006/0149380 A1 | 7/2006 | Lotz et al. |
| 2006/0161153 A1 | 7/2006 | Hawkes et al. |
| 2006/0195093 A1 | 8/2006 | Jahng |
| 2006/0200128 A1 | 9/2006 | Mueller |
| 2006/0200131 A1 | 9/2006 | Chao et al. |
| 2006/0229607 A1 | 10/2006 | Brumfield |
| 2006/0229613 A1 | 10/2006 | Timm et al. |
| 2006/0235385 A1 | 10/2006 | Whipple |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241600 A1 | 10/2006 | Ensign et al. |
| 2006/0241601 A1 | 10/2006 | Trautwein et al. |
| 2006/0241603 A1 | 10/2006 | Jackson |
| 2006/0241757 A1 | 10/2006 | Anderson |
| 2006/0247623 A1 | 11/2006 | Anderson et al. |
| 2006/0247631 A1 | 11/2006 | Ahn et al. |
| 2006/0247637 A1 | 11/2006 | Colleran et al. |
| 2006/0253118 A1 | 11/2006 | Bailey |
| 2006/0264935 A1 | 11/2006 | White |
| 2006/0264937 A1 | 11/2006 | White |
| 2006/0276897 A1 | 12/2006 | Winslow et al. |
| 2006/0282073 A1 | 12/2006 | Simanovsky |
| 2006/0282078 A1 | 12/2006 | Labrom et al. |
| 2007/0016190 A1 | 1/2007 | Martinez et al. |
| 2007/0016194 A1 | 1/2007 | Shaolian et al. |
| 2007/0016201 A1 | 1/2007 | Freudiger |
| 2007/0049936 A1 | 3/2007 | Colleran et al. |
| 2007/0083200 A1 | 4/2007 | Gittings et al. |
| 2007/0088359 A1 | 4/2007 | Woods et al. |
| 2007/0093814 A1 | 4/2007 | Callahan, II et al. |
| 2007/0093820 A1 | 4/2007 | Freudiger |
| 2007/0093821 A1 | 4/2007 | Freudiger |
| 2007/0118122 A1 | 5/2007 | Butler et al. |
| 2007/0123871 A1 | 5/2007 | Jahng |
| 2007/0161994 A1 | 7/2007 | Lowery et al. |
| 2007/0162007 A1 | 7/2007 | Shoham |
| 2007/0167946 A1 | 7/2007 | Triplett et al. |
| 2007/0167947 A1 | 7/2007 | Gittings |
| 2007/0198014 A1 | 8/2007 | Graf et al. |
| 2007/0213719 A1 | 9/2007 | Hudgins et al. |
| 2007/0233068 A1 | 10/2007 | Bruneau et al. |
| 2007/0233072 A1 | 10/2007 | Dickinson et al. |
| 2007/0233090 A1 | 10/2007 | Naifeh et al. |
| 2007/0233091 A1 | 10/2007 | Naifeh et al. |
| 2007/0233092 A1 | 10/2007 | Falahee |
| 2007/0233093 A1 | 10/2007 | Falahee |
| 2007/0233094 A1 | 10/2007 | Colleran et al. |
| 2007/0250061 A1 | 10/2007 | Chin et al. |
| 2007/0270836 A1 | 11/2007 | Bruneau et al. |
| 2007/0270838 A1 | 11/2007 | Bruneau et al. |
| 2007/0276380 A1 | 11/2007 | Jahng et al. |
| 2007/0288009 A1 | 12/2007 | Brown et al. |
| 2007/0288012 A1 | 12/2007 | Colleran et al. |
| 2008/0009864 A1 | 1/2008 | Forton et al. |
| 2008/0021459 A1 | 1/2008 | Lim |
| 2008/0021461 A1 | 1/2008 | Barker et al. |
| 2008/0033433 A1 | 2/2008 | Implicito |
| 2008/0039838 A1 | 2/2008 | Landry et al. |
| 2008/0051787 A1 | 2/2008 | Remington et al. |
| 2008/0065073 A1 | 3/2008 | Perriello et al. |
| 2008/0065075 A1 | 3/2008 | Dant et al. |
| 2008/0065079 A1 | 3/2008 | Bruneau et al. |
| 2008/0071273 A1 | 3/2008 | Hawkes et al. |
| 2008/0077139 A1 | 3/2008 | Landry et al. |
| 2008/0183215 A1 | 7/2008 | Altarac et al. |
| 2008/0195208 A1 | 8/2008 | Castellvi et al. |
| 2008/0262554 A1 | 10/2008 | Hayes et al. |
| 2008/0312693 A1 | 12/2008 | Trautwein et al. |
| 2009/0062868 A1 | 3/2009 | Casutt |
| 2010/0174317 A1 | 7/2010 | Timm et al. |
| 2010/0198270 A1 | 8/2010 | Barker et al. |
| 2010/0222819 A1 | 9/2010 | Timm et al. |

FOREIGN PATENT DOCUMENTS

| | | |
|---|---|---|
| DE | 3639810 A1 | 5/1988 |
| EP | 0128058 B1 | 4/1988 |
| EP | 0669109 B1 | 8/1995 |
| EP | 0982007 | 3/2000 |
| EP | 1281362 A2 | 2/2003 |
| EP | 1330987 A1 | 7/2003 |
| FR | 2612070 A1 | 9/1988 |
| FR | 2615095 A1 | 11/1988 |
| FR | 2844180 A1 | 3/2004 |
| FR | 2880256 B1 | 7/2006 |
| GB | 780652 | 8/1957 |
| GB | 2173104 | 10/1986 |
| GB | 2382304 | 5/2003 |
| KR | 20080072848 | 8/2008 |
| WO | WO 87/07134 | 12/1987 |
| WO | WO 94/21185 | 9/1994 |
| WO | WO 98/27884 | 7/1998 |
| WO | WO 01/45576 | 6/2001 |
| WO | WO 01/91656 | 12/2001 |
| WO | WO 02/07621 | 1/2002 |
| WO | WO 02/07622 | 1/2002 |
| WO | WO 02/17803 | 3/2002 |
| WO | WO 02/39921 | 5/2002 |
| WO | WO 02/43603 | 6/2002 |
| WO | WO 02/102259 | 12/2002 |
| WO | WO 03/007828 | 1/2003 |

| | | | |
|---|---|---|---|
| WO | WO 03/009737 | 2/2003 | |
| WO | WO 03/015647 | 2/2003 | |
| WO | WO 03/037216 | 5/2003 | |
| WO | WO 03/077806 | 9/2003 | |
| WO | WO2004/024011 | 3/2004 | |
| WO | WO2004/034916 | 4/2004 | |
| WO | WO2006/033503 | 3/2006 | |
| WO | WO2006/066685 | 6/2006 | |
| WO | WO2006/105935 | 10/2006 | |
| WO | WO2007064324 | 6/2007 | |
| WO | WO2007/080317 | 7/2007 | |
| WO | WO2008/034130 * | 3/2008 | 606/264 |
| WO | WO2008/073544 | 6/2008 | |

OTHER PUBLICATIONS

Zimmer, Inc. Website, 2007; Zimmer Spine, product description for Dynesis—The Dynamic Stabilization System, 5 pages, <http://www.zimmer com/ctl?template=IN&action=1&op=global&id=9165&pr=Y>.

Ito Medical Instrument website, 2006; ITOIKA Medical Instruments, product description for S-Plate, 15 pages, <http://ito-ika.co.jp/s-plate/splate1.pdf and http://ito-ika.co.jp/s-plate/splate1.pdf>.

"Flexible rods and the case for dynamic stabilization," Jason M. Highsmith, M.D., et al., Neurosurg. Focus, vol. 22, Jan. 2007, pp. 1-5.

"The Spinous Process: The Forgotten Appendage," Kenneth R. Kattan, M. D. eta l., Skeletal Radiology, vol. 6, 1981, pp. 199-204.

"Morphological and functional changes of the lumbar spinous processes in the elderly," R. Scapinelli, Surgical Radiologic Anatomy, vol. 11, 1989, pp. 129-133.

"The Paraspinal Sacrospinalis-Splitting Approach to the Lumbar Spine," Leon L. Wiltse et al., The Journal of Bone & Joint Surgery, vol. 50-A, No. 5, Jul. 1968 pp. 919-926.

Dynamic Reconstruction of the Spine, D.H. Kim et al., Thieme, New York 2006, Chapters 1, 2, 30, 31, 37-43.

International Search Report for PCT/US07/70981 dated Apr. 23, 2008, 7 pages.

International Search Report for PCT/US/2009/058466 dated Apr. 29, 2010, 13 pages.

International Search Report for PCT/US/2009/058460 dated Apr. 29, 2010, 11 pages.

International Search Report for PCT/US/2009/058470 dated Apr. 29, 2010, 12 pages.

International Search Report for PCT/US/2009/066567 dated Jul. 20, 2010, 9 pages.

International Search Report for PCT/US2010/058776 dated Aug. 23, 2011, 4 pages.

* cited by examiner

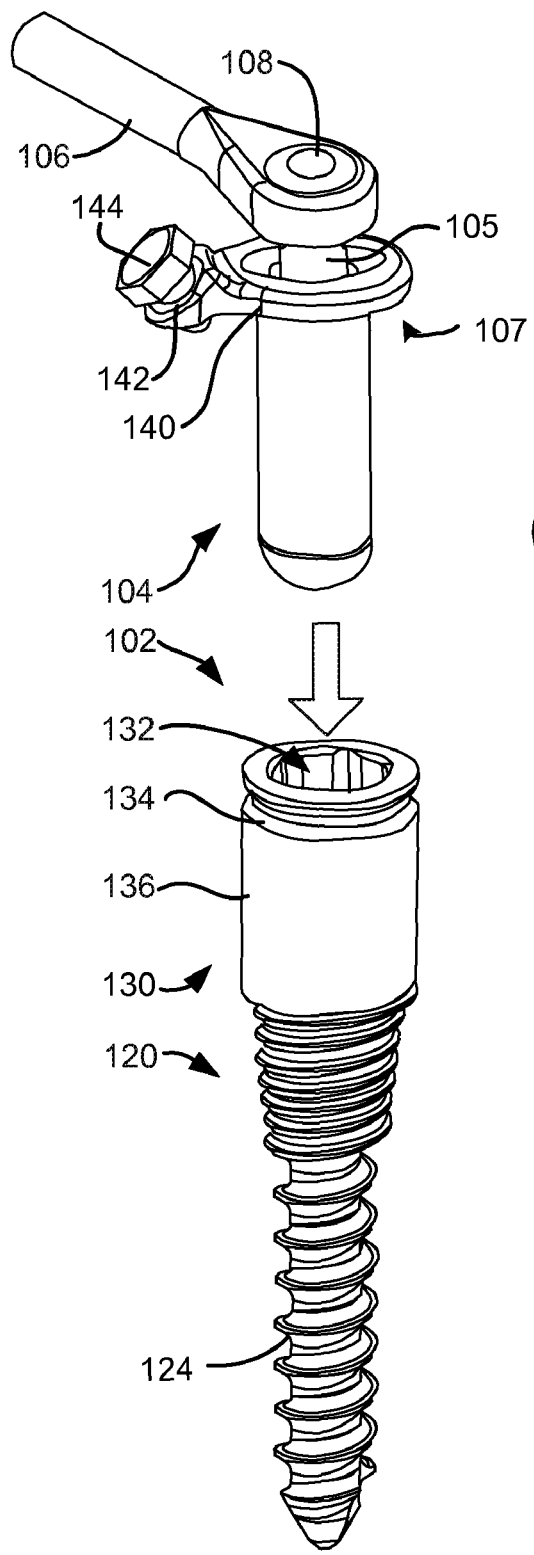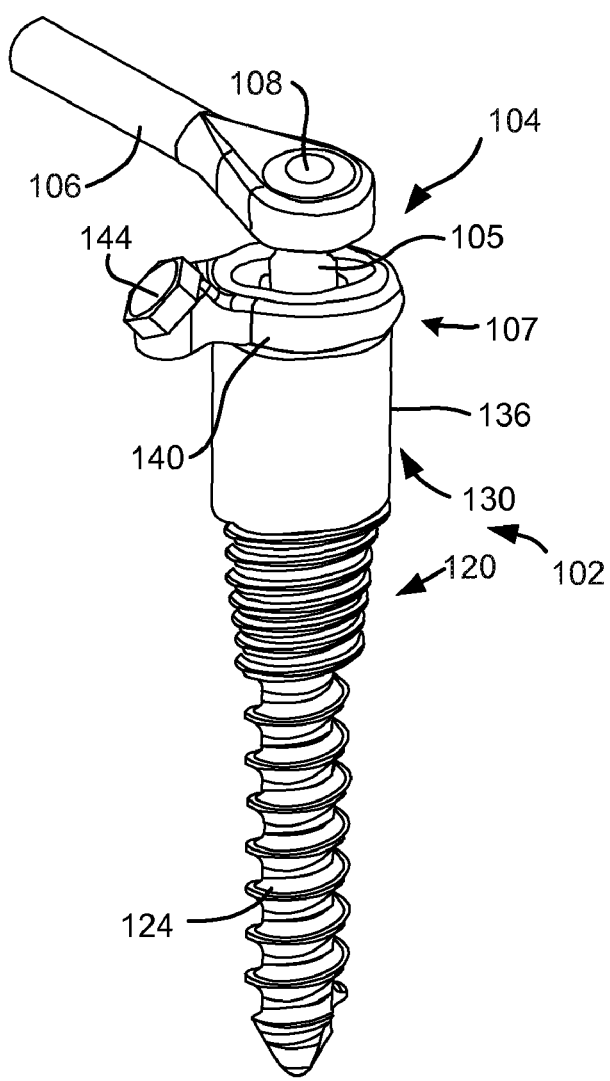
FIG. 1A  FIG. 1B

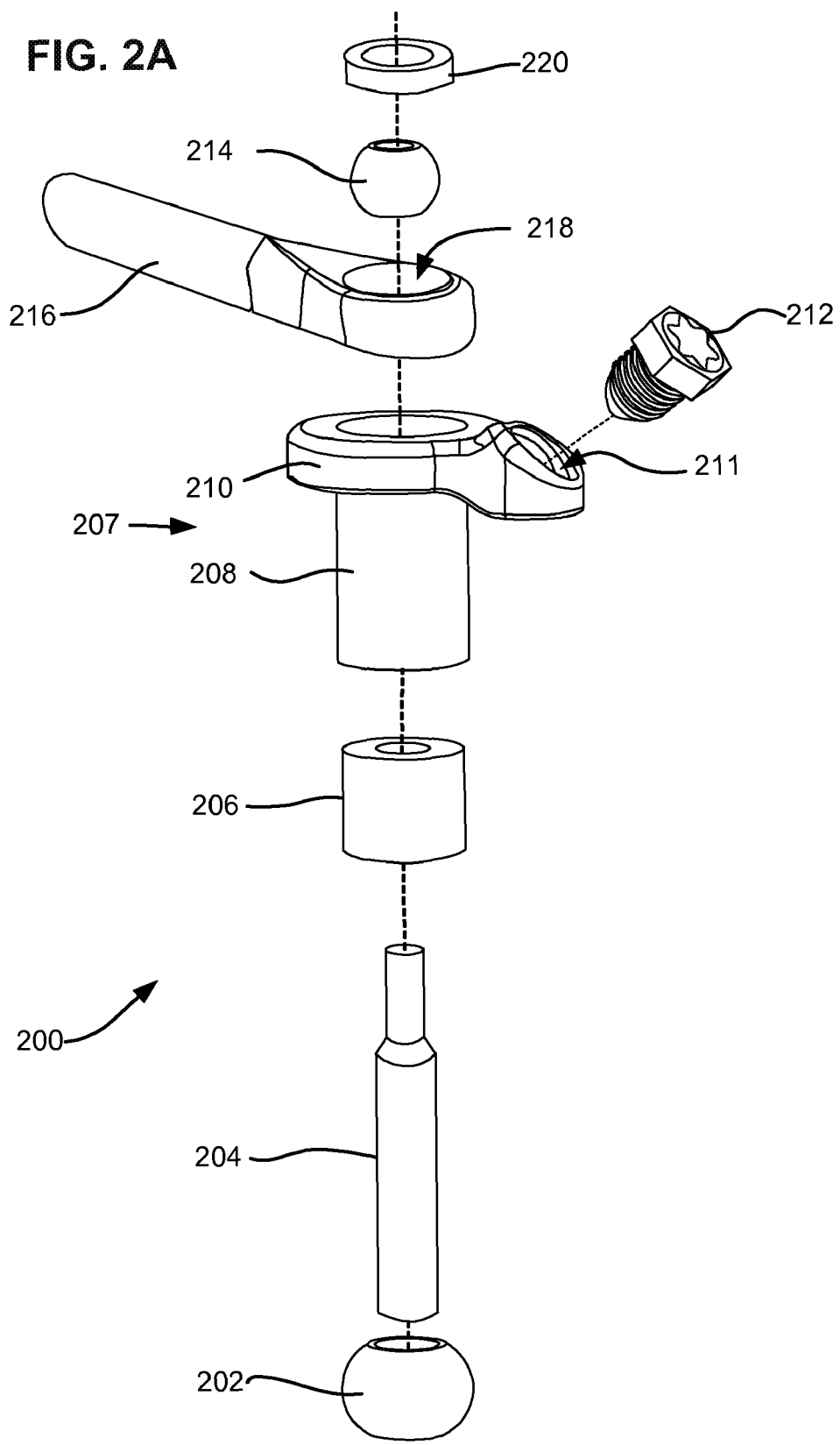

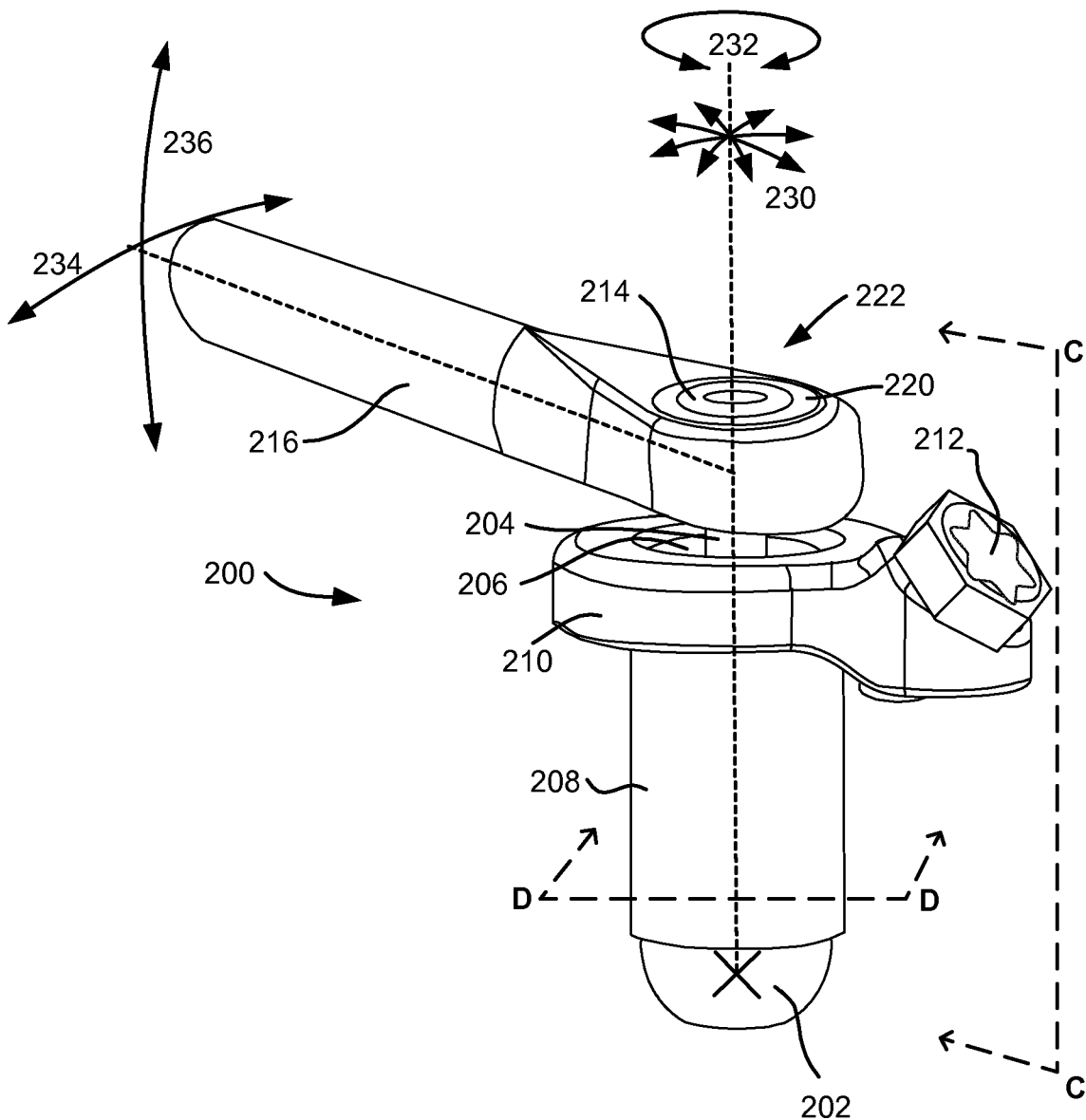

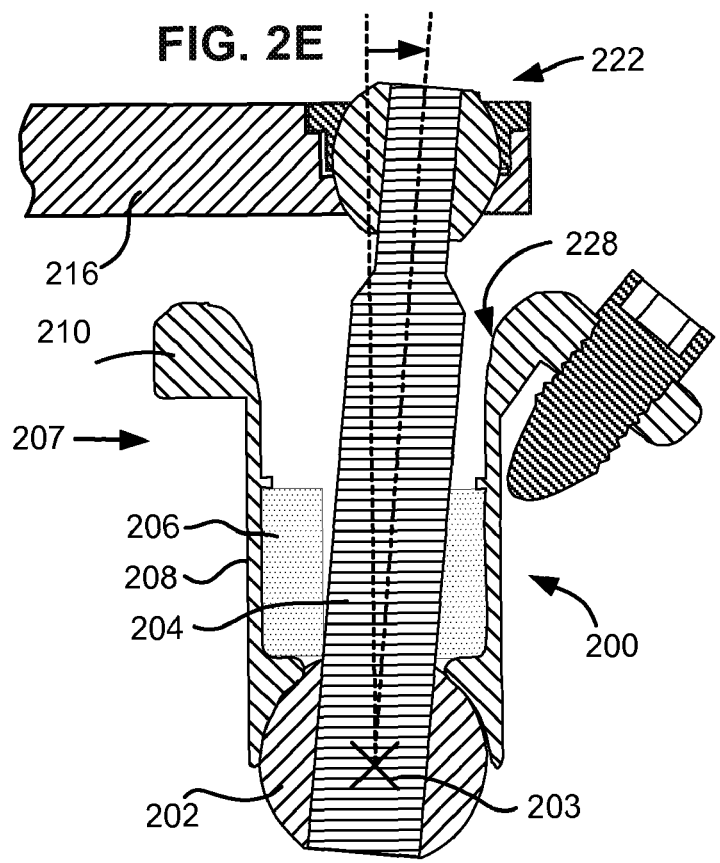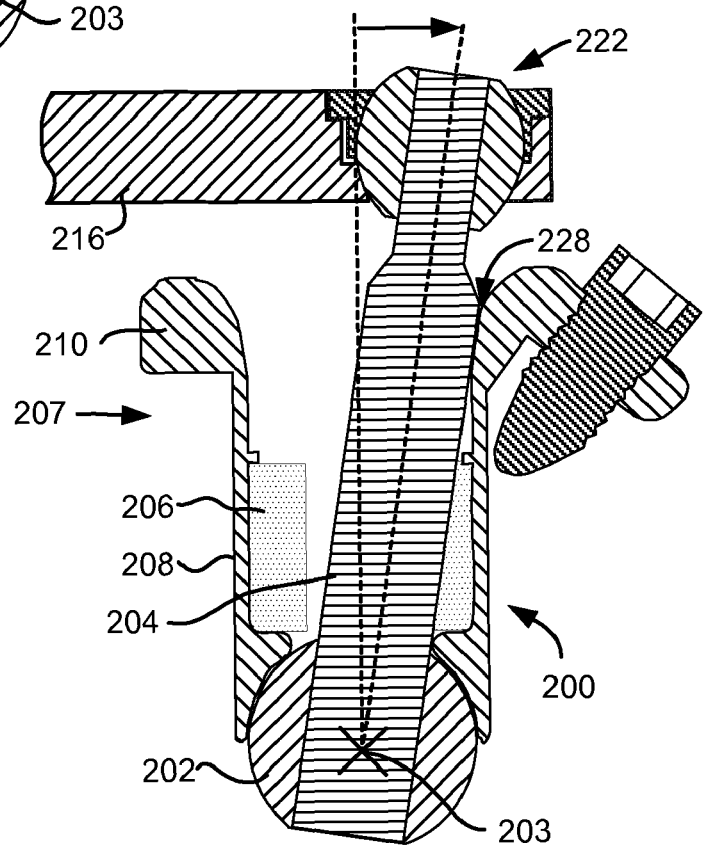

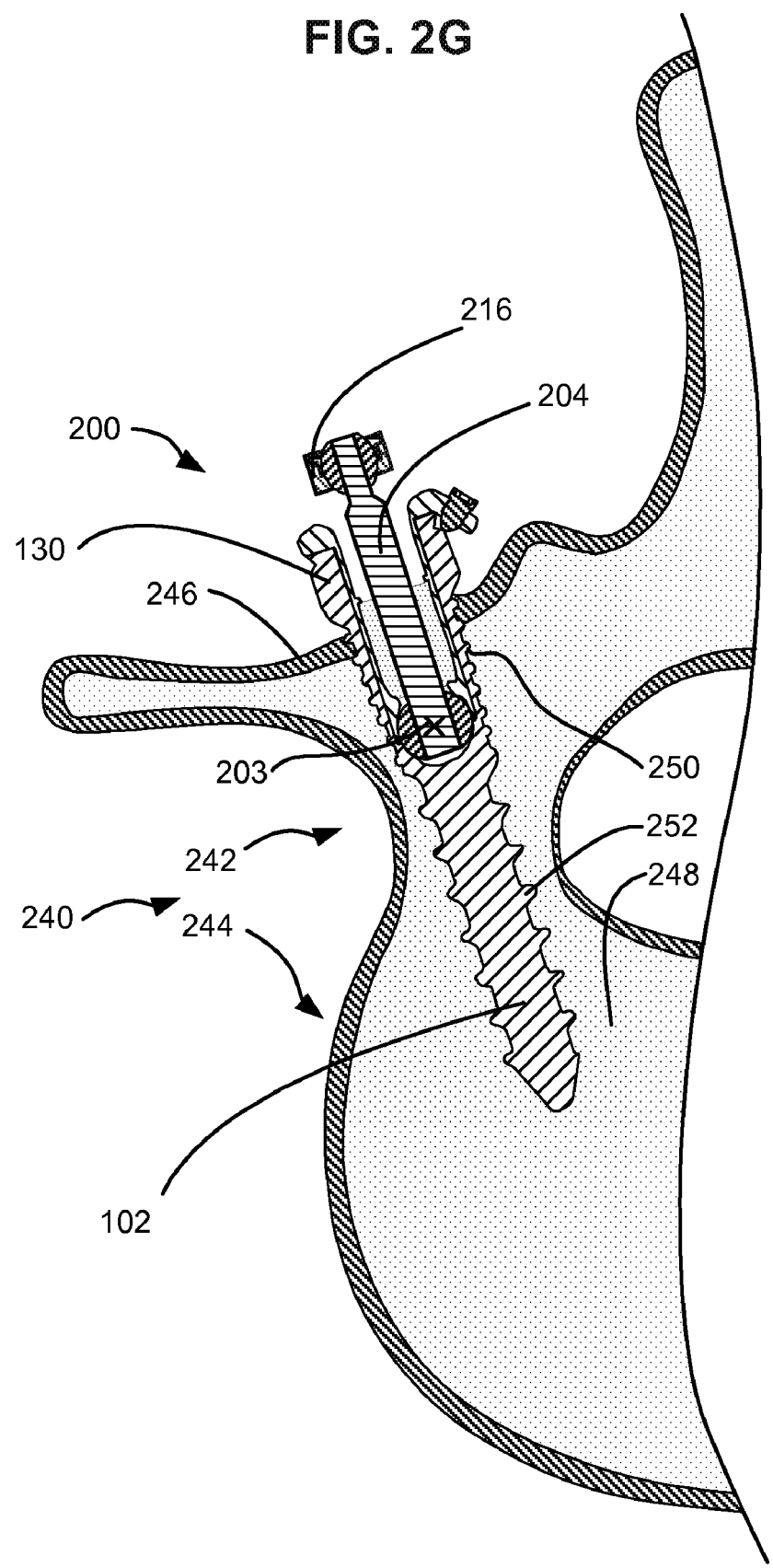

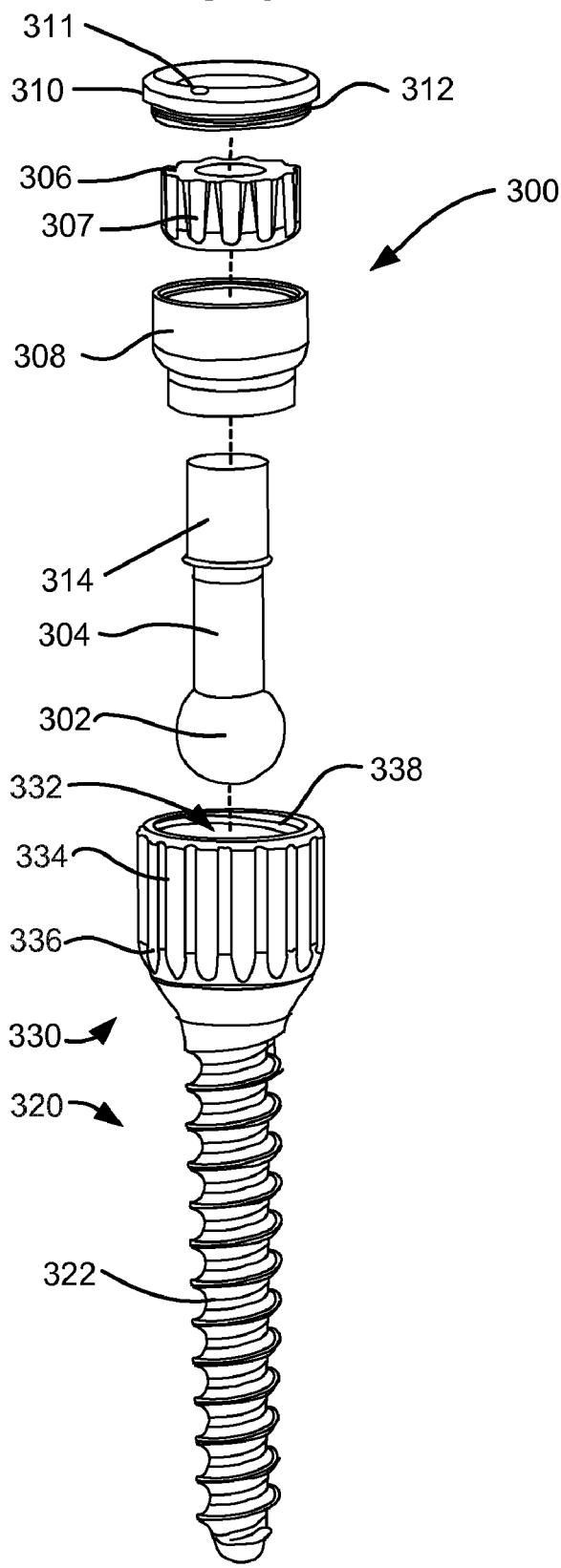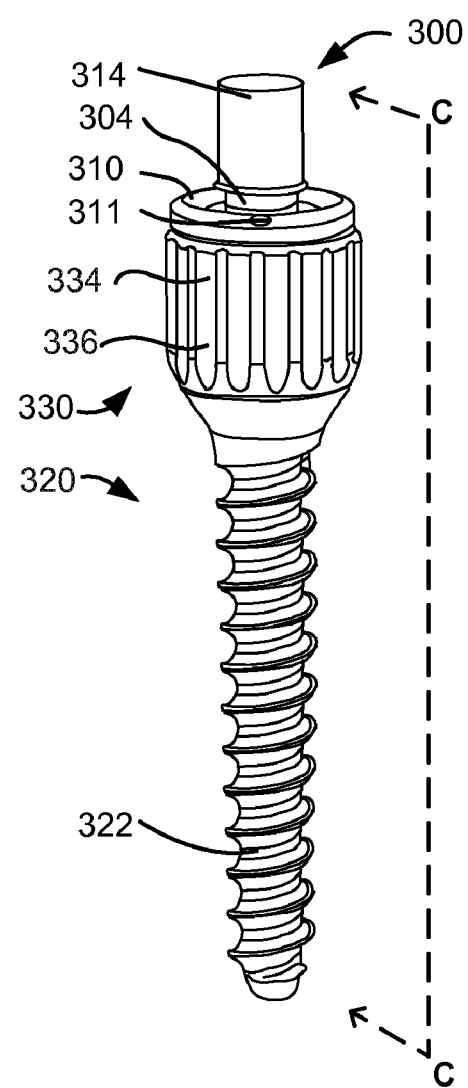

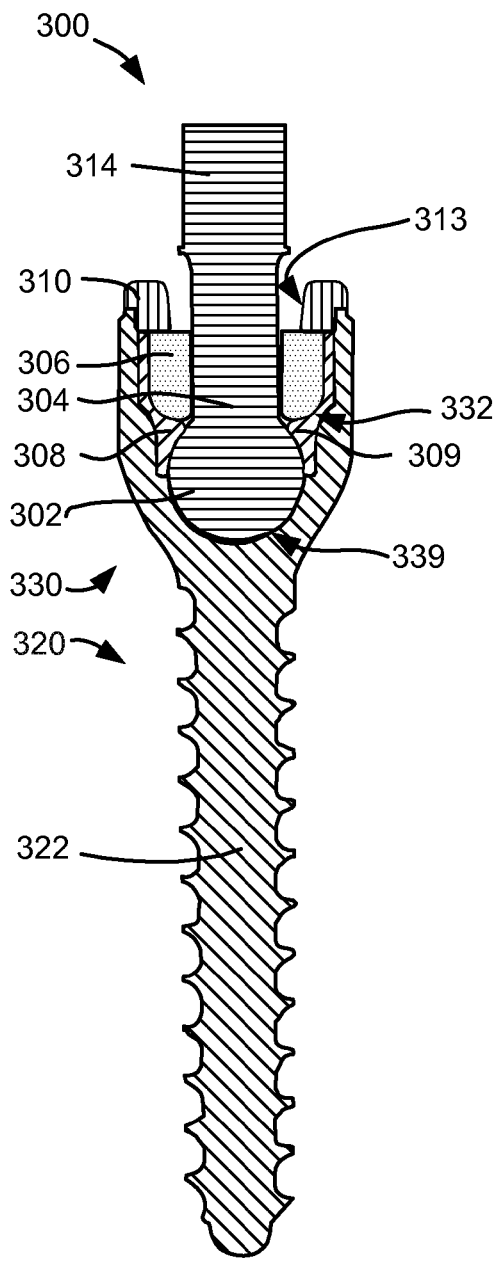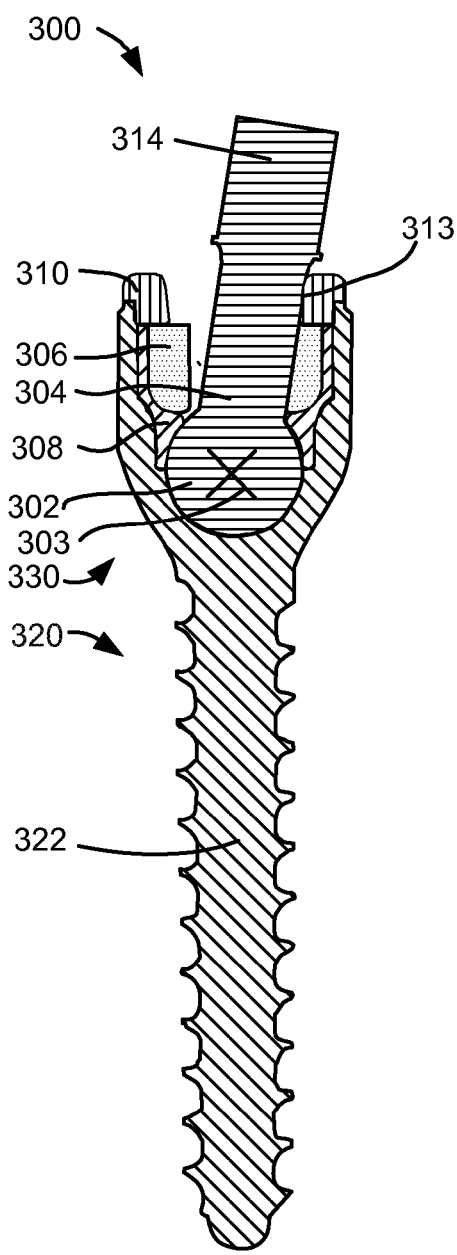

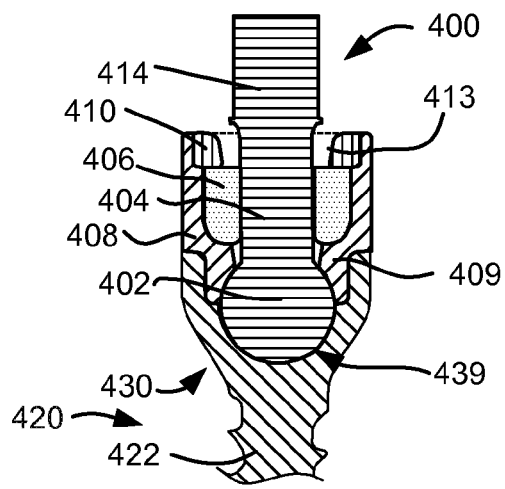
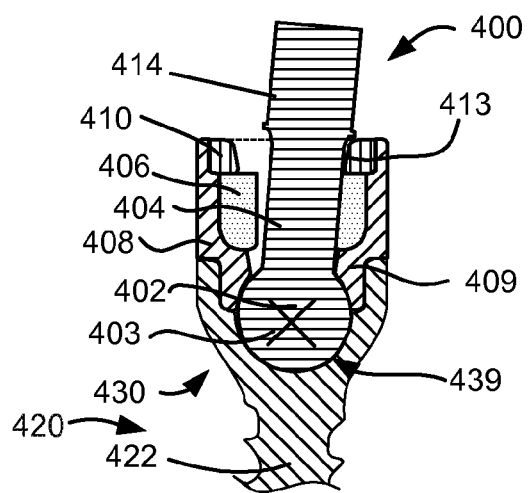
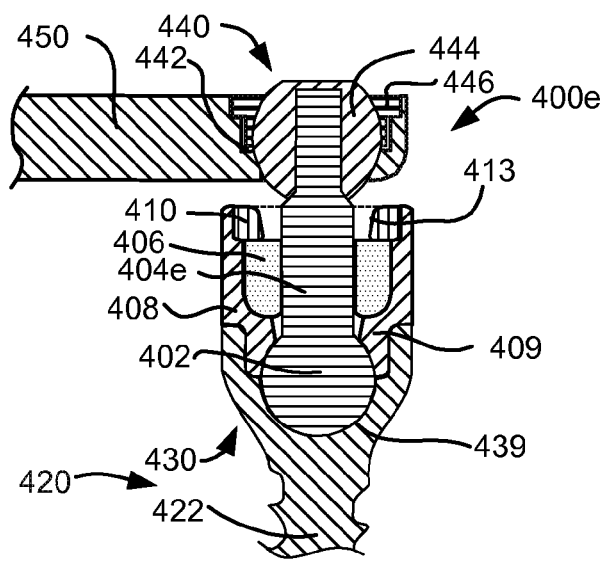

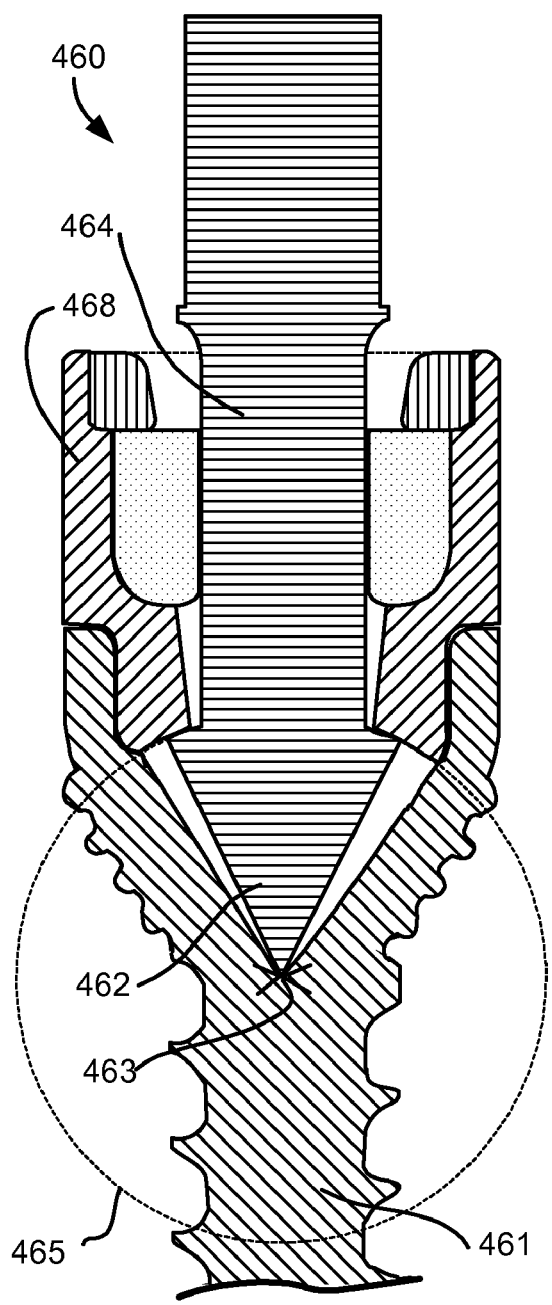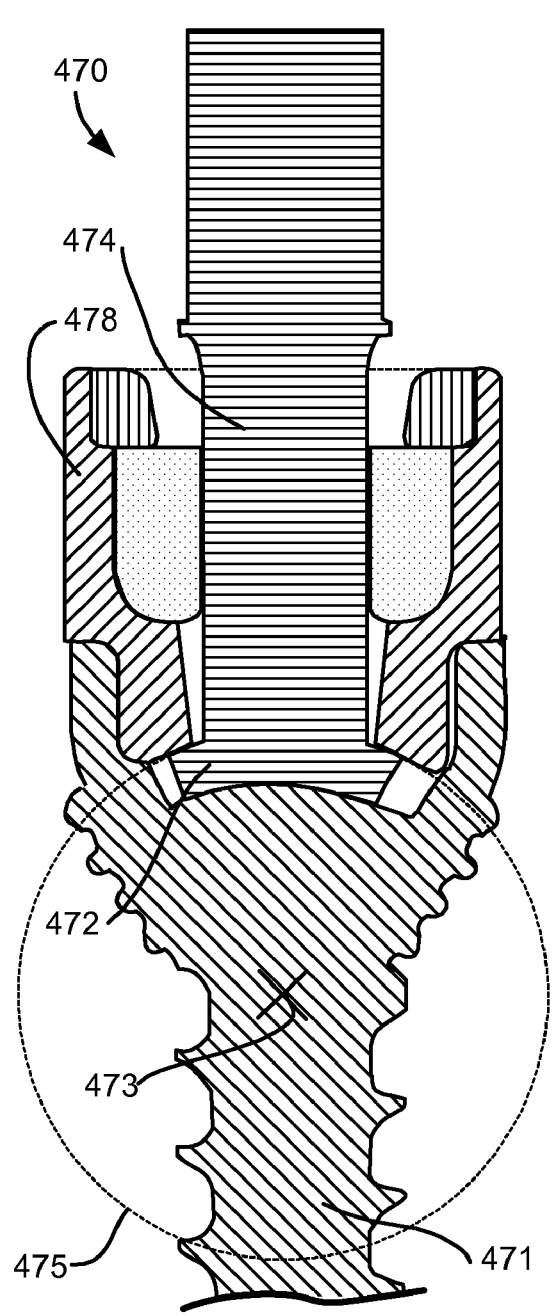

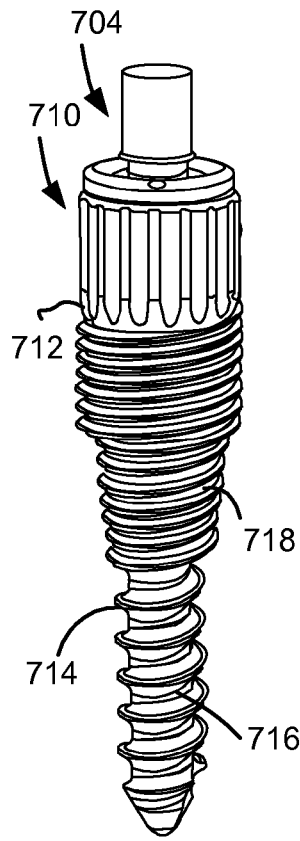
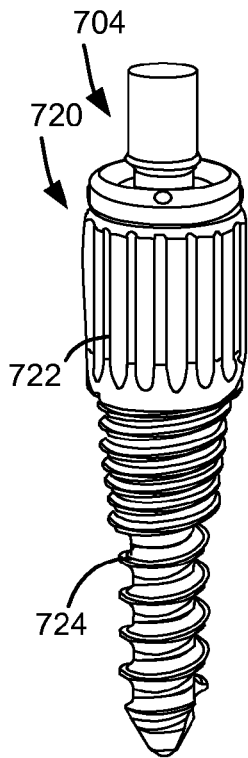
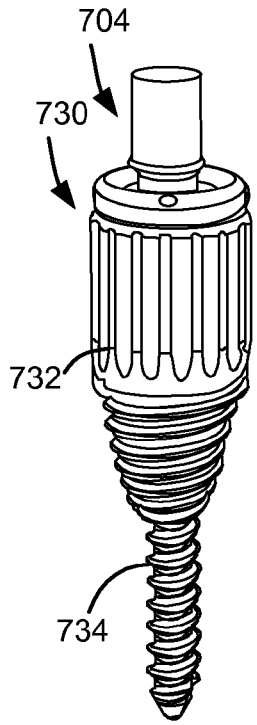
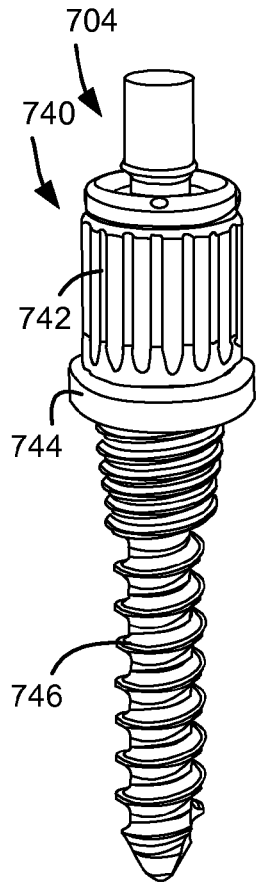
FIG. 7A  FIG. 7B  FIG. 7C  FIG. 7D
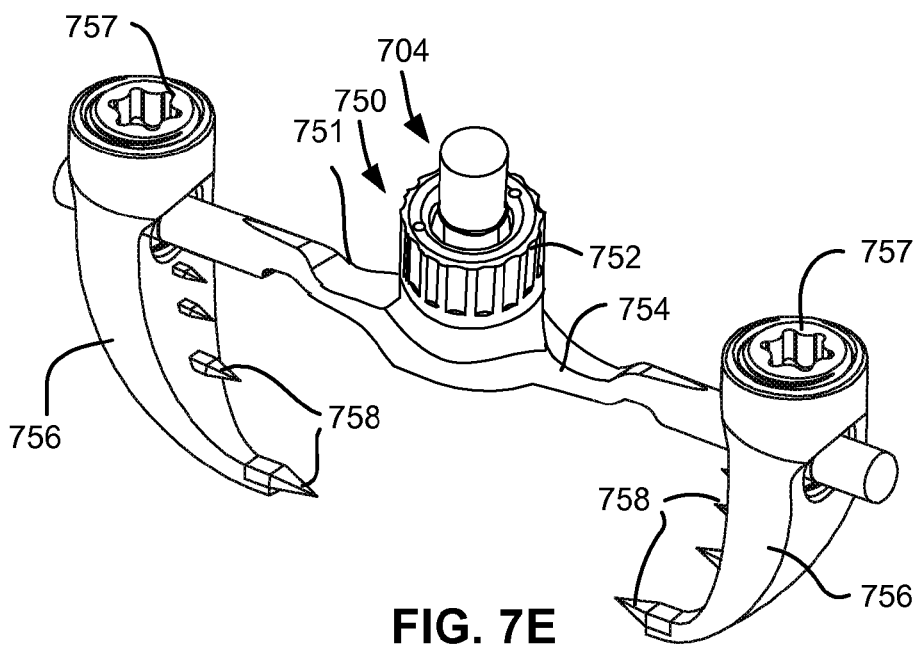
FIG. 7E

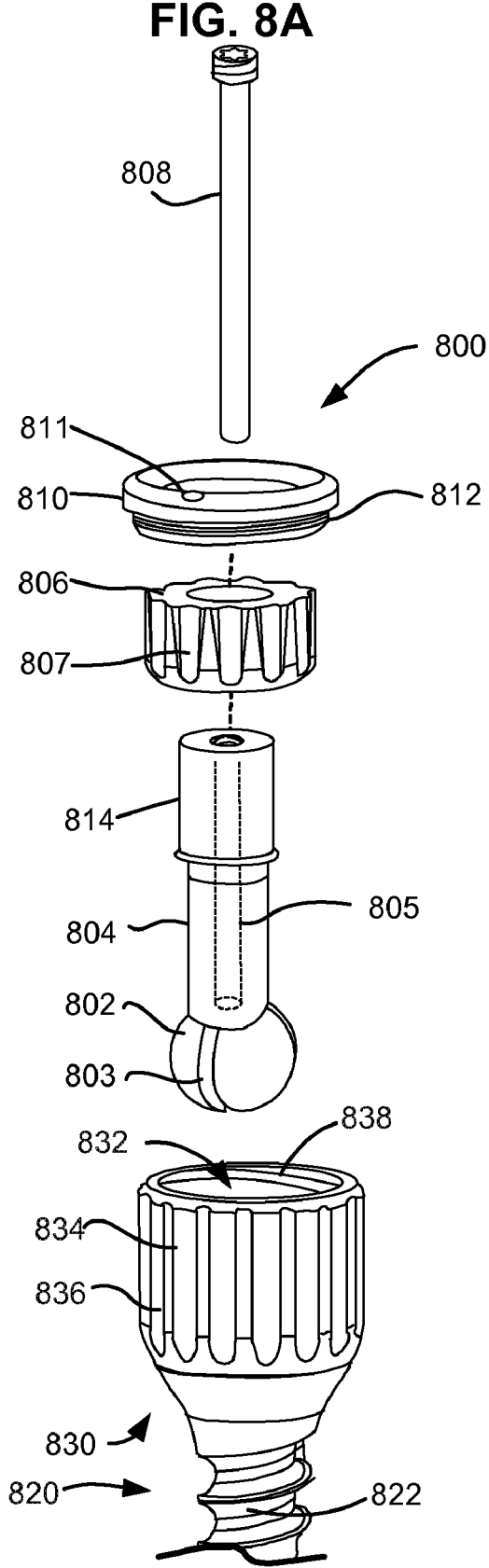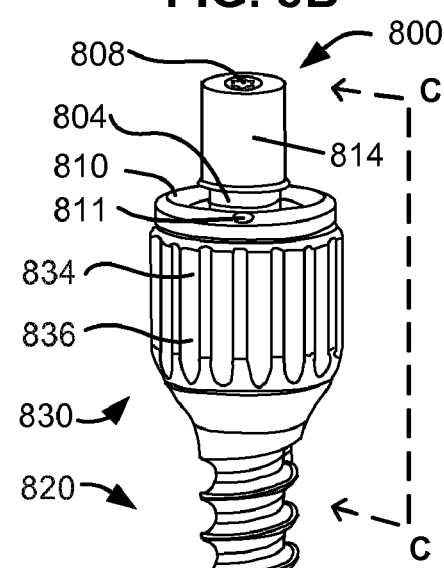
FIG. 8A
FIG. 8B

FIG. 8E
FIG. 8F
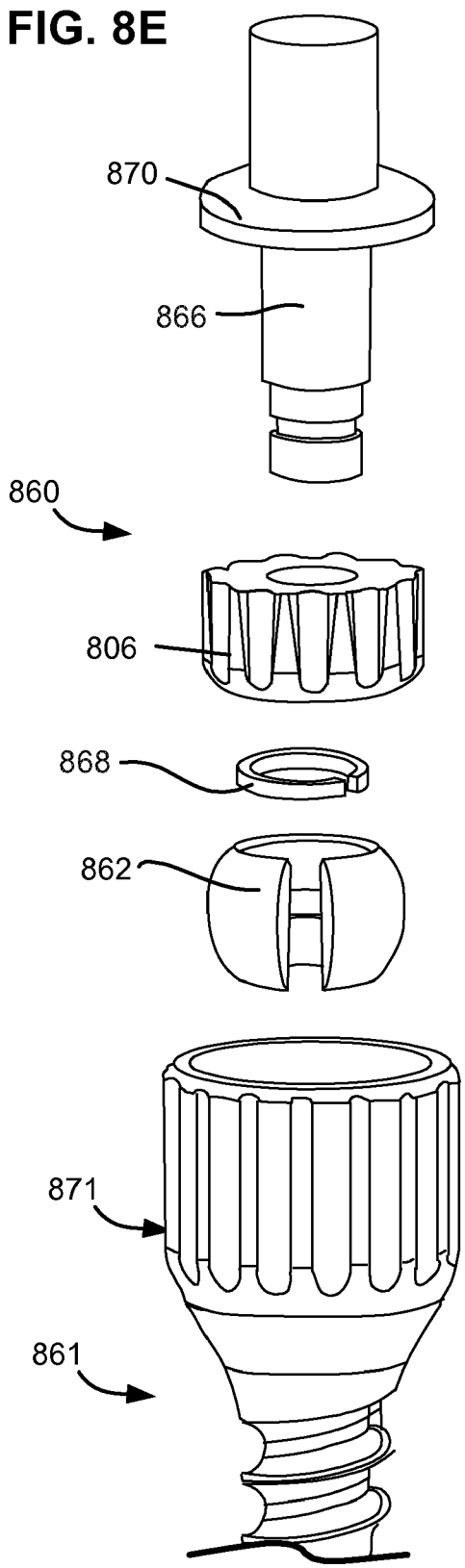
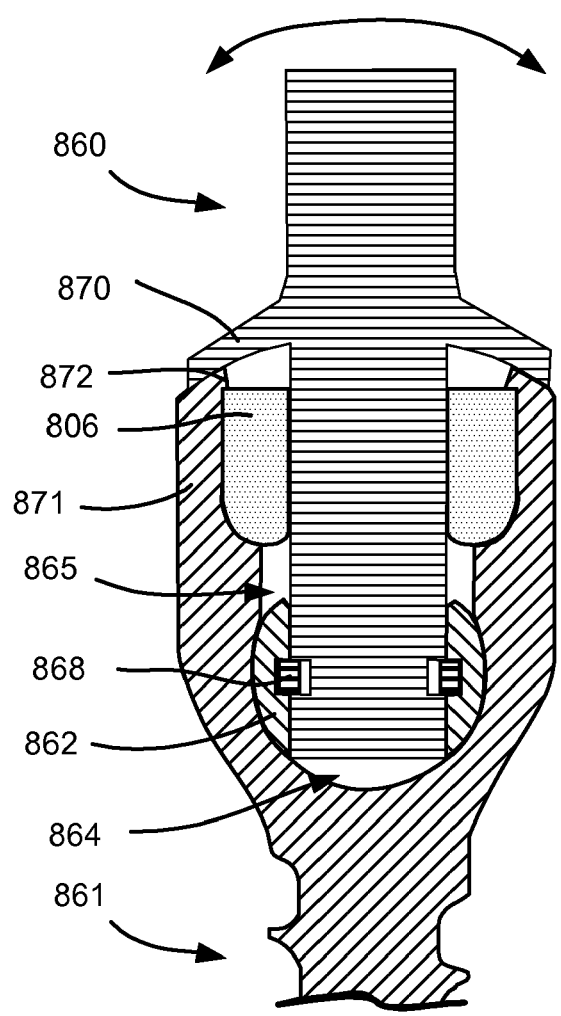

FIG. 9A
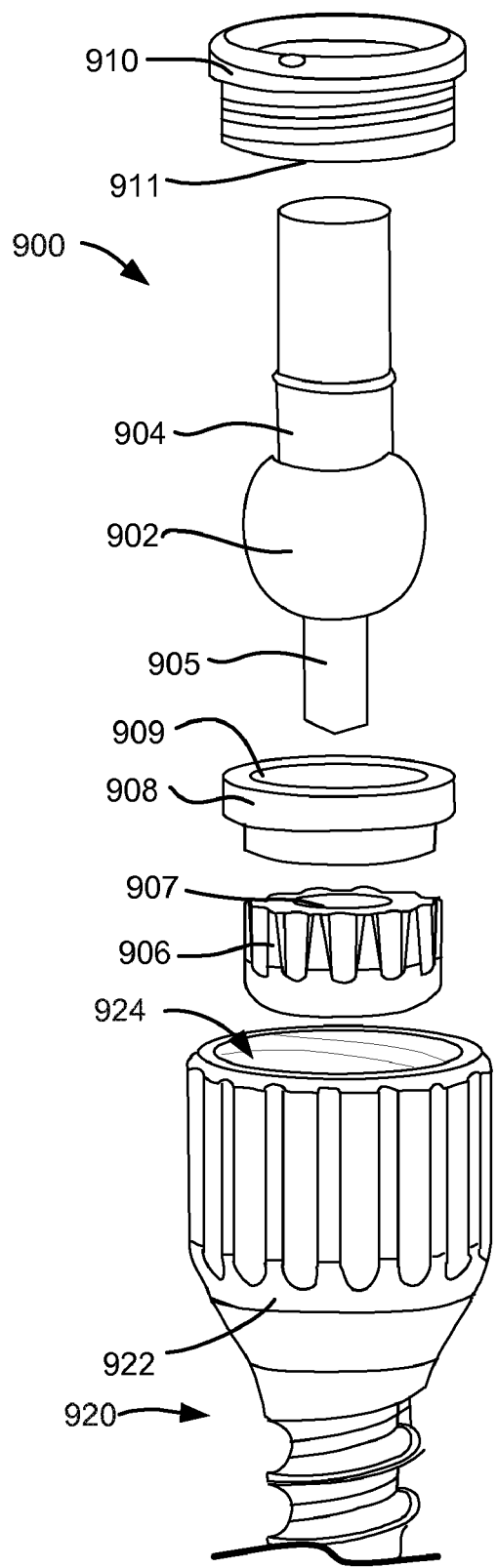
FIG. 9B
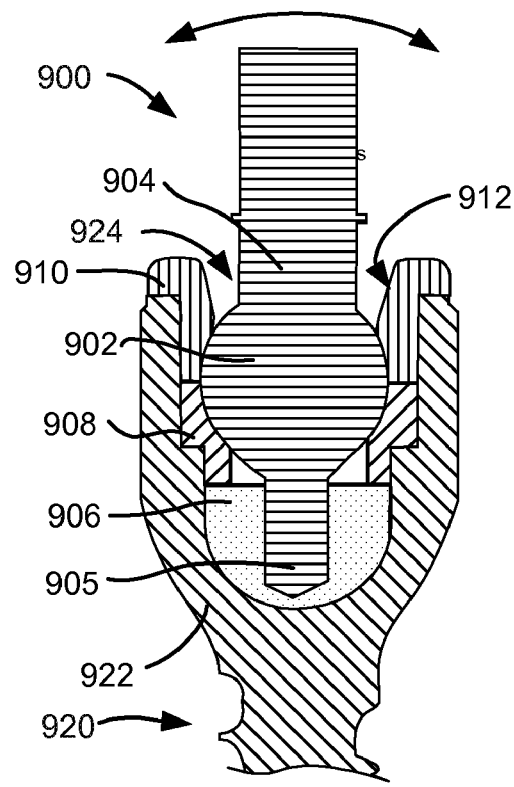
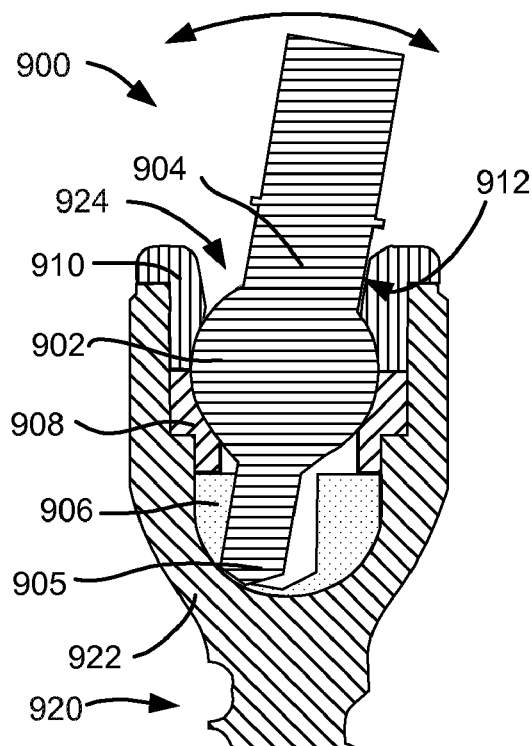
FIG. 9C

FIG. 9G
FIG. 9H
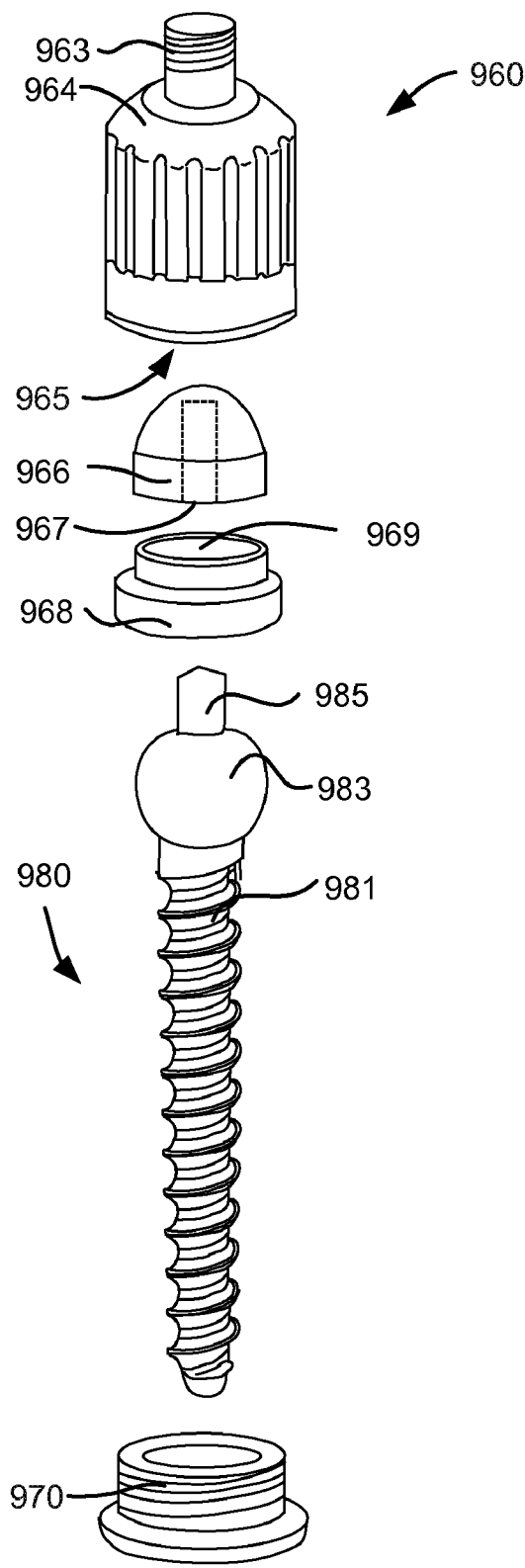
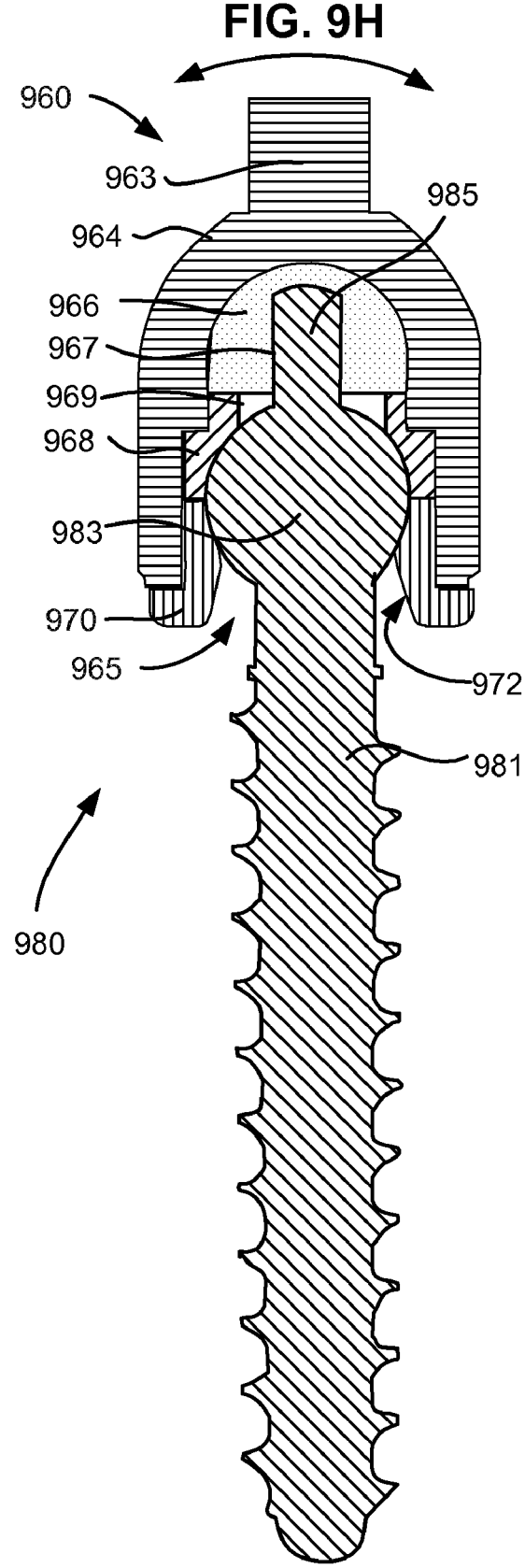

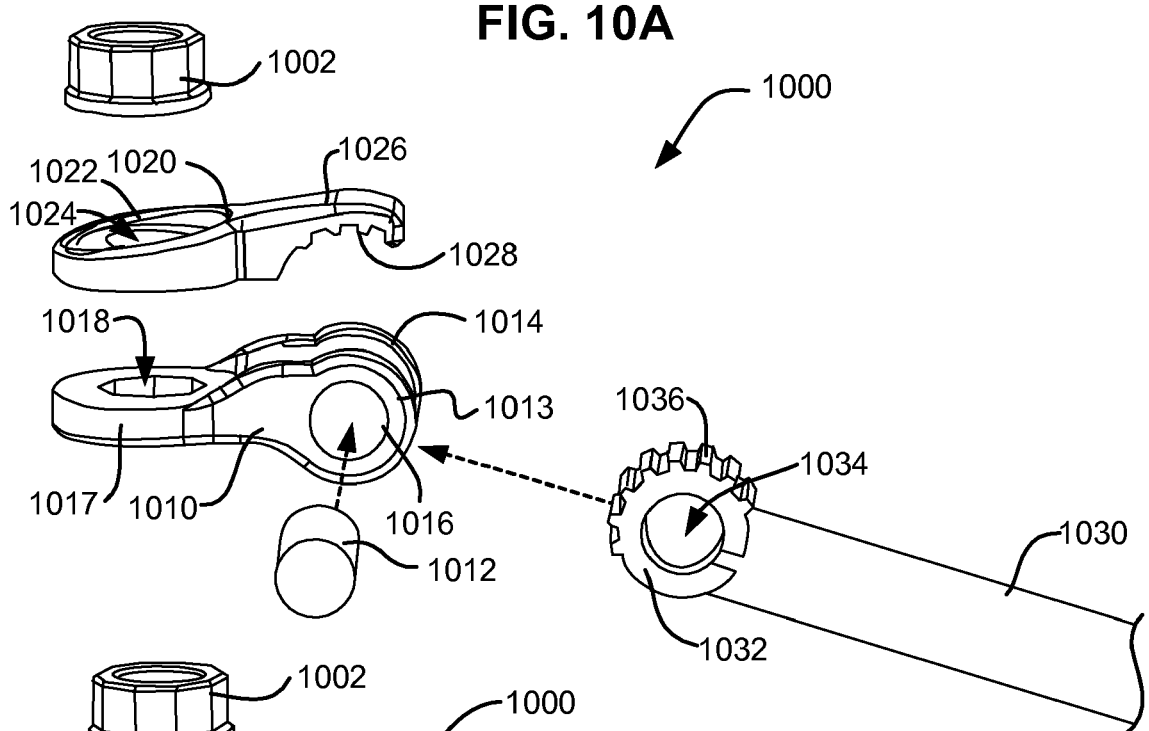
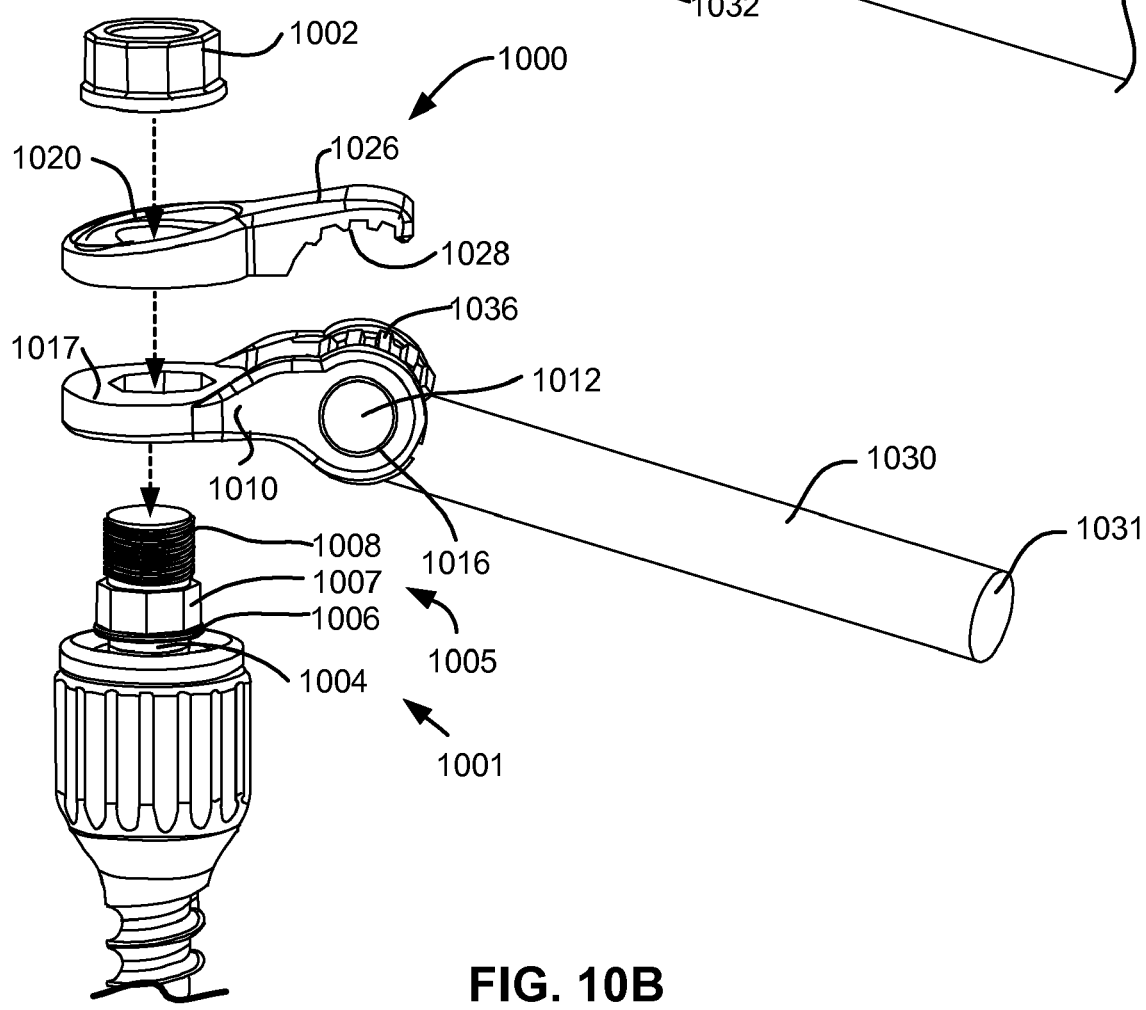

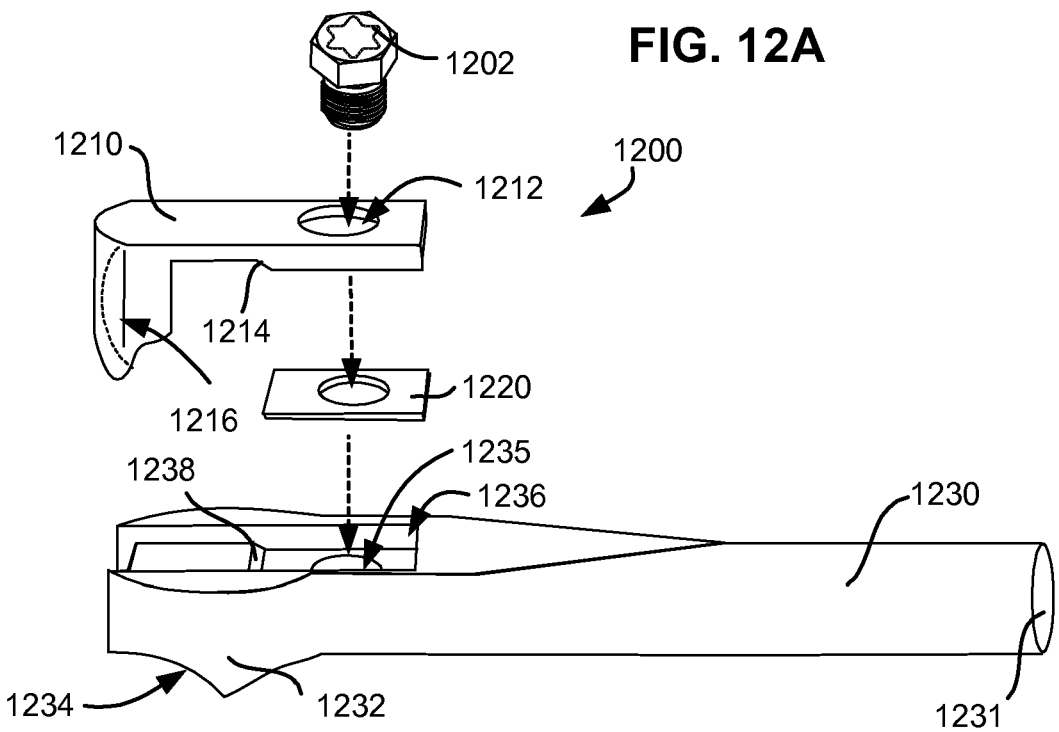
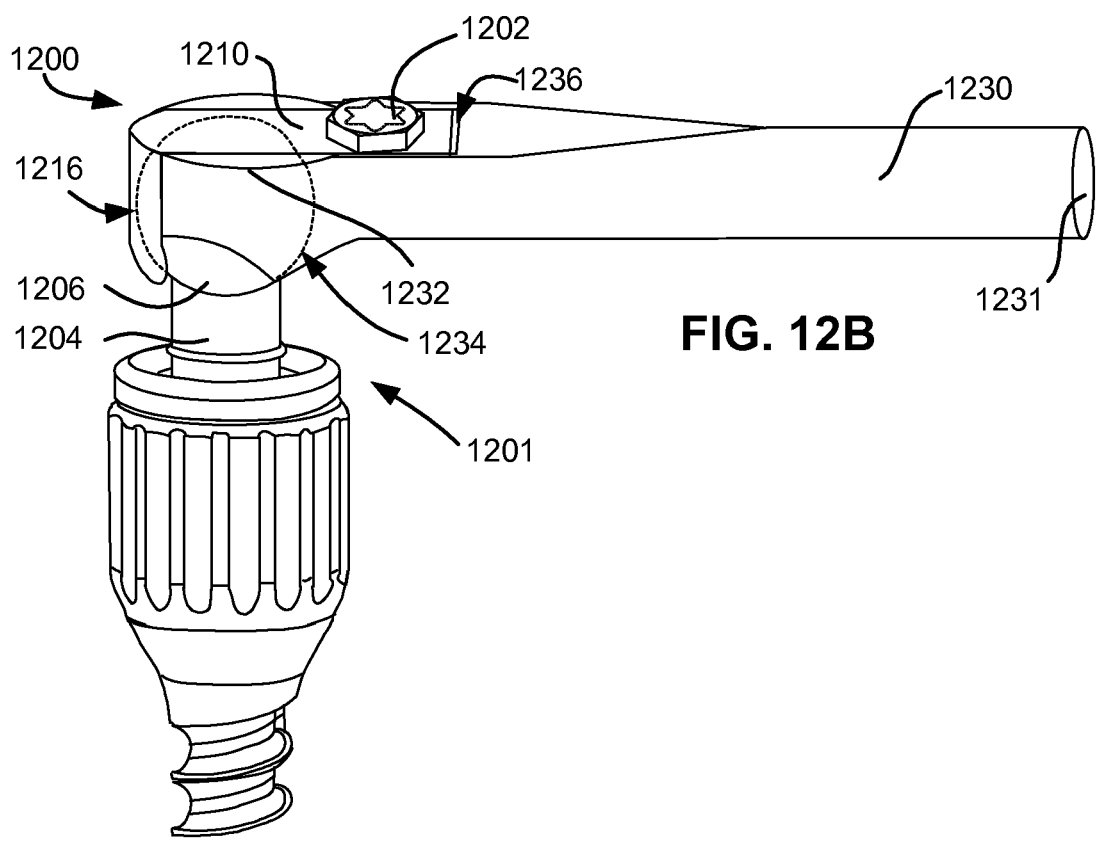

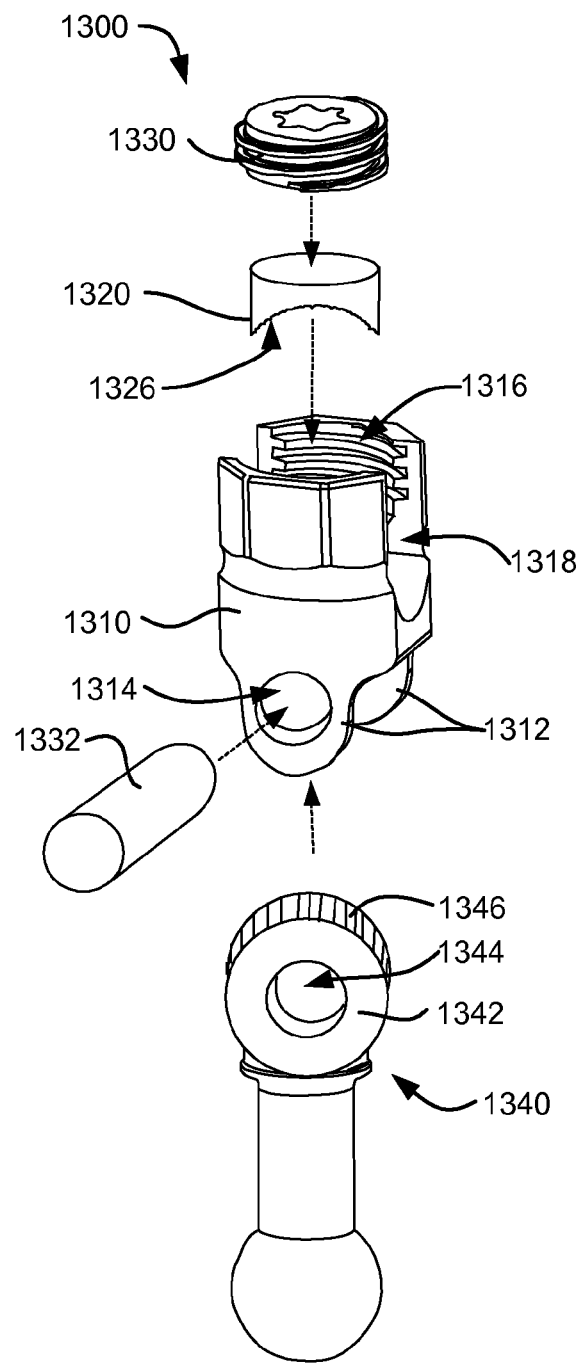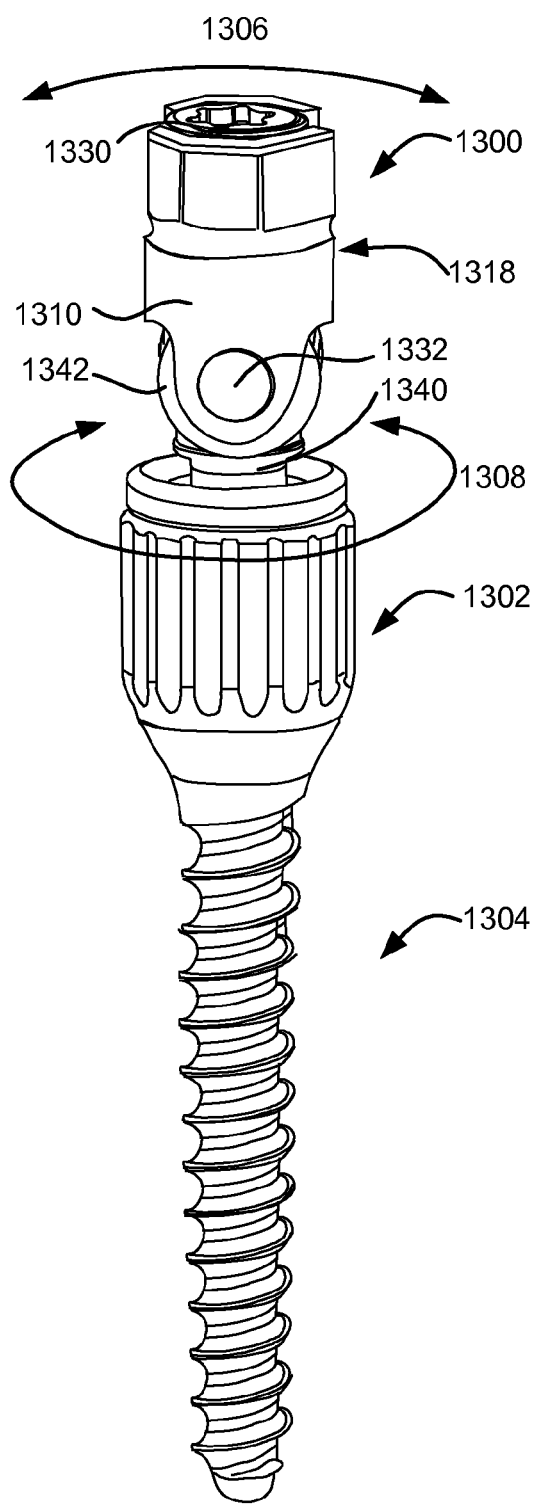

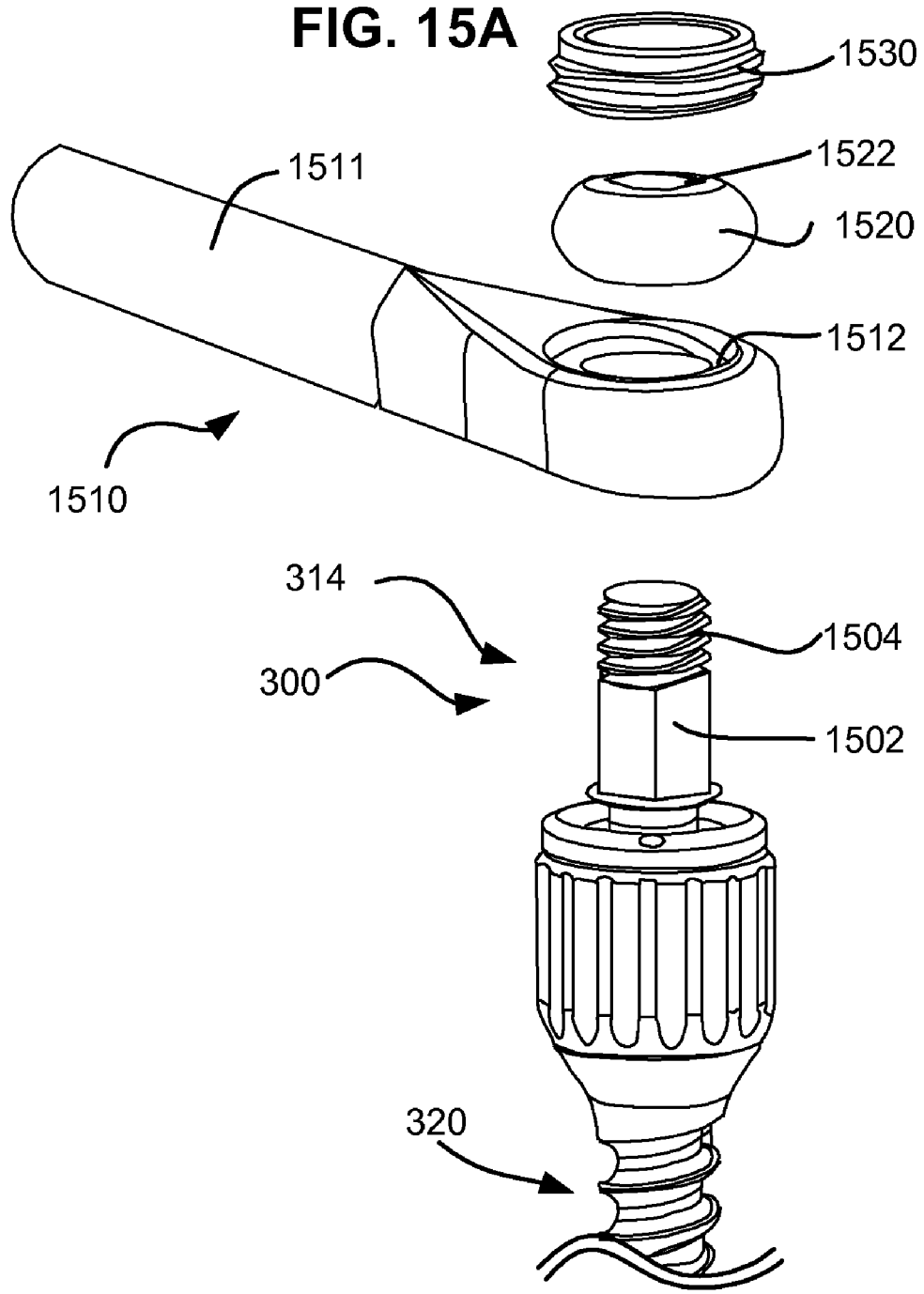

FIG. 15B
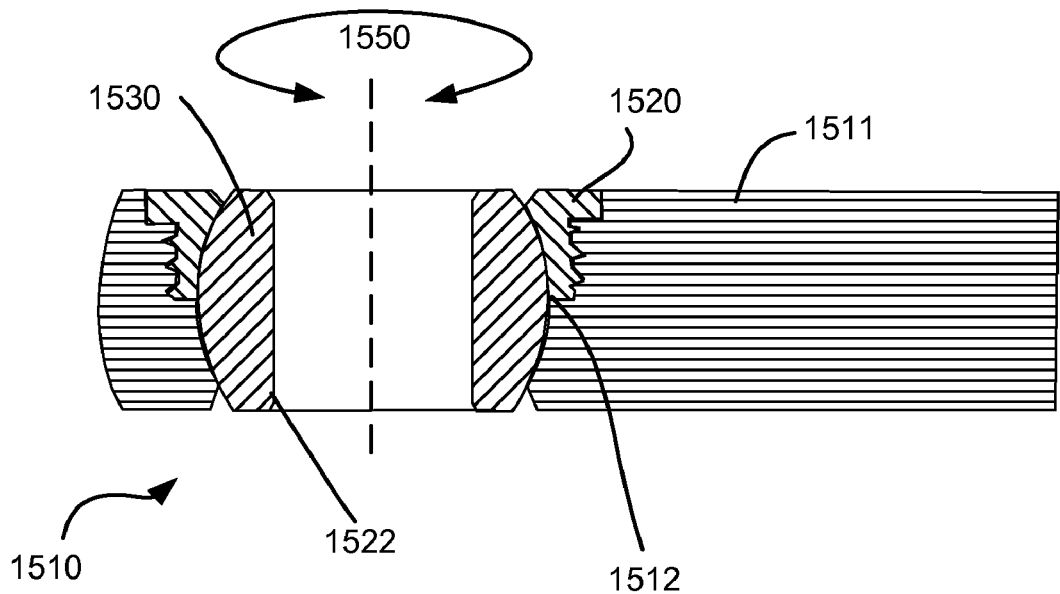
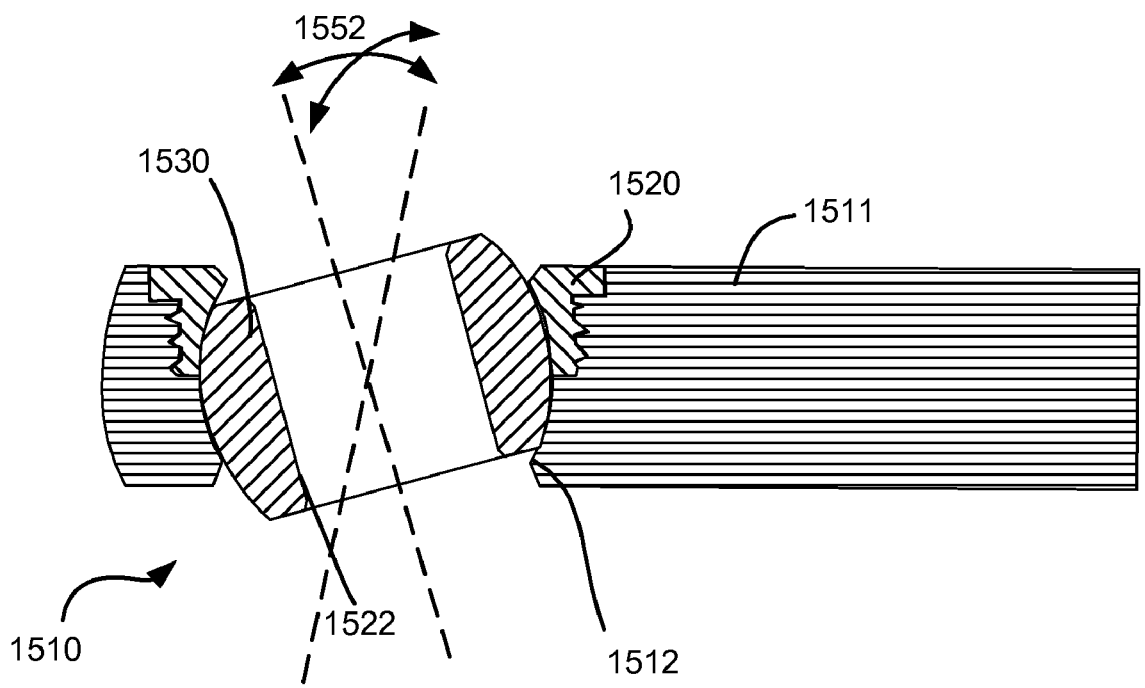
FIG. 15C

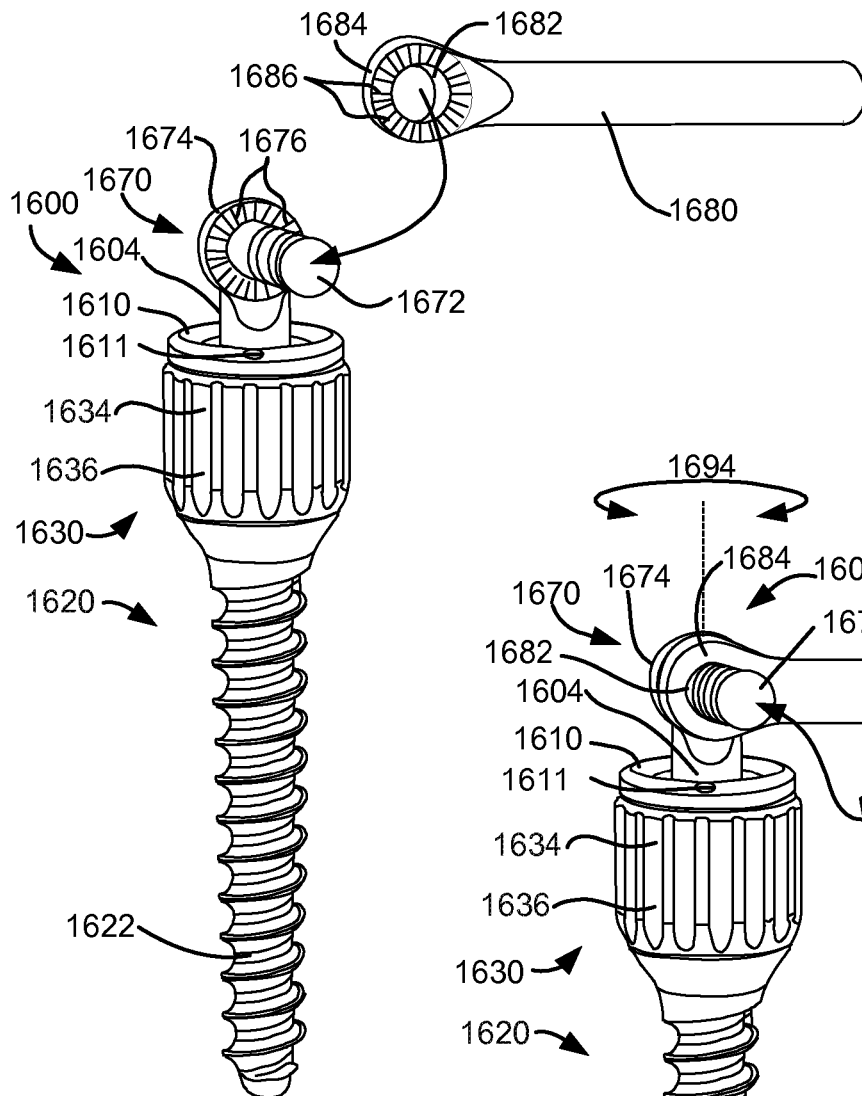
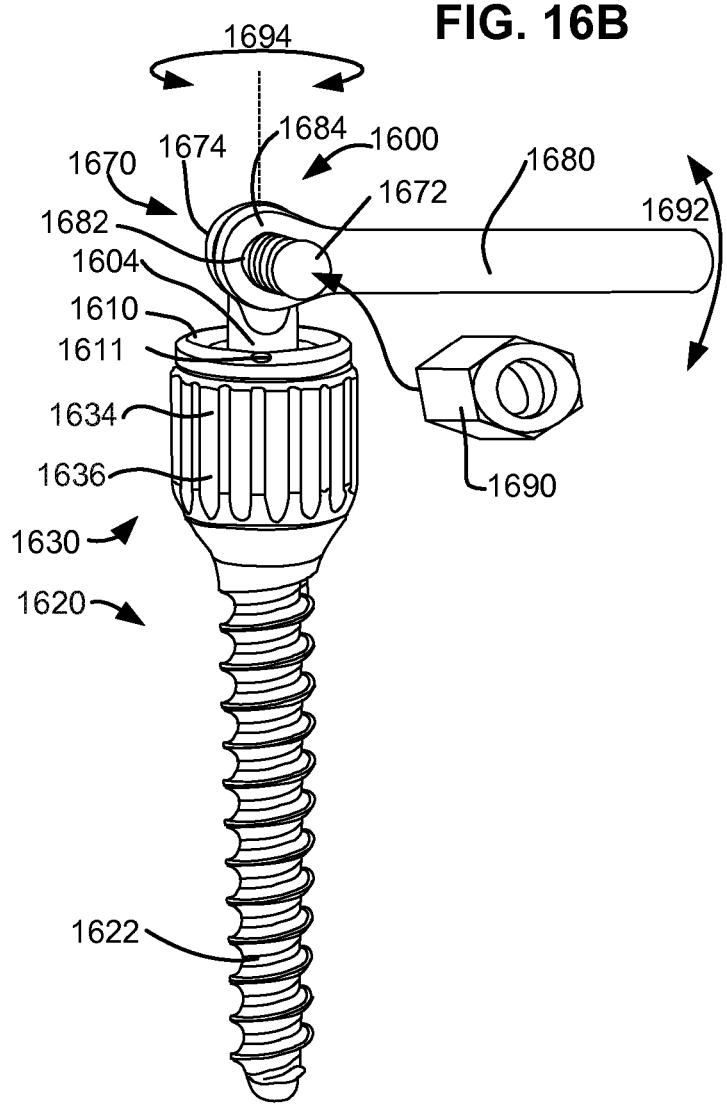
FIG. 16A
FIG. 16B

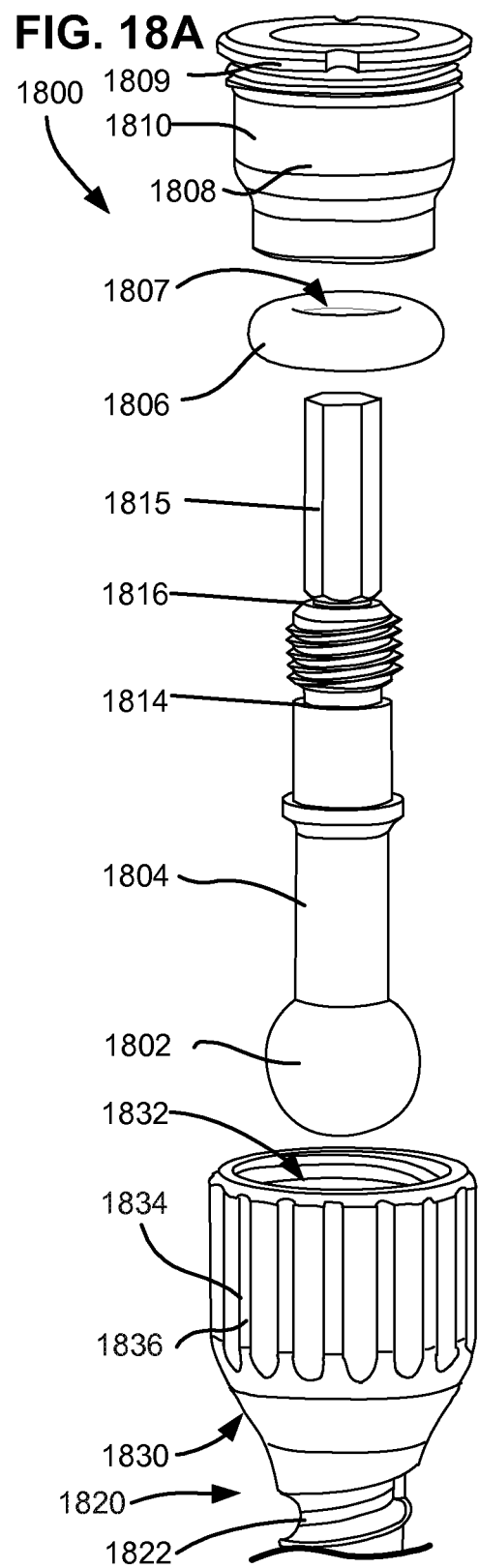
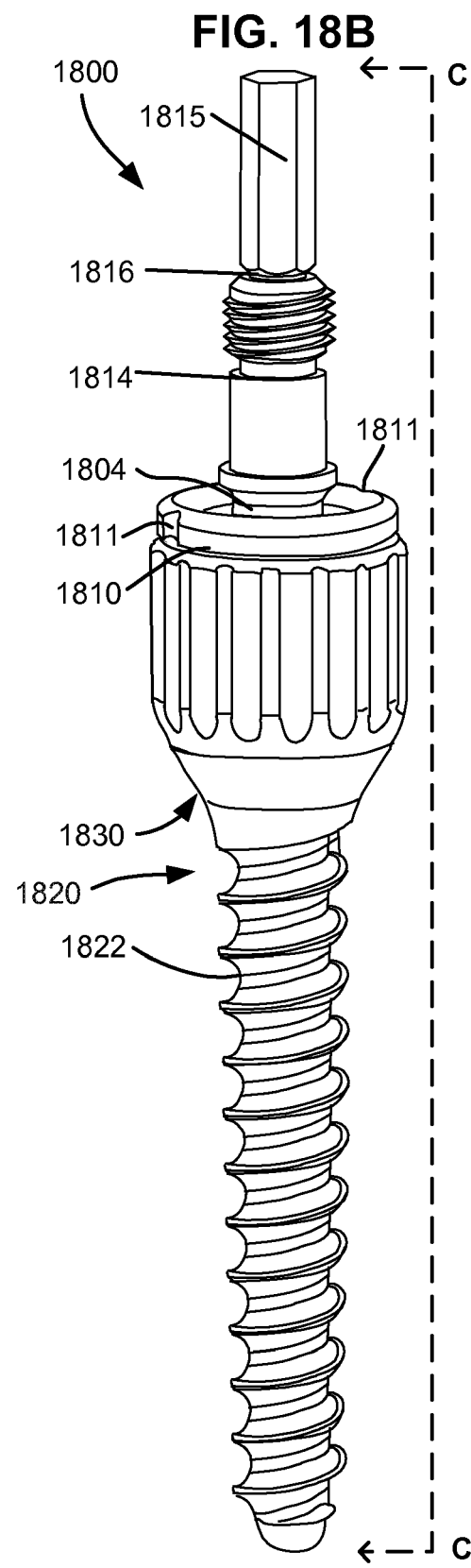

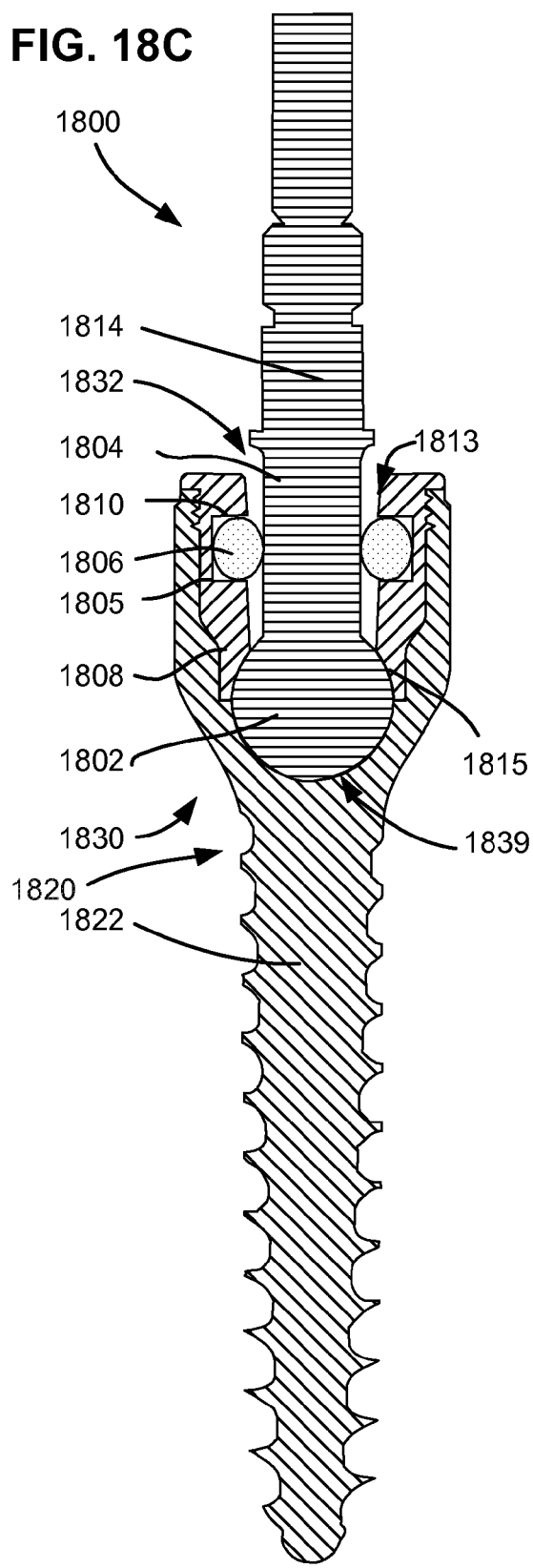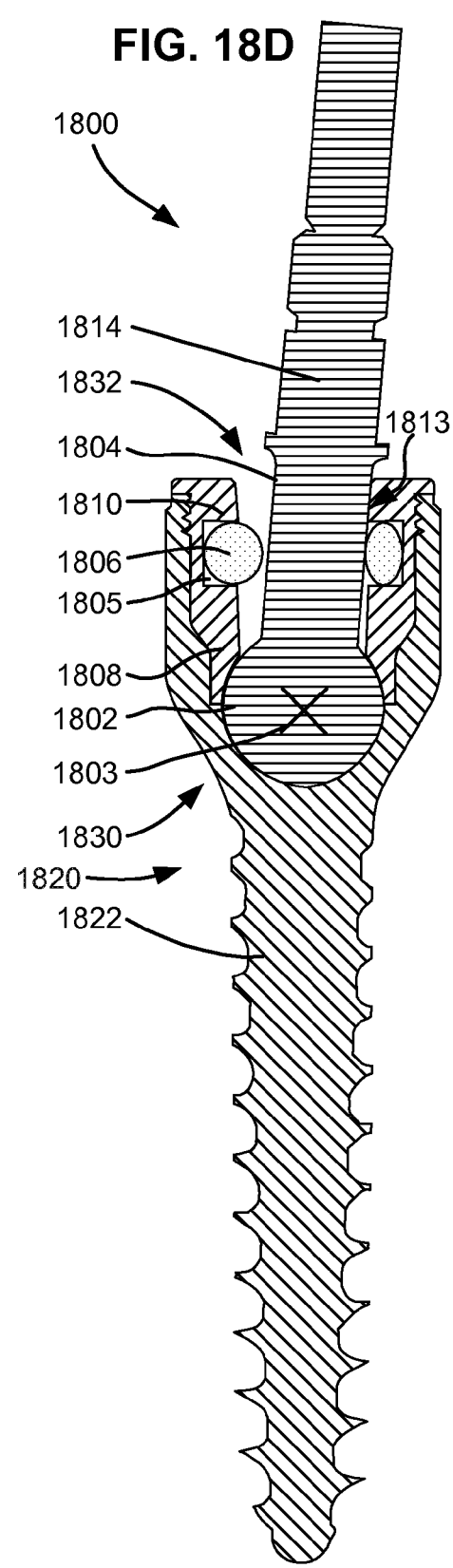

FIG. 19C
FIG. 19D
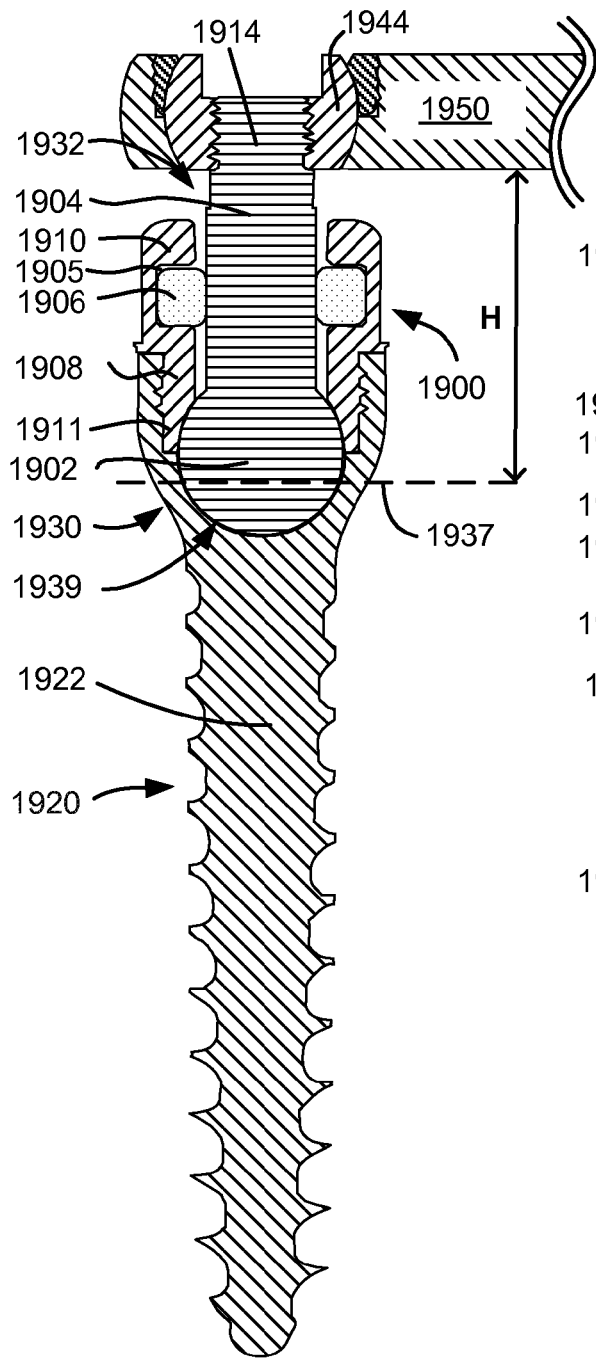
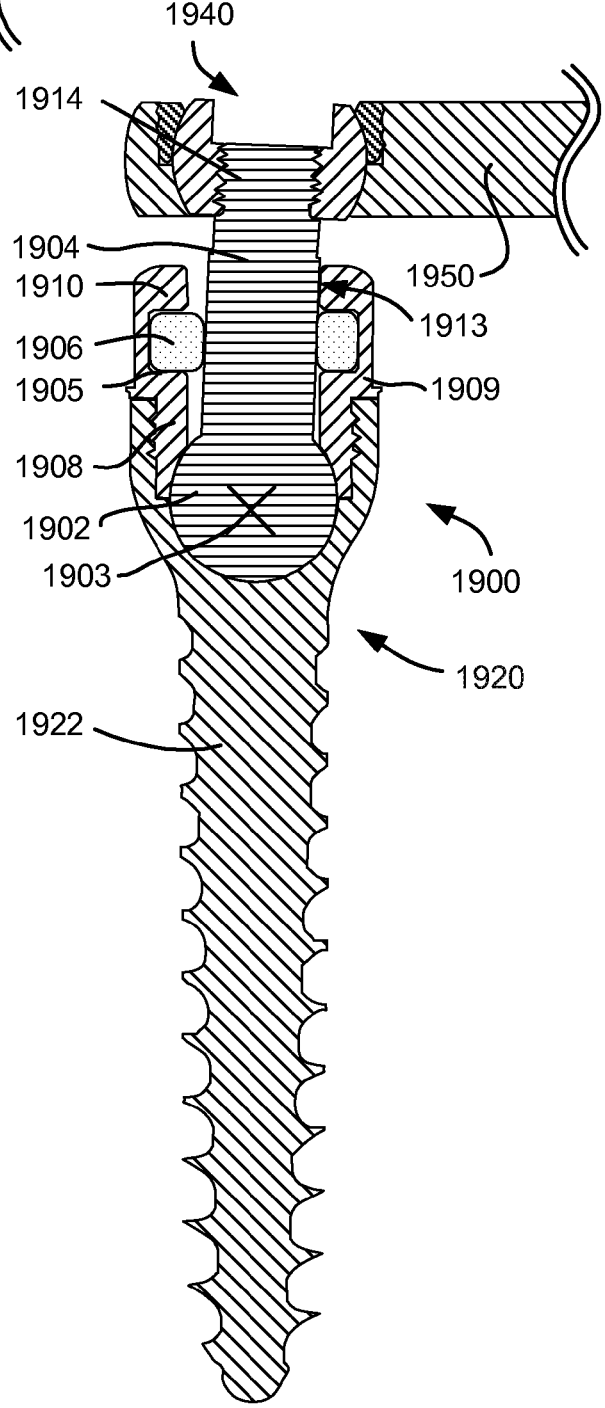

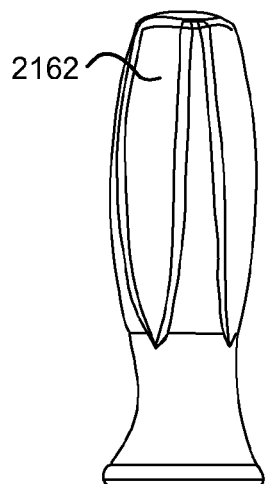
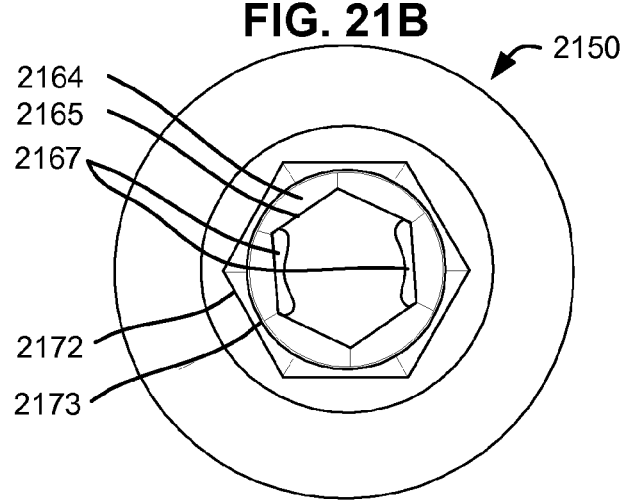
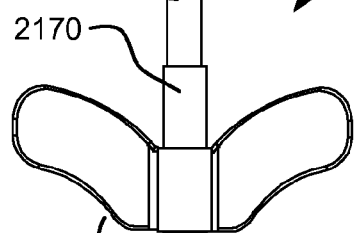
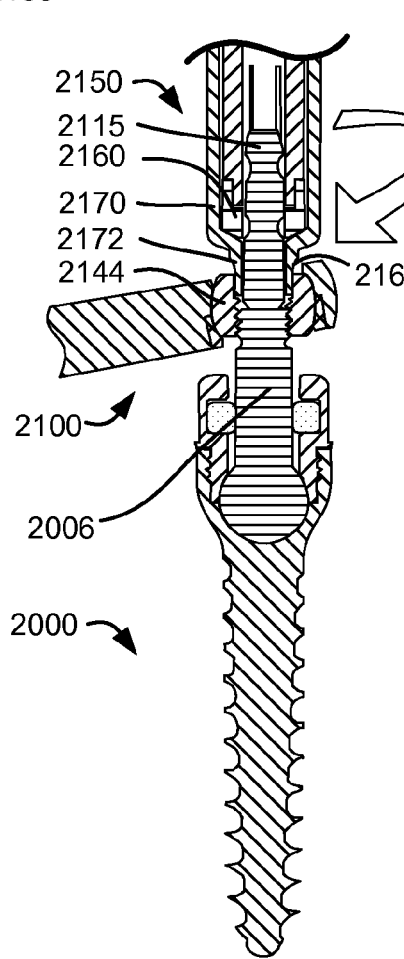
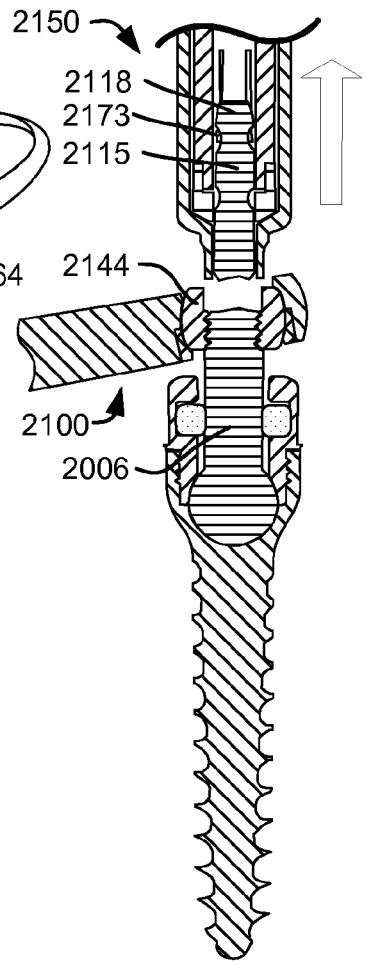

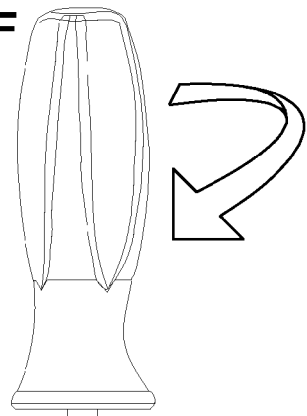
FIG. 21F
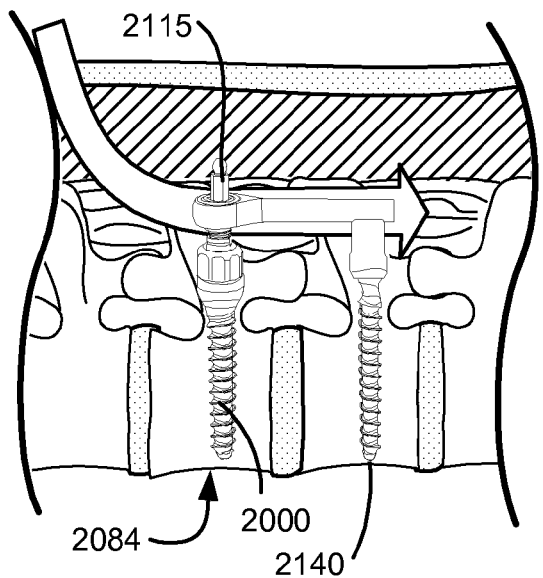
FIG. 21E
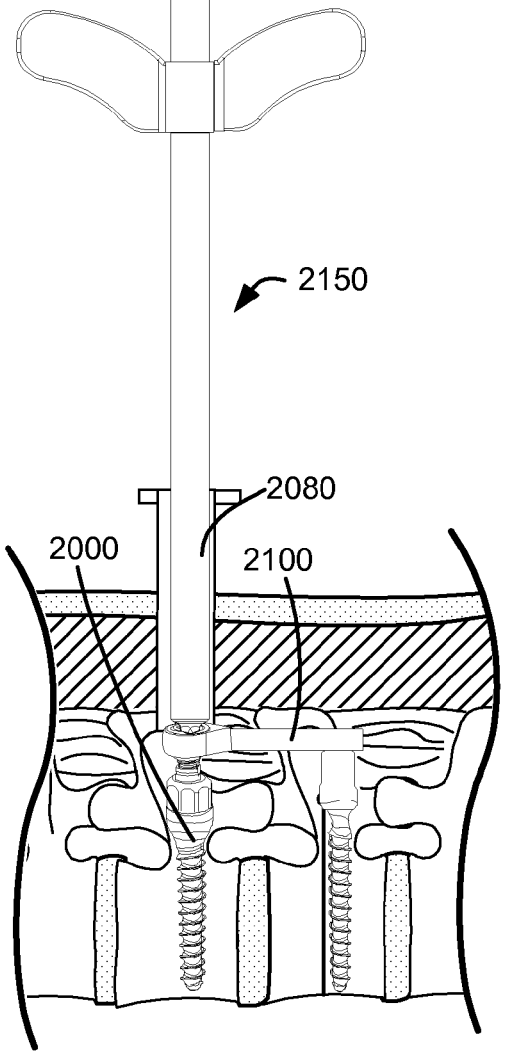

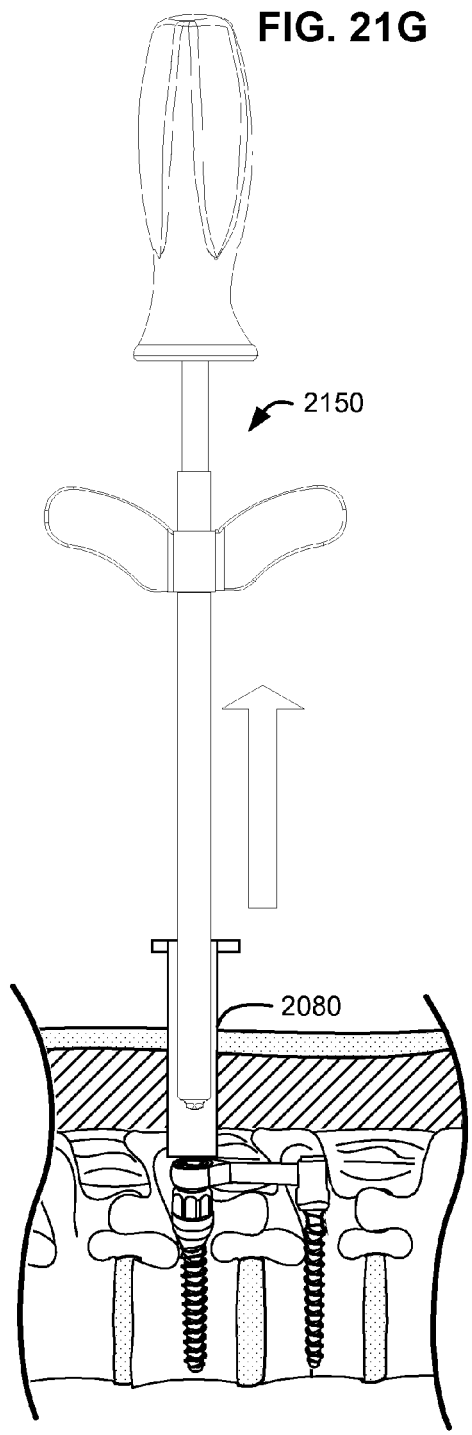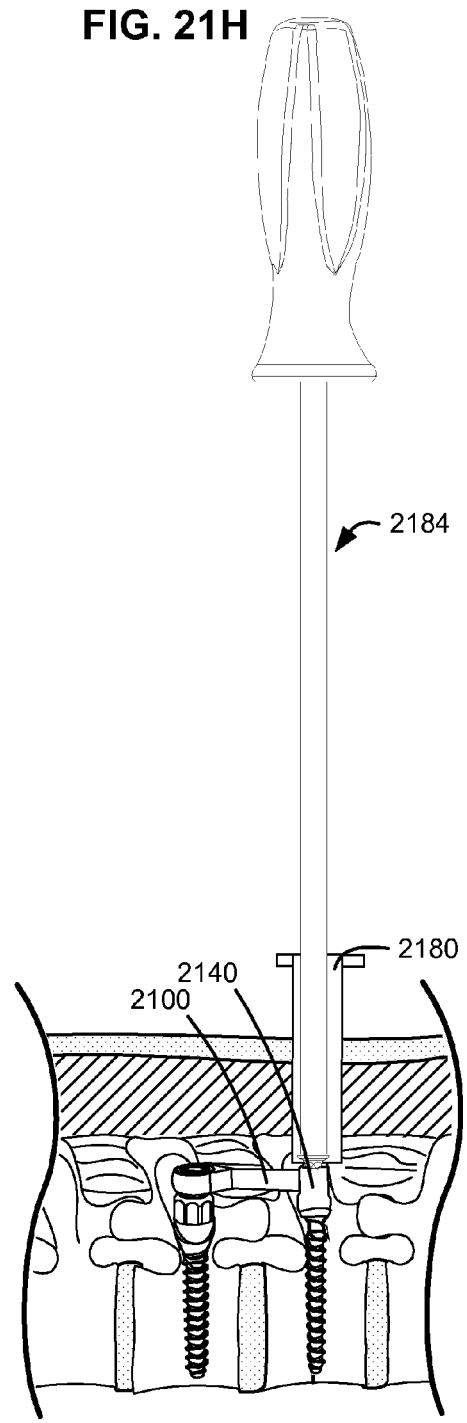

FIG. 22E
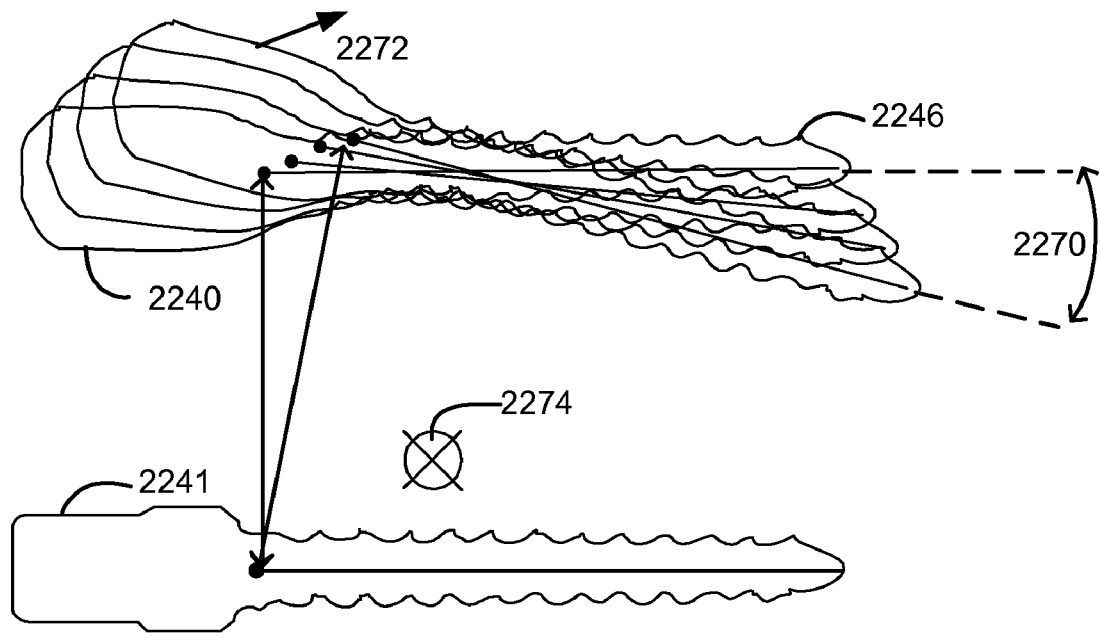
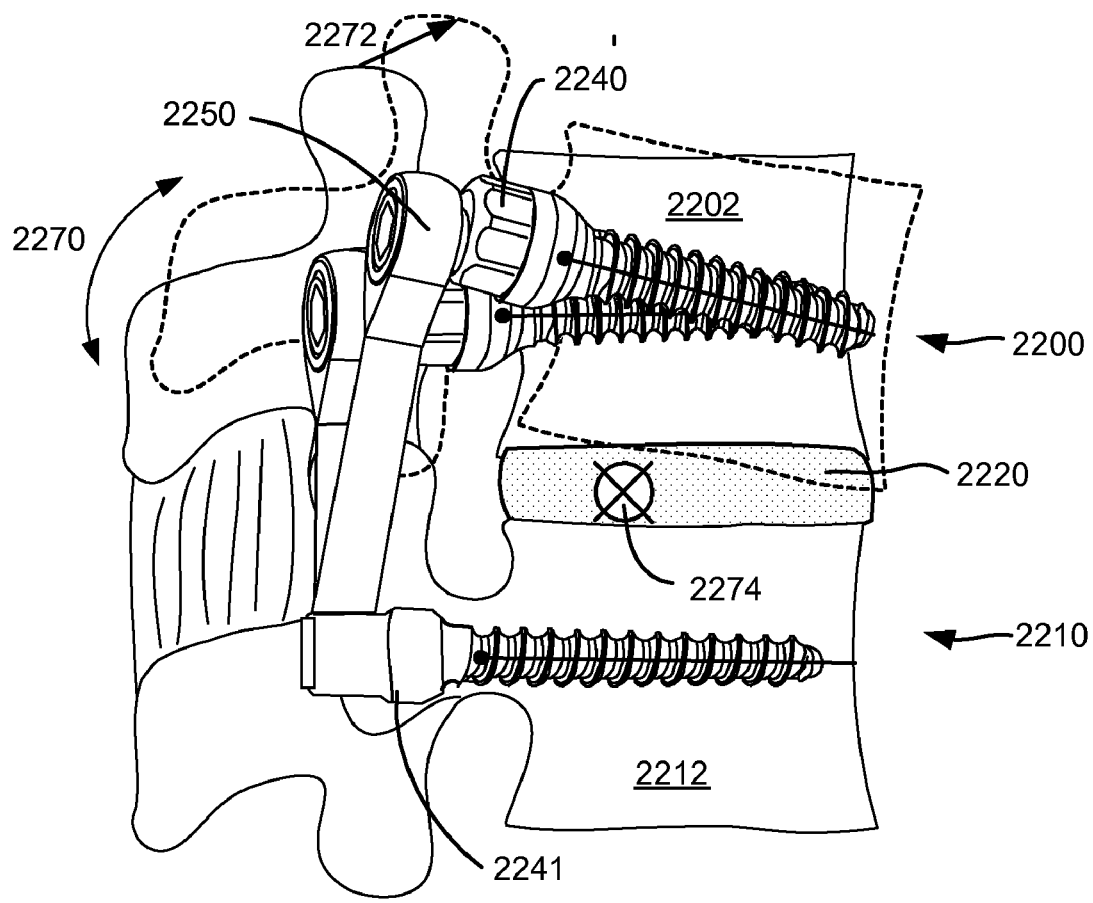
FIG. 22F

LOAD-SHARING BONE ANCHOR HAVING A NATURAL CENTER OF ROTATION AND METHOD FOR DYNAMIC STABILIZATION OF THE SPINE

CLAIM TO PRIORITY

This application claims priority to the following patents and patent applications:

U.S. Provisional Application No. 61/100,593 filed Sep. 26, 2008, entitled "A Spine Implant With A Deflection Rod System Selectively Alignable And Selectively Lockable To A Bone Anchor And Method"; and U.S. Provisional Application No. 61/100,625 filed Sep. 26, 2008, entitled "Versatile Components And Methods For Dynamic Stabilization"; and U.S. Provisional Application No. 61/119,651 filed Dec. 3, 2008, entitled "Load-sharing Component Having A Deflectable Post And Methods For Dynamic Spinal Stabilization"; and U.S. Provisional Application No. 61/122,658 filed Dec. 15, 2008, entitled "Load-sharing Component Having A Deflectable Post And Methods For Dynamic Spinal Stabilization"; and U.S. Provisional Application No. 61/144,426 filed Jan. 13, 2009, entitled "Load-sharing Component Having A Deflectable Post And Methods For Dynamic Spinal Stabilization"; and U.S. Provisional Application No. 61/225,478 filed Jul. 14, 2009, entitled "Load-sharing Component Having A Deflectable Post And Methods For Dynamic Spinal Stabilization"; and U.S. Provisional Application No. 61/167,789 filed Apr. 8, 2009, entitled "Load-sharing Component Having A Deflectable Post And Spring And Methods For Dynamic Spinal Stabilization"; and U.S. Provisional Application No. 61/217,556 filed Jun. 1, 2009, entitled "Load-sharing Component Having A Deflectable Post And Axially-Compressible Spring And Methods For Dynamic Spinal Stabilization".

The present application is a continuation-in-part of U.S. Patent Application No. 12/130,395, filed May 30, 2008, entitled "A Deflection Rod System For A Dynamic Stabilization And Motion Preservation Spinal Implantation System And Method" which claims priority to U.S. Provisional Application No. 61/031,598 filed Feb. 26, 2008 and entitled "A Deflection Rod System For A Dynamic Stabilization And Motion Preservation Spinal Implantation System And Method".

The present application is also a continuation-in-part of U.S. patent application Ser. No. 12/130,095, filed May 30, 2008, entitled "A Spine Implant With A Deflection Rod System Including A Deflection Limiting Shield Associated With A Bone Screw And Method" which claims priority to U.S. Provisional Application No. 61/057,340 filed May 30, 2008, entitled "A Spine Implant With A Deflection Rod System Aligned With A Bone Anchor And Method".

All of the afore-mentioned patent applications are incorporated herein by reference in their entireties.

CROSS-REFERENCES TO RELATED APPLICATIONS

This application is related to all of the afore-mentioned patent applications. This application is also related to all of the following applications including:

U.S. patent application Ser. No. 12/566,478, filed Sep. 24, 2009, entitled "A Modular In-Line Deflection Rod And Bone Anchor System And Method For Dynamic Stabilization Of The Spine"; and U.S. patent application Ser. No. 12/566,485, filed Sep. 24, 2009, entitled "Versatile Polyaxial Connector Assembly And Method For Dynamic Stabilization Of The Spine"; and U.S. patent application Ser. No. 12/566,487, filed Sep. 24, 2009, entitled "Versatile Offset Polyaxial Connector And Method For Dynamic Stabilization Of The Spine"; and U.S. patent application Ser. No. 12/566,491, filed Sep. 24, 2009, entitled "Load-Sharing Bone Anchor Having A Deflectable Post and Method For Dynamic Stabilization Of The Spine"; and U.S. patent application Ser. No. 12/566,494, filed Sep. 24, 2009, entitled "Load-Sharing Component Having A Deflectable Post And Method For Dynamic Stabilization Of The Spine"; and U.S. patent application Ser. No. 12/566,498, filed Sep. 24, 2009, entitled "Load-Sharing Bone Anchor Having A Durable Compliant Member And Method For Dynamic Stabilization Of The Spine"; and U.S. patent application Ser. No. 12/566,504, filed Sep. 24, 2009, entitled "Load-Sharing Bone Anchor Having A Deflectable Post With A Compliant Ring And Method For Stabilization Of The Spine"; and U.S. patent application Ser. No. 12/566,507, filed Sep. 24, 2009, entitled "Load-Sharing Bone Anchor Having A Deflectable Post With A Compliant Ring And Method For Stabilization Of The Spine"; and U.S. patent application Ser. No. 12/566,511, filed Sep. 24, 2009, entitled "Load-Sharing Bone Anchor Having A Deflectable Post And Method For Stabilization Of The Spine"; and U.S. patent application Ser. No., 12/566,516, filed Sep. 24, 2009, entitled "Load-Sharing Bone Anchor Having A Deflectable Post And Method For Stabilization Of The Spine"; and U.S. patent application Ser. No., 12/566,519, filed Sep. 24, 2009, entitled "Dynamic Spinal Rod And Method For Dynamic Stabilization Of The Spine"; and U.S. patent application Ser. No. 12/566,522, filed Sep. 24, 2009, entitled "Dynamic Spinal Rod Assembly And Method For Dynamic Stabilization Of The Spine"; and U.S. patent application Ser. No. 12/566,529, filed Sep. 24, 2009, entitled "Configurable Dynamic Spinal Rod And Method For Dynamic Stabilization Of The Spine"; and U.S. patent application Ser. No. 12/566,531, filed Sep. 24, 2009, entitled "A Spinal Prosthesis Having A Three Bar Linkage For Motion Preservation And Dynamic Stabilization Of The Spine"; and U.S. patent application Ser. No. 12/566,534, filed Sep. 24, 2009, entitled "Surgical Tool And Method For Implantation of A Dynamic Bone Anchor"; and U.S. patent application Ser. No. 12/566,547, filed Sep. 24, 2009, entitled "Surgical Tool And Method For Connecting A Dynamic Bone Anchor and Dynamic Vertical Rod"; and U.S. patent application Ser. No. 12/566,551, filed Sep. 24, 2009, entitled "Load-Sharing Bone Anchor Having A Deflectable Post And Centering Spring And Method For Dynamic Stabilization Of The Spine"; and U.S. patent application Ser. No. 12/566,553, filed Sep. 24, 2009, entitled "Load-Sharing Component Having A Deflectable Post And Centering Spring And Method For Dynamic Stabilization Of The Spine"; and U.S. patent application Ser. No. 12/566,559, filed Sep. 24, 2009, entitled "Load-Sharing Bone Anchor Having A Deflectable Post And Axial Spring And Method For Dynamic Stabilization Of The Spine".

All of the afore-mentioned patent applications are incorporated herein by reference in their entireties.

BACKGROUND OF INVENTION

Back pain is a significant clinical problem and the costs to treat it, both surgical and medical, are estimated to be over $2 billion per year. One method for treating a broad range of degenerative spinal disorders is spinal fusion. Implantable medical devices designed to fuse vertebrae of the spine to treat have developed rapidly over the last decade. However, spinal fusion has several disadvantages including reduced range of motion and accelerated degenerative changes adjacent the fused vertebrae.

Alternative devices and treatments have been developed for treating degenerative spinal disorders while preserving motion. These devices and treatments offer the possibility of treating degenerative spinal disorders without the disadvantages of spinal fusion. However, current devices and treatments suffer from disadvantages e.g., complicated implantation procedures; lack of flexibility to conform to diverse patient anatomy; the need to remove tissue and bone for implantation; increased stress on spinal anatomy; insecure anchor systems; poor durability, and poor revision options. Consequently, there is a need for new and improved devices and methods for treating degenerative spinal disorders while preserving motion.

SUMMARY OF INVENTION

The present invention includes a spinal implant system and methods that can dynamically stabilize the spine while providing for the preservation of spinal motion. Embodiments of the invention provide a dynamic stabilization system which includes: versatile components, adaptable stabilization assemblies, and methods of implantation. An aspect of embodiments of the invention is the ability to stabilize two, three and/or more levels of the spine by the selection of appropriate components of embodiments of the invention for implantation in a patient. Another aspect of embodiments of the invention is the ability to accommodate particular anatomy of the patient by providing a system of versatile components which may be customized to the anatomy and needs of a particular patient and procedure. Another aspect of the invention is to facilitate the process of implantation and minimize disruption of tissues during implantation.

Thus, the present invention provides new and improved systems, devices and methods for treating degenerative spinal disorders by providing and implanting a dynamic spinal stabilization assembly which supports the spine while preserving motion. These and other objects, features and advantages of the invention will be apparent from the drawings and detailed description which follow.

BRIEF DESCRIPTION OF THE DRAWINGS

FIGS. 1A and 1B are perspective views of a deflection system component mounted to an anchor system component according to an embodiment of the present invention.

FIG. 2A is an exploded view of a deflection rod according to an embodiment of the present invention.

FIG. 2B is a perspective view of the deflection rod assembly of FIG. 2A, as assembled.

FIGS. 2E and 2F are sectional views of the deflection rod assembly of FIGS. 2A and 2B showing deflection of the post.

FIG. 2G is a transverse sectional view of a vertebra illustrating the implantation of the deflection rod assembly of FIGS. 2A and 2B.

FIG. 3A is an exploded view of an alternative deflection rod assembly according to an embodiment of the present invention.

FIG. 3B is a perspective view of the deflection rod assembly of FIG. 3A, as assembled.

FIG. 3C is a sectional view of the deflection rod assembly of FIGS. 3A and 3B.

FIG. 3D is a sectional view of the deflection rod assembly of FIGS. 3A and 3B showing deflection of the post.

FIG. 4C is a sectional view of the deflection rod assembly of FIGS. 4A and 4B.

FIG. 4D is a sectional view of the deflection rod assembly of FIGS. 4A and 4B showing deflection of the post.

FIG. 4E is a sectional view of an alternative deflection rod assembly according to an embodiment of the present invention.

FIG. 4F is a sectional view of an alternative deflection rod assembly according to an embodiment of the present invention.

FIG. 4G is a sectional view of an alternative deflection rod assembly according to an embodiment of the present invention.

FIGS. 7A-7E are perspective views of alternative combinations of deflection rods and bone anchors according to embodiments of the present invention.

FIGS. 8A-8H show alternative deflection rods having different mechanisms to secure the deflectable post to the deflection rod assembly and/bone anchor.

FIGS. 9A-9C show an alternative deflection rod assembly according to an embodiment of the invention.

FIGS. 9G and 9H show an alternative deflection rod assembly according to an embodiment of the invention.

FIGS. 10A-10E show a locking hinged mechanism for connecting a deflection rod assembly to a vertical rod according to an embodiment of the invention.

FIGS. 12A-12D show a locking receiver mechanism for connecting a vertical rod to a post terminating in a ball according to an embodiment of the invention.

FIGS. 13A and 13B show a deflection rod assembly having a pivoting head according to an embodiment of the invention.

FIGS. 15A-15C show views of a preferred deflection rod, bone anchor and vertical rod.

FIGS. 16A-16B show perspective views show a deflection rod assembly having an adjustable vertical rod connector according to an embodiment of the invention.

FIG. 18A is an exploded view of an alternative deflection rod assembly according to an embodiment of the present invention.

FIG. 18B is a perspective view of the deflection rod assembly of FIG. 18A, as assembled.

FIG. 18C is a sectional view of the deflection rod assembly of FIGS. 18A and 18B.

FIG. 18D is a sectional view of the deflection rod assembly of FIGS. 18A and 18B showing deflection of the post.

FIG. 19C is a sectional view of the deflection rod assembly of FIGS. 19A and 19B.

FIG. 19D is a sectional view of the deflection rod assembly of FIGS. 19A and 19B showing deflection of the post.

FIG. 21A shows a perspective view of an attachment tool for securing a dynamic vertical rod to a dynamic bone anchor according to an embodiment of the invention.

FIG. 21B shows a detailed view of the head of the attachment tool of FIG. 21A.

FIGS. 21C and 21D show detailed sectional views of the head of the attachment tool of FIG. 21A in relation to a dynamic vertical rod and bone anchor.

FIG. 21E-21H are a lateral views of the lumbar spine illustrating steps to secure a dynamic vertical rod to a dynamic bone anchor assembly using the attachment tool of FIG. 21A according to an embodiment of the invention.

FIG. 22E is a graph illustrating the kinematics of a dynamic spine stabilization prosthesis including the dynamic bone anchor of FIGS. 22C and 22D.

FIG. 22F is a lateral views of the spine illustrating the kinematics of the spine supported by a dynamic spine stabilization prosthesis of FIG. 22E.

DETAILED DESCRIPTION OF THE PREFERRED EMBODIMENTS

Figure 1C:
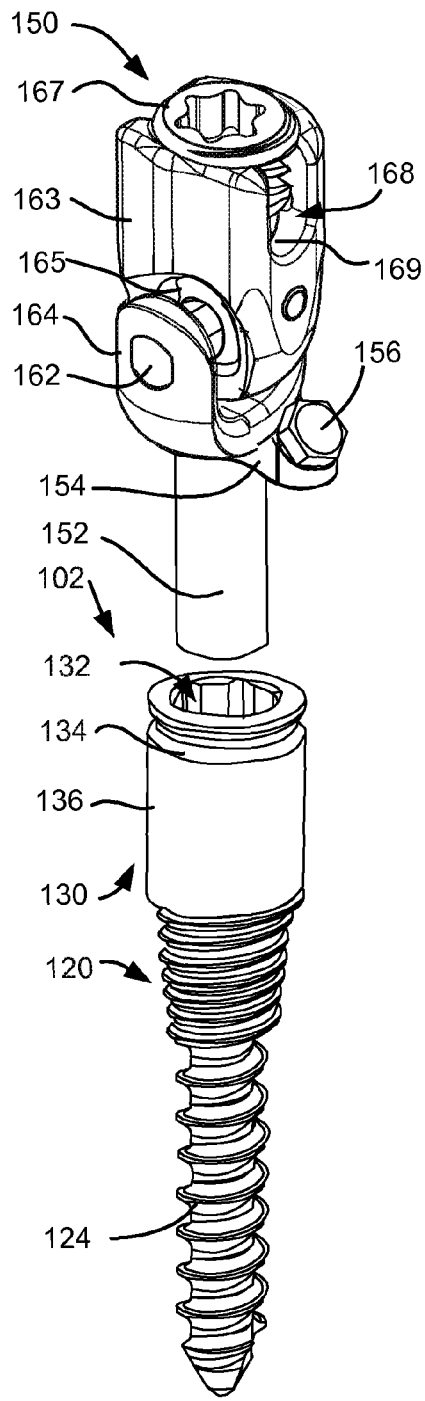
FIG. 1C is a perspective view of a connection system component mounted to an anchor system component according to an embodiment of the present invention.

The present invention includes a versatile spinal implant system and methods which can dynamically stabilize the spine while providing for the preservation of spinal motion. Alternative embodiments can be used for spinal fusion. An aspect of the invention is restoring and/or preserving the natural motion of the spine including the quality of motion as well as the range of motion. Still, another aspect of the invention is providing for load sharing and stabilization of the spine while preserving motion.

Another aspect of the invention is to provide a modular system which can be customized to the needs of the patient. Another aspect of embodiments of the invention is the ability to stabilize two, three and/or more levels of the spine by the selection of appropriate components for implantation in a patient. Another aspect of the invention is the ability to provide for higher stiffness and fusion at one level or to one portion of the spine while allowing for lower stiffness and dynamic stabilization at another adjacent level or to another portion of the spine. Embodiments of the invention allow for fused levels to be placed next to dynamically stabilized levels. Such embodiments of the invention enable vertebral levels adjacent to fusion levels to be shielded by providing a transition from a rigid fusion level to a dynamically stable, motion preserved, and more mobile level.

Embodiments of the present invention provide for assembly of a dynamic stabilization system which supports the spine while providing for the preservation of spinal motion. The dynamic stabilization system has an anchor system, a deflection system, a vertical rod system and a connection system. The anchor system anchors the construct to the spinal anatomy. The deflection system provides dynamic stabilization while reducing the stress exerted upon the bone anchors and spinal anatomy. The vertical rod system connects different levels of the construct in a multilevel assembly and may in some embodiments include compound deflection rods. The connection system includes coaxial connectors and offset connectors which adjustably connect the deflection system, vertical rod system and anchor system allowing for appropriate, efficient and convenient placement of the anchor system relative to the spine. Alternative embodiments can be used for spinal fusion.

Embodiments of the invention include a construct with an anchor system, a deflection system, a vertical rod system and a connection system. The deflection system provides dynamic stabilization while reducing the stress exerted upon the bone anchors and spinal anatomy. The anchor system anchors the deflection system to the spine. The connection system connects the deflection system to the vertical rod system. The vertical rod system connects dynamic stabilization system components on different vertebra to provide load sharing and dynamic stabilization.

Embodiments of the present invention include a deflection rod assembly which provides load sharing while preserving range of motion and reducing stress exerted upon the bone anchors and spinal anatomy. The deflection rod assembly includes a deflectable post mounted within a bone anchor. Deflection of the deflectable post is controlled by a compliant sleeve. A contact surface of the deflection rod is positioned to limit deflection of the deflectable post. The force/deflection properties of the deflection rod assembly may be adapted to the anatomy and functional requirements of the patient.

Common reference numerals are used to indicate like elements throughout the drawings and detailed description; therefore, reference numerals used in a drawing may or may not be referenced in the detailed description specific to such drawing if the associated element is described elsewhere. The first digit in a three digit reference numeral indicates the series of figures in which the referenced item first appears. Likewise the first two digits in a four digit reference numeral.

The terms "vertical" and "horizontal" are used throughout the detailed description to describe general orientation of structures relative to the spine of a human patient that is standing. This application also uses the terms proximal and distal in the conventional manner when describing the components of the spinal implant system. Thus, proximal refers to the end or side of a device or component closest to the hand operating the device, whereas distal refers to the end or side of a device furthest from the hand operating the device. For example, the tip of a bone screw that enters a bone would conventionally be called the distal end (it is furthest from the surgeon) while the head of the screw would be termed the proximal end (it is closest to the surgeon).

Dynamic Stabilization System

FIGS. 1A-1F introduce components of a dynamic stabilization system according to an embodiment of the present invention. The components include anchor system components, deflection rods, vertical rods and connection system components, including for example coaxial and offset connectors. The components may be implanted and assembled to form a dynamic stabilization system appropriate for the anatomical and functional needs of a patient.

FIG. 1A shows a bone anchor 102 and a deflection rod 104 connected to a vertical rod 106 by a ball joint 108. Deflection rod 104 is an example of a component of the deflection rod assembly system. Deflection rod 104 is a component having controlled flexibility which allows for load sharing. The deflection rod 104 provides stiffness and support where needed to support the loads exerted on the spine during normal spine motion, which loads, the soft tissues of the spine are no longer able to accommodate since these spine tissues are either degenerated or damaged. Load sharing is enhanced by the ability to select the appropriate stiffness of the deflection rod in order to match the load sharing characteristics desired. For embodiments of this invention, the terms "deflection rod" and "loading rod" can be used interchangeably. Deflection rods, deflection rod mountings and alternative deflection rods are described in more detail below.

Deflection rod 104 includes a deflectable post 105 which may deflect relative to a mount 107. Mount 107 is adapted to secure the deflectable post 105 to bone anchor 102. Mount 107 is received within cavity 132 of bone anchor 102. When received in cavity 132, mount 107 is secured into a fixed position relative to bone anchor 102. Deflectable post 105 may still deflect in a controlled manner relative to bone anchor 102 thereby provide for load sharing while preserving range of motion of the patient. The stiffness/flexibility of deflection of the deflectable post 105 relative to mount 107/ bone anchor 102 may be controlled and/or customized as will be described below.

As shown in FIG. 1A, mount 107 is designed to be received within a cavity 132 of bone anchor 102. As shown in FIG. 1A, mount 107 includes a collar 140. A threaded aperture 142 extends obliquely through collar 140. The threaded aperture 142 receives a locking set screw 144 which, when seated (FIG. 1B), engages the housing 130 of bone anchor 102. Locking set screw 144 is positioned within threaded aperture 142 through collar 140. The locking set screw 144 thereby secures the mount 107 of deflection rod 104 in place within the housing 130 of bone anchor 102.

As shown in FIG. 1A, deflection rod 104 is oriented in a co-axial, collinear or parallel orientation to bone anchor 102. This arrangement simplifies implantation, reduces trauma to structures surrounding an implantation site, and reduces system complexity. Arranging the deflection rod 104, co-axial with the bone anchor 102 can substantially transfer a moment (of) force applied by the deflectable post 105 from a moment force tending to pivot or rotate the bone anchor 102 about the axis of the shaft, to a moment force tending to act perpendicular to the axis of the shaft. The deflection rod can thereby effectively resist repositioning of the deflection rod and/or bone anchor 102 without the use of locking screws or horizontal bars to resist rotation. Further examples of coaxial deflection rods are provided below. Each of the deflection rods described herein may be used as a component of a dynamic stabilization system.

Bone anchor 102 is an example of a component of the anchor system. Bone anchor 102 includes a bone screw 120 and housing 130. As shown in FIG. 1A, bone anchor 102 is a bone screw 120 having one or more threads 124 which engage a bone to secure the bone anchor 102 onto a bone. The anchor system may include one or more alternative bone anchors known in the art e.g. bone hooks, expanding devices, barbed devices, threaded devices, adhesive and other devices capable of securing a component to bone instead of or in addition to bone screw 120.

As shown in FIG. 1A, bone anchor 102 includes a housing 130 at the proximal end. Housing 130 includes a cavity 132 for receiving deflection rod 104. Cavity 132 is coaxial with threaded bone screw 120. Housing 130 also comprises a groove 134 for securing deflection rod 104 within housing 130. As shown in FIG. 1A, groove 134 is located at the proximal end of housing 130. Groove 134 is designed to be engaged by the locking mechanism of a component mounted within cavity 132. For example, groove 134 is designed to be engaged by locking set screw 144 of deflection rod 104. When deflection rod 104 has been positioned within cavity 132 of bone anchor 102 as shown in FIG. 1B, locking set screw 144 is tightened to engage groove 134 of housing 130 thus securing deflection rod 104 within housing 130. Alternative mechanisms and techniques may be used to secure the deflection rod to the bone anchor including for example, welding, soldering, bonding, and/or mechanical fittings including threads, snap-rings, locking washers, cotter pins, bayonet fittings or other mechanical joints.

Bone anchor 102 also includes a coupling 136 to which other components may be mounted. As shown in FIG. 1A, coupling 136 is the external cylindrical surface of housing 130. Housing 130 thus provides two mounting positions, one coaxial mounting position and one external mounting position. Thus, a single bone anchor 102 can serve as the mounting point for one, two or more components. A deflection rod 104 may be coaxially mounted in the cavity 132 of the housing and one or more additional components may be externally mounted to the outer surface 136 of the housing. For example, a component of the connection system may be mounted to the outer surface 136 of the housing—such a connector may be called an offset head or offset connector. In some applications a component of the connection system may be coaxially-mounted in the cavity 132 in place of a deflection rod 104—such a connector may be called a coaxial head or coaxial connector.

It is desirable to have a range of different connectors which are compatible with the anchor system and deflection system. The connectors may have different attributes, including for example, different degrees of freedom, range of motion, and amount of offset, which attributes may be more or less appropriate for a particular relative orientation and position of two bone anchors and/or patient anatomy. It is desirable that each connector be sufficiently versatile to connect a vertical rod to a bone anchor in a range of positions and orientations while being simple for the surgeon to adjust and secure. It is desirable to provide a set of connectors which allows the dynamic stabilization system to be assembled in a manner that adapts a particular dynamic stabilization assembly to the patient anatomy rather than adapting the patient anatomy for implantation of the assembly (for example, by removing tissue\bone to accommodate the system). In a preferred embodiment, the set of connectors comprising the connection system have sufficient flexibility to allow the dynamic stabilization system to realize a suitable dynamic stabilization assembly in all situations that will be encountered within the defined patient population.

In some embodiments of the present invention, a connection system component, e.g. a polyaxial connector may be mounted in the cavity 132 of a bone anchor 102 to secure the bone anchor to vertical rod 106. For example, FIG. 1C shows coaxial head 150 which is a polyaxial connector which is coaxially mounted within the cavity 132 of the housing 130 of bone anchor 102. Coaxial head 150 is an example of a coaxial head or coaxial connector. Bone anchor 102 is the same bone anchor previously described with respect to FIGS. 1A and 1B. Coaxial head 150 comprises a rod 152 which is designed to fit within cavity 132 of housing 130. Coaxial head 150 also comprises a collar 154 and locking set screw 156. Locking set screw 156 is configured to engage groove 134 of bone anchor 102 in the same way as locking set screw 144 of deflection rod 104. Rod 152 and cavity 132 may in some case be circular in section (e.g. cylindrical), in which case rod 152 can rotate within cavity 132 until locked into place by locking set screw 156. In alternative embodiments, rod 152 may be polygonal in section such that it fits in one of a fixed number of possible positions.

Referring again to FIG. 1C, attached to rod 152 of coaxial head 150 is a yoke 164. Yoke 164 is connected to a ball 165 by a hexagonal pin 162. A saddle 163 is also mounted to ball 165 such that saddle 163 can pivot about two orthogonal axes relative to yoke 164. Saddle 163 has an aperture 168 through which a vertical rod may be passed. On one side of aperture 168 is a plunger 169. On the other side of aperture 168 is a locking set screw 167. When a vertical rod 106 (not shown) is positioned within aperture 168 and locking set screw 167 is tightened down, the locking set screw 167 forces the vertical rod 106 down onto the plunger 169. Plunger 169 is, in turn, forced down by the vertical rod 106 against ball 165. Plunger 169 engages ball 165, and ball 165 engages hexagonal pin 162, to lock saddle 163 in position relative to yoke 164 and secure a rod (e.g. vertical rod 106) to saddle 163. In this way, tightening set screw 167 secures the vertical rod 106 to the coaxial head 150 and also locks orientation of the coaxial head 150.

The ability to coaxially mount coaxial head 150 to a bone anchor 102 has several advantages over a standard polyaxial bone screw in which a polyaxial connector is an integral part of the device and may not be removed or exchanged. The bone anchor 102 is simpler to install and there is no risk of damage to the polyaxial connector during installation. A single coaxial head 150 can be manufactured and designed to mount to a range of different bone anchors thus allowing bone anchors to be selected as appropriate for the patient anatomy. After the bone anchor is installed, the orientation of the yoke 164 can be adjusted without changing the screw depth (this is not possible in a standard polyaxial bone screw without also turning the screw). After the bone anchor is implanted, one of a range of different coaxial heads may be installed without requiring removal of the bone anchor. Likewise, if a revision is required, the coaxial head may be exchanged for a different component without necessitating removal of the bone anchor 102.

Figure 1D:
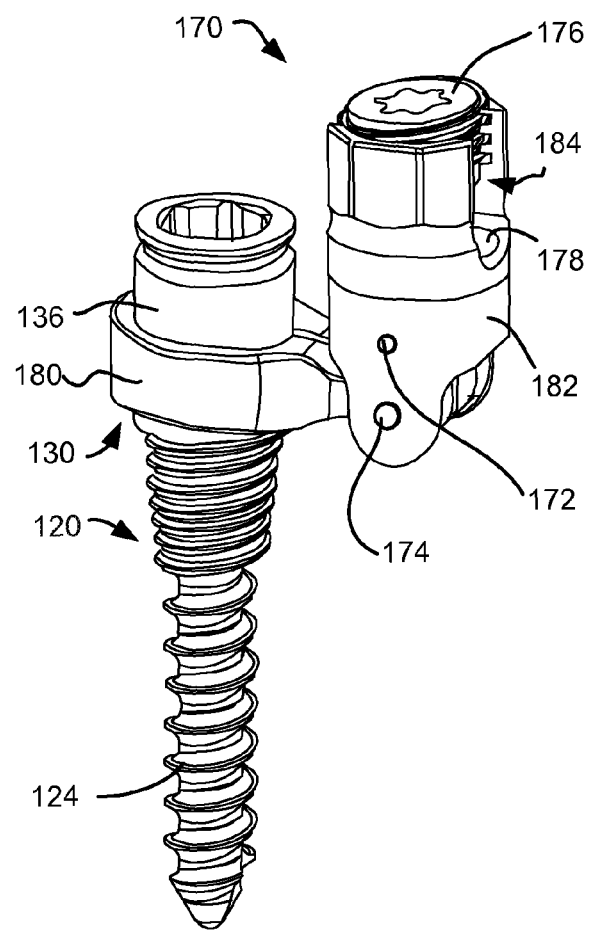
FIG. 1D is a perspective view of a different connection system component mounted to an anchor system component according to an embodiment of the present invention.

As described above, bone anchor 102 has housing 130 which can accept one coaxially-mounted component (e.g. a coaxial head) and one externally-mounted component (e.g. an offset connector). FIG. 1D shows a component of the connection system which may be mounted externally to housing 130 of bone anchor 102 in conjunction with a coaxially-mounted component. FIG. 1D shows a perspective view of offset connector 170 mounted externally to housing 130 of bone anchor 102 in which a deflection rod 104 is coaxially mounted. Connector 170 may be termed an offset head or offset connector.

Offset connector 170 comprises six components and allows for two degrees of freedom of orientation and two degrees of freedom of position in connecting a vertical rod to a bone anchor. The six components of offset connector 170 are dowel pin 172, pivot pin 174, locking set screw 176, plunger 178, clamp ring 180 and saddle 182. Saddle 182 has a slot 184 sized to receive a rod which may be a vertical rod, e.g. vertical rod 106 of FIG. 1A. Locking set screw 176 is mounted at one end of slot 184 such that it may be tightened to secure a rod within slot 184.

Clamp ring 180 is sized such that, when relaxed it can slide freely up and down the housing 130 of bone anchor 102 and rotate around housing 130. However, when locking set screw 176 is tightened on a rod, the clamp ring 180 grips the housing and prevents the offset connector 170 from moving in any direction. Saddle 182 is pivotably connected to clamp ring 180 by pivot pin 174. Saddle 182 can pivot about pivot pin 174. However, when locking set screw 176 is tightened on a rod, the plunger 178 grips the clamp ring 180 and prevents further movement of the saddle 182. In this way, operation of the single set screw 176 serves to lock the clamp ring 180 to the housing 130 of the bone anchor 102, fix saddle 182 in a fixed position relative to clamp ring 180 and secure a rod within the slot 184 of offset connector 170.

The above-described coaxial connector and offset connector are provided by way of example only. Alternative embodiments of coaxial heads and offset connectors can be found in U.S. Provisional Patent Application No. 61/100,625, filed Sep. 26, 2008 entitled "Versatile Assembly Components And Methods For A Dynamic Spinal Stabilization System" (Attorney Docket No.: SPART-01043US0) which is incorporated by reference. These coaxial heads and offset connectors may be used in conjunction with the components herein described to permit assembly of a dynamic stabilization system appropriate to the functional needs and anatomy of a particular patient. In addition screws having an integrated connector may also be utilized to anchor components of the dynamic stabilization system in fixed relationship to a vertebra, for example polyaxial screws.

The components of the dynamic stabilization system may be assembled and implanted in the spine of a patient to provide a multilevel dynamic stabilization assembly which provides dynamic stabilization of the spine and load sharing. In some embodiments, the first step is implantation of bone anchors in the vertebrae. In other embodiments, the bone anchors may be implanted with the deflection rod/connection component already installed.

Figure 1E:
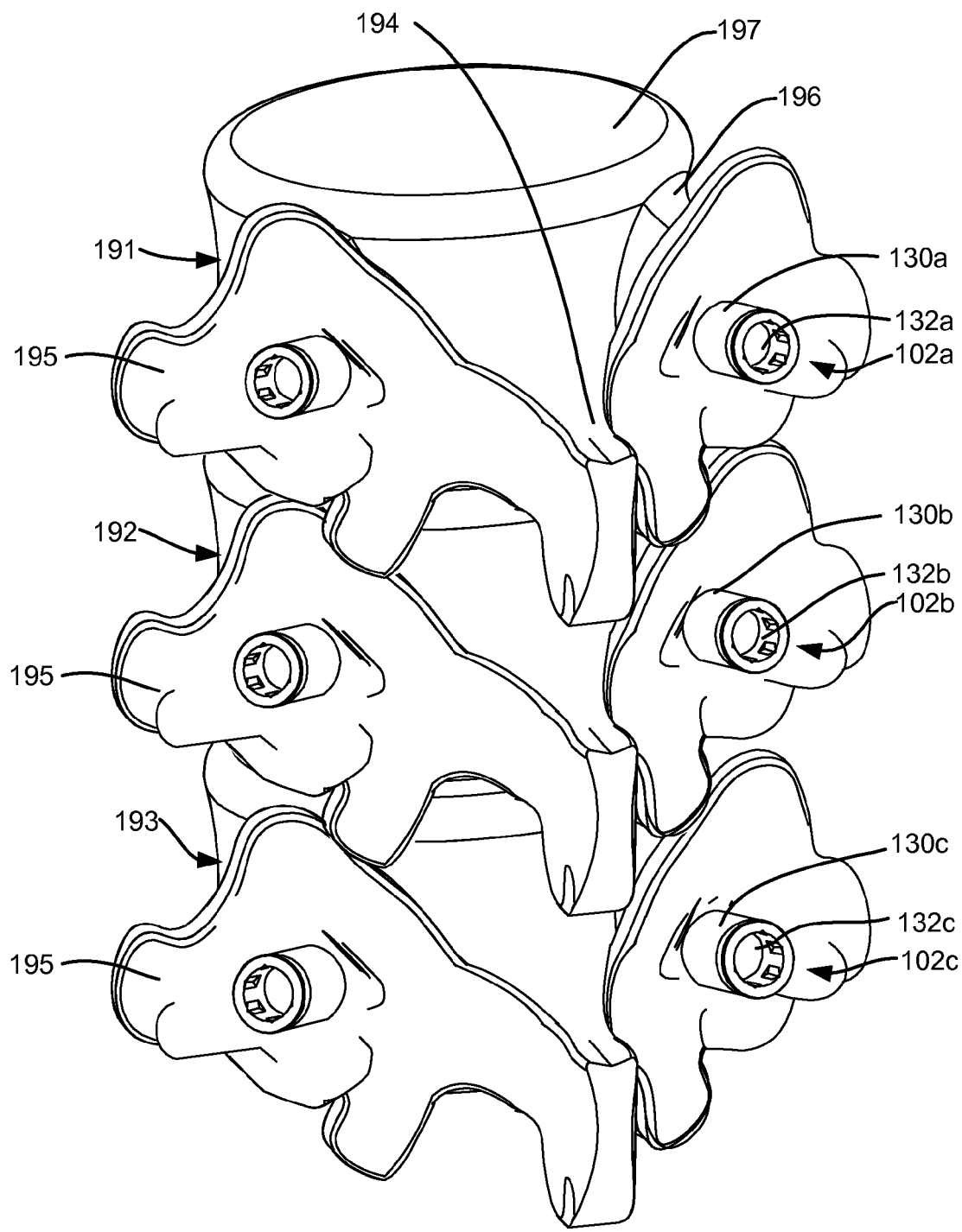
FIG. 1E is a posterior view of an anchor system for a multi-level dynamic stabilization assembly utilizing the anchor components of FIGS. 1A to 1D according to an embodiment of the present invention.

FIG. 1E, shows three adjacent vertebrae 191, 192 and 193. As a preliminary step, bone anchors 102a, 102b and 102c have been implanted in the vertebrae 191, 192 and 193 on the right side of the spinous process 194 between the spinous process 194 and the transverse process 195. A driver is inserted into the cavity 132a, 132b, 132c in order to drive the threaded portion of each bone anchor into the bone. In preferred procedures, the bone anchor is directed so that the threaded portion is implanted within one of the pedicles 196 angled towards the vertebral body 197. The threaded region of each bone anchor is fully implanted in the vertebrae 191, 192 and 193. A driver may alternatively and/or additionally engage the exterior surface of housing 130 in order to implant the bone anchor. The driver may have a torque-measuring and/or torque limiting function to assist in accurate implantation of the bone screw and avoid excess force being applied to the vertebrae. In alternative embodiments, the bone screw may incorporate a torque limiting element, for example a secondary head which breaks away when the driver torque exceeds a predetermined torque limit. See, e.g. FIGS. 7F-7H and accompanying text.

As shown in FIG. 1E, the housings 130a, 130b, 130c of each bone anchor remain partly or completely exposed above the surface of the vertebrae so that one or more of a connection system component and deflection component can be secured to each bone anchor 102a, 102b and 102c. Coaxial components may be coaxially-mounted inside each of cavities 132a, 132b, and 132c. Offset heads/connectors may also be externally-mounted to the outside surface of each of housings 130a, 130b and 130c. Note that bone anchors are also implanted on the left side of the spine.

Figure 1F:
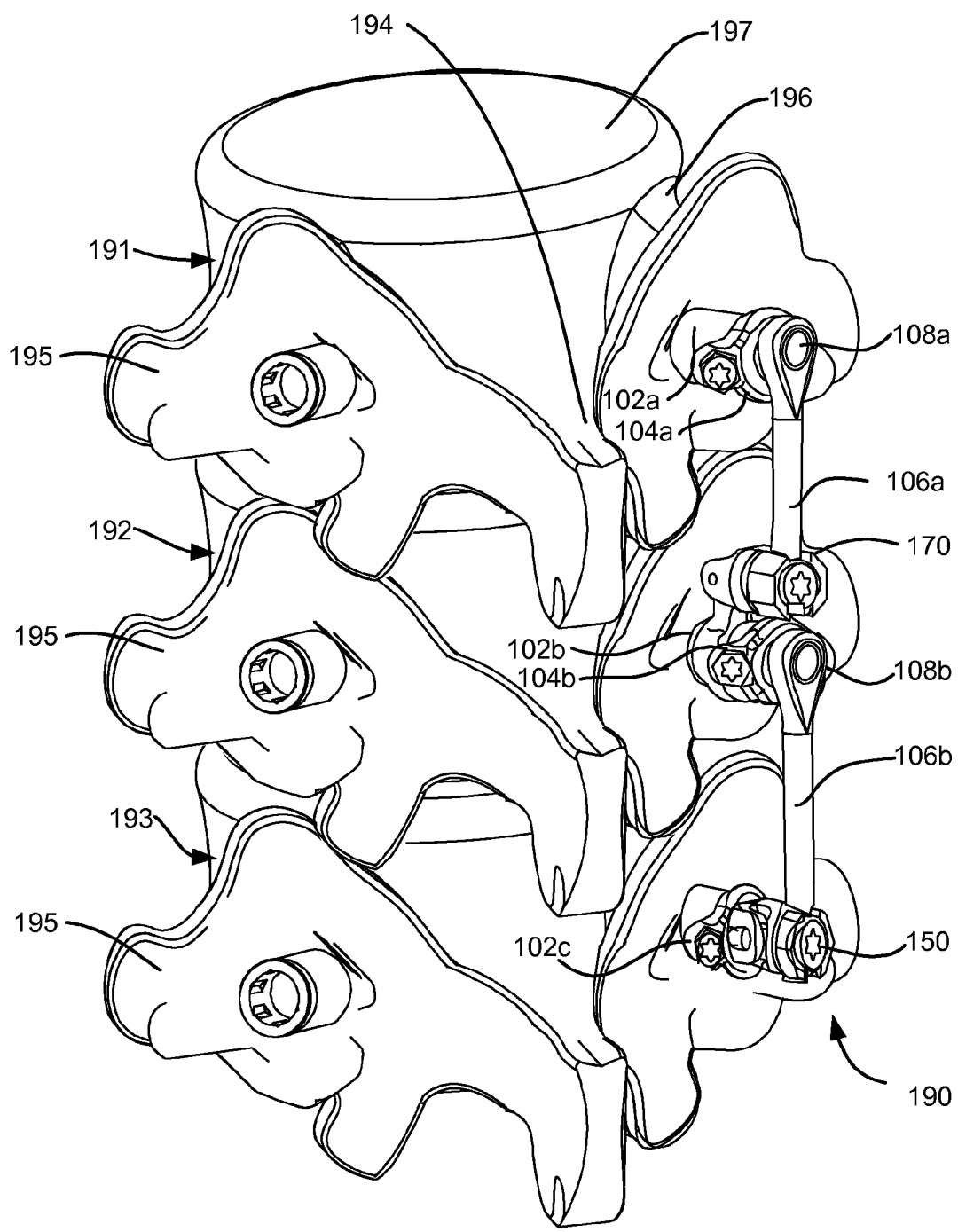
FIG. 1F is a posterior view of a multi-level dynamic stabilization assembly utilizing the components of FIGS. 1A to 1E according to an embodiment of the present invention.

After installation of the bone anchors, the deflection system components, vertical rod systems components and connection system components may be installed and assembled. FIG. 1F shows one way to assemble deflection system components and connection system components. As shown in FIG. 1F, a coaxial head 150 is installed in bone anchor 102c. An offset connector 170 is mounted externally to the housing of bone anchor 102b. A deflection rod 104a is coaxially mounted in the housing of bone anchor 102a. A deflection rod 104b is coaxially mounted in the housing of bone anchor 102b. A vertical rod 106a is connected at one end to deflection rod 104a by ball joint 108a. Vertical rod 106a is connected at the other end by in-line connector 170 to bone anchor 102b. A second vertical rod 106b is connected at one end to deflection rod 104b by ball joint 108b. Vertical rod 106b is connected at the other end by coaxial head 150 to bone anchor 102c.

The dynamic stabilization assembly 190 of FIG. 1E thus has a vertical rod 106a, 106b stabilizing each spinal level (191-192 and 192-193). Each of the vertical rods 106a, 106b is secured rigidly at one end to a bone anchor (102b, 102c). Each of the vertical rods 106a, 106b is secured at the other end by a ball joint 108a, 108b to a deflection rod 104a, 104b thereby allowing for some movement and load sharing by the dynamic stabilization assembly. Offset connector 170 and coaxial head 150 permit assembly of dynamic stabilization assembly 190 for a wide range of different patient anatomies and/or placements of bone anchors 102a, 102b and 102c. An identical or similar dynamic stabilization assembly would preferably be implanted on the left side of the spine. It should be noted that dynamic stabilization assembly 190 does not require horizontal bars or locking screws thereby reducing the exposure of tissue and/or bone to foreign bodies compared to systems with this additional hardware. The dynamic stabilization assembly of FIG. 1F, thereby, has a small footprint, potentially reducing the amount of displacement of tissue and/or bone, reducing trauma to tissue and/or bone during surgery. Further, the smaller footprint can reduce the amount of tissue that needs to be exposed during implantation.

The particular dynamic stabilization assembly shown in FIG. 1G is provided by way of example only. It is an aspect of preferred embodiments of the present invention that a range of components be provided and that the components may be assembled in different combinations and organizations to create different assemblies suitable for the functional needs and anatomy of different patients. Also, deflection rods having different force deflection characteristics may be incorporated at different spinal levels in accordance with the anatomical and functional requirements. Dynamic stabilization may be provided at one or more motion segments and in some cases dynamic stabilization may be provided at one or more motion segments in conjunction with fusion at an adjacent motion segment. Particular dynamic stabilization assemblies may incorporate combinations of the bone anchors, vertical rods, deflection rods, offset and coaxial connectors described herein, in the related applications incorporated by reference, and standard spinal stabilization and/or fusion components, for example screws, rods and polyaxial screws.

Deflection Rods/Loading Rods

One feature of embodiments of the present invention is the load sharing and range of motion provided by a deflection rod. The deflection rod provides stiffness and support where needed to support the loads exerted on the spine during normal spine motion thereby recovering improved spine function without sacrificing all motion. The deflection rod also isolates the anchor systems components from forces exerted by the dynamic stabilization assembly thereby reducing stress on the bone anchors and the bone to which they are attached. Moreover, by selecting the appropriate stiffness of the deflection rod or loading rod to match the physiology of the patient and the loads that the patient places on the spine, a better outcome is realized for the patient.

The deflection rod includes a deflectable post, a compliant sleeve and a mount. The deflectable post and mount are typically made of biocompatible metal or metals, e.g. titanium and stainless steel. The sleeve is made of a compliant material, for example a compliant polymer. The mount secures the deflection rod to an anchoring device in a manner which allows deflection of the deflectable post. The deflectable post is configured to connect to the vertical rod system. The deflectable post may deflect relative to the mount by compressing the compliant material of the sleeve. The deformation of the sleeve imparts force/deflection characteristics to the deflectable post. The movement of the post relative to the mount allows controlled movement of the bone anchor (and vertebra in which it is implanted) relative to the vertical rods thereby supporting the vertebrae to which the bone anchors are attached while allowing movement of the vertebrae.

Deflection rods can be manufactured in a range from highly rigid configurations to very flexible configurations by appropriate selection of the design, materials and dimensions of the post, sleeve and mount. Deflection rods having a particular stiffness/flexibility may be selected for use in a dynamic stabilization assembly based upon the physiological needs of a particular patient. In a preferred embodiment deflection rod stiffness/flexibility is selected to provide load sharing in conjunction with from 50% to 100% of the normal range of motion of a patient and more preferably 70% to 100% of the normal range of motion of a patient.

In some cases, certain of the deflection rods of a dynamic stabilization assembly can have a different stiffness or rigidity or flexibility than other of the deflection rods. Thus, in the same assembly, a first deflection rod can have a first flexibility or stiffness or rigidity, and a second deflection rod can have a second different flexibility or stiffness or rigidity depending on the needs of the patient. Particular embodiments of a dynamic stabilization assembly may utilize deflection rods having different deflection properties for each level and/or side of the dynamic stabilization assembly. In other words, one portion of a dynamic stabilization assembly may offer more resistance to movement than the other portion based on the design and selection of different stiffness characteristics, if that configuration benefits the patient.

Figure 2C:
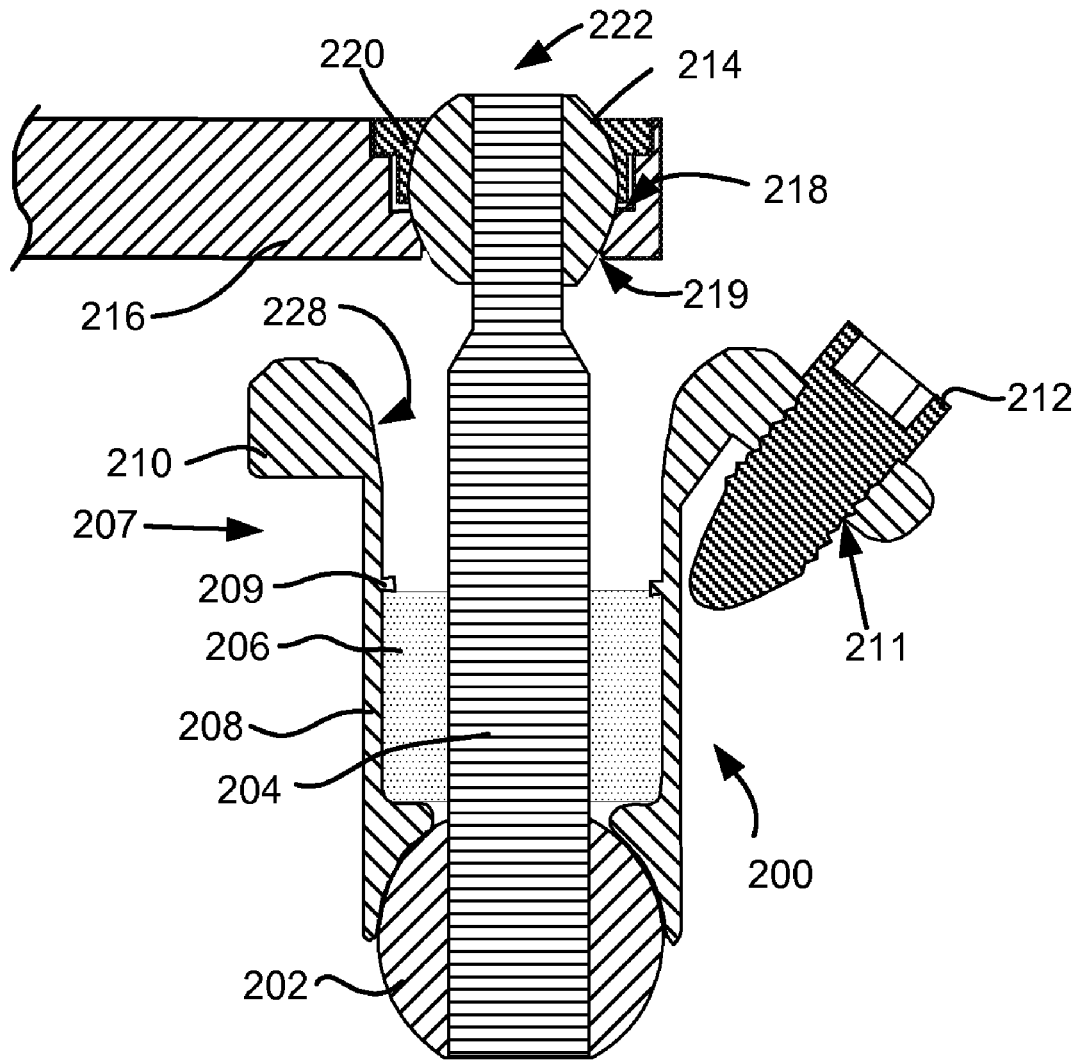
FIG. 2C is a sectional view of the deflection rod assembly of FIGS. 2A and 2B.

FIGS. 2A through 2G illustrate the design and operation of a first embodiment of a deflection rod according to an embodiment of the present invention. FIG. 2A shows an exploded view of deflection rod 200. Deflection rod 200 includes retainer 202, deflectable post 204, sleeve 206, shield 208, collar 210, screw 212 and ball 214. Deflection rod 200 connects to vertical rod 216 at a ball joint which includes ball 214, pocket 218 and cap 220. Shield 208 and collar 210 are securely attached to each other (or formed in one piece) and make up the mount 207. A threaded aperture 211 passes obliquely through collar 210. Threaded aperture 211 is configured to receive a screw 212. Sleeve 206 is made of a compliant material which permits movement of deflectable post 204 relative to shield 208. Deflectable post 204 may thus pivot in any direction about the center of ball-shaped retainer 202 as shown by arrows 230. The sleeve 206 controls and limits the deflection of the deflectable post 204. The deflectable post 204 can also rotate about the longitudinal axis of the post and the bone anchor as shown by arrow 232.

Referring now to FIG. 2B, which shows a perspective view of a fully assembled deflection rod 200. When assembled, deflectable post 204 is positioned within sleeve 206; sleeve 206 is positioned within shield 208. Ball 214 is connected to the proximal end of deflectable post 204 to provide a component of a ball joint for connecting deflection rod 200 to a vertical rod 216. Ball 214 may be formed in one piece with deflectable post 204 or may be securely attached to deflectable post 204 using a joint, for example, a threaded joint, welded joint, adhesive joint. Retainer 202 is attached to the distal end of deflectable post 204 to prevent deflectable post 204 from being pulled out of sleeve 206.

As shown in FIG. 2A, the retainer 202 may be a ball-shaped retainer 202. Retainer 202 may be formed in one piece with deflectable post 204 or may be securely attached to deflectable post 204. The retainer 202 may be attached by laser welding, soldering or other bonding technology. For example, retainer 202 in the form of a ball, disk, plate or other shape may be laser welded to the distal end of deflectable post 204. Alternatively, retainer 202 may mechanically engage the deflectable post 204 using, for example, threads. For example, a lock ring, toothed locking washer, cotter pin or other mechanical device can be used to secure deflectable post 204 within shield 208.

The ball 214 of deflection rod 200 is received in a pocket of vertical rod 216. Cap 220 secures ball 214 within the pocket of vertical rod 216 creating a ball joint 222 which allows vertical rod 216 to rotate 360 degrees around the axis of deflectable post 204 (as shown by arrow 234) and also tilt away from the plane perpendicular to the axis of deflectable post 204 (as shown by arrow 236). Thus, the vertical rod 216 is allowed to rotate and/or have tilting and/or swiveling movements about a center which corresponds with the center of ball 214 of ball joint 222. Ball 214 can also be displaced relative to shield 208 by deflection of deflectable post 204 (as shown by arrows 230).

FIG. 2C shows a sectional view of a fully assembled deflection rod 200 along the axis indicated by line C-C of FIG. 2B. As shown in FIG. 2C, sleeve 206 occupies the space between deflectable post 204 and shield 208 and is compressed by deflection of deflectable post 204 towards shield 208 in any direction. In some embodiments, sleeve 206 may be formed separately from deflection rod 200. For example, deflectable post 204 and sleeve 206 may be press fit into shield 208. Alternatively or additionally, a biocompatible adhesive may be used to bond the sleeve 206 to the shield 208 and/or deflectable post 204. Alternatively, sleeve 206 may be formed in place by positioning the deflectable post 204 within the shield 208 and then filling the space between the deflectable post 204 and the shield 208 with liquid polymer (polymer reagents) and allowing the polymer to solidify (polymerize).

FIG. 2C, also illustrates the internal detail of ball joint 222 which connects vertical rod 216 and deflectable post 204 of deflection rod 200. Vertical rod 216 includes disk-shaped pocket 218 at one end. The proximal end of deflectable post 204 is passed through aperture 219 in disk-shaped pocket 218 of the vertical rod 216. The diameter of deflectable post 204 is smaller than the diameter of aperture 219. Once the proximal end of deflectable post 204 is passed through the aperture 219, ball 214 is attached to deflectable post 204 using threading, fusing, gluing, press fit and/or laser welding techniques, for example. The diameter of the aperture 219 is less than the diameter of ball 214 to prevent ball 214 from passing back through aperture 219. Once ball 214 is positioned within the disk-shaped pocket 218 of vertical rod 216, cap 220 is threaded, fused, glued, press fit and/or laser welded, for example, into pocket 218 thereby securing ball 214 within disk shaped pocket 218. FIG. 2C also shows an optional ridge 209 on the interior of shield 208 for retaining sleeve 206.

Figure 2D:
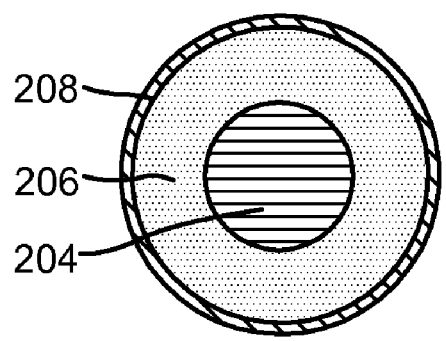
FIG. 2D is a sectional view of the deflection rod assembly of FIGS. 2A and 2B.

FIG. 2D shows a sectional view of a fully assembled deflection rod 200 along the axis indicated by line D-D of FIG. 2B. As shown in FIG. 2D, sleeve 206 occupies the space between deflectable post 204 and shield 208 and is compressed by deflection of deflectable post 204 towards shield 208 in any direction. Sleeve 206 resists deflection of deflectable post 204 outwardly from a position that is collinear with the longitudinal axis of sleeve 206. The dimensions and material of sleeve 206 may be adjusted to generate the desired deflection/load characteristics for the deflection rod.

FIGS. 2E and 2F illustrate deflection of deflectable post 204. Applying a force to ball-joint 222 causes deflection of deflectable post 204 relative to mount 207 including shield 208 (and any bone anchor to which it may be mounted). Initially deflectable post 204 pivots about a pivot point 203 indicated by an X. In this embodiment pivot point 203 is located at the center of ball-shaped retainer 202. In other embodiments however, pivot point may positioned at a different location. As shown in FIG. 2E, deflection of deflectable post 204 initially compresses the material of sleeve 206 between deflectable post 204 and shield 208. The force required to deflect deflectable post 204 depends upon the dimensions of deflectable post 204, sleeve 206 and shield 208 as well as the attributes of the material of sleeve 206.

By changing the dimensions of deflectable post 204, sleeve 206 and shield 208, the deflection characteristics of deflection rod 200 can be changed. The stiffness of components of the deflection rod can be, for example, increased by increasing the diameter of the post and/or by decreasing the diameter of the inner surface of the shield and deflection guide. Additionally, increasing the diameter of the post will increase the stiffness of the deflection rod while decreasing the diameter of the post will decrease the stiffness of the deflection rod. Alternatively and/or additionally changing the materials which comprise the components of the deflection rod can also affect the stiffness and range of motion of the deflection rod. For example, making sleeve 206 out of stiffer and/or harder material reduces deflection of deflectable post 204.

The stiffness of the deflection rod may thus be varied or customized according to the needs of a patient. The deflection characteristics of the deflection rod can be configured to approach the natural dynamic motion of the spine, while giving dynamic support to the spine in that region. It is contemplated, for example, that the deflection rod can be made in stiffness that can replicate a 70% range of motion and flexibility of the natural intact spine, a 50% range of motion and flexibility of the natural intact spine and a 30% range of motion and flexibility of the natural intact spine. In some cases, a kit is provided to a doctor having a set of deflection rods with different force/deflection characteristics from which the doctor may select the deflection rods most suitable for a particular patient. In other cases, the surgeon may select deflection rods prior to the procedure based upon pre-operative assessment.

Sleeve 206 is preferably made of a compliant biocompatible polymer. Sleeve 206 may, for example, be made from a polycarbonate urethane (PCU) such as Bionate®. If the sleeve is comprised of Bionate®, a polycarbonate urethane or other hydrophilic polymer, the sleeve can also act as a fluid-lubricated bearing for rotation of the deflectable post 204 relative to the longitudinal axis of the deflectable post 204 (see arrow 232 of FIG. 2B). In a preferred embodiment, the sleeve is made of PCU, is 2 mm thick when uncompressed and may be compressed to about 1 mm in thickness by deflection of the post.

The sleeve may also include polymer regions having different properties. For example, the sleeve can include concentric rings of one or more polymers with each ring having a different hardness of stiffness or durometer. For example, each successive ring from the center outward can have a higher hardness or stiffness or durometer so that as the post is deflected outwardly from a position that is collinear with the longitudinal axis of the sleeve provides increased resistance to further deflection. The sleeve may also be designed to provide different force deflection characteristics in different directions. The deflectable post could also be designed so that less resistance occurs with increased deflection of the post.

As shown in FIG. 2F, after further deflection, deflectable post 204 comes into contact with limit surface 228 of shield 208. Limit surface 228 is oriented such that when deflectable post 204 makes contact with limit surface 228, the contact is distributed over an area to reduce stress on deflectable post 204 and limit surface 228. As depicted, limit surface 228 is configured such that as the deflectable post 204 deflects into contact with limit surface 228, limit surface 228 is aligned/flat relative to deflectable post 204 in order to present a larger surface to absorb any load and also to reduce stress on deflectable post 204 and limit surface damage. Additional deflection may cause elastic deformation of deflectable post 204. Because deflectable post 204 is relatively stiff, the force required to deflect deflectable post 204 increases significantly after contact of deflectable post 204 with shield 208. In a preferred embodiment, deflectable post 204 may deflect from 0.5 mm to 2 mm in any direction before making contact with limit surface 228. More preferably, deflectable post 204 may deflect approximately 1 mm before making contact with limit surface 228.

Thus, as load or force is first applied to the deflection rod by the spine, the deflection of the deflection rod responds about linearly to the increase in the load during the phase when deflection of deflectable post 204 causes compression of sleeve 206 as shown in FIG. 2E. After about 1 mm of deflection, when deflectable post 204 contacts limit surface 228 (as shown in FIG. 2F) the deflection rod becomes stiffer. Thereafter, a greater amount of load or force needs to be placed on the deflection rod in order to obtain the same incremental amount of deflection that was realized prior to this point because further deflection requires bending of deflectable post 204. Accordingly, the deflection rod provides a range of motion where the load supported increases about linearly as the deflection increases and then with increased deflection the load supported increases more rapidly in a non-linear manner in order to provide stabilization. Put another way, the deflection rod becomes stiffer as the deflection/load increases. In a dynamic stabilization assembly incorporating the deflection rod, the load sharing and deflection is provided by the deflection rod between the deflectable post and the bone screw or the overall bone anchor such as bone anchor 102 and to a lesser degree or not in the vertical rod such as the vertical rod 106 (FIG. 1B).

FIG. 2G is a sectional view illustrating the implantation of deflection rod 200 in a vertebra 240. As shown in FIG. 2G, bone anchor 102 is oriented such that is passes through pedicle 242 into vertebral body 244. Note that the length of bone anchor 102 is selected based upon the anatomy of the patient. Thus shorter bone anchors are used in smaller vertebrae and longer bone anchors are used in larger vertebrae. As shown in FIG. 2G, bone anchor 102 has shallower threads 250 adjacent housing 130. Threads 250 engage the harder cortical bone 246 on the surface of the vertebra 240. Bone anchor 102 has deeper threads 252 towards the distal end of bone anchor 102. Threads 252 engage the softer cancellous bone 248 within the vertebral body 244.

As shown in FIG. 2G, deflection rod 200 is mounted within bone anchor 102 such that pivot point 203 is positioned below the surface of vertebra 240. Deflectable post 204 pivots about this pivot point 203 positioned within vertebra 240. This is advantageous in that it places pivot point 203 of deflectable post 204 closer to the vertebral body 244 and thus closer to the natural instantaneous center of rotation of the spine. Placing pivot point 203 closer to the vertebral body 244 promotes natural motion and reduces non physiological forces on the bones and strain on the system. Placing the pivot point 203 closer to the vertebral body 244 also helps isolate bone anchor 102 from the relative motion between vertebra 240 and the vertical rod 216 which connects one vertebra to another vertebra. Pivot point 203 is preferably at or below the surface of the vertebra and more preferably pivot point 203 is within the cancellous bone 248 of the vertebrae 240. Even more preferably, the pivot point 203 is positioned with the pedicle 242 of the vertebra 240. In some cases, pivot point 203 may be positioned within vertebral body 244.

Alternative Deflection Rods/Loading Rods

Figure 3E:
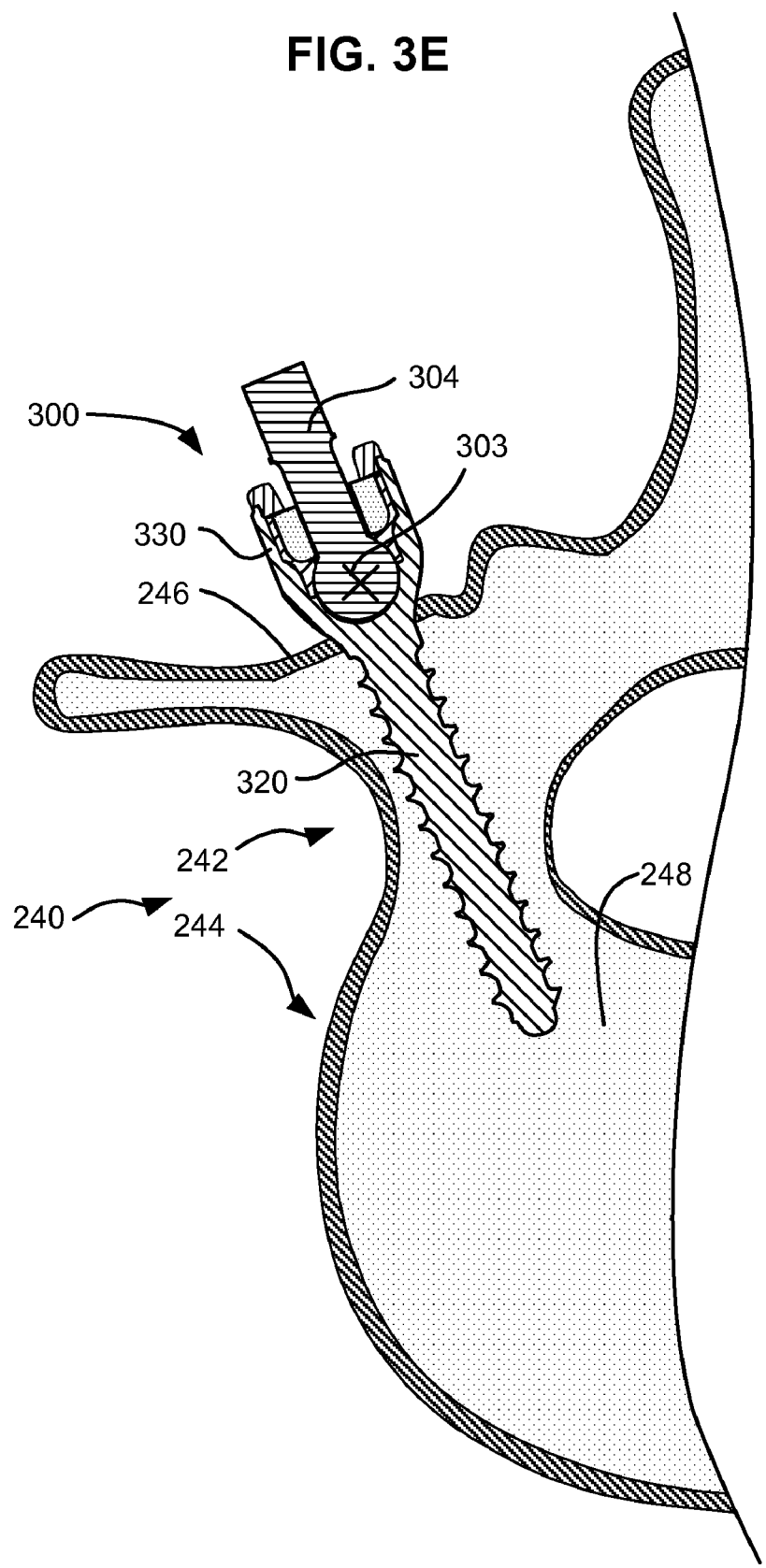
FIG. 3E is a transverse sectional view of a vertebra illustrating the implantation of the deflection rod assembly of FIGS. 3A and 3B.

FIGS. 3A-3H illustrate a first alternative deflection rod 300. FIG. 3A shows an exploded view of alternative deflection rod 300. Deflection rod 300 includes ball-shaped retainer 302, deflectable post 304, sleeve 306, shield 308, collar 310, and mount 314. In this embodiment, retainer 302 is a spherical structure formed in one piece with deflectable post 304. Mount 314, in this embodiment, is the proximal end of deflectable post 304 suitable for connecting to a vertical rod. A ball may be used in place of mount 314 as previously described. In this embodiment, mount 314 is formed in one piece with deflectable post 304 and retainer 302. In alternative embodiments, deflectable post 304 may be formed separately from and securely attached to one or more of mount 314 and retainer 302 by laser welding, soldering or other bonding technology. Alternatively, deflectable post 304 may be formed separately and mechanically engage one or more of mount 314 and retainer 302 using, for example, threads. For example, a lock ring, toothed locking washer, cotter pin or other mechanical device can be used to secure deflectable post 304 to one or more of mount 314 and retainer 302.

Sleeve 306 is made of a compliant material which permits movement of deflectable post 304 relative to shield 308. The sleeve 306 effectively controls and limits the deflection of the deflectable post 304. Sleeve 306 is preferably made of a compliant biocompatible polymer such as PCU by way of example only. The properties of the material and dimensions of the sleeve 306 are selected to achieve the desired force/deflection characteristics for deflectable post 304. In a preferred embodiment, the sleeve is made of PCU (Bionate® 80A) and is 2 mm thick when uncompressed and may be compressed to about 1 mm in thickness by deflection of the post. Sleeve 306 may also be shaped to modify the compliance of sleeve 306, for example by providing flutes 307. Sleeve 306 fits inside shield 308 surrounding deflectable post 304.

Deflection rod 300 is configured to be mounted in a bone anchor 320, which comprises a bone screw 322 connected to a housing 330. Housing 330 has a cavity 332 oriented along the axis of bone anchor 320 at the proximal end and configured to receive deflection rod 300. Housing 330 also has an outer surface 334 adapted for mounting a component e.g. an offset connector. Housing 330 may in some embodiments be cylindrical as previously described. As shown in FIG. 3A, outer surface 334 of housing 330 is provided with splines/flutes 336. Splines/flutes 336 may be engaged by a driver that mates with splines/flutes 336 for implanting bone anchor 320.

Referring now to FIG. 3B, which shows a perspective view of a deflection rod 300 assembled with a bone anchor 320. When assembled, deflectable post 304 is positioned within sleeve 306 of FIG. 3A; sleeve 306 is positioned within shield 308 of FIG. 3A. Deflectable post 304, sleeve 306 and shield 308 are then placed in the cavity 332 of FIG. 3A of bone anchor 320. Threaded collar 310 is then secured in the threaded proximal end of cavity 332. Threaded collar 310 has two sockets 311 for receiving the pins of a pin wrench to allow threaded collar 310 to be tightened to threads 338 of housing 330. Threaded collar 310 is laser welded to housing 330 after installation to further secure the components. Threaded collar 310 secures deflectable post 304, sleeve 306 and shield 308 within cavity 332 of bone anchor 320.

FIG. 3C shows a sectional view of a deflection rod 300 assembled with a bone anchor 320 along the axis indicated by line C-C of FIG. 3B. As shown in FIG. 3C, sleeve 306 occupies the space between deflectable post 304 and shield 308 and is compressed by deflection of deflectable post 304 towards shield 308 in any direction. Retainer 302 fits into a hemispherical pocket 339 in the bottom of cavity 332 of housing 330. Shield 308 includes a flange 309 which secures ball-shaped retainer 302 within hemispherical pocket 339 while allowing rotation of ball-shaped retainer 302. Collar 310 secures both shield 308 and sleeve 306 within housing 330. If sleeve 306 is comprised of Bionate®, a polycarbonate urethane or other hydrophilic polymer, sleeve 306 can act as a fluid lubricated bearing and allow the post to also rotate about the longitudinal axis of the post and the bone anchor. Other materials and configurations can also allow the post to rotate about the longitudinal axis of the post and the bone anchor.

FIG. 3D illustrates the deflection of deflectable post 304. Applying a force to mount 314 causes deflection of deflectable post 304 of deflection rod 300. Initially deflectable post 304 pivots about a pivot point 303 indicated by an X. Deflectable post 304 may pivot about pivot point 303 in any direction. Concurrently or alternatively, deflectable post 304 can rotate about the long axis of deflectable post 304 (which also passes through pivot point 303). In this embodiment, pivot point 303 is located at the center of ball-shaped retainer 302. As shown in FIG. 3D, deflection of deflectable post 304 initially compresses the material of sleeve 306. The force required to deflect deflectable post 304 depends upon the dimensions of deflectable post 304, sleeve 306 and shield 308 as well as the attributes of the material of sleeve 306.

After further deflection, deflectable post 304 comes into contact with limit surface 313 of collar 310. Limit surface 313 is oriented such that when deflectable post 304 makes contact with limit surface 313, the contact is distributed over an area to reduce stress on deflectable post 304. After deflectable post 304 comes into contact with limit surface 313, further deflection requires deformation (bending) of deflectable post 304.

In a preferred embodiment, deflectable post 304 is a titanium post 5 mm in diameter. Deflectable post 304 is relatively stiff, and the force required to deflect deflectable post 304 therefore increases significantly after contact of deflectable post 304 with collar 310. In a preferred embodiment, deflectable post 304 may deflect from 0.5 mm to 2 mm in any direction before making contact with limit surface 313. More preferably, deflectable post 304 may deflect approximately 1 mm before making contact with limit surface 313.

The inner diameter of the collar 310 may be different in different collars so that the distance between limit surface 313 and deflectable post 304 is different in different deflection rods. This allows for the manufacture of deflection rods having a larger or smaller range of deflection before contact between the post and the limit surface. In this way, deflection rods may be manufactured having different ranges of motion. Moreover, the distance between limit surface 313 and deflectable post 304 need not be the same in all directions such that the range of motion of the deflection rod is different in different directions.

Referring to FIG. 3D, as load or force is first applied to the deflection rod 300 by the spine, the deflection of deflectable post 304 responds about linearly to the increase in the load during the phase when deflection of deflectable post 304 causes compression of sleeve 306. After about 1 mm of deflection, deflectable post 304 contacts limit surface 313 and the deflection rod becomes substantially stiffer. A greater amount of load or force needs to be placed on the deflection rod in order to obtain the same amount of incremental deflection that was realized prior to this point because further deflection requires bending of deflectable post 304. The amount of deflection caused by the load applied is a non-linear function, in this embodiment. The deflection rod provides a range of motion where the load supported increases about linearly as the deflection increases and then with increased deflection the load supported increases more rapidly (upon contact of the post with the limit surface). Alternatively, if desired, this embodiment could be designed such that the rate of change of the amount of deflection could be a linear function for a larger range of motion by; for example, increasing the distance between limit surface 313 and deflectable post 304.

FIG. 3E is a sectional view illustrating the implantation of a deflection rod 300 in a vertebra 240. As shown in FIG. 3E, bone anchor 320 is oriented such that is passes through pedicle 242 into vertebral body 244. Note that the length of bone anchor 320 is selected based upon the anatomy of the patient. Thus shorter bone anchors are used in smaller vertebrae and longer bone anchors are used in larger vertebrae. As shown in FIG. 3E, housing 330 of bone anchor 320 is mounted entirely above the surface of vertebra 240. Pivot point 303 of deflection rod 300 is positioned within housing 330 such that pivot point 303 is, in this embodiment, positioned close to but outside of vertebra 240.

Figure 3F:
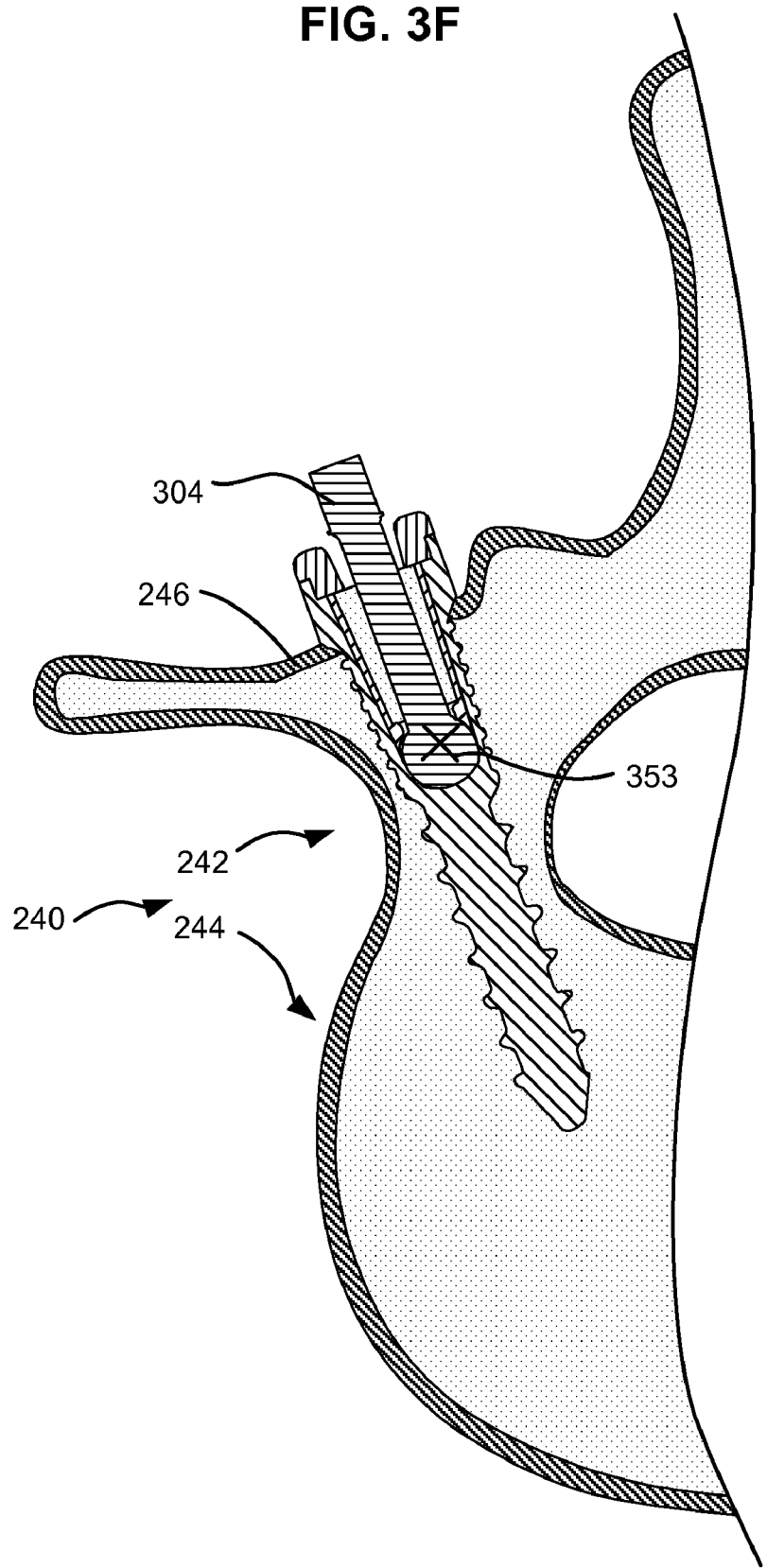
FIG. 3F is a transverse sectional view of a vertebra illustrating the implantation of an alternative deflection rod.

In an alternative embodiment, as shown in FIG. 3F, deflectable post 304 pivots about a pivot point 353 positioned within vertebra 240. This is advantageous in that it places pivot point 353 of deflectable post 304 closer to the vertebral body 244 and thus the natural instantaneous center of rotation of the spine. Placing the pivot point 353 closer to the vertebral body 244 promotes natural motion and reduces non-physiological forces on the bones and strain on the dynamic stabilization assembly. In particular, placing the pivot point 353 closer to the vertebral body 244 helps isolate bone anchor 320 from the relative motion between vertebra 240 and a vertical rod of the dynamic stabilization assembly which connects one level of the spine to the adjacent level. Pivot point 353 is preferably at or below the surface of the vertebra 240. More preferably, the pivot point 353 is positioned with the pedicle 242 of the vertebra 240. In some cases, pivot point 353 may be positioned within vertebral body 244.

Figure 3G:
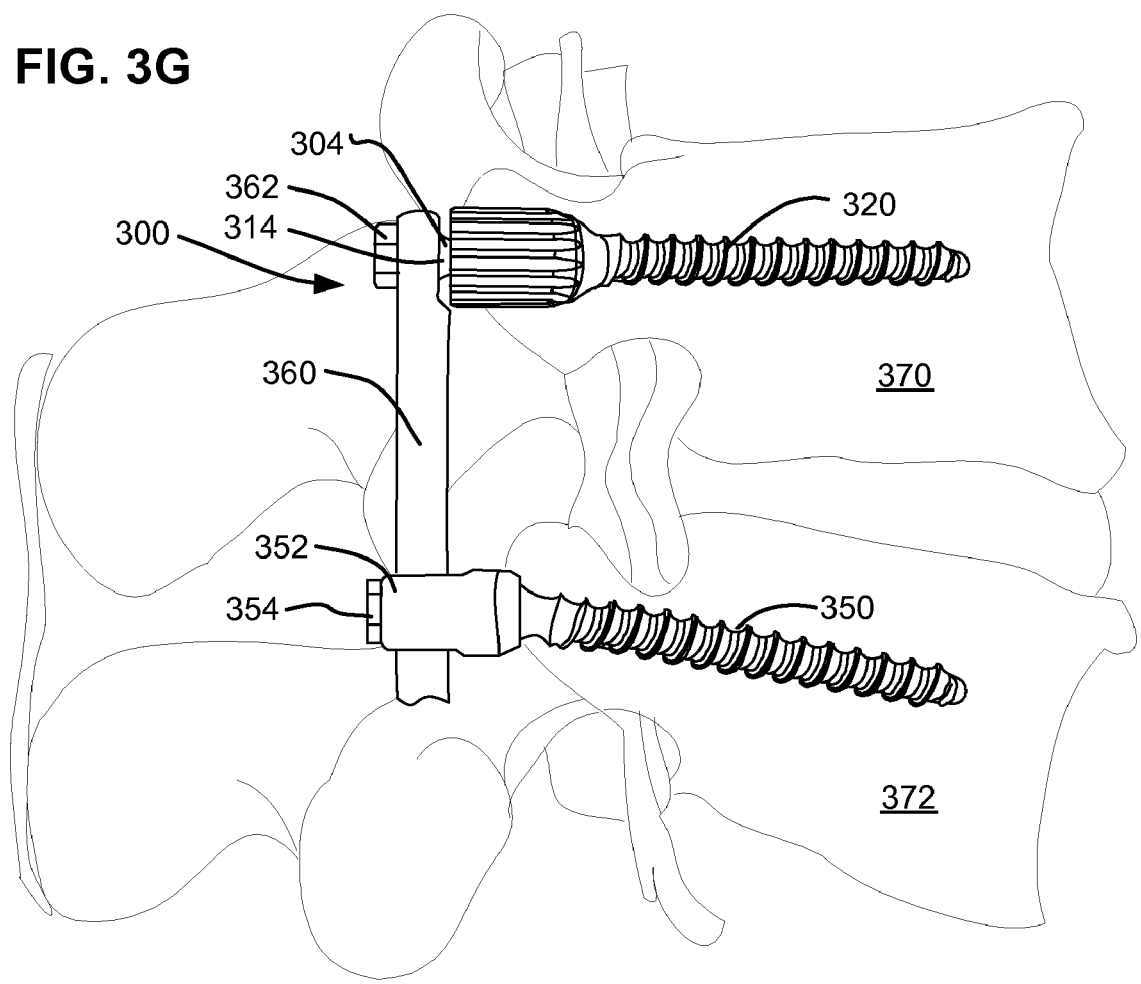
FIG. 3G is a lateral view of a multi-level dynamic stabilization assembly utilizing the deflection rod assembly of FIGS. 3A-3B according to an embodiment of the present invention.

FIG. 3G shows a lateral view of a dynamic stabilization assembly utilizing deflection rod 300. As shown in FIG. 3G, deflection rod 300 is installed in bone anchor 320. Bone anchor 320 is implanted in one vertebra 370 (see e.g. FIG. 3E). A polyaxial screw 350 is implanted in a second vertebra 372. A vertical rod 360 is secured at one end to mount 314 of deflection rod 300. Mount 314 in this embodiment passes through an aperture in vertical rod 360. The proximal end of mount 314 is threaded so that vertical rod 360 may be secured to mount 314 with a threaded nut 362. In this embodiment, as shown in FIG. 3G, the vertical rod 360 is secured rigidly to deflectable post 304. The rigid connection provides a relatively stiff assembly. However, where greater range of motion is desired, deflectable post 304 may be provided with a ball end and vertical rod 360 may be connected to deflectable post 304 by a ball joint as previously described with respect to FIGS. 1A-1B.

Vertical rod 360 is mounted at the other end to the polyaxial head 352 of polyaxial screw 350. This screw may be a standard polyaxial screw, for example, a 5.5 mm polyaxial screw available in the marketplace. This screw may, alternatively, be a bone anchor with a polyaxial head e.g. the polyaxial head previously described with respect to FIG. 1C. In a preferred embodiment, vertical rod 360 is a titanium rod 5.5 mm in diameter as used in rigid spinal implants. The vertical rod 360 is secured to polyaxial head 352 using a threaded fitting, set screw 354, for example. The vertical rod 360 thereby supports the vertebrae while deflection rod 300 provides for load sharing and allows relative motion of vertebra 370 relative to vertebra 372. Thus, the dynamic stabilization assembly provides dynamic stabilization of the spine. The dynamic stabilization assembly may be expanded to two or more levels using an offset connector mounted to the housing 330 of bone anchor 320. It is to be understood that an offset connector can include a fluted ring to assist in engaging the housing 330 (see e.g. shape of open wrench 380 in FIG. 3H). Thus, a modular system is provided which provides for the creation of a multi-level dynamic stabilization assembly.

Figure 3H:
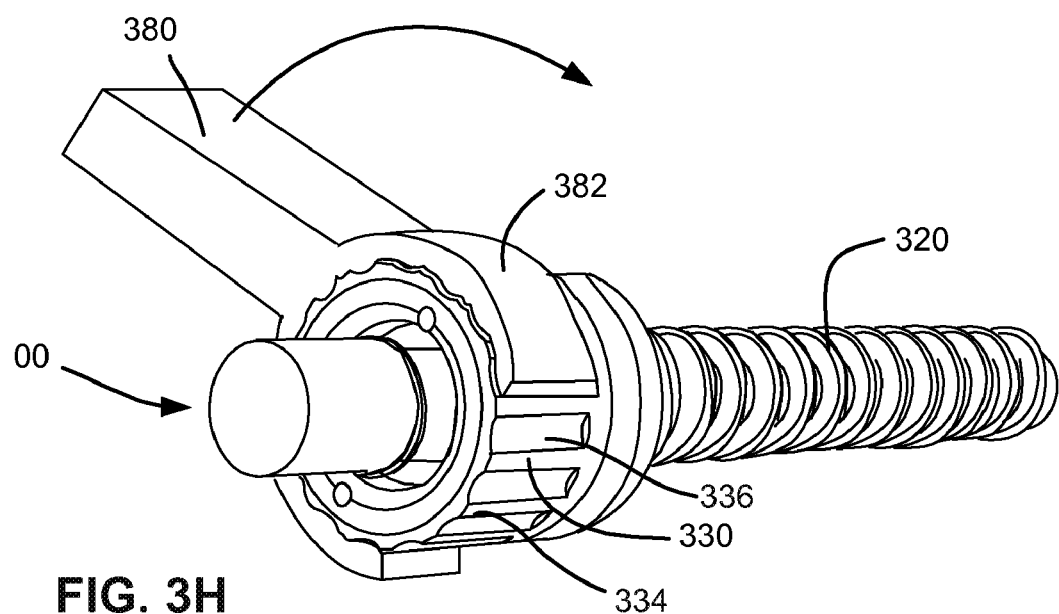
FIG. 3H is an oblique view of an offset connector mounted to the deflection rod assembly of FIGS. 3A-3B according to an embodiment of the present invention.

FIG. 3H illustrates an open wrench 380 for driving bone anchor 320 into position. Bone anchor 320 of FIG. 3H has a housing 330. A deflection rod 300 is installed in housing 330 and secured in place by threaded collar 310 (FIGS. 3A and 3B). Threaded collar 310 engages threads interior to housing 330. Collar 310 has two apertures 311 which may be engaged by a pin wrench to tighten collar 310 to housing 330. Collar 310 may also be welded to housing 330 to further secure deflection rod 300 with housing 330. In this embodiment deflection rod 300 is designed to be preassembled with bone anchor 320 prior to implantation.

As shown in FIG. 3H, the exterior surface 334 of housing 330 is provided with surface features in the form of a plurality of splines 336. Splines 336 are oriented parallel to the longitudinal axis of bone anchor 320 and project from housing 330 at regular intervals. Open wrench 380 has a head 382 designed to engage the exterior surface 334 of housing 330. With such a tool, the housing 330 can be engaged and rotated about the longitudinal axis of the bone anchor 320 in order to drive the bone anchor into the bone. Open wrench 380 may be provided with a torque limiting or torque measuring component to facilitate installation of bone anchor 320. In alternative embodiments a socket may be used to engage housing 330 in place of an open wrench.

Figure 3I:
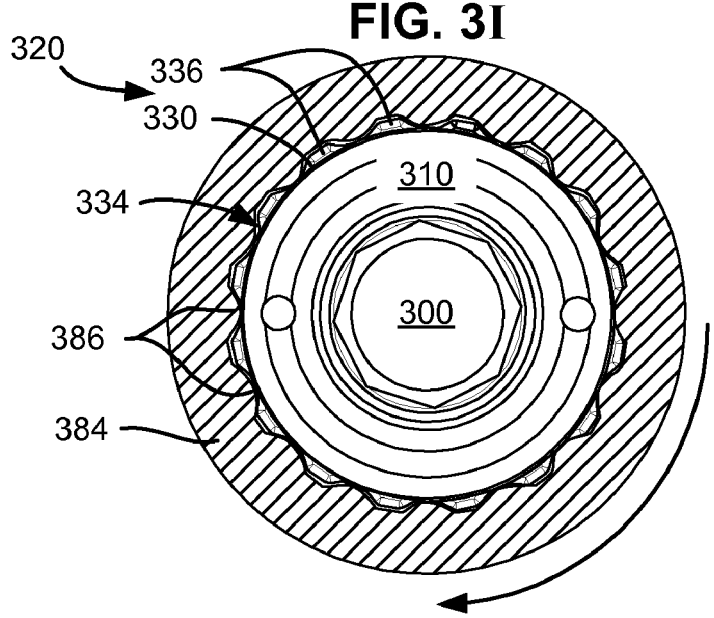
FIG. 3I shows a socket with interior features adapted to engage features of the housing of a deflection rod assembly according to an embodiment of the present invention.

FIG. 3I shows a plan view of bone anchor 320 and deflection rod 300 observed from the deflection rod end of the assembly. As shown in FIG. 3I there are 16 splines 336 evenly spaced around the exterior surface 334 of housing 330. The diameter of collar 310 is the same or smaller as the minimum diameter of housing 330 in the region of the splines 336 to allow engagement of the splines 336 by a complementary tool or connector without interference from collar 310. In other embodiments there may be a greater or lesser number of splines.

FIG. 3I shows a sectional view of a socket wrench 384 suitable for engaging housing 330. Socket wrench 384 has a plurality of splines 386 complementary to splines 336 of housing 330. Socket wrench 384 may therefore be slipped over deflection rod 300 and housing 330 and positioned as shown in FIG. 3I. When in position, socket wrench 384 may be used to rotate housing 330 to install bone anchor 320 in a bone (or remove the bone anchor from the bone). Socket wrench 384 should be complementary in interior profile to the exterior profile 334 of housing 330. Socket wrench 384 need not have as many splines 386 as housing 330 has splines 336 so long as splines 386 are correctly positioned to engage some or all of the splines 336 of housing 330. An open wrench or other driver may be designed with the same engagement surface to engage some or all of the splines 336 of housing 330.

Figure 3J:
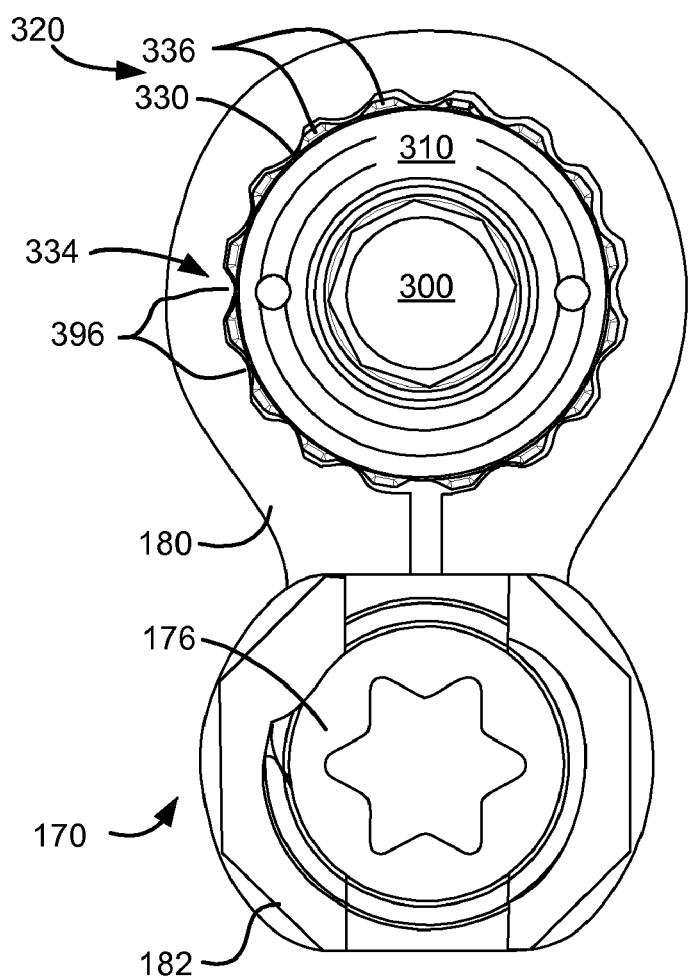
FIG. 3J shows a connector with interior features adapted to engage features of the housing of a deflection rod assembly according to an embodiment of the present invention.

Likewise, connectors that engage the housing of a bone anchor may also be readily adapted to engage splines 336 of housing 330. By way of example, FIG. 3J shows connector 170 of FIG. 1D adapted to engage splines 336. Connector 170 mounts externally of the housing 330 of a bone anchor 320. The components of connector 170 shown in FIG. 3J include locking set screw 176, clamp ring 180 and saddle 182. As shown in FIG. 3J, clamp ring 180 has, on the inside diameter, a plurality of splines 396 complementary to splines 336 of housing 330. Clamp ring 180 may therefore be slipped over deflection rod 300 and housing 330 and positioned as shown in FIG. 3J after implantation of bone anchor 320 in a vertebra. Splines 396 engage splines 336 of housing 330. Clamp ring 180 is prevented by splines 396 and 336 from free rotation around housing 330. This is advantageous in that increases the stability of the dynamic stabilization assembly by preventing the clamp ring 180 from slipping around housing 330 under load. When clamp ring 180 is positioned at the desired angle relative to bone anchor 320, set screw 176 may be tightened onto a vertical rod (not shown) to clamp the vertical rod to the saddle 182 and also tighten clamp ring 180 against the exterior surface 334 of housing 330. Thus connector 180 may be used to securely attach a vertical rod to the housing 330 of bone anchor 320.

Clamp ring 180 (and thus connector 170) may be installed in any of 16 positions around housing 330 (22.5 degrees separation between positions). If smaller granularity of positioning is required, a larger number of splines 336 may be used. Clamp ring 180 should be complementary in interior profile to the exterior surface 334 of housing 330. Clamp ring 180 need not have as many splines 396 as housing 330 has splines 336 so long as the splines 396 are correctly positioned to engage some or all of the splines 336 of housing 330. A clamp ring 180 as shown in FIG. 1D without any splines may still be used to engage housing 330.

Other connectors may be similarly adapted to engage the splines 336 of housing 330 of bone anchor 320. Likewise, the other bone anchors discussed herein may be provided with splines on the exterior of the housing to facilitate installation and enhance the mounting of connectors. In alternative embodiments, different surface features may be utilized on the surface of a housing for engagement by a tool or connector. For example, a housing may be made polygonal in exterior section and have 8, 3, 12, 16 or more sides. A tool or connector for use with such a housing would have a complementary interior profile designed to engage the 8, 3, 12, 16 or more sides. Alternatively, a housing may be provided with a plurality of apertures at regular intervals. A tool or connector for use with such a housing may be provided with a one or more of pins designed to engage the apertures in a plurality of positions in the manner of a pin wrench. Conversely the housing may be provided with one or more protruding pins and the tool or connector with a plurality of complementary apertures. Alternatively, one or both of the housing and connector may be provided with shallow surface features such as dots, dimples, ridges or the like designed to increase the frictional engagement of the housing and connector. In the latter case, the features of the housing and connector need not necessarily be complementary to one another and the connector and housing may be free to engage one another at any angular position.

Figure 4A:
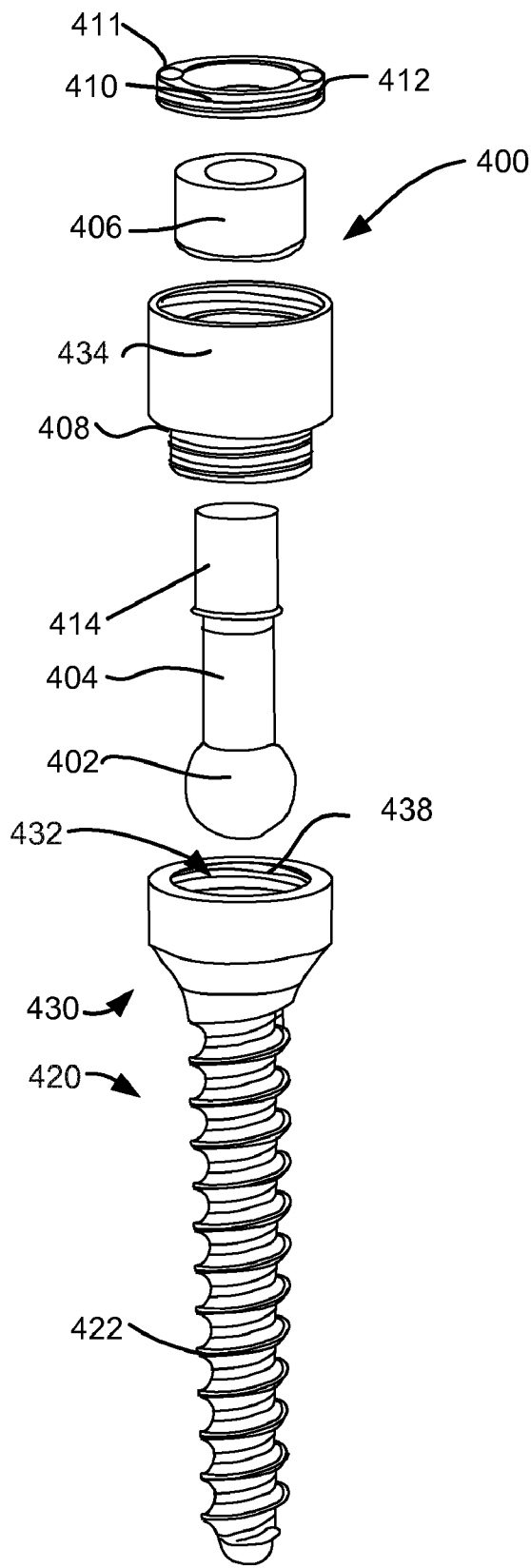
FIG. 4A is an exploded view of an alternative deflection rod assembly according to an embodiment of the present invention.

FIGS. 4A-4D illustrate a second alternative deflection rod 400. FIG. 4A shows an exploded view of an alternative deflection rod 400. Deflection rod 400 includes retainer 402, deflectable post 404, sleeve 406, shield 408, collar 410, and mount 414. In this embodiment, retainer 402 is a ball-shaped structure formed in one piece with deflectable post 404. Mount 414 is suitable for connecting to a vertical rod. A ball may be used in place of mount 414 as previously described. In this embodiment, mount 414 is formed in one piece with deflectable post 404. In a preferred embodiment, mount 414, ball-shaped retainer 402 and deflectable post 404 are formed from a single piece of titanium. In alternative embodiments, deflectable post 404 may be formed separately from, and securely attached to, one or more of mount 414 and retainer 402 by laser welding, soldering or other bonding technology. Alternatively, deflectable post 404 may be formed separately and mechanically engage one or more of mount 414 and retainer 402 using, for example, threads, a lock ring, toothed locking washer, cotter pin or other mechanism.

Sleeve 406 is made of a compliant material which permits movement of deflectable post 404 relative to shield 408. The sleeve 406 controls deflection of the deflectable post 404. Sleeve 406 is preferably made of a compliant biocompatible polymer. The properties of the material and dimensions of the sleeve 406 and deflectable post 404 are selected to achieve the desired force/deflection characteristics for deflectable post 404. In a preferred embodiment, the sleeve is made of PCU, is 2 mm thick when uncompressed and may be compressed to about 1 mm in thickness by deflection of the post. Sleeve 406 may also be shaped to modify the compliance of sleeve 406, for example by providing flutes 407 (not shown). Sleeve 406 fits inside shield 408 surrounding deflectable post 404.

Deflection rod 400 is configured to be mounted in a bone anchor 420, which comprises a bone screw 422 connected to a housing 430. Housing 430 has a short cavity 432 oriented along the axis of bone anchor 420 at the proximal end and configured to receive the threaded distal end of shield 408. Shield 408 also has an outer surface 434 adapted for mounting an offset connector. Outer surface 434 may, in some embodiments, be cylindrical or may have surface features, for example flutes as previously discussed. Note that in this embodiment, the deflection rod is arranged coaxially with bone anchor 422. In particular, post 404 of deflation rod 400 is arranged coaxially with bone anchor 422.

Figure 4B:
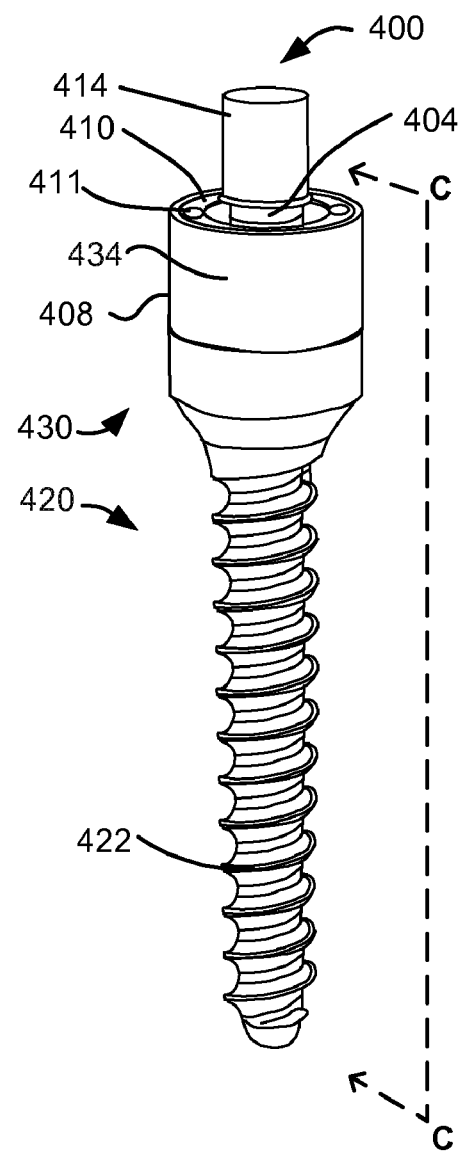
FIG. 4B is a perspective view of the deflection rod assembly of FIG. 4A, as assembled.

Referring now to FIG. 4B, which shows a perspective view of a fully assembled deflection rod 400. When assembled, deflectable post 404 is positioned within sleeve 406; sleeve 406 is positioned within shield 408. Retainer 402 of FIG. 4A and the threaded distal end of shield 406 (see FIG. 4A) are then placed in short cavity 432 (not shown) of bone anchor 420. Shield 408 is tightened to housing 430 using the threads and may also be laser welded to further secure shield 408 to housing 430. Threaded collar 410 is then secured in the threaded proximal end of shield 408. Threaded collar 410 has two sockets 411 for receiving the pins of a pin wrench to allow threaded collar 410 to be tightened to threads 438 (see FIG. 4A) of shield 408. Threaded collar 410 may also be laser welded to shield 408 after installation to further secure the components.

FIG. 4C shows a sectional view of deflection rod 400 assembled with a bone anchor 420 along the axis indicated by line C-C of FIG. 4B. As shown in FIG. 4C, ball-shaped retainer 402 fits into a hemispherical pocket 439 inside housing 430. Shield 408 includes a flange 409 which holds ball-shaped retainer 402 within hemispherical pocket 439. Collar 410 secures sleeve 406 within shield 408. Collar 410 also provides a limit surface 413 for limiting deflection of deflectable post 404. Sleeve 406 occupies the space between deflectable post 404 and shield 408 and is compressed by deflection of deflectable post 404 towards shield 408 in any direction.

FIG. 4D illustrates the deflection of deflectable post 404. Applying a force to mount 414 causes deflection of deflectable post 404 of deflection rod 400. Initially deflectable post 404 pivots about a pivot point 403 indicated by an X. Deflectable post 404 may pivot in any direction about pivot point 403. In this embodiment, pivot point 403 is located at the center of ball-shaped retainer 402. Pivot point 403 may be positioned closer to the distal end of bone screw 422, for example by projecting a virtual pivot point. As shown in FIG. 4D, deflection of deflectable post 404 initially compresses the material of sleeve 406. The force required to deflect deflectable post 404 depends upon the dimensions of deflectable post 404, sleeve 406 and shield 408 as well as the attributes of the material of sleeve 406. After further deflection, deflectable post 404 comes into contact with limit surface 413 of collar 410.

Limit surface 413 is shaped and oriented to reduce the possibility of wear and damage to deflectable post 404 due to contact with limit surface 413. For example, limit surface 413 is oriented such that when deflectable post 404 makes contact with limit surface 413, the contact is distributed over an area to reduce wear and stress on deflectable post 404. After deflectable post 404 comes into contact with limit surface 413, further deflection requires deformation of deflectable post 404. Because deflectable post 404 is relatively stiff, the force required to deflect deflectable post 404 will increase significantly after contact of deflectable post 404 with collar 410. In a preferred embodiment, deflectable post 404 may deflect from 0.5 mm to 2 mm in any direction before making contact with limit surface 413. More preferably, deflectable post 404 may deflect approximately 1 mm before making contact with limit surface 413.

As depicted in FIG. 4D, when load or force is first applied to the deflection rod by the spine, the deflection of the deflection rod responds about linearly to the increase in the load during the phase when deflection of deflectable post 404 causes compression of sleeve 406. After about 1 mm of deflection, when deflectable post 404 contacts limit surface 413 the deflection rod becomes stiffer. A greater amount of load or force needs to be placed on the deflection rod in order to obtain the same amount of deflection that was realized prior to this point because further deflection requires bending of deflectable post 404. The relationship between deflection and load is thus a non-linear function. Accordingly, the deflection rod of this example provides a range of motion where the load supported increases about linearly as the deflection increases and then with increased deflection the load supported increases more rapidly in a non-linear manner in order to provide dynamic stabilization.

FIG. 4E shows a modified version 400e of deflection rod 400. All parts are the same with the exception that deflectable post 404e is modified to receive a ball 444. Ball 444 is received in a pocket 442 at one end of vertical rod 450. Ball 444 is secured within pocket 442 by cap 446. Ball 444 forms part of ball joint 440 which connects deflectable post 404e to vertical rod 450. Ball joint 440 allows greater range of motion and reduces torsional stresses on the dynamic stabilization assembly and the bones to which it is attached. However, using a ball-joint in place of a fixed connection between the vertical rod and post also reduces the stiffness of the assembly. Thus the choice of ball-joint or fixed connection is a trade-off between stiffness and range of motion. The choice will be made based on the patient's anatomy and functional requirements.

Deflection rod 400 and bone anchor 420 may be used in the same manner as previously described. Deflection rod 400 may be utilized, for example, to provide load sharing and dynamic stabilization. Deflection rod 400 may be connected to another level of a spine using a vertical rod connected to a polyaxial screw at that level or another deflection rod and bone anchor. By utilizing offset connectors mounted to the exterior surface of shield 408, deflection rod 400 can connect to both adjacent vertebrae thereby providing the ability to construct a multi-level dynamic spinal stabilization assembly suitable for providing load sharing and stabilization.

FIG. 4F shows a sectional view of an alternative embodiment of a deflection rod 460. As shown in FIG. 4F post 464 includes a retainer 462 which is engaged by sleeve 468 to secure post 464 to bone screw 461. In deflection rod 460, retainer 462 is a cone-shaped portion of a sphere instead of spherical in shape. Retainer 462 pivots about pivot point 463 marked by an X. Dotted line 465 shows the diameter of a spherical retainer having the same effective pivot point. The conical retainer 462 requires a lower volume while providing an effective pivot point closer to the distal end of bone screw 461. The conical retainer can be accommodated in a smaller cavity within bone screw 461. This allows bone screw 461 to be stronger while allowing pivot point 463 to be placed closer to the instantaneous center of rotation of the spine. Placing the pivot point 463 closer to the instantaneous center of rotation of the spine also helps isolate the bone anchor from the relative motion between the vertebrae. When implanted, pivot point 463 is preferably positioned at or below the surface of the vertebra. More preferably, pivot point 463 is positioned within the pedicle or vertebral body of a vertebra. This retainer may be substituted for the retainers in the other deflection rods described herein.

FIG. 4G shows a sectional view of another alternative embodiment of a deflection rod 470. As shown in FIG. 4G post 474 includes a retainer 472 which is engaged by sleeve 478 to secure post 474 to bone screw 471. In deflection rod 470, retainer 472 is segment of the surface of a sphere instead of being spherical. Retainer 472 pivots about pivot point 473 marked by an X. Dotted line 475 shows the diameter of a spherical retainer having the same effective pivot point. The center of the sphere (if complete) is outside of retainer 472. However, post 474 behaves as if pivoting about this virtual pivot point (so-called because it is external to the pivot mechanism). Retainer 472 requires a lower volume than a spherical retainer. Retainer 472 can therefore be accommodated in a smaller cavity within bone screw 471. This allows bone screw 471 to be stronger while allowing pivot point 473 to be placed closer to the instantaneous center of rotation of the spine. Placing the pivot point 473 closer to the instantaneous center of rotation of the spine also helps isolate the bone anchor from the relative motion between the vertebrae. When implanted, pivot point 473 is preferably positioned at or below the surface of the vertebra. More preferably pivot point 473 is positioned within the pedicle or vertebral body of a vertebra. This retainer may be substituted for the retainers in the other deflection rods described herein.

Deflection/Load Response Curve

Figure 5A:
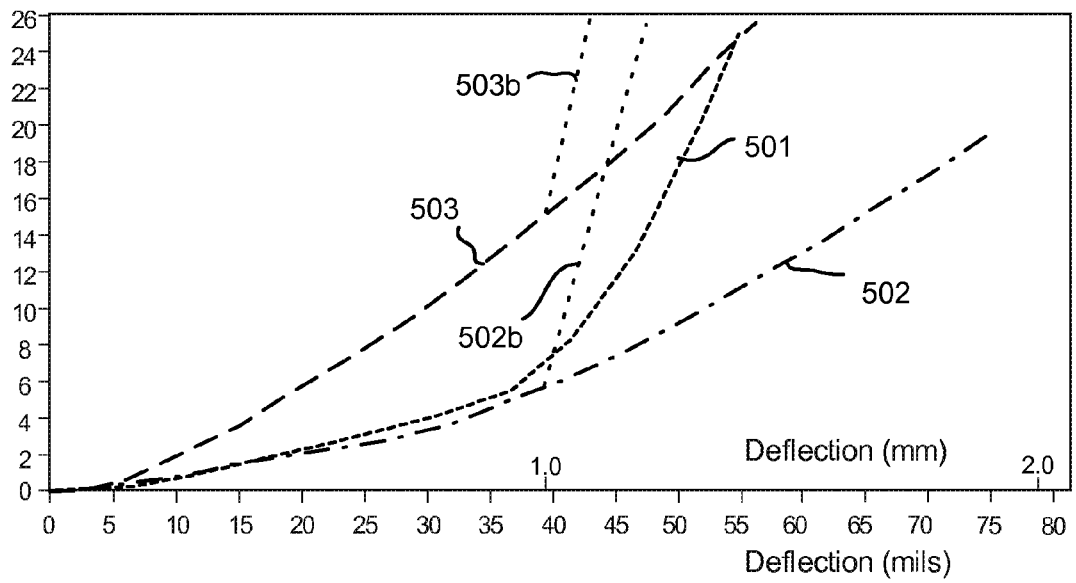
FIG. 5A is a graph showing the deflection/force response curves of various embodiments of deflection rods according to embodiments of the present invention.

As previously stated, the deflection response of a deflection rod can be customized based on the choice of design, dimensions and materials. It is contemplated, for example, that the deflection rod can be made in stiffness that can replicate a 70% range of motion and flexibility of the natural intact spine, a 50% range of motion and flexibility of the natural intact spine and a 30% range of motion and flexibility of the natural intact spine for providing in a kit for a doctor to use. FIG. 5A is a graph showing the deflection/force response of three different deflection rod assemblies.

Figure 5B:
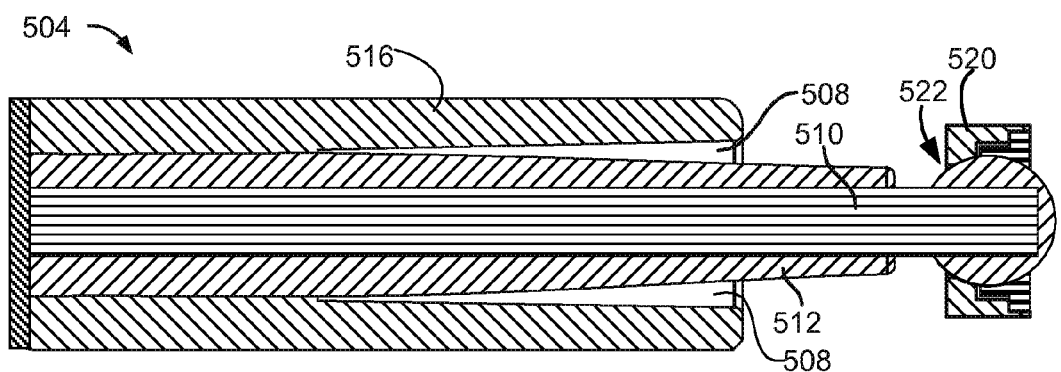
FIG. 5B is a sectional view of an alternative deflection rod.

Curve 501 shows the force/deflection response of a deflection rod that is a little stiffer than a 70% stiffness deflection rod. The deflection rod 504 tested to generate the force/deflection curve 501 shown in FIG. 5A is shown schematically in FIG. 5B. Deflection rod 504 has a PEEK sleeve 512 of about 4 mm in diameter at its largest diameter and a deflectable post 510 made of Nitinol. Sleeve 512 and deflectable post 510 are press fit inside a sleeve 516. There is a gap 508 between the sleeve 512 and shield 516 which allows initial deflection of deflectable post 510 without compression of sleeve 512. The working length of the deflection rod 504 is about 26 mm. The deflectable post 510 is connected by a ball-joint 522 to the vertical rod 520. The deflection of the deflectable post 510 post in response to load applied on the vertical rod 522 is shown by the curve 501. As is evident from FIG. 5A, the deflection/force curve 501 is non-linear. At about 1 mm of deflection, sleeve 512 makes contact with the shield 516 and further deflection requires compressions of sleeve 512 as well as bending of the deflectable post 510. The deflection rod 504 therefore responds more stiffly as the load increases. As the deflection increases, the stiffness of the deflection rod increases such that the force required per unit of additional deflection increases in response to the load placed on the spine and deflection rod. This can be observed in the force/deflection curve as an increase in the slope of the curve 501.

Curve 502 shows the force/deflection response of an alternative deflection rod. The deflection rod tested to generate the force/deflection curve 502 shown in FIG. 5A is of the same general design as deflection rod 300 of FIGS. 3A-3C. The deflection rod has a 2 mm thick sleeve of Bionate® PCU having a durometer of 80. The deflectable post is made of titanium and varies between 4 mm and 5 mm in diameter. The length of the deflectable post (including retaining ball and ball joint) is about 20 mm. The deflection rod is connected by a ball-joint to the vertical rod. The deflection of the deflectable post in response to load applied on the vertical rod is shown by the curve 502. As is evident from curve 502 the deflection rod responds gradually more stiffly as the load increases. Curve 502 was obtained without a collar and limit surface. In deflection rods made according to the designs illustrated in FIGS. 3A-3H and 4A-4D, the stiffness of the deflection rod should increase at about 1 mm of deflection the deflectable post makes contact with the limit surface. This is illustrated in the predicted force/deflection curve 502b as a sudden increase in slope of the curve. Thus, as the deflection increases, the stiffness of the deflection rod increases such that the force required per unit of additional deflection increases rapidly in response to the load placed on the spine and deflection rod.

Curve 503 shows the force/deflection response of an alternative deflection rod. The deflection rod tested to generate the force/deflection curve 502 shown in FIG. 5A is of the same general design as deflection rod 300 of FIGS. 3A-3C. The deflection rod tested to generate the force/deflection curve 503 shown in FIG. 5A also has a 2 mm thick sleeve of Bionate® PCU having a durometer of 80. The deflectable post is made of titanium and varies between 4 mm and 5 mm in diameter. The length of the deflectable post (including retaining ball and mount) was about 20 mm. The deflection rod is, however, connected by a rigid connection between the mount and the vertical rod (instead of a ball-joint). The deflection of the post in response to load applied on the vertical rod is shown by the curve 503. As is evident from curve 503 the deflection rod responds much more stiffly than when connected via a ball-joint. Curve 503 was also obtained without a collar and limit surface. In deflection rods made according to the designs illustrated in FIGS. 3A-3H and 4A-4D, the stiffness of the deflection rod should increase further at about 1 mm of deflection when the post makes contact with the limit surface. This is illustrated in the predicted force/deflection curve 503b as a sudden increase in the slope of the curve. Thus, as the deflection increases, the stiffness of the deflection rod increases such that the force required per unit of additional deflection increases rapidly in response to the load placed on the spine and deflection rod.

As depicted in FIG. 5A, as load or force is first applied to the deflection rod by the spine, the deflection of the deflection rod responds about linearly to the increase in the load. After the post makes contact with the limit surface, the deflection rod responds more stiffly. In this region, a greater amount of load or force needs to be placed on the deflection rod in order to obtain the same amount of deflection that was realized prior to this point. Accordingly, the deflection rod of this example provides a range of motion where the load supported increases about linearly as the deflection increases and then with increased deflection the load supported increases more rapidly in a non-linear manner. The transition from lower stiffness to higher stiffness region depends upon the distance between the deflectable post and the limit surface of the collar. This distance may be customized as previously described so that the transition occurs after the desired amount of deflection, for example after about 1 mm of deflection or after about 2 mm of deflection.

Deflection Rods Having Anisotropic Deflection Characteristics

The deflection system of the present invention provides in some embodiments the ability to control stiffness for extension, flexion, lateral bending and axial rotation, and to control stiffness for each of these motions independently of the other motions. The characteristics of the deflection rod can be changed, for example, by adjusting the diameter of post and/or the thickness of the sleeve and/or the distance between the post and the limit surface. For example, FIGS. 6A-6D show cross-sections through alternative embodiments of the deflection rod 200 of FIG. 2B along the line D-D. Similar variations could be made of the other deflection rods described herein e.g. deflection rod 300 of FIGS. 3A-3C and deflection rod 400 of FIGS. 4A-4C.

Figure 6A:
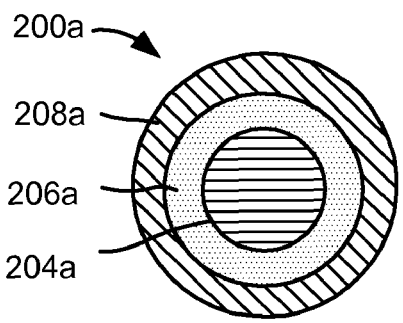
FIGS. 6A-6H are sectional views of alternative deflection rods according to embodiments of the present invention.

In FIG. 6A, the shield 208a is uniformly thicker and sleeve 206a of deflection rod 200a is uniformly thinner than that of deflection rod 200. As a consequence, deflection post 204a with the cross-section shown in FIG. 6A is stiffer/less flexible in all directions.

Figure 6B:
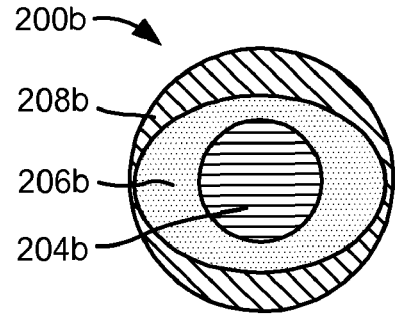

However, the deflection characteristics need not be isotropic. A bias can be introduced in the deflection rod by varying the inner surface of the shield and/or the thickness of the sleeve in different positions around the post. As shown in FIG. 6B, shield 208b is designed such that the sleeve 206b of deflection rod 200b is thicker on the left and right sides of deflectable post 204b than in the top and bottom sides (relative to the page). A deflection rod 200b having the cross-section shown in FIG. 6B is thus stiffer in the up and down directions and more flexible in the left and right directions.

Figure 6C:
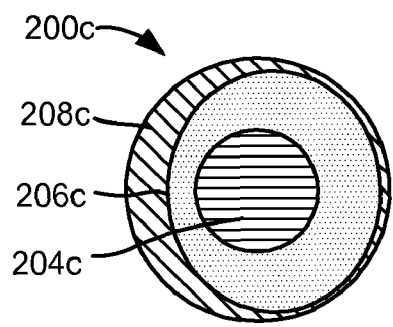

As shown in FIG. 6C, shield 208c is designed so that sleeve 206c of deflection rod 200c is thicker on the right, top, and bottom sides of deflectable post 204c than on the left side. A deflection rod 200c having the cross-section shown in FIG. 6C is thus stiffer in the left direction and more flexible in the right, up and down directions.

Figure 6D:
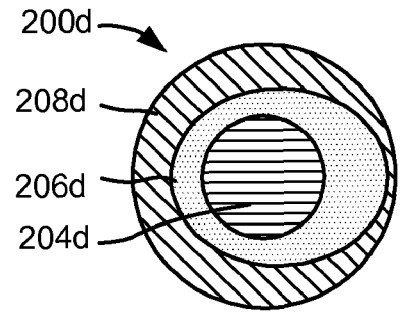

As shown in FIG. 6D, shield 208d is designed so that sleeve 206d of deflection rod 200d is thicker on the right side of deflectable post 204d than on the left, top, or bottom sides. Deflection rod 200d having the cross-section shown in FIG. 6D is, thus, more flexible in the right direction than in any of the other directions.

The characteristics of the deflection rod can also be changed by, for example, adjusting the compliance of the sleeve. For example, using PCU with different durometer ratings and or using different materials. Making the entire sleeve of a less compressible material for example will make the deflection rod stiffer, e.g. a larger load will be required to cause the same deflection. Conversely, making the entire sleeve of a more compressible material for example will make the deflection rod more flexible, e.g. a smaller load will be required to cause the same deflection. However, the deflection characteristics need not be isotropic. A bias can be introduced in the deflection rod 200 by having material with different compliance in different regions of the sleeve. This can be achieved, for example, using a multi-shot injection molding technique to make the sleeve and using PCUs having different durometer ratings in the multi-shot injection process. For example, FIGS. 6E-6H show cross-sections through alternative embodiments of the deflection rod 200 of FIG. 2B along the line D-D in which the sleeves have regions with different properties.

Figure 6E:
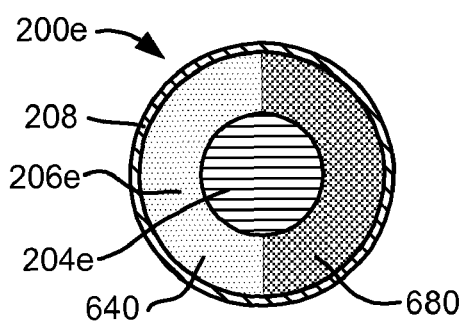

As shown in FIG. 6E, sleeve 206e of deflection rod 200e has a region of more compliant material 640 on the left side of deflectable post 204e and a region of less compliant material 680 on the right side (relative to the page). Accordingly, material 640 can have a different durometer value than material 680. Both can be a polymer. A deflection rod 200e having the cross-section shown in FIG. 6E is thus stiffer in the right direction and more flexible in the left direction.

Figure 6F:
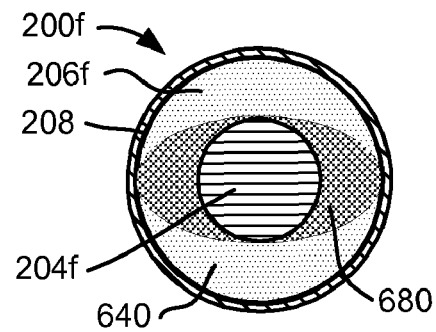

As shown in FIG. 6F, sleeve 206f of deflection rod 200f has a region of more compliant material 640 on the top and bottom sides of deflectable post 204f and a region of less compliant material 680 on the left and right sides (relative to the page). A deflection rod 200f having the cross-section shown in FIG. 6E is thus stiffer in the left and right directions and more flexible in the up and down directions.

Figure 6G:
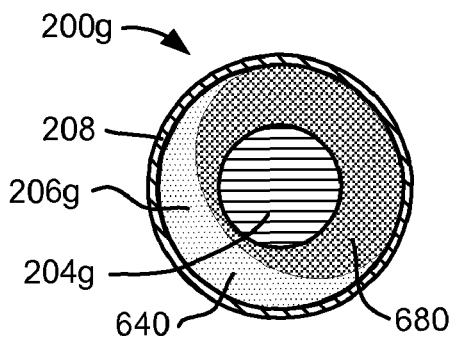

As shown in FIG. 6G, sleeve 206g of deflection rod 200g has a region of more compliant material 640 on the left and bottom sides of deflectable post 204g and a region of less compliant material 680 on the top and right sides (relative to the page). A deflection rod 200g having the cross-section shown in FIG. 6G is thus stiffer in the up and right directions and more flexible in the down and left directions.

Figure 6H:
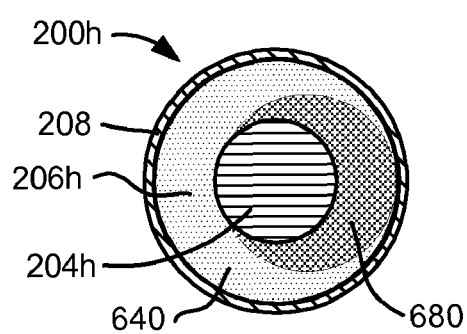

As shown in FIG. 6H, sleeve 206h of deflection rod 200h has a region of more compliant material 640 on the left, top, and bottom sides of deflectable post 204h and a region of less compliant material 680 on the right side (relative to the page). A deflection rod 200h having the cross-section shown in FIG. 6H is thus stiffer in the right direction and more flexible in the other directions.

Furthermore, by varying the shape of the collar, the distance between the post and the limit surface of the collar may also be varied. By making the distance shorter, the amount of deflection can be reduced that occurs before the dramatic increase in stiffness caused by contact with the limit surface. The collar may be shaped to reduce the gap between the post and the limit surface uniformly or may be shaped to reduce the gap between the post and the limit surface more in some directions than in others (anisotropically).

In embodiments where the deflection rod has anisotropic force-deflection response, it is important to ensure that the deflection rod is implanted in the correct orientation. The deflection rod is therefore provided with discernable visual or physical characteristics (e.g. an arrow, color, indentation or other observable indicator) which guide the surgeon to the correct orientation of implantation. When correctly installed, a deflection rod with anisotropic force-deflection response may be used to control stiffness for extension, flexion, lateral bending and axial rotation independently. For example, if a deflection rod is more flexible in the upward direction (relative to the spine after implantation—the head direction being up), the post can deflect more when the spine is placed in flexion and can deflect less when the spine is placed in extension. In effect, this arrangement is more restrictive with respect to movement of the spine with the spine in extension and less restrictive with respect to the movement of the spine with the spine in flexion. Conversely, if the deflection rod is more compliant in the down direction (relative to the spine after implantation—the head direction being up), the post can deflect more when the spine is placed in extension and can deflect less when the spine is placed in flexion. In effect, this arrangement is more restrictive with respect to movement of the spine in flexion and less restrictive with respect to the movement of the spine in extension.

Alternative Bone Anchors

FIGS. 7A through 7H illustrate some possible variations in bone anchors of the anchoring system. The bone anchors each have a housing compatible with the deflection rods of the deflection system and the offset heads/connectors of the connector system. In some embodiments, the bone anchors are installed prior to implantation of the bone anchors in the body. In alternative embodiments, the bone anchors may be implanted in the body before installation of a deflection rod.

Bone anchor 710 of FIG. 7A is a bone screw having a threaded region 714 which extends up over most of a housing 712. A deflection rod 704 is installed in housing 712. The threaded region 714 may extend over a greater or lesser amount of housing 712 depending upon such factors as the length of the bone screw, the type of bone in which the screw is to be implanted and the desired height to which the housing 712 will extend above the bone surface after implantation. Bone anchor 710 may be useful to lower the depth of the pivot point of the deflection rod 704 closer to the natural instantaneous center of rotation of the spine. Note also that the distal thread depth 716 may be deeper than the proximal thread depth 718. The distal thread depth 716 is adapted for engagement of the soft cancellous bone while the proximal thread depth 718 is adapted for engagement of the harder cortical bone at the surface of the vertebra.

Bone anchor 720 of FIG. 7B is a bone screw in which the screw-only section 724 is shorter in length than in bone screw 710 of FIG. 7A. A deflection rod 704 is installed in housing 722. Different lengths of screw-only section may be useful in different patients or different vertebrae as the size of the bone in which the anchor needs be implanted may vary considerably. For example, short bone screws are desirable where the dynamic stabilization system is to be implanted in smaller vertebrae. The physician may determine the length of bone screw appropriate for a particular patient by taking measurements during the procedure of by determining measurements from non-invasive scanning, for example, X-ray NMR, and CT scanning. Note however, that housing 722 is preferably the same size and shape as the housings of the other bone anchors so as to be compatible with the same deflection rods and connectors.

Bone anchor 730 of FIG. 7C is a bone screw in which the screw-only section 734 has a smaller diameter and is shorter in length than in bone screw 710 of FIG. 7A. A deflection rod 704 is installed in housing 732. Different diameters of screw-only section may be useful in different patients or different vertebrae as the size of the bone in which the anchor needs be implanted may vary considerably. For example, smaller diameter bone screws may be desirable where the dynamic stabilization system is to be implanted in smaller vertebrae. The physician may determine the diameter of bone screw appropriate for a particular patient by taking measurements during the procedure by determining measurements from non-invasive scanning, for example, X-ray NMR, and CT scanning. Note however, that housing 732 is preferably the same size and shape as the housings of the other bone anchors to be compatible with the same deflection rods and connectors.

Bone anchor 740 of FIG. 7D is a bone screw in which the housing 742 has a rim 744 extending away from housing 742 where it transitions to the threaded region 746. A deflection rod 704 is installed in housing 742. Rim 744 may serve to retain an offset head mounted to housing 742 in a way that it can rotate freely around housing 742 during installation. Rim 744 may also serve to widen the contact area between the bone anchor 740 where it meets the bone of the vertebra. This can act as a stop preventing over-insertion. This can also provide a wide base for stabilizing the housing against lateral motion and torque. Note that housing 742 is preferably the same size and shape as the housings of the other bone anchors so as to be compatible with the same deflection rods and connectors.

Bone anchor 750 of FIG. 7E illustrates a bone hook device 751 having a housing 752. A deflection rod 704 is installed in housing 752. Bone hook device 751 comprises a bar 754 to which housing 752 is rigidly connected. At either end of bar 754 is a bone hook 756 having a set screw 757 for securing the bone hook 756 to the bar 754. Each bone hook 756 has a plurality of sharp points 758 for engaging and securing the bone hook 756 to a vertebra. During use, the bone hooks 756 are urged towards each other until the sharp points engage and/or penetrate the surface of a bone. Set screws 757 are tightened to secure bone hooks 756 in position relative to bar 754 and thus secure housing 752 relative to the bone. Different arrangements of bone hooks and bars may be made suitable for attachment of the housing 752 to different types, sizes, shapes and locations of vertebra. Note that housing 752 is preferably the same size and shape as the housings of the other bone anchors so as to be compatible with the same deflection rods and connectors.

In some embodiments, the bone anchors may be provided with a torque-limiting and/or breakaway head which is engaged by a driver to drive the bone anchor into the vertebra. The torque-limiting and/or breakaway head is designed to prevent further driving of the bone anchor into the vertebra when the torque applied by the driver exceeds a predetermined torque limit. In preferred embodiments, the torque limit is selected so that the torque required to drive the bone anchor into a vertebra is lower than the torque limit. In preferred embodiments, when the bone anchor is fully implanted in the vertebra, further rotation of bone anchor requires significantly higher torque which is higher than the torque limit. Thus, when bone anchor is fully implanted in the vertebra, the driver torque exceeds the torque limit and torque-limiting and/or breakaway head prevents the bone anchor from being driven further into the bone. In some cases, the torque limit may be reached prior to complete installation of the bone anchor. In such cases, the bone anchor may be removed and a new bone anchor installed—the cavity in the bone in which the bone anchor is to be installed may be enlarged to facilitate implantation of the second bone anchor thereby reducing the torque necessary to implant the bone anchor.

Figures 7F, 7G, 7H:
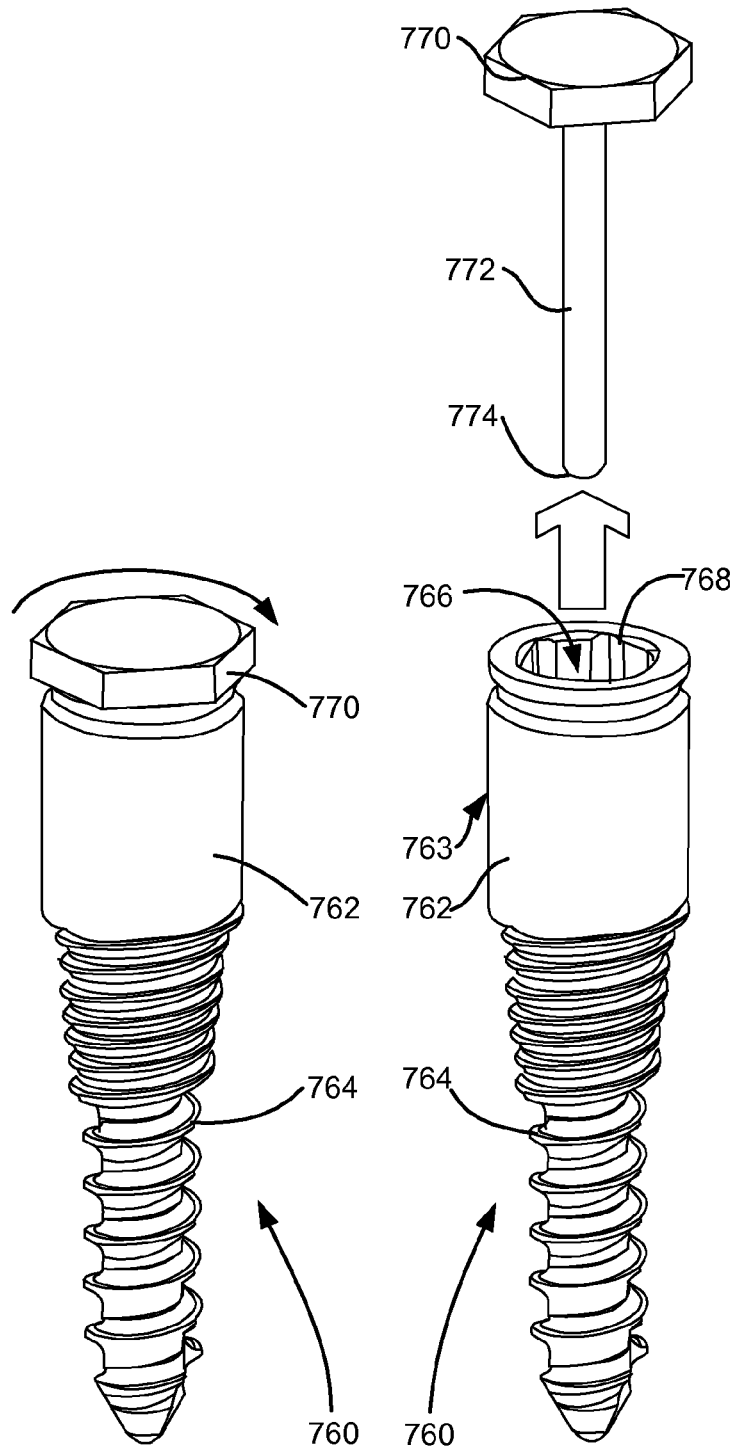
FIGS. 7F-7H are perspective and sectional views of an alternative bone anchors having a torque-limiting breakaway head according to an embodiment of the present invention.

Bone anchor 760 of FIGS. 7F-7H is a bone screw having a head 770 extending beyond a housing 772. Housing 772 is preferably the same size and shape as the housings of the other bone anchors so as to be compatible with the same deflection rods and connectors. Head 770 is a torque-limiting head which is designed to break away from bone anchor 760 when the torque applied to head 770 exceeds a predetermined torque limit. Head 770 may be a hex head (as shown) or may be of another design suitable for being driven by an installation tool for example a wrench or other driver, including, for example, slotted, Phillips, square, Allen, and Torx heads. During installation, a driver (for example a hex socket) engages head 770 and rotates bone anchor 760 to drive threaded region 764 into a vertebra. In preferred embodiments, the torque limit is selected so that the torque required to drive threaded region 764 into a vertebra is lower than the torque limit. In preferred embodiments, when the threaded region 764 is fully implanted in the vertebra, further rotation of bone anchor 760 requires significantly higher torque which is higher than the torque limit. Thus, when the threaded region 764 is fully implanted in the vertebra, the driver torque exceeds the torque limit and the head 770 breaks away from bone anchor 760 as shown in FIG. 7G.

As shown in FIG. 7G, when the torque limit is exceeded, head 770 breaks away from bone anchor 760. Head 770 may then be removed from cavity 766 of bone anchor 760. Cavity 766 may contain internal features 768 designed to engage a driver to permit removal of bone anchor 760, if necessary or desired. Alternatively or additionally, the exterior surface 763 of housing 762 may be provided with features for example knurling or splines (not shown but see, e.g., FIG. 7A) which allow a driver to engage the external surface 763 of housing 762 to permit removal of bone anchor 760 if necessary or desired. As shown in FIG. 7G, head 770 comprises a shaft 772 which extends into cavity 766 of housing 762. When head 770 has been removed, cavity 766 is open, to receive a deflection system component or connection system component as previously described (not shown).

FIG. 7H shows an enlarged sectional view of bone anchor 760 through head 770. As shown in FIG. 7H, head 770 is connected by shaft 772 to bone anchor 760. Shaft 772 has a neck 774 of smaller diameter than the remainder of shaft 772. The neck 774 is therefore subjected to higher stress than the remainder of shaft 772. The diameter and material of neck 774 is selected to control the torque limit. For a particular material, reducing the diameter of the neck reduces the maximum torque which can be transmitted by the head before the neck shears off. When the torque limit is exceeded, the shaft 772 shears off at the neck 774. Neck 774 is positioned so that, when neck 774 is sheared, any portion of shaft 772 which remains attached to bone anchor 760 is positioned so as not to obstruct installation of a deflection system component or connection system component within cavity 766. As shown in FIG. 7H, for example, neck 774 may be positioned within a depression 767 in the distal end of cavity 766. When neck 774 shears off, cavity 766 is clear for installation of another component. In some cases, head 770 and shaft 772 may be formed in one piece with bone anchor 760. In other embodiments, head 770 and shaft 772 may be formed separately from bone anchor 760 and subsequently securely connected to bone anchor 760 by a bonded, welded or mechanical joint.

Alternative Deflection Rods/Loading Rods

One feature of embodiments of the present invention is load sharing provided by the deflection rod. The deflection rod provides stiffness and support where needed to support the loads exerted on the spine during normal spine motion thereby recovering improved spine function without sacrificing all motion. The deflection rod also isolates the anchor system components from forces exerted by the dynamic stabilization assembly thereby reducing stress on the bone anchors and the bone to which they are attached. In particular embodiments, the deflection rods of the present invention are oriented coaxial with the longitudinal axis of the bone anchor to which they are attached or in which they are incorporated. Moreover, by selecting the appropriate stiffness of the deflection rod or loading rod to match the physiology of the patient and the loads that the patient places on the spine, a better outcome is realized for the patient.

Figure 8C:
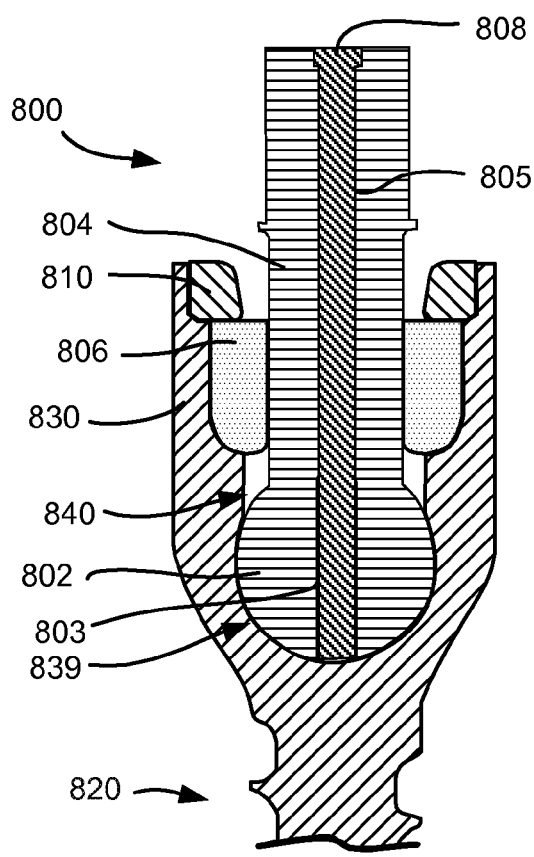

FIGS. 8A-8H shows alternative deflection rods having different mechanisms to secure the deflectable post to the deflection rod and/or the bone anchor. The mechanisms of FIGS. 8A-8H may be adapted for use in other of the deflection rods described herein. For example, FIGS. 8A-8C illustrate one alternative embodiment of a deflection rod/loading rod. Deflection rod 800 of FIGS. 8A-8C is similar in design and function to deflection rod 300 of FIGS. 3A-3E. However, deflection rod 800 utilizes a different mechanism to secure the ball-shaped retainer to the housing of the bone anchor than is used in deflection rod 300.

FIG. 8A shows an exploded view of alternative deflection rod 800. Deflection rod 800 includes ball-shaped retainer 802, post 804, sleeve 806, locking pin 808, collar 810, and mount 814. In this embodiment, ball-shaped retainer 802 is formed in one piece with post 804. Ball-shaped retainer 802 is split along the longitudinal axis of post 804 by one or more slots 803. Slots 803 allow ball-shaped-retainer 802 to deform to have a reduced diameter. A shaft 805 passes from the proximal end of mount 814 through post 804 and communicates with the one or more slots 803. A locking pin 808 may be inserted through shaft 805 to occupy space in the one or more slots 803. With locking pin 808 secured in place, ball-shaped retainer 802 is locked at its normal diameter and may not be compressed to a smaller diameter.

Sleeve 806 fits inside cavity 832 of housing 830 surrounding post 804. Sleeve 806 is made of a compliant material which permits movement of post 804 relative to housing 830. Deflection rod 800 is configured to be mounted in a bone anchor 820, which comprises a bone screw 822 connected to a housing 830. Housing 830 has a cavity 832 oriented along the axis of bone anchor 820 at the proximal end and configured to receive deflection rod 800. Housing 830 also has an outer surface 834 adapted for mounting a component, e.g. an offset connector. As shown in FIG. 8A, outer surface 834 of housing 830 is provided with flutes 836. Flutes 836 may be engaged by a driver for implanting bone anchor 820.

Referring now to FIG. 8B, which shows a perspective view of a deflection rod 800 assembled with a bone anchor 820. When assembled, deflectable post 804 is positioned within sleeve 806 of FIG. 8A. Post 804 and sleeve 806 are then placed in the cavity 832 of bone anchor 820 (See FIG. 8A). Locking pin 808 is then inserted into shaft 805 (not shown) to secure ball-shaped retainer 802 to bone anchor 820. Locking pin 808 may also be laser welded to mount 814 after installation to further secure the components. Threaded collar 810 is then secured in the threaded proximal end of cavity 832. Threaded collar 810 has two sockets 811 for receiving the pins of a pin wrench to allow threaded collar 810 to be tightened to threads 838 of housing 830. Threaded collar 810 is laser welded to housing 830 after installation to further secure the components. Threaded collar 810 secures sleeve 806 within cavity 832 of bone anchor 820.

FIG. 8C shows a sectional view of a deflection rod 800 assembled with a bone anchor 820 along the axis indicated by line C-C of FIG. 8B. As shown in FIG. 8C, sleeve 806 occupies the space between post 804 and housing 830. Sleeve 806 is compressed by deflection of post 804 towards housing 830 in any direction. Ball-shaped retainer 802 fits into a pocket 839 in the bottom of cavity 832 (not shown) of housing 830. Pocket 839 has the shape of a major spherical cap (a spherical cap comprising greater than half of the sphere). Consequently, the entrance aperture 840 to pocket 839 is narrower than the major diameter of pocket 839. Ball-shaped retainer 802 has the same diameter as the major diameter of pocket 839; however, in the absence of locking pin 808, ball-shaped retainer 802 may be compressed sufficiently to pass through aperture 840. However, after ball-shaped retainer has been pushed into pocket 839 and locking pin 808 has been installed in shaft 805 and slot 803, ball shaped retainer 802 can no longer be compressed and is therefore locked into pocket 839 while still allowing rotation of ball-shaped retainer 802. Collar 810 secures sleeve 806 within housing 830. The deflection rod 800 of FIG. 8A-8C does not include a shield between sleeve 806 and housing 830. By removing the thickness of the shield, the size/strength properties of the device may be enhanced.

Figure 8D:
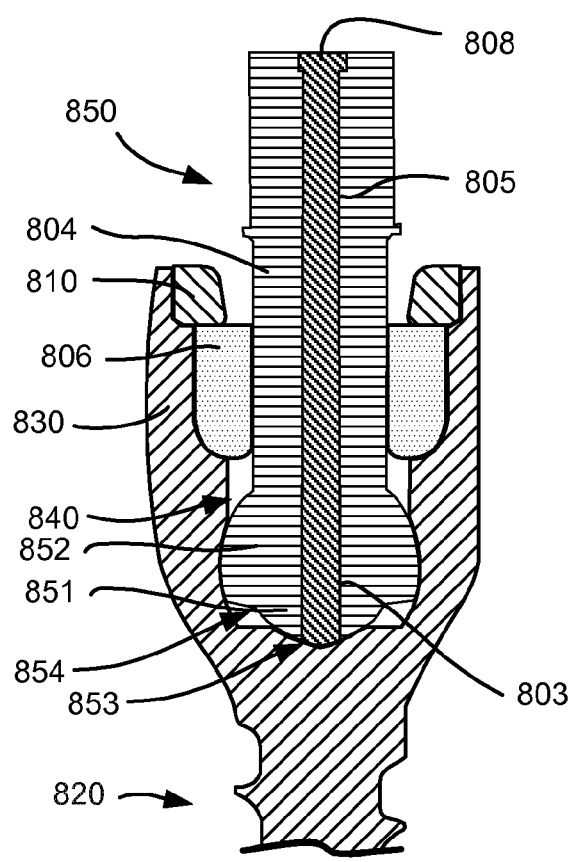

As shown in FIG. 8D, an alternative deflection rod 850 may utilize retainer 852 which is a portion of a sphere rather than spherical. In other aspects, the deflection rod 850 is similar to deflection rod 800 of FIGS. 8A-8C. However, a full sphere may be unnecessary for retainer 852 where, as here, the post 804 is limited by collar 810 to a few degrees of deflection. Over the range of deflection permitted, the spherical segment retainer 852 maintains sufficient contact with the wall of pocket 854 to secure retainer 852 within pocket 854. The lower portion 851 of retainer 852 is, in this embodiment, a sphere having a smaller diameter than the upper portion, but having the same center of rotation. Pocket 852 can likewise be reduced in size by truncating the major spherical cap to form a pocket 854 in the shape of a spherical segment (which includes the center and thus maximum diameter of the sphere). A smaller lower pocket 853 of the same diameter as the lower sphere serves to locate the retainer during its travel. As a consequence less material needs to be removed to form pocket 854 and the strength of bone anchor 850 is therefore enhanced. Other shapes of retainer and pocket may also be used so long as they secure post 804 to bone anchor 820 and allow the desired range of travel for post 804.

FIGS. 8E and 8F, show exploded and sectional views of an alternative deflection rod 860 which uses a retainer in the form of a split-ring 862. Split spherical ring 862 fits in pocket 864 in bone anchor 861. Pocket 864 has the shape of a major spherical cap (a spherical cap comprising greater than half of the sphere). Consequently, the entrance aperture 865 to pocket 864 is narrower than the major diameter of pocket 864. Split-ring 862 has the same diameter as the major diameter of pocket 864. However, split-ring retainer 862 may be compressed sufficiently to pass through aperture 865. After split-ring retainer 862 has been pushed into pocket 864, post 866 is pushed into the central aperture of split-ring retainer 862. With post 866 locked into the central aperture of split-ring retainer 862, split-ring retainer 862 can no longer be compressed and is therefore locked into pocket 864 while still allowing rotation of retainer 862. Post 866 can be secured to split-ring retainer 862 with an internal split-ring 868. Other fittings such as threads, clips and or tabs may also be utilized to secure post 866 to split-ring retainer 862. Alternatively bonding technology may be used to secure post 866 to split-ring retainer 862, e.g. laser welding.

Deflection rod 860 may be provided with a collar similar to collar 810 of FIGS. 8A-8C. However, FIGS. 8E and 8F show an alternative embodiment in which post 866 includes a flange 870. Flange 870 is shaped to remain in close proximity to the top surface of housing 871 of bone anchor 861 as post 866 pivots. Flange 870 retains sleeve 806 within housing 871 without need of a collar. The interior surface of housing 871 is shaped to provide the limit surface 872 to limit deflection of post 866. By removing the thickness of the shield and the need for a separate collar, the size/strength properties of the device may be enhanced.

Figure 8G:
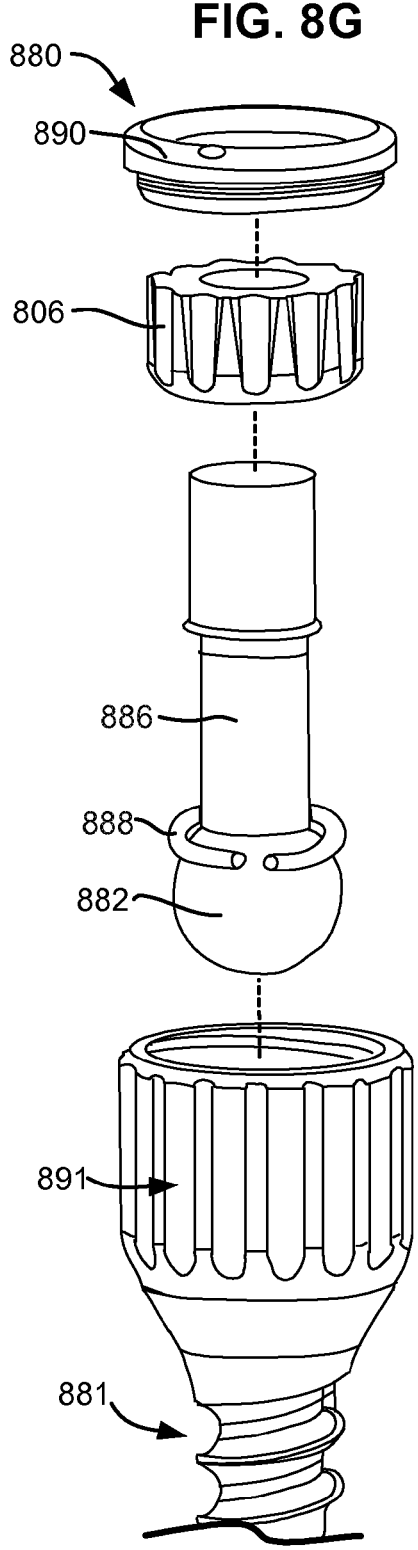
Figure 8H:
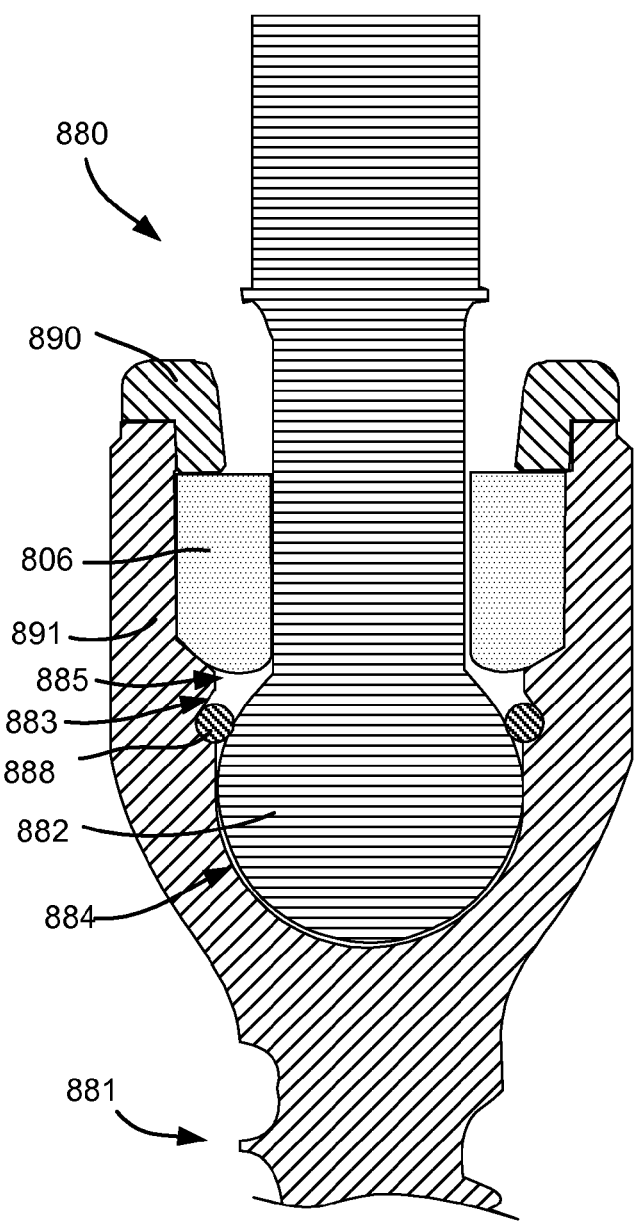

A ball may be locked in a ball-joint pocket in a variety of ways. Some suitable methods and devices for locking a ball in a ball-joint assembly are disclosed in U.S. Pat. No. 4,666,330 titled "Ball Joint Assembly" to O'Connell et al. which is incorporated herein by reference in its entirety. FIGS. 8G and 8H, show exploded and sectional views of an alternative deflection rod 880 which uses a ball-shaped retainer 882. Ball-shaped retainer 882 fits in pocket 884 in bone anchor 881. Pocket 884 is hemispherical. The entrance aperture 885 to pocket 884 is the same diameter as ball-shaped retainer 882. However, entrance aperture 885 includes a groove 883 which receives a split-ring 888. Split-ring 888 has a larger diameter than aperture 885 but split-ring 888 is compressed slightly during installation. After passing through aperture 885, split-ring 888 expands outwards to occupy groove 883. Split-ring 888, when positioned in groove 883, reduces the effective diameter of aperture 885 and prevents removal of ball-shaped retainer 882. Sleeve 806 is then inserted in housing 891 of bone anchor 881. Collar 890 secures sleeve 806 within housing 891 of bone anchor 881. By removing the thickness of the shield, the size/strength properties of the device may be enhanced.

In some embodiments, as described above, the deflection rod includes a deflectable post, an outer sleeve, and a mount which includes a shield positioned around the sleeve. The movement of the deflectable post relative to the mount allows controlled movement of the bone anchor (and vertebra in which it is implanted) relative to the vertical rods thereby supporting the vertebrae to which the bone anchors are attached while allowing movement of the vertebrae. However, as illustrated in FIGS. 9A-9H controlled movement of the deflectable post (or other connection point for vertical rods) relative to a bone anchor may be achieved using a number of alternative designs for deflection rods/loading rods. In general, each mechanism includes a linkage by which deflection of the deflectable post is tied to compression of a compliant component. The compression of the compliant component imparts the deflection rod so formed with the force/deflection characteristics necessary or desirable for the application.

FIGS. 9A-9C show views of an alternative deflection rod 900 according to an embodiment of the invention. FIG. 9A shows an exploded view of the deflection rod 900. FIGS. 9B and 9C show sectional views of the deflection rod 900 with FIG. 9C illustrating deflection of deflection rod 900 under load. Referring first to FIG. 9A, deflection rod 900 is assembled in cavity 924 of housing 922 of bone anchor 920. A compliant sleeve 906 is first placed into cavity 924. Sleeve 906 is annular and has a central opening 907. Retaining ring 908 is then inserted into cavity 924. The lower surface of retaining ring 908 is adapted to engage compliant sleeve 906 and secure it into position. The upper surface of retaining ring 908 has a pocket 909 adapted to receive the lower portion of a ball 902. Deflectable post 904 is attached to the top of ball 902. A control rod 905 extends from the bottom of ball 902. Control rod 905 is shaped to fit through retaining ring 908 into the central opening 907 of sleeve 906. With control rod 905 positioned inside sleeve 906 and ball 902 in contact with retaining ring 908, a threaded collar 910 is tightened into the upper end of cavity 924. The lower surface 911 of collar 910 is shaped to form the top half of a pocket in which ball 902 may rotate. Collar 910 has sockets for a pin wrench or other features allowing the collar to be secured to bone anchor 920. Collar 910 may also be bonded or welded into place.

FIG. 9B shows a sectional view of deflection rod 900 when fully assembled. As shown in FIG. 9B control rod 905 is surrounded by sleeve 906. Ball 902 is secured in a pocket formed by retaining ring 908 and collar 910. Post 904 may pivot in any direction and rotate about its long axis. However, as shown in FIG. 9C, when post 904 pivots, control rod 905 also pivots (in the opposite direction) compressing the material of sleeve 906. Compression of sleeve 906 by control rod 905 imparts the deflectable post 904 with a controllable force/load response which can be customized as previously described. A limit surface 912 of collar 910 is designed to make contact with deflectable post 910 after a predetermined deflection. Further deflection of the proximal end of deflectable post 904 after contact with limit surface 912 requires bending of deflectable post 904. Thus, the stiffness of deflectable post 904 will typically increase dramatically upon contact between deflectable post 904 and limit surface 912.

Figure 9D:
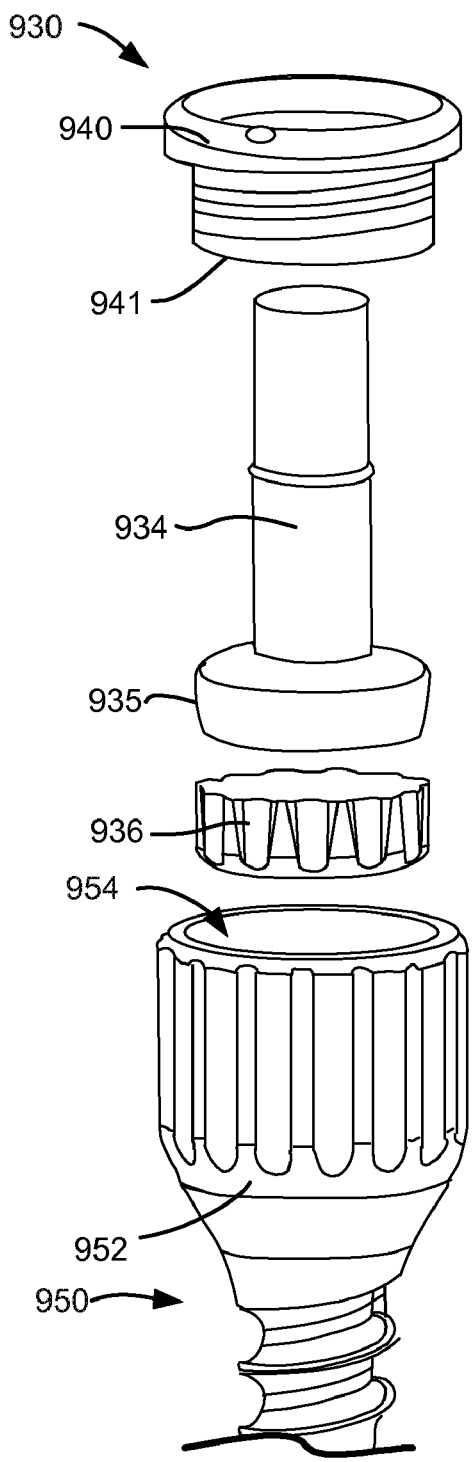
FIGS. 9D-9F show an alternative deflection rod assembly according to an embodiment of the invention.
Figure 9E:
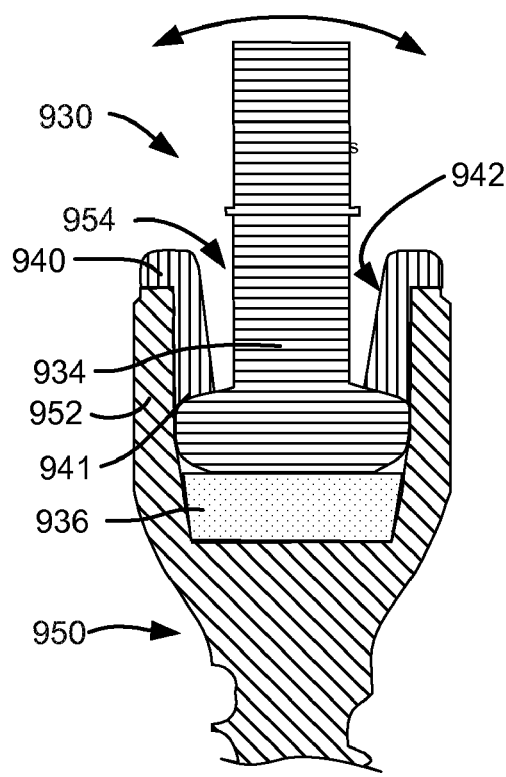
Figure 9F:
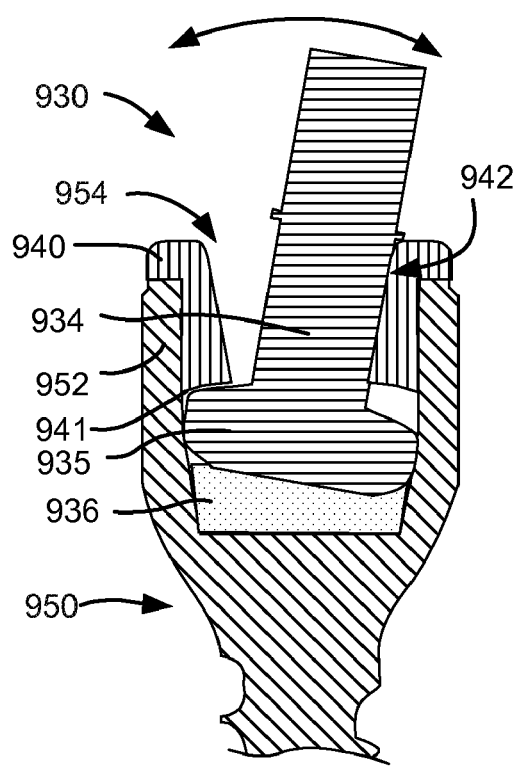

FIGS. 9D-9F show views of an alternative deflection rod 930 according to an embodiment of the invention. FIG. 9D shows an exploded view of the deflection rod 930. FIGS. 9E and 9F show sectional views of the deflection rod 930 with FIG. 9F illustrating deflection of deflection rod 930 under load. Referring first to FIG. 9D, deflection rod 930 is assembled in cavity 954 of housing 952 of bone anchor 950. A compliant disc 936 is first placed into cavity 954. With compliant disc 936 in position, deflectable post 934 is then inserted into cavity 954. Deflectable post 934 has a control disc 935 at the distal end. Control disc 935 fits snuggly against compliant disc 936. Collar 940 is then secured into the end of cavity 954. The lower surface 941 of collar 940 is shaped to form the top portion of a pocket in which control disc 935 may pivot and rotate. The edges of control disc 935 and the walls of cavity 954 are radiussed so that control disc 935 may pivot over the desired range of travel. Collar 940 may also be bonded or welded into place.

FIG. 9E shows a sectional view of deflection rod 930 when fully assembled. As shown in FIG. 9E control disc 935 sits on top of compliant disc 936. Control disc 935 is secured in a pocket formed by the walls of cavity 954 and collar 940. Deflectable post 934 may pivot in any direction and rotate about its long axis. However, as shown in FIG. 9F, when deflectable post 934 pivots, control disc 935 also pivots compressing the material of compliant disc 936. Compression of compliant disc 936 by control disc 935 imparts the deflectable post 934 with a controllable force/load response which can be customized as previously described. A limit surface 942 of collar 940 is designed to make contact with deflectable post 930 after a predetermined deflection. Further deflection of the proximal end of deflectable post 934 after contact with limit surface 942 requires bending of deflectable post 934. Thus the stiffness of deflectable rod 930 will typically increase dramatically upon contact between deflectable post 934 and limit surface 942.

FIGS. 9G and 9H show views of an alternative deflection rod 960 according to an embodiment of the invention. FIG. 9G shows an exploded view of the deflection rod 960. FIG. 9H shows a sectional view of the deflection rod 960. Referring first to FIG. 9G, deflectable post 964 has a cavity 965 which receives a portion of bone anchor 980. Deflectable post 964 also has a threaded mount 963 to which a vertical rod may be secured. A compliant sleeve 966 is first placed into cavity 965. Compliant sleeve 966 has a central opening 967. A retaining ring 968 is then placed in cavity 965. Retaining ring 968 has a central opening 969. Bone anchor 980 comprises a bone screw 981, a ball 983 and a control rod 985. Control rod 985 is passed through central opening 969 of retaining ring 968 and into central opening 967 of compliant sleeve 966. Lastly, threaded collar 970 is screwed into the opening 965. Threaded collar 970 combines with retaining ring 968 to form a pocket shaped to receive ball 983. Ball 983 is secured between retaining ring 968 and collar 970 but can rotate and pivot relative to deflectable post 964. Collar 970 may also be bonded or welded into place.

FIG. 9H shows a sectional view of deflection rod 960 when fully assembled. As shown in FIG. 9G, compliant sleeve disc 966 sits around control rod 985. Deflectable post 964 may pivot in any direction and rotate about its long axis. However, when deflectable post 964 pivots, control rod 985 compresses the material of sleeve 966. Compression of sleeve 966 by control rod 985 imparts the deflectable post 964 with a controllable force/load response which can be customized as previously described. A limit surface 972 of collar 970 is designed to make contact with bone anchor 980 after a predetermined deflection. Further deflection of deflectable post 964 after contact between bone anchor 980 and limit surface 972 requires bending of deflectable post 964 or bone anchor 980. Thus the stiffness of deflectable rod 960 will typically increase dramatically upon contact between bone anchor 980 and limit surface 972.

Alternate Mechanisms for Mounting a Vertical Rod to a Deflection Rod

In order to utilize deflection rods of the present invention to construct a dynamic stabilization assembly, the deflection rod is coupled with a vertical rod. The deflection rod may be coupled to the vertical rods in a fixed, pivoting or flexible manner depending on the requirements of the dynamic stabilization assembly. One mechanism for coupling a deflection rod to a vertical rod is the ball-joint 222 illustrated for example in FIGS. 2A-2C and FIGS. 2E-2G. As shown in FIG. 2B, the vertical rod 216 is coupled to the deflectable post 204 by the ball-joint 222 in a manner that allows the vertical rod 216 to rotate about the long axis of the deflectable post 204 and also pivot relative to the deflectable post 204. These two degrees of freedom are present both during implantation and also in the completed dynamic stabilization assembly. By comparing FIGS. 2C, 2E and 2F, it can be seen that the angle between the vertical rod 216 and deflectable post 204 changes as deflectable post 204 is deflected. This change in angle is accommodated by rotation of ball 214 in ball joint 222.

A second mechanism for coupling a deflection rod to a vertical rod is the threaded mount 314 of deflection rod 300 illustrated in FIGS. 3A-3H. As shown in FIG. 3G, the vertical rod 360 is secured to threaded mount 314 by a nut 362. The vertical rod 360 can be rotated around mount 314 before nut 362 is tightened but, thereafter, vertical rod 360 is rigidly secured to deflectable post 304. After completion of the dynamic stabilization assembly, vertical rod can still rotate around the long axis of bone anchor 320 because deflectable post 304 may rotate relative to the long axis of bone anchor 320. However, the angle between vertical rod 360 and deflectable post 304 is fixed. Thus, any angle change between vertical rod 360 and deflectable post 304 resulting from movement of the vertebra must be accommodated by deformation (bending) of vertical rod 360 and deflectable post 304. Vertical rod 360 and deflectable post 304 are relatively stiff and thus, the dynamic stabilization assembly is stiff as compared to a dynamic stabilization assembly which may accommodate the angle change without bending of the vertical rod and deflectable post using e.g. a ball-joint.

Thus, the mechanism by which the vertical rod is coupled to a deflection rod affects the ease by which the dynamic stabilization system may be assembled and also the stiffness of the dynamic stabilization assembly. FIGS. 10A-12X show a range of alternative mechanisms for coupling the deflectable post of a deflection rod to the vertical rod to create the dynamic stabilization assembly.

FIGS. 10A-10E show a hinged coupling 1000 for connecting a deflection rod to a vertical rod according to an embodiment of the invention. Hinged coupling 1000 is designed to be mounted to the threaded proximal end of a deflectable post of a deflection rod. Hinged coupling 1000 may be used with and deflection rod having a suitable proximal mount, for example, deflection rod 300 of FIGS. 3A-3H.

FIG. 10A shows an exploded view of hinged coupling 1000. Hinged coupling 1000 comprises clevis 1010, clevis pin 1012, locking plate 1020 and a vertical rod 1030. Hinged coupling 1000 is held in place by a nut 1002. Vertical rod 1030 is configured to be received by clevis 1010. One end of vertical rod 1030 includes a disc 1032 having a central aperture 1034. The circumference of disc 1032 is provided with locking features, for example, teeth 1036. Disc 1032 is received between arms 1013, 1014 of clevis 1010. Pin 1012 is then inserted through aperture 1016 which passes through both arms 1013, 1014. Pin 1012 also passes through central aperture 1034 of disc 1032 of vertical rod 1030. Pin 1012 is secured to clevis 1010, either with a mechanical fitting and/or by bonding, for example threads and/or laser welding. With pin 1012 in place, vertical rod 1030 is secured to clevis 1010 but may pivot about the axis of clevis pin 1012.

Clevis 1010 also has a mounting plate 1017 having an aperture 1018 therethrough for receiving the deflectable post of a deflection rod. Aperture 1018 may be circular or may be polygonal (as shown). Where aperture 1018 is polygonal (non-circular) it may engage a similarly polygonal post in such a way as to prevent rotation of mounting plate 1017 relative to the post. This is advantageous in that such rotation may cause nut 1002 to be loosened. Moreover, the deflectable of the deflection rods of the present invention can typically rotate relative to the bone anchor and thus rotation of the mounting plate 1017 is a redundant and therefore unnecessary degree of freedom. In embodiments where the post to which the hinged coupling 1000 is connected may not rotate, it may be desirable to provide a mounting by which mounting plate 1017 may rotate around the post, however in such cases, care must be taken to ensure that nut 1002 or such other fastener that is used secures the mounting plate in position while allowing such rotation.

FIG. 10B shows hinged coupling 1000 ready for installation on a deflection rod 1001. Deflection rod 1001 has at the end of deflectable post 1004 a mount 1005 for receiving mounting plate 1016 of hinged coupling 1000. Mount 1005 has a lip 1006, a polygonal portion 1007 and a threaded portion 1008. Lip 1006 provides a mechanical stop to catch mounting plate 1017. Polygonal portion 1007 fits snuggly in polygonal aperture 1018 to preclude rotation of mounting plate 1017 relative to deflectable post 1004. In use, aperture 1018 is placed over mount 1005 until mounting plate 1017 contacts lip 1006 and polygonal portion 1007 is received with aperture 1018.

Figure 10C:
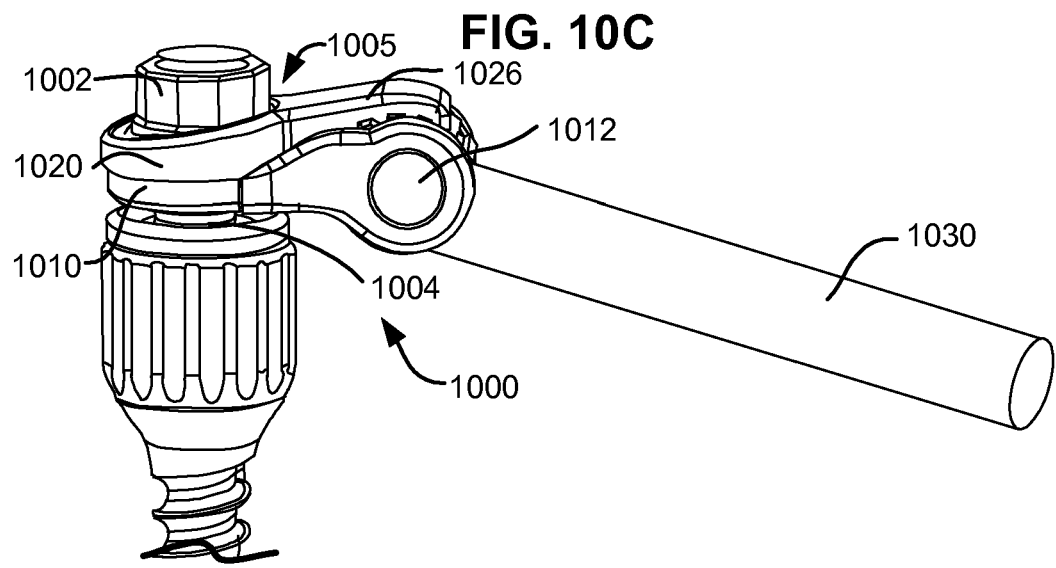

After mounting plate 1017 is positioned, vertical rod 1030 is oriented in the desired direction and angle relative to deflectable post 1004. Typically, vertical rod 1030 is oriented by securing the free end 1031 to another device on another vertebra of the spine, e.g. a bone screw, polyaxial screw, or deflection rod. When vertical rod 1030 is correctly positioned, locking plate 1020 may be installed. Locking plate 1020 includes mounting plate 1022 having an aperture 1024 adapted to be received over mount 1005 of deflectable post 1004. A locking arm 1026 projects from mounting plate 1022. Locking arm 1026 is adapted to fit between arms 1013, 1014 of clevis 1010 and engage vertical rod 1030 to secure vertical rod 1030 at the desired angle with deflection post 1004. Locking arm 1026 is provided with locking features, for example, teeth 1028 for engaging the circumference of disc 1032 of vertical rod 1030. In this embodiment, teeth 1028 of locking arm 1026 engage teeth 1036 of vertical rod 1030 to lock vertical rod 1030 at a fixed angle relative to deflectable post 1004. Clevis 1010 and locking plate 1020 are secured in place by nut 1002 which engages threaded portion 1008 of mount 1005 to secure vertical rod 1030 to deflectable post 1004. FIG. 10C shows vertical rod 1030 secured to deflectable post 1004 by hinged coupling 1000 with vertical rod 1030 at a fixed angle relative to deflectable post 1004.

Figure 10D:
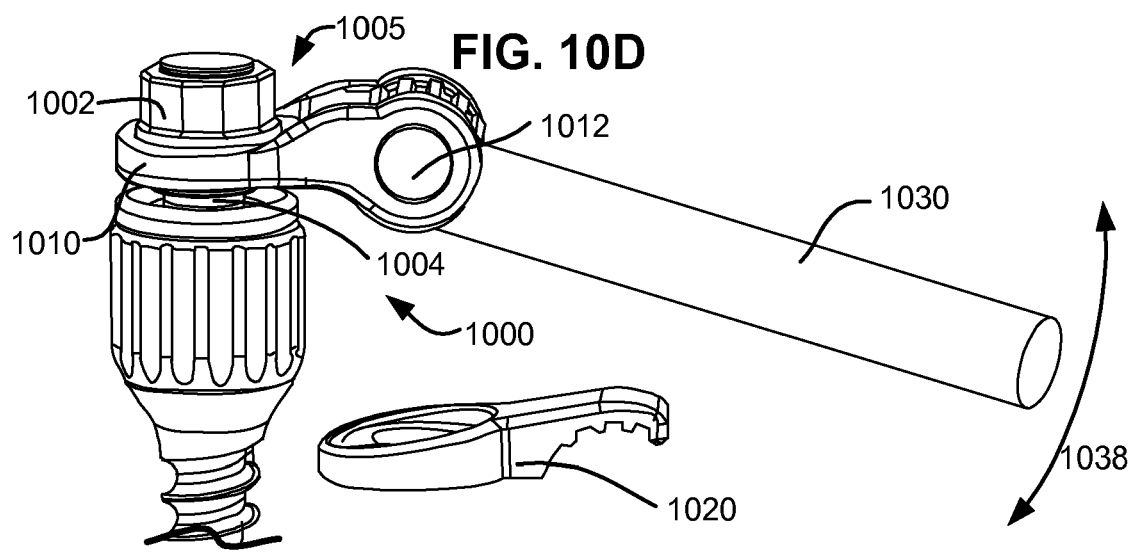

In an alternative mode of installation shown in FIG. 10D, locking plate 1020 may be omitted. In such case, nut 1002 is used to secure clevis 1010 to mount 1005 of deflectable post 1004. In the absence of locking plate 1020, vertical rod 1030 is free to pivot about pivot pin 1012 even after installation and securing of vertical rod 1030 to deflectable post 1004 (see arrow 1038). Thus, vertical rod 1030 is provided with an additional degree of freedom of motion as finally implanted. As described above, the resulting dynamic stabilization assembly will have reduced stiffness and greater range of motion than an embodiment in which the angle between the vertical rod and deflectable post is invariant.

Figure 10E:
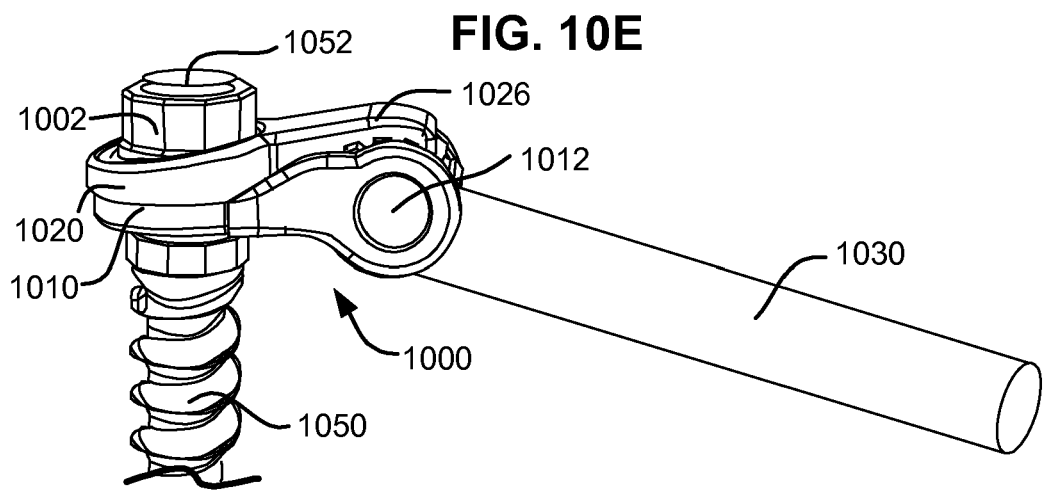

Referring to FIG. 10E, hinged coupling 1000 may also be used to secure vertical rod 1030 to a standard bone anchor 1050 having a fixed threaded post 1052. Hinged coupling 1000 may be used with or without locking plate 1020 depending upon if it is desired to have vertical rod 1030 pivot relative to the bone anchor 1050 after installation. When used in conjunction with a standard bone anchor, hinged coupling functions as a polyaxial head in that it allows the direction and angle of vertical rod 1030 to be adjusted relative to bone anchor 1050 during installation thereby facilitating implantation of a spinal implant assembly.

FIGS. 11A-11D show an alternative ball-joint 1100 for connecting a deflection rod to a vertical rod according to an embodiment of the invention. Ball-joint 1100 is designed to be mounted to the threaded proximal end of a deflectable post of a deflection rod. Ball-joint 1100 may however be used with any deflection rod (or bone anchor) having a suitable proximal mount, for example, deflection rod 300 of FIGS. 3A-3H.

Figure 11A:
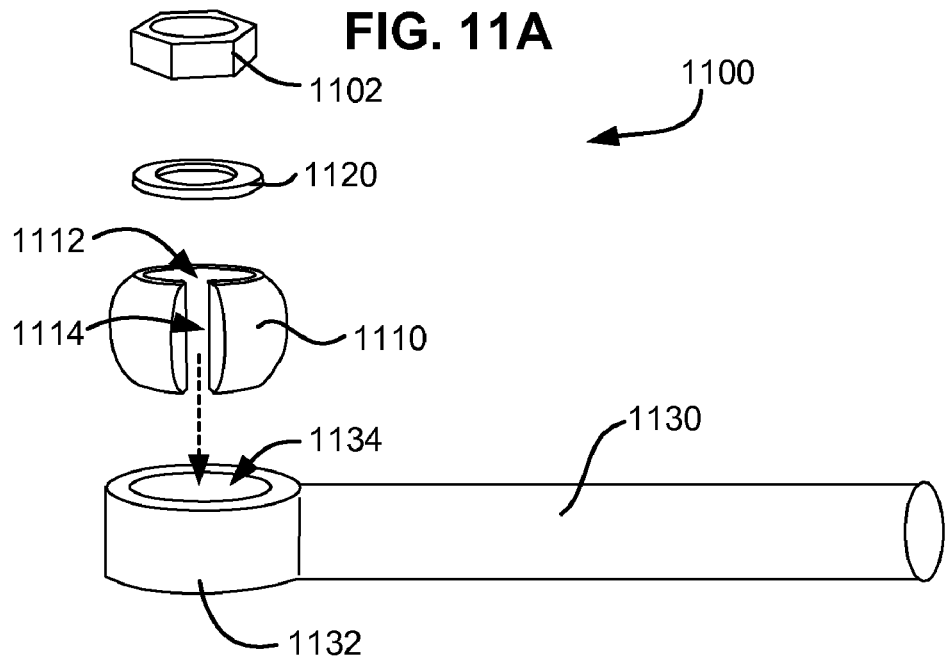
FIGS. 11A-11D show a locking ball-joint mechanism for connecting a deflection rod assembly to a vertical rod according to an embodiment of the invention.

FIG. 11A shows an exploded view of ball-joint 1100. Ball-joint 1100 includes split spherical bearing 1110, locking washer 1120 and a vertical rod 1130. Ball-joint 1100 is held in place by a nut 1102. Vertical rod 1130 is configured to receive split spherical bearing 1110. One end of vertical rod 1130 includes a disc 1132 having a pocket 1134. Pocket 1134 is shaped like a segment of a sphere and has a larger diameter in the interior than at the surface of disc 1132. Split spherical bearing 1110 has the same diameter as the largest diameter of pocket 1134. However, split spherical bearing 1110 has a central aperture 1112 and a gap 1114 which allows split spherical bearing 1110 to be compressed and inserted into pocket 1134. When split spherical bearing 1110 is correctly positioned within pocket 1134 it is allowed to expand into position. Expansion of bearing 1110 secures it within pocket 1134, when split spherical bearing 1110 is ready for mounting.

Figure 11B:
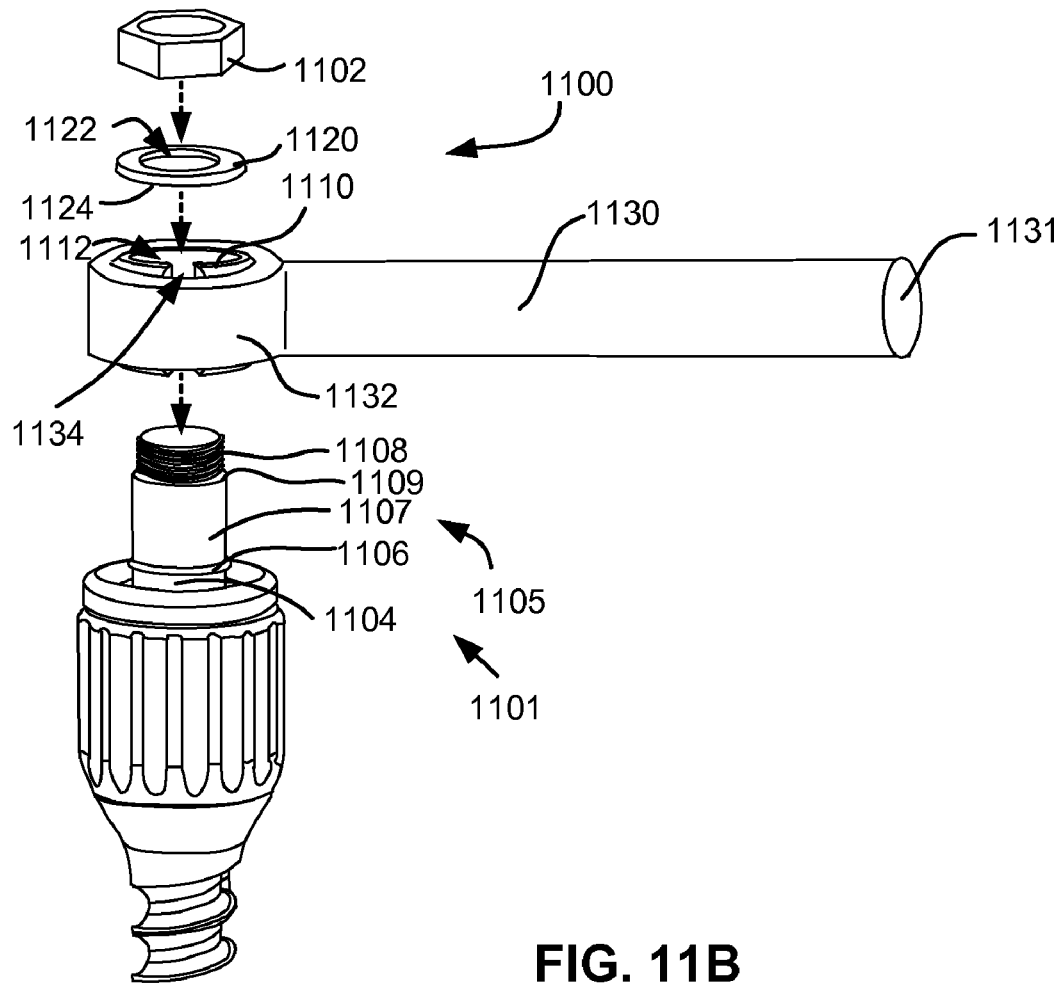

FIG. 11B shows split spherical bearing 1110 mounted within pocket 1134 of vertical rod 1130 ready for installation on a deflection rod 1101. Split spherical bearing 1110 protrudes on either side of disc 1132 to provide adequate spacing for the movement of disc 1132. Central aperture 1112 may be circular (as shown) or may be polygonal. Where aperture 1112 is polygonal (non-circular) it may engage a similarly-shaped polygonal post in such a way as to prevent rotation of bearing 1110 relative to deflectable post 1104. This is advantageous in that such rotation may cause nut 1102 to be loosened. Moreover, deflectable post 1104 of the deflection rods of the present invention can typically rotate relative to the bone anchor and thus rotation of spherical bearing 1110 is a redundant and therefore unnecessary degree of freedom.

As shown in FIG. 11B, deflection rod 1101 has at the end of deflectable post 1104 a mount 1105 for receiving mounting plate 1116 of ball-joint 1100. Mount 1105 has a lip 1106, a cylindrical portion 1107 and a threaded portion 1108. Lip 1106 provides a mechanical stop to catch bearing 1110. Cylindrical portion 1107 fits snuggly in aperture 1112 to preclude compression of split spherical bearing 1110 and thereby preventing split spherical bearing 1110 from being removed from pocket 1134. In use, aperture 1112 is placed over mount 1105 until split spherical bearing 1110 contacts lip 1106 and cylindrical portion 1107 is received with aperture 1112.

After bearing 1110 is positioned, vertical rod 1130 is oriented in the desired direction and angle relative to deflectable post 1104. Typically, vertical rod 1130 is oriented by securing the free end 1131 to another device on another vertebra of the spine, e.g. a bone screw, polyaxial screw, or deflection rod. When vertical rod 1130 is correctly positioned, locking washer 1120 may be installed. Locking washer 1120 has an aperture 1124 adapted to be received over mount 1105 of deflectable post 1104. Aperture 1124 is smaller than shoulder 1109 of mount 1105. Locking washer 1120 has a lower lip 1122 designed, in one orientation, to push down on bearing 1110. In the other orientation, locking washer 1120 is blocked by shoulder 1109 before locking washer 1120 can compress bearing 1110. Bearing 1110 and locking washer 1120 are secured in place by nut 1102 which engages threaded portion 1108 of mount 1105 to secure vertical rod 1130 to deflectable post 1104.

Figure 11C:
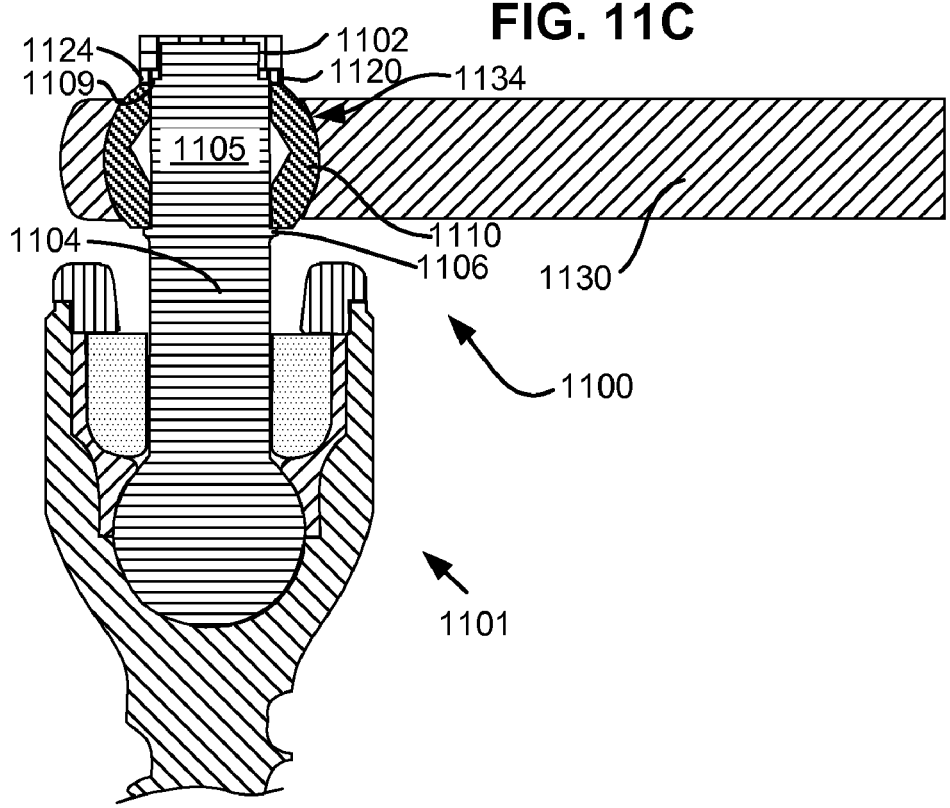

FIG. 11C shows vertical rod 1130 secured to deflectable post 1104 by ball-joint 1100 with vertical rod 1130 at a fixed angle relative to deflectable post 1104. As shown in FIG. 11C, split spherical bearing 1110 is engaged on one side by lip 1106 of mount 1105. On the other side, split spherical bearing 1110 is engaged by lip 1124 of locking washer 1120 which extends past shoulder 1109 of mount 1105. As nut 1102 is tightened, split spherical bearing 1110 is compressed between washer 1120 and lip 1106. Split spherical bearing 1110 is designed so that, in response to compression by nut 1102, it shrinks in height and expands in diameter. For example, split spherical bearing 1110 may be provided with interior relief. When split spherical ring 1110 increases in diameter, it engages the surface of pocket 1134 sufficiently to preclude further movement of bearing 1110 relative to rod 1130. Thus, by tightening nut 1102, vertical rod 1130 is secured to deflectable post 1104 and the angle between vertical rod 1130 and deflectable post 1104 is fixed.

Figure 11D:
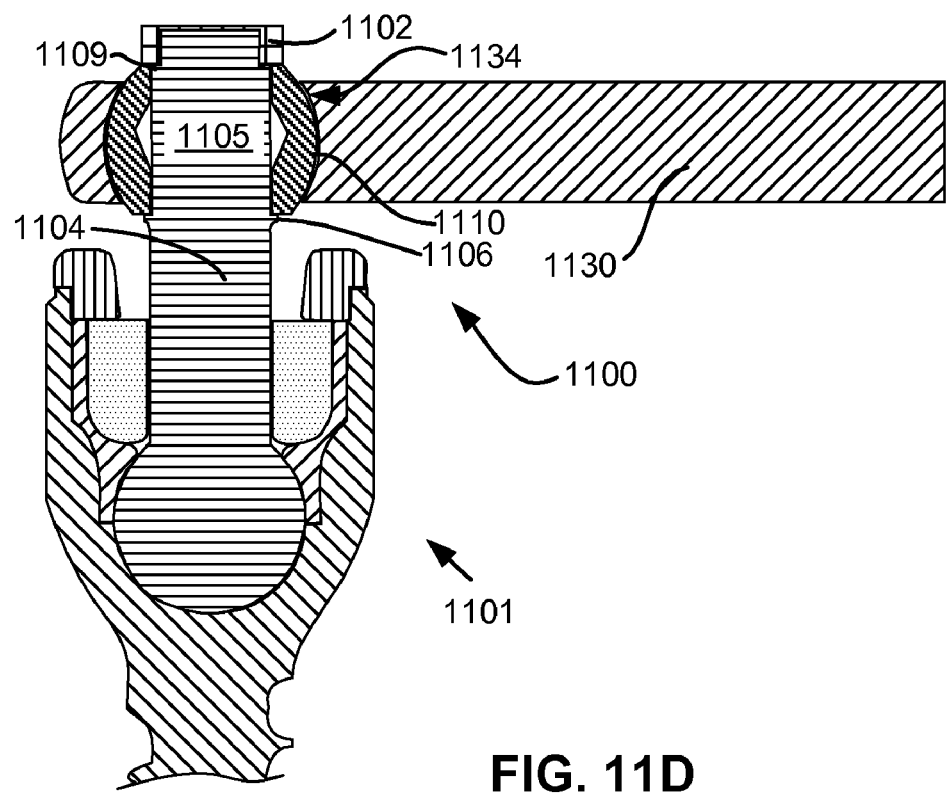

In an alternative mode of installation shown in FIG. 11D, locking washer 1120 may be omitted. In such case, nut 1102 is used to secure split spherical bearing 1110 to mount 1105 of deflectable post 1104. In the absence of locking washer 1120, nut 1102 cannot compress split spherical bearing 1110 because nut 1102 does not extend beyond shoulder 1109 of mount 1105. As a consequence, split spherical bearing 1110 is not compressed and may therefore still rotate within pocket 1134 of vertical rod 1130. Thus, in this mode, vertical rod 1130 is free to pivot about bearing 1110 even after installation and securing of vertical rod 1130 to deflectable post 1104 (see arrow 1138). Thus vertical rod 1130 is provided with additional freedom of motion as finally implanted. As described above, the resulting dynamic stabilization assembly will have reduced stiffness and greater range of motion than an embodiment in which the angle between the vertical rod and deflectable post is invariant. Ball joint 1100 may similarly be used (in either mode) to secure vertical rod 1130 to a conventional bone anchor having a fixed threaded post (see, e.g., bone anchor 1050 of FIG. 10E).

Figure 11E:
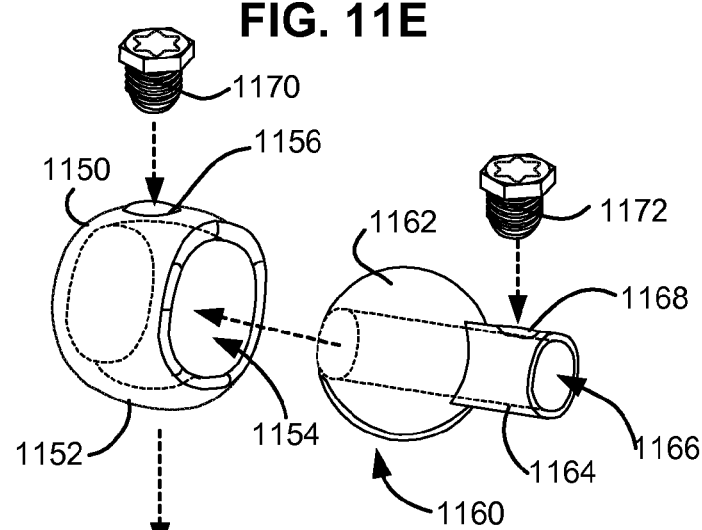
FIGS. 11E-11F show a locking receiver mechanism attached to a deflection rod assembly for connecting the deflection rod assembly to a vertical rod according to an embodiment of the invention.
Figure 11F:
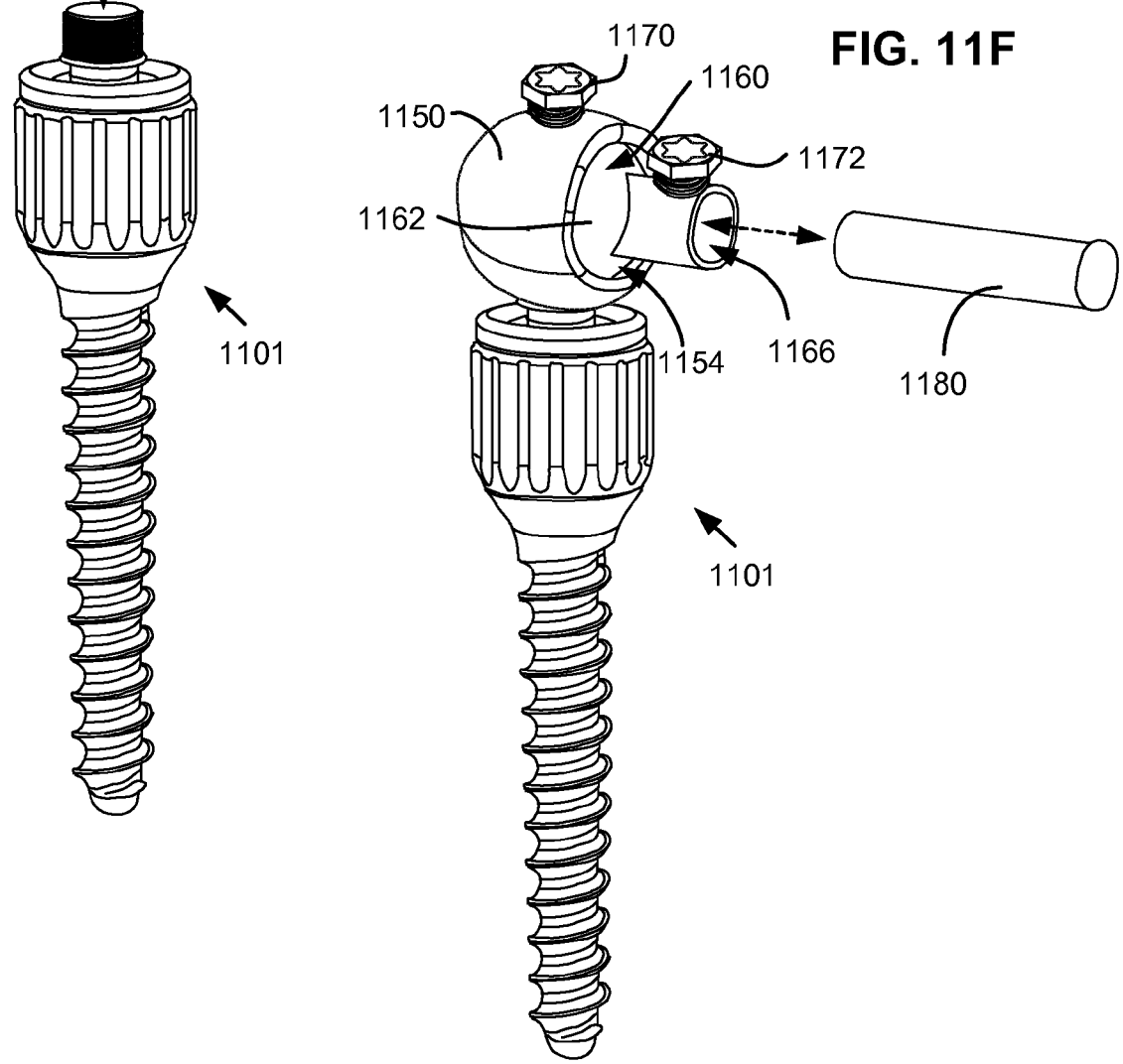

In alternative embodiments, shown in FIGS. 11E and 11F, a socket for a split spherical bearing is mounted to the deflection rod itself. A vertical rod may be slipped into the split spherical bearing and may be locked in position and angle by two set screws. FIG. 11E shows an exploded view of the components which include socket 1150, bearing 1160 and screws 1170 and 1172. Socket 1150 includes a lower fitting 1152 (e.g. a threaded aperture) for attaching socket 1150 to deflection rod 1101. Socket 1150 may also be bonded to deflection rod 1101 by e.g. laser welding, or may, in some cases, be formed in one piece with the deflectable post of the deflection rod 1101. Socket 1150 has an internal pocket 1154 which is the same diameter as spherical bearing 1160. Socket 1150 also has an upper threaded aperture 1156 for receiving set screw 1170.

Spherical bearing 1160 has a spherical section 1162, a sleeve 1164, a central passage 1166 and a threaded aperture 1168. Spherical section 1162 is provided with a split or other structural relief mechanism that allows it to be pressed into the pocket 1154 of socket 1150 (in the absence of a vertical rod). Sleeve 1164 extends from one side of spherical section 1162. Central passage 1166 extends through sleeve 1164 and spherical section 1162 and is sized so that a vertical rod may slide therethrough. Threaded aperture 1168 intersects passage 1166 such that, when inserted, locking set screw 1172 may secure a vertical rod 1180 within passage 1166.

Spherical bearing 1160 is pressed into socket 1150 and socket 1150 is secured to deflection rod 1101 prior to implantation in a patient as shown in FIG. 11F. A vertical rod 1180 may then be inserted through central passage 1166 of spherical bearing 1160 (shown in FIG. 11E). When vertical rod 1180 is at the desired position, set screw 1172 may be tightened to secure the vertical rod 1180 within passage 1166. At this point, the vertical rod 1180 is secured to deflection rod 1101. Spherical bearing 1160 is secure within pocket 1154 of socket 1150 because, with vertical rod in position, spherical section 1162 may no longer be compressed sufficiently to remove it from pocket 1154. However, spherical section 1162 may still rotate within pocket 1154 and thus the angle between deflection rod 1101 and vertical rod 1180 can change.

In some embodiments vertical rod 1180 may be oriented to the desired angle and then screw 1170 may be tightened. Screw 1170 engages the spherical section 1162 of bearing 1160 and pushes it against the wall of socket 1154 thereby locking bearing 1160 in a fixed position. As previously described, locking the angle of the vertical rod 1180 relative to the deflection rod 1101 increases the stiffness of the system. However, if less stiffness and more range of motion is required, screw 1170 can be removed and bearing 1160 left free to rotate within pocket 1154 after final assembly.

FIGS. 12A-12D show another ball-joint mechanism for connecting a deflection rod to a vertical rod according to an embodiment of the invention. In the embodiment of FIGS. 12A-12D, the vertical rod is provided with a locking ball receiver 1200 which can be secured to a deflection rod 1201 having a deflectable post 1204 which terminates in a ball 1206. The locking ball receiver 1200 can be secured to the ball 1206 in two modes. In one mode, the locking ball receiver 1200 is secured to the ball 1206 so that it cannot be removed from the ball 1206 but can still rotate and pivot relative to the ball 1206. In the other mode, the locking ball receiver 1200 is secured to the ball 1206 such that it cannot be removed from the ball 1206 and nor can it rotate and pivot relative to the ball 1206.

FIG. 12A shows an exploded view of receiver 1200. Receiver 1200 includes clamp 1210, washer 1220 and is attached to vertical rod 1230. The receiver 1200 is positioned at one end of vertical rod 1230 and includes a pocket 1234. Pocket 1234 is shaped like a portion of a sphere having the same diameter as ball 1206. The entrance to pocket 1234 is the same diameter as ball 1206 or larger so that ball 1206 may be inserted into pocket 1234 during connection of vertical rod 1230 to deflectable post 1204. Clamp 1210 has a pocket 1216 also shaped like a portion of a sphere having the same diameter as ball 1206. Pocket 1216 can be moved away from pocket 1234 to allow the insertion of ball 1206. Pocket 1216 can be moved towards pocket 1234 to secure ball 1206 within pocket 1234.

Clamp 1210 is held in place by a screw 1202. During assembly, screw 1202 is passed through an aperture 1212 in clamp 1210. Aperture 1212 is larger than screw 1202. Clamp 1210 fits within slot 1236 in receiver 1200. Slot 1236 includes a ramp 1238 which engages a ramp 1214 of clamp 1210. Engagement of ramp 1238 with ramp 1214 causes tightening of clamp 1210 as clamp 1210 is brought closer to the bottom of slot 1236. Screw 1202 passes into a threaded aperture 1235 in vertical rod 1230 so that tightening of screw 1202 draws clamp 1210 towards the bottom of slot 1236. In some modes, washer 1220 is positioned between clamp 1210 and the bottom of slot 1236 thereby spacing clamp 1210 from the bottom of slot 1236 and limiting the clamping action of clamp 1210.

As shown in FIG. 12B, deflectable post 1204 has at the end of deflectable post 1204 ball 1206 to which receiver 1200 may be mounted. Ball 1206 may be formed in one piece with deflectable post 1204 or may be formed separately and subsequently securely attached. FIG. 12B shows receiver 1200 positioned over ball 1206 of a deflectable post 1204. Ball 1206 is slipped into pocket 1234 with clamp 1210 removed or loosely attached to vertical rod 1230. After ball 1206 is positioned within pocket 1234, vertical rod 1230 is oriented in the desired direction and angle relative to deflectable post 1204. Typically vertical rod 1230 is oriented by securing the free end 1231 to another device on another vertebra of the spine, e.g. a bone screw, polyaxial screw, or deflection rod. When vertical rod 1230 is correctly positioned, screw 1202 may be tightened. As screw 1202 is tightened, ramp 1238 pushes on ramp 1214 to push pocket 1216 towards pocket 1234. If washer 1220 is present, the approach of pocket 1216 towards pocket 1234 is limited by the washer 1220 so that clamp 1210 does not lock to ball 1206. If washer 1220 is absent, clamp 1210 is forced into contact with ball 1206 by the tightening of screw 1202.

Figure 12C:
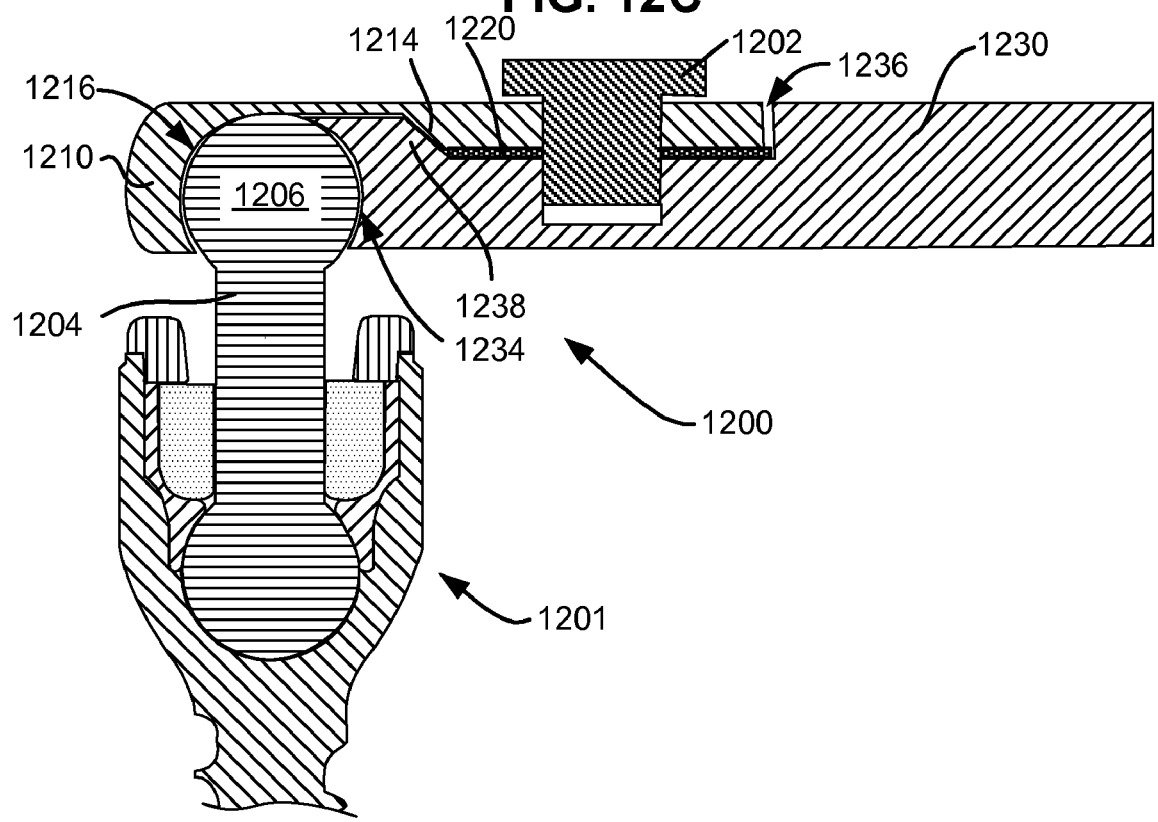

FIG. 12C shows a sectional view of vertical rod 1230 secured to deflectable post 1204 by receiver 1200. As shown in FIG. 12C, ball 1206 is trapped between pocket 1216 of clamp 1210 and pocket 1234 of vertical rod 1230. Pockets 1216 and 1234 combine to form a pocket which traps ball 1206. As screw 1202 is tightened, pocket 1216 is pushed further towards pocket 1234 by the interaction or ramps 1214 and 1238. However, where washer 1220 is present, the approach of pocket 1216 towards pocket 1234 is halted before any clamping pressure is applied to ball 1206. Thus, vertical rod 1230 may still rotate and pivot relative to ball 1206 after screw 1202 has been tightened. Thus, vertical rod 1230 is provided with an additional degree of freedom of motion as finally implanted. As described above, the resulting dynamic stabilization assembly will have reduced stiffness and greater range of motion than an embodiment in which the angle between the vertical rod and deflectable post is invariant.

Figure 12D:
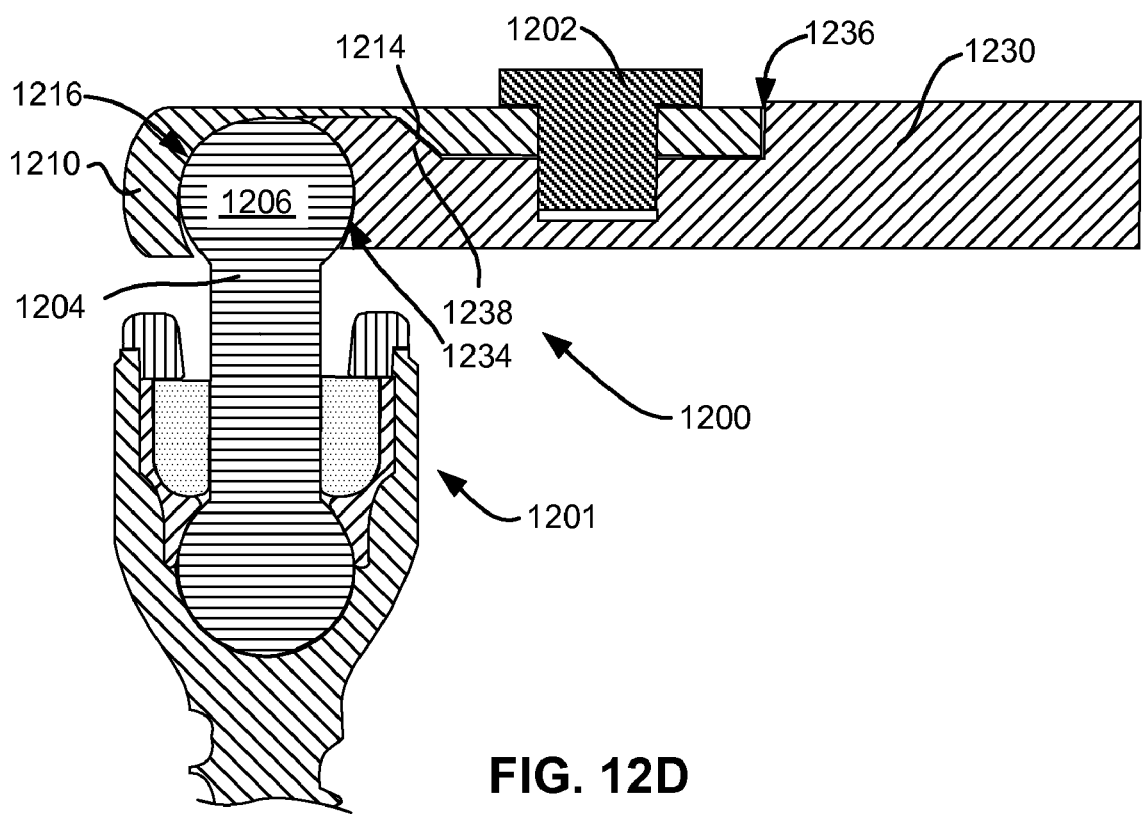

In an alternative mode of installation shown in FIG. 12D, washer 1220 (not shown) may be omitted. In the absence of washer 1220, clamp 1210 can be moved closer to the bottom of slot 1236. As screw 1202 is tightened, pocket 1216 is pushed further towards pocket 1234 by the interaction or ramps 1214 and 1238. Now that washer 1220 (not shown) is absent, the approach of pocket 1216 towards pocket 1234 is not halted until clamping pressure is applied to ball 1206. As a consequence, vertical rod 1230 is fixed to ball 1206 and cannot rotate or pivot relative to ball 1206. As described above, the resulting dynamic stabilization assembly will have increased stiffness but less range of motion than an embodiment in which the angle between the vertical rod and deflectable post may vary. The receiver may similarly be used (in either mode) to secure vertical rod 1230 to a standard bone anchor having a fixed threaded post e.g. bone anchor 1050 of FIG. 10E).

FIGS. 13A and 13B show another mechanism for connecting a deflection rod to a vertical rod according to an embodiment of the invention. FIGS. 13A and 13B show a deflection rod having a pivoting head according to an embodiment of the invention. In the embodiment of FIGS. 13A-13B, the deflection rod has an integrated connector 1300 which can be secured to a vertical rod. The connector 1300 can be secured to the vertical rod in two modes. In one mode the connector 1300 is secured to the vertical rod so that it cannot be removed from the connector 1300 but can still pivot relative to the deflection rod. In the other mode, the connector 1300 is secured to the vertical rod such that it cannot be removed from the connector 1300 and nor can it pivot relative to the deflection rod.

FIG. 13A shows an exploded view of connector 1300. Connector 1300 includes saddle 1310, plunger 1320, set screw 1330, pivot pin 1332 and is attached to a deflectable post 1340 of a deflection rod 1302. Deflectable post 1340 has a disk-shaped mount 1342 at the proximal end. Mount 1342 has a central aperture 1344 sized to receive pivot pin 1332. Saddle 1310 is approximately tube shaped with a bore 1316 which passes through the long axis of saddle 1310. At one end of saddle 1310 is a clevis 1312 sized to receive disk-shaped mount 1342. Clevis 1312 has an aperture 1314 which passes through clevis 1312 and is sized to receive pivot pin 1332. To assemble connector 1300, disk-shaped mount 1342 is inserted into clevis 1312 and pivot pin 1332 is passed through aperture 1314 and aperture 1344. Pivot pin 1332 is then secured to one or both sides of clevis 1312 using mechanical means and/or bonding e.g. laser welding. Saddle 1310 is then free to pivot relative to deflectable post 1340 around the axis of pivot pin 1332.

Bore 1316 now communicates with disk-shaped mount 1342. A plunger 1320 may now be introduced into bore 1316. Plunger 1320 has surface features, for example, ribs 1326 designed to engage the surface features of disk-shaped mount 1342. The end of saddle 1310 opposite clevis 1312 has a slot 1318 which passes therethrough. Slot 1318 is sized to receive a vertical rod. At the closed end slot 1318 intersect the position of plunger 1320. At the open end of slot 1318, bore 1316 is threaded to receive set screw 1330. When a vertical rod (not shown) is inserted into slot 1318, tightening of set screw 1330 forces the vertical rod down in slot 1318 towards plunger 1320 which is in turn pushed down into contact with disk-shaped mount 1342.

FIG. 13B shows connector 1300 assembled with a deflection rod 1302 and bone anchor 1304. As assembled, connector 1300 may pivot about the axis of pivot pin 1332 as shown by arrow 1306. Connector 1300 may also rotate around the long axis of bone anchor 1304 as shown by arrow 1308. Rotation 1308 is possible because deflectable post 1340 may rotate around its long axis within deflection rod 1302.

Figure 14A:
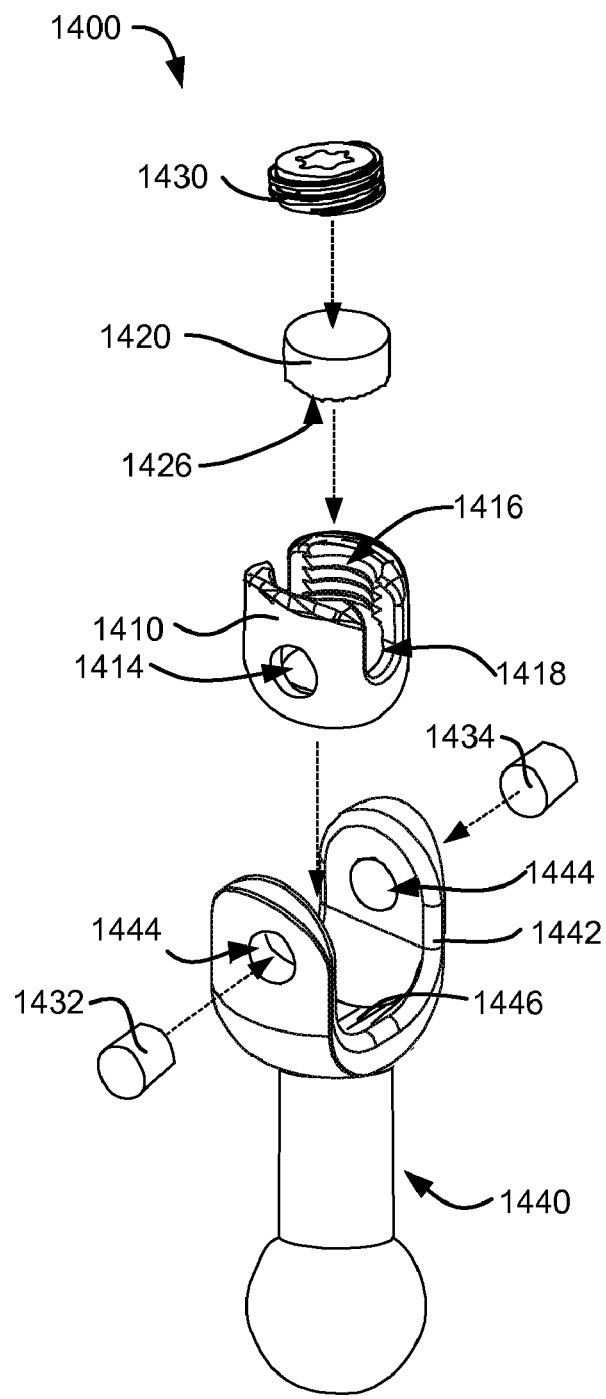
FIGS. 14A and 14B show a deflection rod assembly having a pivoting head according to an embodiment of the invention.
Figure 14B:
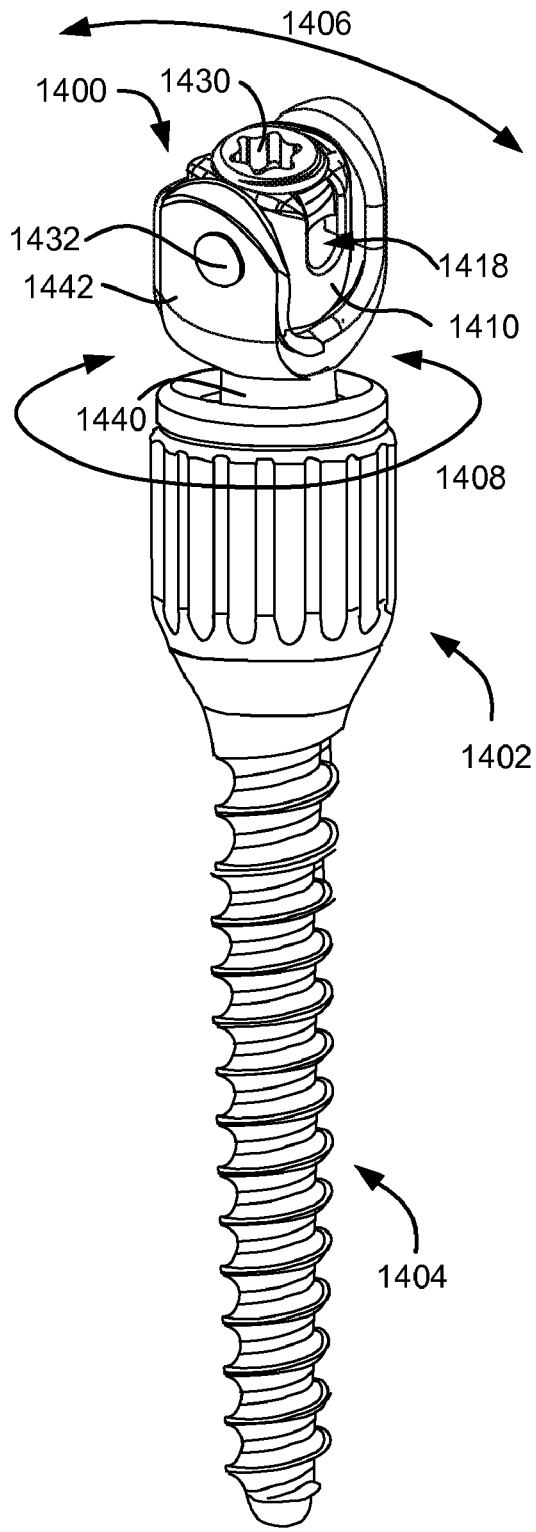

FIGS. 14A and 14B show another mechanism for connecting a deflection rod to a vertical rod according to an embodiment of the invention. FIGS. 14A and 14B show a deflection rod having a pivoting head according to an embodiment of the invention. In the embodiment of FIGS. 14A and 14B, the deflection rod has an integrated connector 1400 which can be secured to a vertical rod. The connector 1400 can be secured to the vertical rod in two modes. In one mode, the connector 1400 is secured to the vertical rod so that it cannot be removed from the connector 1400 but can still pivot relative to the deflection rod. In the other mode, the connector 1400 is secured to the vertical rod such that it cannot be removed from the connector 1400 and nor can it pivot relative to the deflection rod.

FIG. 14A shows an exploded view of connector 1400. Connector 1400 includes saddle 1410, plunger 1420, set screw 1430, pivot pins 1432, 1434 and is attached to a deflectable post 1440 of a deflection rod 1402 (see FIG. 14B). Deflectable post 1440 has clevis 1442 at the proximal end. Clevis 1442 has an aperture 1444 which passes through both arms of clevis 1442 and is configured to receive pivot pins 1432, 1434. Saddle 1410 is approximately tube shaped with a bore 1416 which passes through the long axis of saddle 1410. Clevis 1442 has an aperture 1414 which passes through clevis 1412 and is sized to receive pivot pins 1432, 1434. To assemble connector 1400, saddle 1410 is inserted into clevis 1442 and pivot pins 1432, 1434 are passed through apertures 1444 into apertures 1414. Pivot pins 1432, 1434 is then secured to both sides of clevis 1442 using mechanical means and/or bonding e.g. laser welding. Saddle 1410 is then free to pivot relative to deflectable post 1440 around the axis of pivot pins 1432, 1434.

Bore 1416 now communicates with ribbed surface 1446 of clevis 1442. A plunger 1420 may now be introduced into bore 1416. Plunger 1420 has surface features, for example, ribs 1426 designed to engage the ribbed surface 1446 of clevis

1442. The proximal end of saddle 1410 has a slot 1418 which passes therethrough. Slot 1418 is sized to receive a vertical rod (not shown). At the closed end, slot 1418 intersects the position of plunger 1420. At the open end of slot 1418, bore 1416 is threaded to receive set screw 1430. When a vertical rod (not shown) is inserted into slot 1418, tightening of set screw 1430 forces the vertical rod down in slot 1418 towards plunger 1420 which is in turn pushed down into contact with ribbed surface 1446 of clevis 1442. Contact between plunger 1420 and clevis 1442 locks saddle 1410 so that it can no longer pivot relative to the plunger. However, in an alternative configuration, plunger 1420 is omitted, and set screw 1430 can be used to lock the vertical rod (not shown) to the saddle 1410 while still allowing saddle 1410 to pivot with respect to clevis 1442.

FIG. 14B shows connector 1400 assembled with a deflection rod 1402 and bone anchor 1404. As assembled, connector 1400 may pivot about the axis of pivot pin 1432 as shown by arrow 1406. Connector 1400 may also rotate around the long axis of bone anchor 1404 as shown by arrow 1408. Rotation 1408 is possible because deflectable post 1440 may rotate around its long axis within deflection rod 1402. A vertical rod (not shown) may be inserted into slot 1418. Tightening set screw 1430 secures the vertical rod to the saddle 1410. If plunger 1420 is present, tightening set screw 1430 also locks the relative positions of saddle 1410 and clevis 1442 preventing pivoting after implantation. If plunger 1420 is absent, tightening set screw 1430 does not lock saddle 1410 to clevis 1442 and the saddle 1410 may still pivot after implantation. As described above, the resulting dynamic stabilization assembly will have reduced stiffness and greater range of motion in an embodiment that allows pivoting between the vertical rod and deflectable post rod after implantation than an embodiment in which the angle between the vertical rod and deflectable post is locked.

FIG. 15A illustrates a preferred embodiment of the deflection rod 300 and bone anchor 320 of FIG. 3A. As shown in FIG. 15A, mount 314 of deflection rod 300 includes a polygonal section 1502 for secure mounting to a vertical rod component. Polygonal section 1502 may be hexagonal, octagonal or the like. Polygonal section 1502 is shaped to match the shape of a receiver in the vertical rod component (not shown) such that when the two are mounted together there will be no rotation. As shown in FIG. 15A, the proximal end of mount 314 is threaded 1504 to receive a fastener to secure a vertical rod component to mount 314. Deflection rod 300 is otherwise as previously described.

FIG. 15A also shows a preferred embodiment of vertical rod 1510 for use with deflection rod 300. As shown in FIG. 15A, vertical rod 1510 comprises a rod 1511 which is preferably a 5.5 mm diameter titanium rod. Vertical rod 1510 has a pocket 1512 at one end sized to receive a ball 1520. Ball 1520 is preferably a cobalt chrome ball. Ball 1520 has a polygonal aperture 1522 designed to closely engage the polygonal section 1502 of mount 314. Ball 1520 is inserted into pocket 1512 and secured into place with threaded cap 1530. Pocket 1512 is threaded to receive cap 1530. Ball 1520 is placed in pocket 1512 and then cap 1530 is screwed into the threaded portion of pocket 1512. Cap 1530 is preferably titanium and may be laser welded or otherwise secured to vertical rod 1510 after assembly. The components of vertical rod 1510—titanium rod 1511, titanium cap 1530 and cobalt chrome ball 1520 are assembled prior to use.

FIGS. 15B and 15C shows a sectional view through vertical rod 1510 after assembly. FIG. 15B shows ball 1520 positioned within pocket 1512 of rod 1511. As shown in FIG. 15B cap 1530 and pocket 1512 capture ball 1530 such that it cannot be removed from vertical rod 1510. Ball 1530 can, however, rotate 360 degrees around the axis of aperture 1522 as shown by arrow 1550. This allows vertical rod 1510 to rotate 360 degrees around the long axis of the deflection rod or bone anchor to which ball 1530 is mounted. Ball 1530 can also tilt from the position shown in FIG. 15B as shown in FIG. 15C by arrows 1552. In a preferred embodiment ball 1530 can tilt 15 degrees in any direction therefore allowing vertical rod 1510 to tilt 15 degrees from perpendicular relative to the deflection rod or bone anchor to which ball 1530 is mounted. Note that the mount 314 and a nut to secure the vertical rod 1510 to mount 314 are designed so not as to interfere with the range of motion either in rotation or tilting.

Vertical rod 1510 may be used with a standard bone anchor, a deflection rod and bone anchor (for example bone anchor 320 and deflection rod 300 of FIG. 15A), or a polyaxial screw. Likewise, the assembly of deflection rod 300 and bone anchor 320 of FIG. 15A may be utilized with vertical rod 1510, but may also be utilized in conjunction with a vertical rod not having a ball joint.

FIGS. 16A and 16B show an alternative embodiment of deflection rod 1600 which includes mount 1670 for connecting the deflection rod to a vertical rod. As shown in FIG. 16A, mount 1670 includes a circular plate 1674; the face of which is parallel to the longitudinal axis of deflectable post 1604. A threaded pin 1672 projects from the center of circular plate 1674. Threaded pin 1672 is perpendicular to the longitudinal axis of deflectable post 1604. On the face of circular plate 1674 surrounding pin 1672 are a plurality of radial splines 1676.

Mount 1670 is designed to mate with vertical rod 1680 as also shown in FIG. 16A. Vertical rod 1680 has at one end a circular plate 1684; the face of which is parallel to the longitudinal axis of vertical rod 1680. An aperture 1682 passes through the center of circular plate 1684 and is sized to receive threaded pin 1672. Aperture 1682 is perpendicular to the longitudinal axis of vertical rod 1680. On the face of circular plate 1684 surrounding aperture 1682 are a plurality of radial splines 1686. The radial splines 1686 of vertical rod 1680 are designed to mate with and engage the splines 1676 of mount 1670.

As shown in FIG. 16B, aperture 1682 of vertical rod 1680 is received over threaded pin 1672 of mount 1670. The angle of vertical rod 1680 is relative to deflectable post 1604 may be adjusted as shown by arrow 1692. Adjustment of the relative angle of deflectable post 1604 and vertical rod 1680 combined with the ability of deflectable post 1604 to rotate about its long axis (as shown by arrow 1694) is relative to bone anchor 1620 provides two degrees of freedom and thus sufficient flexibility of installation to align vertical rod 1680 with a bone anchor implanted in another vertebrae. As shown in FIG. 16B, a nut 1690 engages threaded pin 1672 to secure plate 1674 to plate 1684. Splines 1676 of plate 1674 are arranged facing splines 1686 of plate 1684. When nut 1690 is tightened, splines 1686 engage splines 1676 to prevent rotation of vertical rod 1680 about pin 1672. Thus, when nut 1690 is tightened, the angle between deflectable post 1604 and vertical rod 1680 is fixed. The vertical rod mounting mechanism of FIGS. 16A and 16B may be readily applied to any of the deflection rod systems described herein.

Further Alternative Deflection Rods/Loading Rods

Figure 17A:
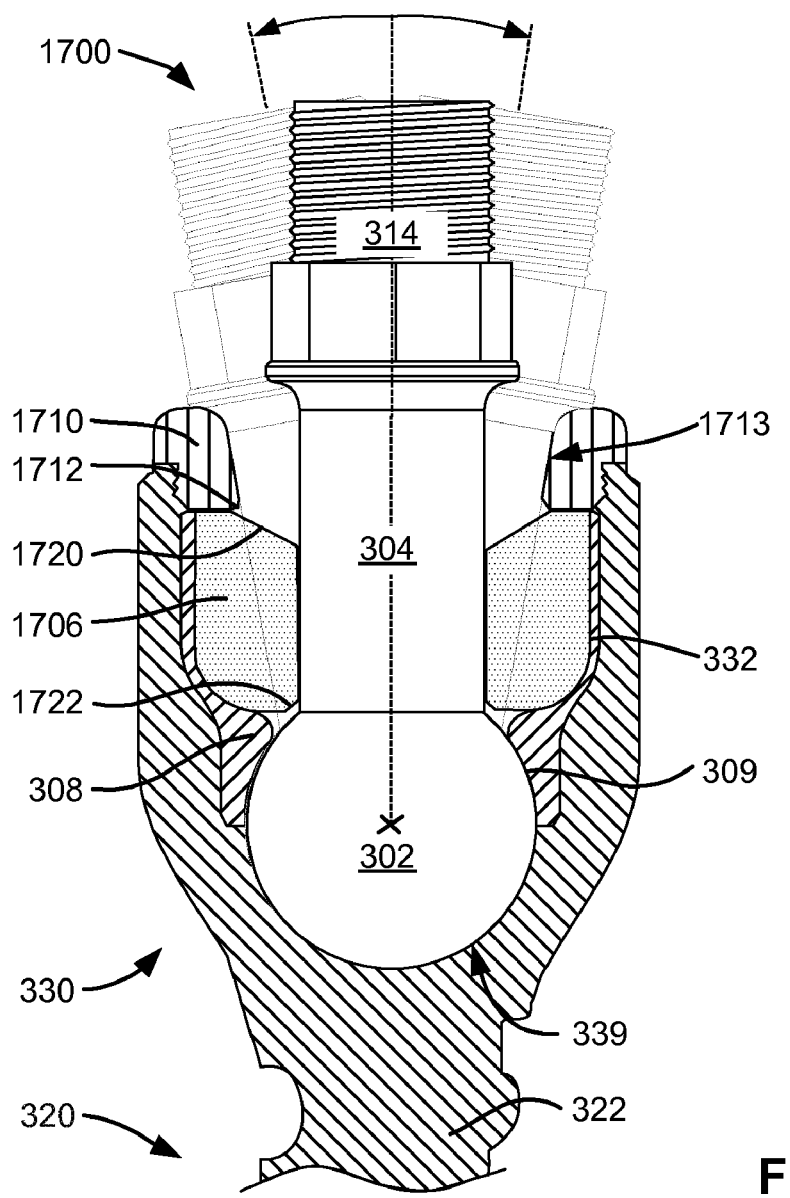
FIG. 17A shows a sectional view of an alternative deflection rod assembly according to an embodiment of the invention.

FIG. 17A shows an alternative deflection rod 1700. FIG. 17A shows the deflectable post 304 and also shows (in dotted lines) the position of deflectable post 304 upon deflection. Deflection rod 1700 has most of the same components as deflection rod 300 of FIGS. 3A-3E. Applicants found, that upon deflection of deflectable post 304 of deflection rod 300 of FIGS. 3A-3E there was a propensity for sleeve 300 of FIGS. 3A-3E to expand longitudinally during compression by deflectable post 304 and become trapped between deflection rod 300 and collar 310. Deflection rod 1700 therefore has a modified sleeve 1706 and modified collar 1710.

As shown in FIG. 17A, sleeve 1706 is provided with a relief 1720 on the upper surface. Relief 1720 allows space for longitudinal expansion of sleeve 1706 during radial compression of sleeve 1706 by post 304. Thus, sleeve 1706 does not become trapped between deflectable post 304 and contact surface 1713 of collar 1710 upon deflection of deflectable post 304 (as shown by dotted lines). This design reduces wear on sleeve 1706 and ensures that deflectable post 304 may freely travel through its designed range of deflection.

As shown in FIG. 17A, collar 1710 may also be provided with a relief 1712 to further assist in preventing sleeve 1706 from becoming trapped between collar 1710 and deflectable post 304. Additionally, sleeve 1706 may be provided with a lower relief 1722 in order to prevent sleeve 1706 from being trapped between deflectable post 304 and shield 308 in the region of retainer 302.

Figure 17B:
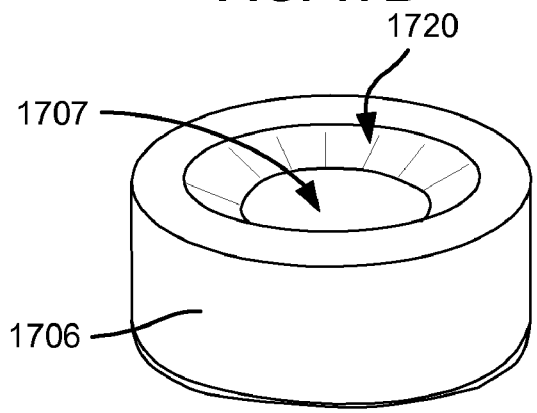
FIG. 17B shows a perspective view of the sleeve of the deflection rod assembly of FIG. 17A.

FIG. 17B shows a perspective view of sleeve 1706. Sleeve 1706 is made of a compliant material which permits movement of deflectable post 304 relative to shield 308 (FIG. 17A). The sleeve 1706 effectively controls the deflection of the deflectable post 304. Sleeve 1706 is preferably made of a compliant biocompatible polymer such as PCU by way of example only. The properties of the material and dimensions of sleeve 1706 are selected to achieve the desired force/deflection characteristics for deflectable post 304 (FIG. 17A). In a preferred embodiment, the sleeve is made of PCU, is 2 mm thick when uncompressed and may be compressed to about 1 mm in thickness by deflection of the post.

As can be seen from FIG. 17B, relief 1720 forms a conical depression in the proximal surface of sleeve 1706 surrounding the central aperture 1707 which receives deflectable post 304 (not shown). The removal of material from the proximal surface of sleeve 1706 (as compared with sleeve 306 of FIGS. 3A-3E) allows room for expansion of sleeve 1706 without sleeve 1706 becoming trapped between deflectable post 304 and collar 1710 (FIG. 17A). Sleeve 1706 may also be shaped to modify the compliance of sleeve 1706, for example by providing additional regions of relief or voids within the body of sleeve 1706 (see, e.g. flutes 307 of FIG. 3A).

Figure 17C:
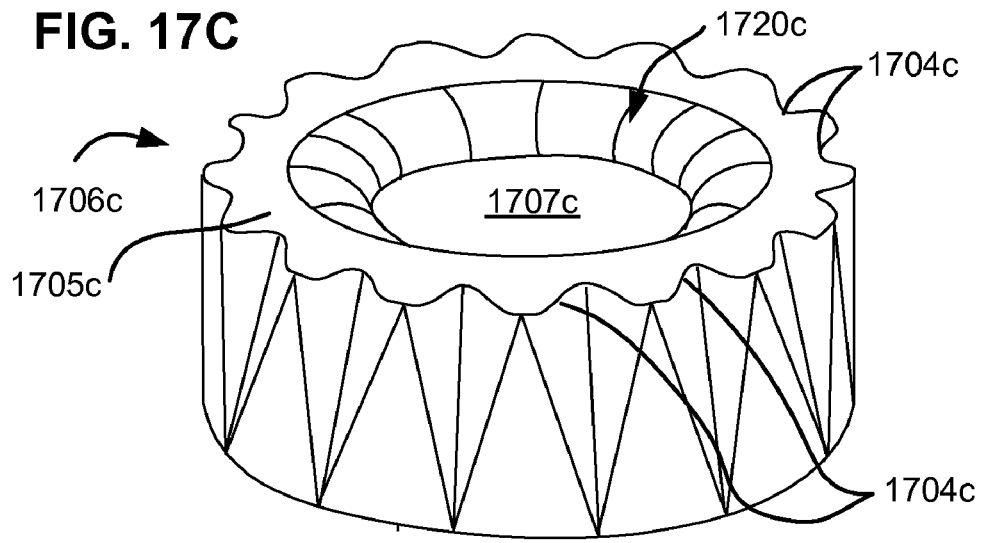
FIGS. 17C-17E show views of alternative sleeves for deflection rod assembly according to embodiments of the present invention.

FIG. 17C shows a perspective view of an alternative sleeve 1706c, also having a relief 1720c in the proximal surface surrounding the central aperture 1707c which receives deflectable post 304. The relief 1720c is curved—the curve extending from the perimeter of central aperture 1707c to the flat region 1705c of sleeve 1706c which is engaged by collar 1710 upon assembly. In this embodiment, the outer circumference of sleeve 1706c is provided with a plurality of scallops 1704c. The scallops are larger in depth at the proximal end of sleeve 1706c (top in FIG. 17C) and taper towards this distal end of sleeve 1706c (bottom in FIG. 17C). Scallops 1704c serve to make the sleeve 1706c more compliant/flexible. In the sleeve 1706c, the scallops make the proximal end of sleeve 1706c more compliant than the distal end of sleeve 1706c. This is advantageous as the geometry of deflection rod 1700 results in greater compression at the proximal end of sleeve 1706c than at the distal end of sleeve 1706c. Increasing the flexibility of the proximal end of sleeve 1706c thus serves to balance out the forces applied to the deflectable post by the proximal and distal regions of sleeve 1706c allowing for a more even distribution of loading and "work" within the sleeve 1706c. Scallops 1704c also serve to reduce the volume of material at the proximal end of sleeve 1706c. During deflection of deflectable post 304 (FIG. 17A) the sleeve 1706c can expand into the void left by scallops 1704c further reducing the possibility that sleeve 1706c will become trapped between deflectable post 304 and collar 1710.

Figure 17D:
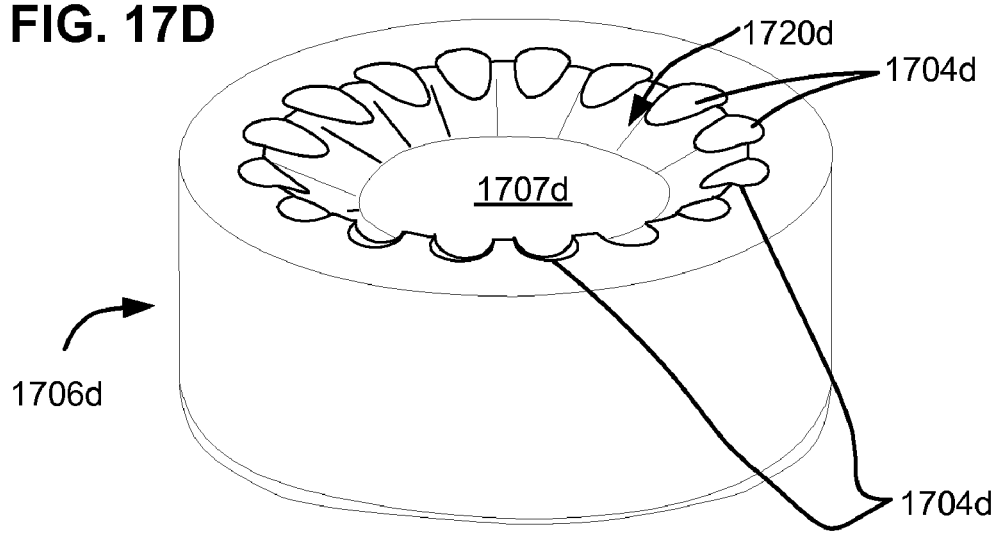

FIG. 17D shows a perspective view of another alternative sleeve 1706d. Sleeve 1706d has a relief 1720d in the proximal surface surrounding the central aperture 1707d. Relief 1720d takes the form of a conical depression in the proximal surface of sleeve 1706d. Sleeve 1706d also has a plurality of voids 1704d which penetrate from the proximal surface of sleeve 1706d into the body of sleeve 1706d along an axis parallel to the axis of central aperture 1707d. As shown in FIG. 17D, voids 1704d are circular in section. Voids 1704d may be, for example cylindrical apertures which pass all the way through sleeve 1706d. Alternatively, the voids 1704d may be cylindrical apertures which pass part of the way but not all of the way through sleeve 1706d. Alternatively, voids 1704d may be conical voids in which the size of the void diminishes as the void passes through sleeve 1706d. The voids serve similar functions as scallops 1704c of FIG. 17C. For example, voids 1704d serve to increase the compliance of the material/region of sleeve 1706d and provide space for the sleeve to be pushed into by deflectable post 304 thereby avoiding pinching between deflectable post 304 and collar 1710 (See FIG. 17A).

Figure 17E:
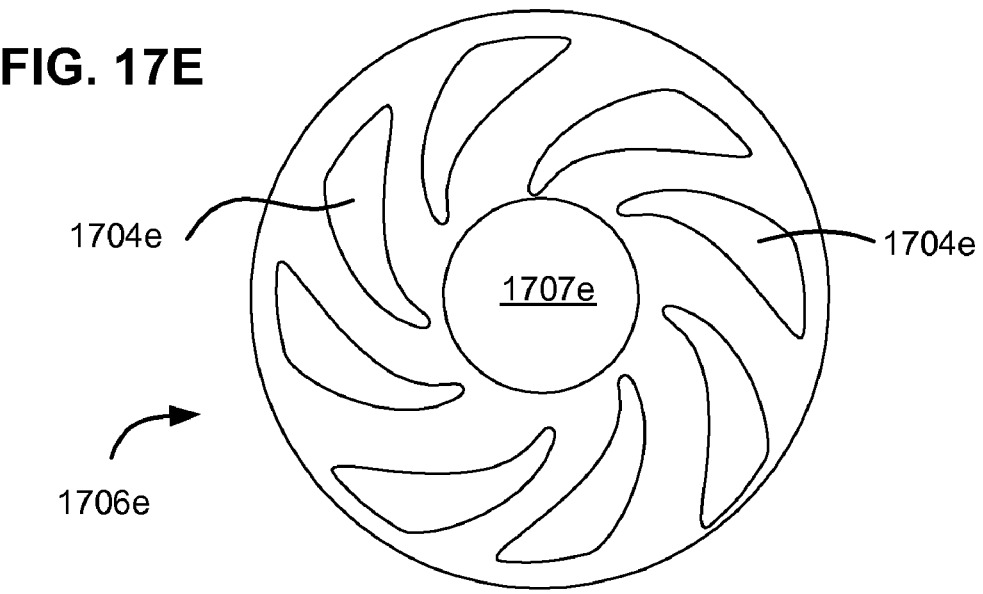

FIG. 17E shows a sectional view of another alternative sleeve 1706e. As shown in FIG. 17E, sleeve 1706e includes a plurality of voids 1704e within the body of sleeve 1706e. Voids 1706e spiral out from a position adjacent central aperture 1707e towards the outer edge of sleeve 1706e. As shown, voids 1704e may be larger towards the outer edge of sleeve 1706e where there is more material. As previously discussed voids 1704e may have a different cross-section at different levels in sleeve 1706e. For example, voids 1704e may have a larger area at the proximal end of sleeve 1706e (closest to collar 1710 of FIG. 17A) than at the distal end of sleeve (closest to retainer 302 of FIG. 17A) thereby increasing the flexibility of sleeve 1706e where deflectable post 304 has the greatest amount of deflection. The voids 1704e serve similar functions as scallops 1704c of FIG. 17C. For example, the voids 1704e serve to increase the compliance of the material/region of sleeve 1706e and provide space for the sleeve 1706e to be pushed into by deflectable post 304 thereby avoiding pinching between deflectable post 304 and collar 1710 (See FIG. 17A).

The sleeves 1706, 1706c, 1706d and 1706e show alternative configurations designed to achieve the function of controlling the movement of a deflectable post. Such sleeves may be incorporated into any of the deflection rod systems described herein. Different designs and combinations of relief and voids than those illustrated may be utilized to adjust the flexibility of the sleeve and prevent pinching of the sleeve between the deflectable post and other components of the deflection rod system.

FIGS. 18A-18D illustrate another alternative deflection rod 1800. FIG. 18A shows an exploded view of alternative deflection rod 1800. FIG. 18B shows the deflection rod assembled with a bone anchor. FIGS. 18C-18D show sectional views of deflection rod 1800 and illustrate deflection of the deflection rod. As shown in FIG. 18A, deflection rod 1800 includes four components: ball-shaped retainer 1802, deflectable post 1804, o-ring 1806, cap 1810.

Deflectable post 1804 has a retainer 1802 at one end. Retainer 1802 is a spherical structure formed in one piece with deflectable post 1804. At the other end of deflectable post 1804 is a mount 1814. Mount 1814, in this embodiment, is suitable for connecting to a vertical rod. A ball may be used in place of mount 1814 as previously described. In this embodiment, mount 1814 is also formed in one piece with deflectable post 1804 and retainer 1802. In alternative embodiments, deflectable post 1804 may be formed separately from and securely attached to one or more of mount 1814 and retainer 1802 by laser welding, soldering or other bonding technology. Alternatively, deflectable post 1804 may be formed separately and mechanically engage one or more of mount 1814 and retainer 1802 using, for example, threads. For example, a lock ring, toothed locking washer, cotter pin or other mechanical device can be used to secure deflectable post 1804 to one or more of mount 1814 and retainer 1802.

As shown in FIG. 18A, mount 1814 may be provided with a hexagonal extension 1815 which may be utilized when securing a vertical rod to mount 1814. Extension 1815 may be gripped by a wrench to prevent rotation of mount 1814 as a nut is tightened onto the threaded region of mount 1814. Extension 1815 may be formed in one piece with mount 1814. A groove 1816 between mount 1814 and extension 1815 reduces the cross-section of material such that extension 1815 breaks away from mount 1814 when a desired torque is achieved. In this way a vertical rod may be secured to mount 1814 and then extension 1815 removed.

Deflection rod 1800 is configured to be mounted in a bone anchor 1820, which comprises a bone screw 1822 connected to a housing 1830. Housing 1830 has a cavity 1832 oriented along the axis of bone anchor 1820 at the proximal end and configured to receive deflection rod 1800. Housing 1830 also has an outer surface 1834 adapted for mounting a component e.g. an offset connector. Housing 1830 may, in some embodiments, be cylindrical as previously described. As shown in FIG. 18A, outer surface 1834 of housing 1830 is provided with splines/flutes 1836. Splines/flutes 1836 may be engaged by a driver that mates with splines/flutes 1836 for implanting bone anchor 1820.

Cap 1810, in this embodiment is designed to perform multiple functions including securing o-ring 1806 as well as securing retainer 1802 in cavity 1832 of bone anchor 1820. Cap 1810, by integrating the functions of the collar and sleeve, reduces the complexity of the deflection rod 1800 and also increases the strength of the deflection rod 1800 or allows a reduction in size for the same strength. Cap 1810 comprises a cylindrical shield section 1808 connected to a collar section 1809. Cap 1810 is designed to mate with aperture 1832 of housing 1830. The shield section 1808 and collar section 1809 are preferably formed in one piece, however, they may be formed separately and then secured together. Shield section 1808 is threaded adjacent collar section 1809 in order to engage threaded aperture 1832. Cap 1810 may alternatively or additionally be joined to housing 1830 by for example laser welding.

O-ring 1806 is made of a compliant material. O-ring 1806 fits within a groove 1805 of shield 1808 of cap 1810 (see FIG. 18C). O-ring 1806 is circular in section but may also be differently shaped to modify the characteristics of o-ring 1806, including, for example, compliance (see FIGS. 8E-8G). O-ring 1806 has a central aperture 1807 through which deflectable post 1804 may be positioned. O-ring 1806 permits movement of deflectable post 1804 relative to shield 1808. The o-ring 1806 effectively controls and limits the deflection of the deflectable post 1804. O-ring 1806 is preferably made of a compliant biocompatible polymer such as PCU by way of example only. The properties of the material and dimensions of the o-ring 1806 are selected to achieve the desired force/deflection characteristics for deflectable post 1804. O-ring 1806 may be made of a compliant implantable polymer having the desired compliance and durability. For example, o-ring 1806 may be made from polycarbonate urethane. In a preferred embodiment, o-ring 1806 may be made from BIONATE®. If the o-ring 1806 is comprised of Bionate®, a polycarbonate urethane or other hydrophilic polymer, the o-ring 1806 can act as a fluid lubricated bearing.

Referring now to FIG. 18B, which shows a perspective view of a deflection rod 1800 assembled with a bone anchor 1820. When assembled, deflectable post 1804 is positioned within cap 1810 which is positioned within housing 1830 of bone anchor 1820. O-ring 1806 (not seen in this view) is first positioned within shield 1808 of cap 1810. Deflectable post 1804 is then positioned through o-ring 1806 and cap 1810. Deflectable post 1804, o-ring 1806 and cap 1810 are then positioned within the cavity 1832 of housing 1830. The cap 1810 is then secured to the threaded proximal end of cavity 1832. Cap 1810 has two sockets 1811 for receiving the pins of a pin wrench to allow cap 1810 to be tightened to housing 1830. Cap 1810 may be, alternatively or additionally, laser welded to housing 1830 after installation to secure the components. Cap 1810 secures deflectable post 1804 and o-ring 1806 within cavity 1832 of bone anchor 1820. (See FIG. 18C).

As shown in FIG. 18B, deflectable post 1804 extends out of housing 1830 and cap 1810 such that mount 1814 is accessible for connection to a vertical rod. There is a gap between deflectable post 1804 and cap 1810 which permits deflection of deflectable post 1804 through a predefined range before deflection is limited by contact with cap 1810.

FIG. 18C shows a sectional view of a deflection rod 1800 assembled with a bone anchor 1820 along the axis indicated by line C-C of FIG. 18B. Retainer 1802 fits into a hemispherical pocket 1839 in the bottom of cavity 1832 of housing 1830. The bottom edge of cap 1810 includes a flange 1815 which secures ball-shaped retainer 1802 within hemispherical pocket 1839 while allowing rotation of ball-shaped retainer 1802. Collar 1809 thereby secures both retainer 1802 and o-ring 1806 within housing 1830. If the o-ring 1806 is comprised of Bionate®, a polycarbonate urethane or other hydrophilic polymer, the o-ring 1806 can act as a fluid lubricated bearing and allow the deflectable post 1804 to also rotate about the longitudinal axis of the deflectable post 1804 and the bone anchor 1820. Other materials and configurations can also allow the post to rotate about the longitudinal axis of the post and the bone anchor.

As shown in FIG. 18C, o-ring 1806 occupies the space between deflectable post 1804 and shield 1808 of cap 1810. O-ring 1806 is secured within groove 1805 of cap 1810. O-ring 1806 may be compressed by deflection of deflectable post 1804 towards shield 1808 in any direction. O-ring 1806 is circular in section and this configuration avoids pinching of o-ring 1806 between deflectable post 1804 and shield 1808. The circular section or o-ring 1806 reduces the area of contact between deflectable post 1804 and o-ring 1806 thereby reducing wear. O-ring 1806 may be slightly larger than the space between the deflectable post and the bottom of groove 1805. This provides preload which reduces slack in the deflection characteristics of the deflection rod 1800. The preload is also useful to reduce the occurrence of slack if the o-ring becomes worn during use.

FIG. 18D illustrates the deflection of deflectable post 1804. Applying a force to mount 1814 causes deflection of deflectable post 1804 of deflection rod 1800. Initially deflectable post 1804 pivots about a pivot point 1803 indicated by an X. Deflectable post 1804 may pivot about pivot point 1803 in any direction. Concurrently or alternatively, deflectable post 1804 can rotate about the long axis of deflectable post 1804 (which also passes through pivot point 1803). In this embodiment, pivot point 1803 is located at the center of ball-shaped retainer

1802. As shown in FIG. 18D, deflection of deflectable post 1804 compresses the material of o-ring 1806. O-ring 1806 is compressed into groove 1805. Groove 1805 may be slightly wider than necessary to accommodate o-ring 1806 in order that o-ring 1806 may expand axially while being compressed radially. The extra space in groove 1805 reduces the possibility that o-ring 1806 will become pinched between deflectable post 1804 and the inside of cap 1810. The force required to deflect deflectable post 1804 depends upon the dimensions of deflectable post 1804, o-ring 1806, groove 1805 and shield 1808 of cap 1810 as well as the attributes of the material of o-ring 1806. The o-ring exerts a centering force back on deflectable post 1804 pushing it back towards a position coaxial with bone anchor 1820.

After further deflection, deflectable post 1804 comes into contact with limit surface 1813 of collar 1809. Limit surface 1813 is oriented such that when deflectable post 1804 makes contact with limit surface 1813, the contact is distributed over an area to reduce stress on deflectable post 1804. After deflectable post 1804 comes into contact with limit surface 1813, further deflection requires deformation (bending) of deflectable post 1804. In a preferred embodiment, deflectable post 1804 is a titanium post 5 mm in diameter. Deflectable post 1804 is relatively stiff, and the force required to deflect deflectable post 1804 therefore increases significantly after contact of deflectable post 1804 with cap 1810. In a preferred embodiment, deflectable post 1804 may deflect from 0.5 mm to 2 mm in any direction before making contact with limit surface 1813. More preferably, deflectable post 1804 may deflect approximately 1 mm before making contact with limit surface 1813.

The inner diameter of the cap 1810 may be different in different caps so that the distance between limit surface 1813 and deflectable post 1804 is different in different deflection rods. This allows for the manufacture of deflection rods having a larger or smaller range of deflection before contact between the post 1804 and the limit surface 1813. In this way deflection rods may be manufactured having different ranges of motion. Moreover the distance between limit surface 1813 and deflectable post 1804 need not be the same in all directions such that the range of motion of the deflection rod is different in different directions.

Referring to FIG. 18D, as load or force is first applied to the deflection rod 1800 by the spine, the deflection of deflectable post 1804 responds about linearly to the increase in the load during the phase when deflection of deflectable post 1804 causes compression of o-ring 1806. After about 1 mm of deflection, deflectable post 1804 contacts limit surface 1813 and the deflection rod becomes substantially stiffer. A greater amount of load or force needs to be placed on the deflection rod in order to obtain the same amount of incremental deflection that was realized prior to this point because further deflection requires bending of deflectable post 1804. The amount of deflection caused by the load applied is a non-linear function, in this embodiment. The deflection rod provides a range of motion where the load supported increases about linearly as the deflection increases and then with increased deflection the load supported increases more rapidly (upon contact of the post with the limit surface). Alternatively, if desired, this embodiment could be designed such that the rate of change of the amount of deflection could be a linear function for a larger range of motion by; for example, increasing the distance between limit surface 1813 and deflectable post 1804.

Figure 18E:
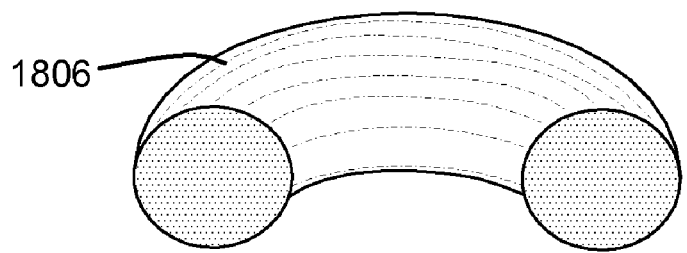
FIG. 18E is a partial sectional view of the o-ring of FIG. 18A.
Figure 18F:
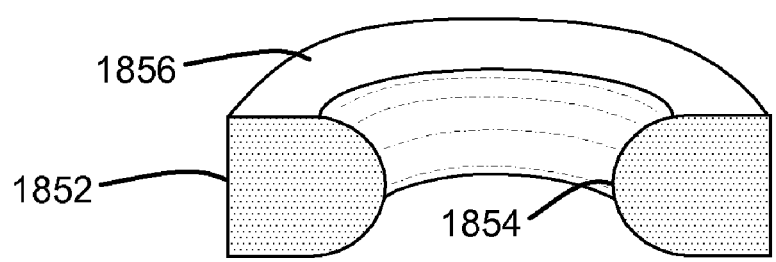
FIG. 18F is a partial sectional view of an alternative o-ring.

FIG. 18E shows a partial sectional view of o-ring 1806. As shown in FIG. 18E, o-ring 1806 is circular in section. The circular section helps reduce the area of contact with deflectable post 1804 (See (FIGS. 18A-18B). The reduced contact results in less wear. However, the o-ring may have different shapes. As shown in FIG. 18F, an o-ring 1856 may have a flat outer edge 1852 for engaging groove 1805 of cap 1810 while still having a curved inner edge 1854 for engaging deflectable post 1804. An o-ring 1856 of this design would be less compliant than o-ring 1806, all other factors being equal. Thus, o-ring 1806 would exert a greater return force upon a deflectable post 1804 for the same amount of deflection.

Figure 18G:
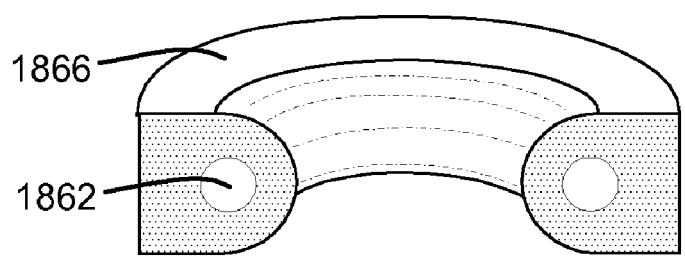
FIG. 18G is a partial sectional view of another alternative o-ring.

As shown in FIG. 18G, the compliance of an o-ring 1866 may also be modified by having a void 1862 (or voids) within o-ring 1866. The voids may contain gas or other fluid and thereby provide pneumatic or hydraulic force/deflection characteristics. As previously discussed, o-rings may be designed that exhibit anisotropic force deflection characteristics by for example having anisotropic variations in shape or material.

Figure 18H:
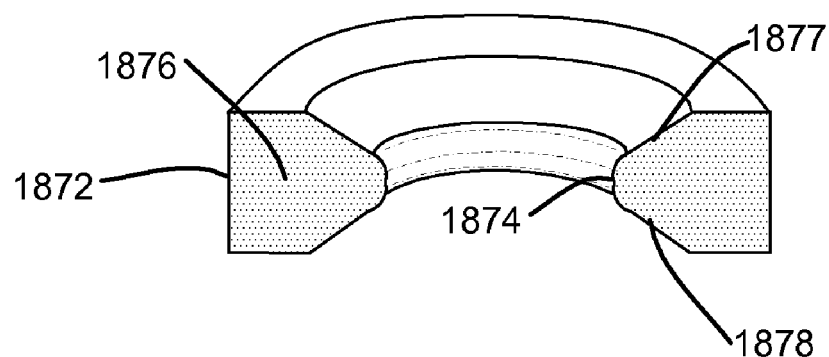
FIG. 18H is a partial sectional view of another alternative o-ring.

FIG. 18H shows another alternative o-ring 1876. O-ring 1876 has a flat outer edge 1872 for engaging groove 1805. O-ring 1876 has a curved inner edge 1874 for engaging deflectable post 1804. O-ring 1876 also has angled reliefs 1877, 1878, one either side of inner edge 1874, which serve to reduce the area of contact between o-ring 1876 and deflectable post 1804.

Figure 19A:
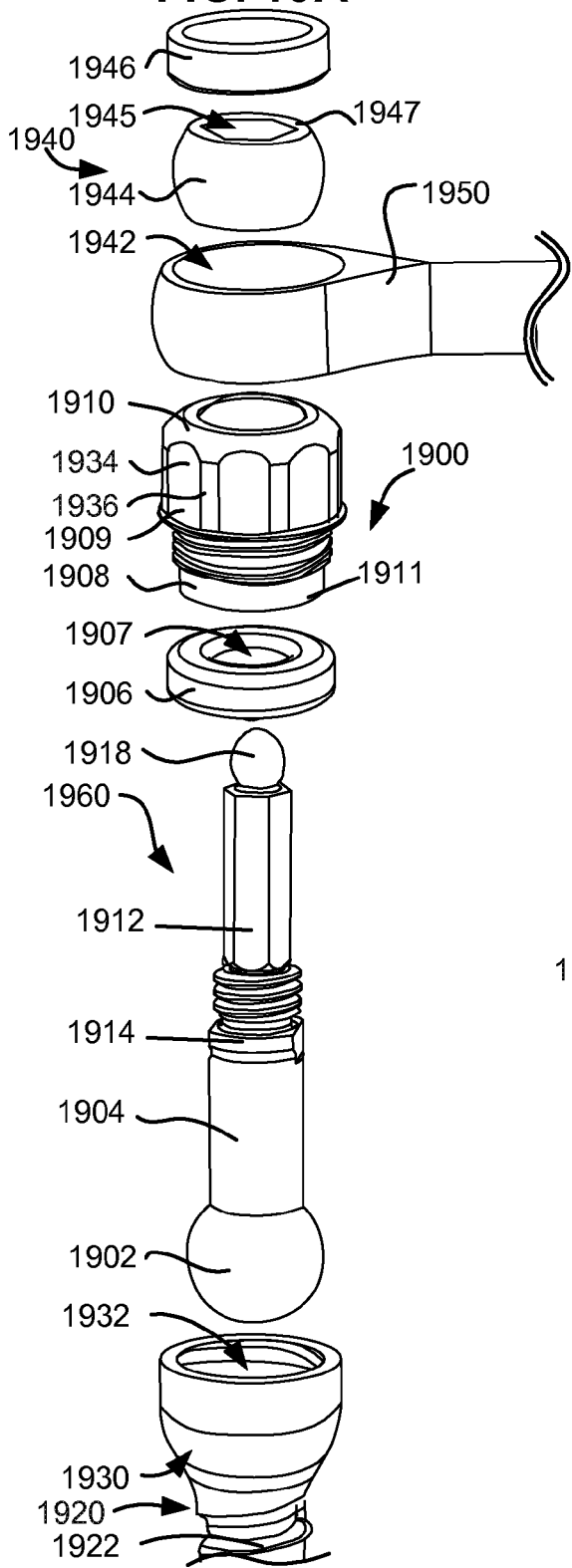
FIG. 19A is an exploded view of an alternative deflection rod assembly according to a preferred embodiment of the present invention.
Figure 19B:
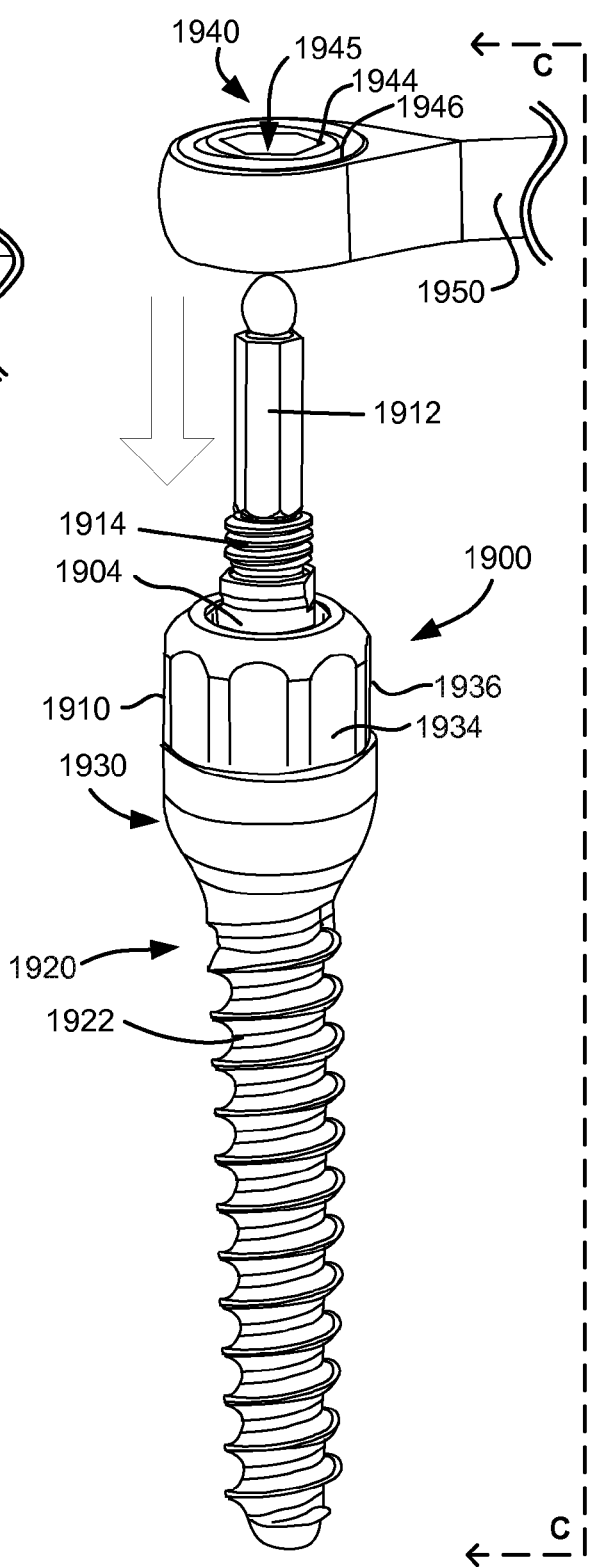
FIG. 19B is a perspective view of the deflection rod assembly of FIG. 19A, as assembled.
Figure 19E:
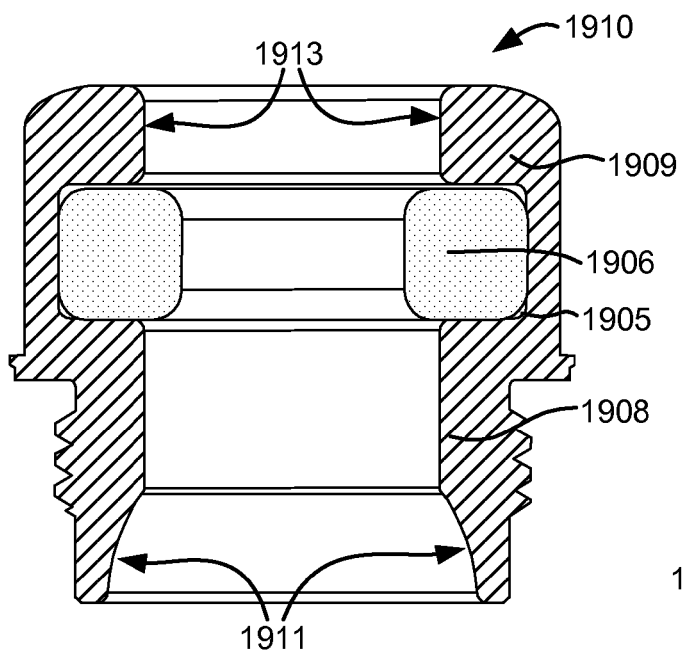
FIGS. 19E-19G show enlarged views of components of the deflection rod assembly of FIGS. 19A-19D.
Figure 19F:
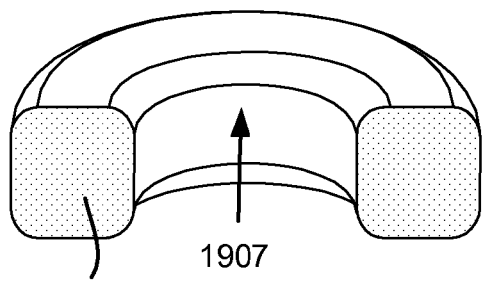

FIGS. 19A-19D illustrate a preferred embodiment of a bone anchor for dynamic stabilization of the spine having an in-line deflection rod assembly 1900 built into a bone anchor 1920. FIGS. 19A-19D also show a preferred embodiment of a dynamic vertical rod 1950 for use with the deflection rod assembly 1900. FIG. 19A shows an exploded view of dynamic vertical rod 1950 and deflection rod assembly 1900 built into a bone anchor 1920. FIG. 19B shows the deflection rod assembled with a bone anchor and dynamic vertical rod. FIGS. 19C-19D show sectional views of deflection rod assembly 1900 and illustrate deflection of the deflection rod. FIGS. 19E and 19F show enlarged views of components of deflection rod assembly 1900.

Referring now to FIG. 19A, deflection rod assembly 1900 includes, in this embodiment, four components: ball-shaped retainer 1902, deflectable post 1904, o-ring 1906 and cap 1910. Retainer 1902 and deflectable post 1904 form the ball rod 1960 as shown in FIG. 19b and will be discussed herein. Deflection rod assembly 1900 is configured to be mounted in a bone anchor 1920, which comprises a bone screw 1922 connected to a housing 1930. Housing 1930 has a cavity 1932 oriented along the axis of bone anchor 1920 at the proximal end and configured to receive deflection rod assembly 1900. In this embodiment, housing 1930 is truncated relative to the bone anchor 1820 of FIG. 18A. Housing 1930 and bone anchor 1920 are preferably formed in one piece from titanium or titanium alloy.

Deflectable post 1904 has a retainer 1902 at one end. Retainer 1902 is a spherical structure formed in one piece with deflectable post 1904. At the other end of deflectable post 1904 is a mount 1914. As shown in FIG. 19A, mount 1914 is a low profile mount configured to fit within a ball joint 1940 of a vertical rod component. Mount 1914 is configured to be secured to a spinal vertical rod component and comprises a threaded cylinder to which the vertical rod component may be secured. An integrated ball may be used in place of mount 1914 as previously described. Mount 1914 includes a male hex extension 1912 which may be engaged by a tool to hold mount 1914 during attachment to a vertical rod. At the proximal end of male hex extension is a feature for securing hex extension 1912 in a tool, in this embodiment a nipple 1918. In a preferred embodiment mount 1914, deflectable post 1904, retainer 1902, hex extension 1912 and nipple 1918 are made in one piece from cobalt chrome allowing for enhanced wear characteristics. Alternatively, titanium or titanium alloy may be used either alone or with a cobalt chrome coating. The combination of mount 1914, deflectable post 1904 and retainer 1902 may be referred to as a ball rod 1960.

Figure 19G:
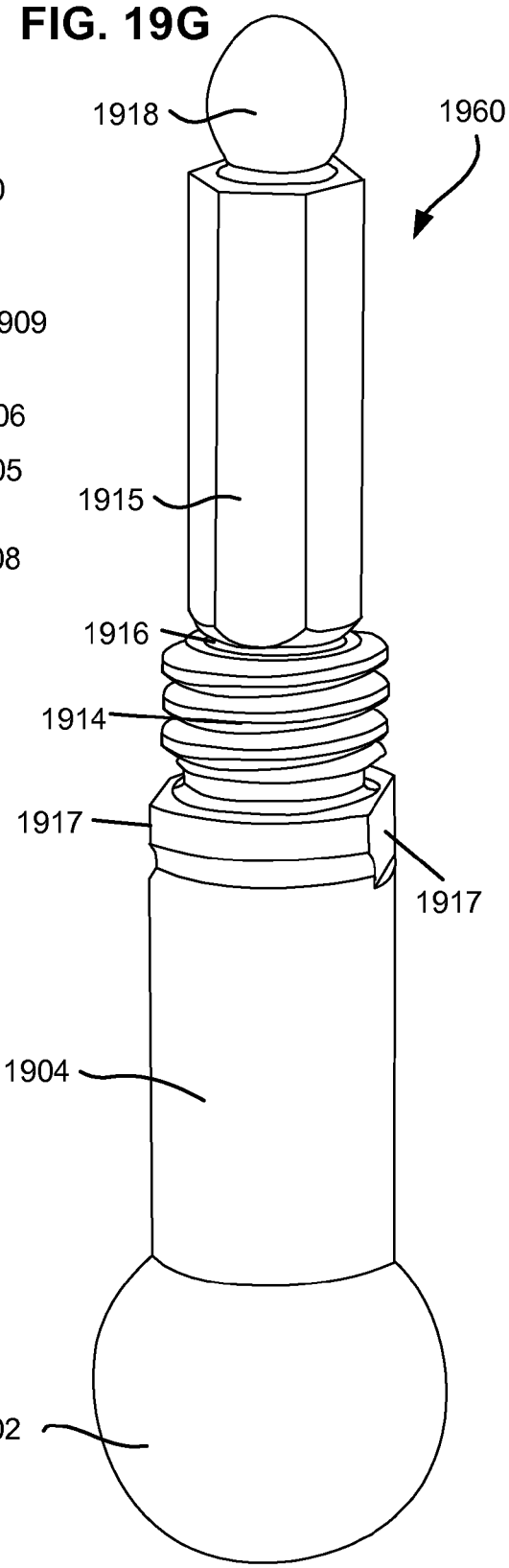

FIG. 19G shows an enlarged perspective view of ball rod 1960. Referring to FIG. 19G, ball rod 1960 is formed in one piece with four main sections, which are, starting from the distal end, ball-shaped retainer 1902, deflectable post 1904, mount 1914 and hex extension 1912. It should be noted that hex extension 1912 also comprises the nipple 1918 on the most proximal end. Hex extension 1915 is breakaway component and nipple 1918 allows hex extension 1915 to be secured by a tool upon breakaway. Where hex extension 1912 meets mount 1914 is a groove 1916. Groove 1916 reduces the diameter of ball rod 1960 such that hex extension 1912 breaks away from mount 1914 when a desired level of torque is reached during attachment of a vertical rod. The breakaway torque is determined by the diameter of remaining material and the material properties. In a preferred embodiment the breakaway torque is approximately 30 foot pounds. Thus, hex extension 1912 breaks away during implantation and is removed. If mount 1914 needs to be removed from a vertical rod, it is necessary to grip another area of the ball rod 1960. Thus, deflectable post 1904 is provided with flats 1917 immediately adjacent mount 1914. Flats 1917 allow ball rod 1960 to be engaged by a tool to remove a vertical rod after hex extension 1912 has been removed.

Referring again to FIG. 19A, a cap 1910, in this embodiment is designed to perform multiple functions including securing o-ring 1906 as well as securing retainer 1902 in cavity 1932 of bone anchor 1920. Cap 1910 is also larger than cap 1810 of FIG. 18A. In the embodiment of FIG. 19A, cap 1910 has an outer surface 1934, with the below discussed splines/flutes 1936, adapted for mounting a component, e.g. an offset connector. Housing 1930 may in some embodiments be cylindrical as previously described. As shown in FIG. 19A, outer surface 1934 of housing 1930 is provided with the splines/flutes 1936. Splines/flutes 1936 may be engaged by a driver that mates with splines/flutes 1936 for implanting bone anchor 1920. Cap 1910, by integrating the functions of the collar and sleeve, reduces the complexity of the deflection rod assembly 1900 and also increases the strength of the deflection rod assembly 1900 or allows a reduction in size for the same strength. Cap 1910 is preferably formed in one piece of titanium or titanium alloy.

As shown in FIG. 19A, cap 1910 comprises a cylindrical shield section 1908 connected to a collar section 1909. Cap 1910 is designed to mate with cavity 1932 of housing 1930. Shield section 1908 is threaded adjacent collar section 1909 in order to engage threaded aperture 1932 of housing 1930. The distal end of shield section 1908 comprises a flange 1911 for securing ball 1902 within housing 1930. FIG. 19E shows a detailed view of cap 1910 in partial section. As shown in FIG. 19E, flange 1911 at the distal end of cylindrical shield section 1908 has a curved surface having the same radius of curvature as ball 1902. The curved surface of flange 1911 in combination with the pocket 1932 in housing 1930 forms a spherical pocket which traps ball 1902 in a manner that allows pivoting and rotation. Inside the central bore of cap 1910 is a circumferential groove 1905 designed to hold an o-ring 1906. Groove 1905 is cut within the interior of collar section 1909. At the distal end of collar section 1909 are the limit surfaces 1913. Groove 1905 is shaped to support o-ring 1906, reduce wear to o-ring 1906 and reduce creep of the o-ring over time. In this embodiment groove 1905 has a rectangular section.

Referring again to FIG. 19A, an o-ring 1906 fits within shield 1908 of cap 1910 between deflectable post 1904 and cap 1910. In a preferred embodiment o-ring 1906 is a ring with a radiussed square section. O-ring 1906 has a round central aperture 1907. Aperture 1907 is slightly smaller than the diameter of deflectable post 1904 to provide some preload on assembly. FIG. 19F shows a detailed view of o-ring 1906 in partial section. FIG. 19E shows o-ring 1906 in position with circumferential groove 1905 of cap 1910. Note that the external diameter of o-ring 1906 is larger than the interior bore diameter of shield 1908/cap 1910. Thus, o-ring 1906 is compressed during assembly and expands within groove 1905 thereby being retained by groove 1905. Note also that the interior diameter of aperture 1907 is smaller than the diameter of the bore of shield 1908 so that o-ring 1906 protrudes from groove 1905 into the bore around deflectable post 1904 (see FIGS. 19C and 19D). This o-ring 1906 is formed by a compliant member that is compressed by deflection of deflectable post 1904. In a preferred embodiment o-ring 1906 is made from polycarbonate urethane (Bionate® 55D or 80A). But other biocompatible polymers with suitable compliance and durability may be used. This material is further described in U.S. Pat. No. 5,133,742, issued Jul. 28, 1992, and entitled and U.S. Pat. No. 5,229,431, issued Jul. 20, 1993, and entitled "Crack-Resistant Polycarbonate Urethane Polymer Prostheses and the Like," both of which are incorporated herein by reference. The o-ring 1906 in FIG. 19F has a preferred shape of flat sides and rounded corners that are transitioned between the flat sides. The flat sides allow the o-ring to fit more securely in groove 1905 and thus distribute the load placed thereon by ball rod 1960 more evenly to reduce wear, creep and deformation of the o-ring. One reason for these advantages is that the flat sides provide more contact surface with the groove 1905 in the cap 1910 and more contact surface with the ball rod 1960.

FIG. 19A also shows the components of a preferred embodiment of a dynamic vertical rod 1950 for use with deflection rod assembly 1900. Dynamic vertical rod 1950 includes a ball 1944 and race 1946. Ball 1944 is preferably made of cobalt chrome alloy for better wear. Ball 1944 may alternatively be made of titanium or titanium alloy with a cobalt chrome coating. Ball 1944 has a central aperture 1945 designed to be secured to mount 1914. Central aperture 1945 is threaded to enable ball 1944 to be secured to the threads of mount 1914. Central aperture 1945 also has a female hex socket 1947 which may mate with a wrench and by which ball 1944 may be tightened to the threaded end of mount 1914. Ball 1944 is received in a spherical pocket 1942 in the end of vertical rod 1950. Ball 1944 is secured in spherical pocket 1942 by race 1946. Race 1946 is secured to vertical rod 1950 by, for example, threads and/or laser welding. When secured, ball 1944 may rotate and pivot in the spherical pocket 1942. Advantageously, there is no nut extending beyond ball 1944 thus reducing the profile of the connection between mount 1914 and vertical rod 1950. To put it another way, the ball 1944 acts as its own nut to secure ball 1944 to mount 1914. Ball joint 1940 allows greater range of motion and reduces torsional stresses on the dynamic stabilization assembly and the bones to which it is attached.

Referring now to FIG. 19B, which shows a perspective view of a deflection rod assembly 1900 assembled with a bone anchor 1920 having a bone screw 1922. When assembled, deflectable post 1904 is positioned within cap 1910 which is positioned within housing 1930 of bone anchor 1920. O-ring 1906 (not seen in this view) is first positioned within shield 1908 of cap 1910. O-ring 1906 is compressed during introduction to cap 1910 and expands into a groove 1905 within cap 1906 (see FIGS. 19C and 19D). A mandrel is used during insertion to prevent damage to o-ring 1906. Deflectable post 1904 is then positioned through o-ring 1906 and cap 1910 with mount 1914 extending from the proximal end of cap 1910. Deflectable post 1904, o-ring 1906 and cap 1910 are then positioned within the cavity 1932 of housing 1930. The cap 1910 is then secured to the threaded proximal end of cavity 1932. Cap 1910 may alternatively or additionally be laser welded to housing 1930 after installation to secure the components. Cap 1910 secures deflectable post 1904 and o-ring 1906 within cavity 1932 of bone anchor 1920 (see FIGS. 19C and 19D). Deflectable post 1904 extends out of housing 1930 and cap 1910 such that mount 1914 is accessible for connection to a vertical rod 1950.

Deflection rod assembly 1900 and bone anchor 1920 are assembled prior to implantation and then implanted in a bone prior to attachment of a dynamic vertical rod or other spinal rod. A special tool may be used to engage cap 1910 during implantation (See FIGS. 20A-20D). Cap 1910 has surface features 1936 for engagement by a wrench to allow cap 1910 to be tightened to housing 1930. For example, cap 1910 may be hexagonal or octagonal in shape or may have splines and/or flutes and/or other registration elements on the surface 1934.

FIG. 19B also shows a perspective view of dynamic vertical rod 1950 secured to deflection rod assembly 1900. Dynamic vertical rod 1950 is assembled by placing ball 1944 in pocket 1942 of rod 1950. Race 1946 is then secured into pocket 1942 by threads and/or laser welding. Once assembled ball 1944 is free to pivot and rotate with the spherical pocket of dynamic vertical rod 1950. Central aperture 1945 is accessible from either end of pocket 1942 for attachment of deflectable post 1904. To attach the dynamic deflection rod assembly 1950 to deflectable post 1904, ball 1944 is threaded onto the threads of mount 1914 and tightened into place with a special tool (see FIGS. 21A-21D). Hex extension 1912 breaks away when sufficient torque is applied to lock ball 1944 to mount 1914 and hex extension 1912 is then removed.

FIG. 19C shows a sectional view of a deflection rod assembly 1900 assembled with a bone anchor 1920 along the axis indicated by line C-C of FIG. 19B. Retainer 1902 fits into a hemispherical pocket 1939 in the bottom of cavity 1932 of housing 1930. The bottom edge of cap 1910 includes a curved flange 1911 which secures ball-shaped retainer 1902 within hemispherical pocket 1939 while allowing rotation of ball-shaped retainer 1902. As shown in FIG. 19C, o-ring 1906 occupies the space between deflectable post 1904 and shield 1908 of cap 1910. O-ring 1906 is secured within groove 1905 of cap 1910. Cap 1910 thereby secures both retainer 1902 and o-ring 1906 within housing 1930. O-ring 1906 may be compressed by deflection of deflectable post 1904 towards shield 1908 in any direction. Deflectable post 1904 may pivot about ball-shaped retainer 1902 up to 1 mm in any direction before contacting cap 1910 (approximately 3 degrees in a preferred embodiment). Dashed line 1937 shows the approximate level of the bone surface when bone anchor 1920, having a bone screw 1922, is implanted. In a preferred embodiment the distance H representing the height of mount 1914 (and thus dynamic vertical rod 1950) above the bone surface is 16 mm. Also shown in FIG. 19C is dynamic vertical rod 1950. Dynamic vertical rod has been secured to deflectable post 1904 by securing ball 1944 to mount 1914.

FIG. 19D illustrates the deflection of deflectable post 1904. Applying a force to mount 1914 through vertical rod 1950 and ball joint 1940 causes deflection of deflectable post 1904 of deflection rod assembly 1900. Initially, deflectable post 1904 pivots about a pivot point 1903 indicated by an X. Deflectable post 1904 may pivot about pivot point 1903 in any direction. Concurrently or alternatively, deflectable post 1904 can rotate about the long axis of deflectable post 1904 (which also passes through pivot point 1903). In this embodiment, pivot point 1903 is located at the center of ball-shaped retainer 1902. As shown in FIG. 19D, deflection of deflectable post 1904 compresses the material of o-ring 1906. O-ring 1906 is compressed into groove 1905. Groove 1905 may be slightly wider than necessary to accommodate o-ring 1906 in order that o-ring 1906 may expand axially while being compressed radially. The extra space in groove 1905 reduces the possibility that o-ring 1906 will become pinched between deflectable post 1904 and the inside of cap 1910. The force required to deflect deflectable post 1904 depends upon the dimensions of deflectable post 1904, o-ring 1906, groove 1905 and shield 1908 of cap 1910 as well as the attributes of the material of o-ring 1906. The o-ring 1906 exerts a centering force back on deflectable post 1904 pushing it back towards a position coaxial with bone anchor 1920. Note that due to ball joint 1940, vertical rod 1950 may also pivot relative to deflectable post 1904 and rotate relative to deflectable post 1904 without compressing o-ring 1906.

After further deflection, deflectable post 1904 comes into contact with limit surface 1913 of collar section 1909 of cap 1910. Limit surface 1913 is oriented such that when deflectable post 1904 makes contact with limit surface 1913, the contact is distributed over an area to reduce stress on deflectable post 1904. After deflectable post 1904 comes into contact with limit surface 1913, further deflection requires deformation (bending) of deflectable post 1904. In a preferred embodiment, deflectable post 1904 is a titanium post 5 mm in diameter. Deflectable post 1904 is relatively stiff, and the force required to deflect deflectable post 1904 therefore increases significantly after contact of deflectable post 1904 with cap 1910. In a preferred embodiment, deflectable post 1904 may deflect from 0.5 mm to 2 mm in any direction before making contact with limit surface 1913. More preferably, deflectable post 1904 may deflect approximately 1 mm before making contact with limit surface 1913.

Implantation and Assembly Tools

FIGS. 20A-20D and 21A-21F show various steps in the implantation and connection of a dynamic stabilization assembly utilizing embodiments of the dynamic bone anchor and dynamic vertical rod described herein. The implantation and assembly is preferably performed in a minimally invasive manner and, thus, tools are provided to facilitate installation and assembly through cannulae. These tools can also be used in open procedures. One suitable minimally invasive approach to the lumbar spine is the paraspinal intermuscular approach. This approach is described for example in "The Paraspinal Sacraspinalis-Splitting Approach to the Lumber Spine," by Leon L. Wiltse et al., *The Journal of Bone & Joint Surgery*, Vol. 50-A, No. 5, July 1968, which is incorporated herein by reference. In general the patient is positioned prone. Incisions are made posterior to the vertebrae to be stabilized. The dorsal fascia is opened and the paraspinal muscle is split to expose the facet joints and lateral processes of the vertebra. Dynamic bone anchors according to embodiments of the present invention and conventional pedicle screws are placed in the vertebrae as necessary for the selected assembly. The screws are placed lateral to the facet joints and angled in towards the vertebral body. The dynamic rods according to embodiments of the present invention are then inserted into position adjacent the dynamic bone anchors according to embodiments of the present invention, screws and conventional pedicle screws. The balls of the dynamic rods according to embodiments of the present invention are then secured to the deflectable posts of the dynamic bone anchors according to embodiments of the present invention the other end of the dynamic rod is then connected to the conventional screws with the desired interpedicular distance. The implantation of the dynamic bone anchors and connection of the dynamic rods can be facilitated by the implantation tool (FIGS. 20A-20D) and connection tool (FIGS. 21A-21F) described below.

Figure 20A:
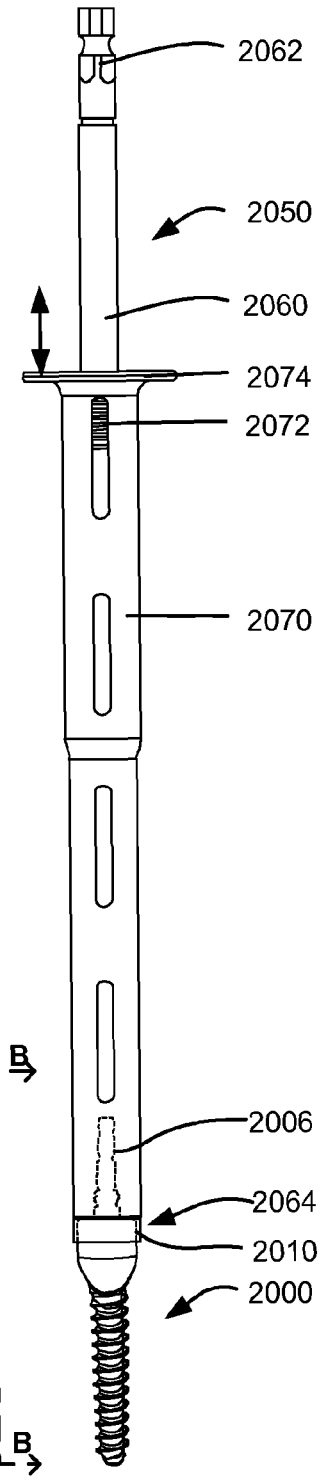
FIG. 20A shows a perspective view of an implantation tool for a dynamic bone anchor according to an embodiment of the invention.

FIG. 20A shows a perspective view of an implantation tool 2050 for use in implanting a dynamic bone anchor 2000. Dynamic bone anchor 2000 may for example be the assembly of deflection rod assembly 1900 and bone anchor 1920 as shown in FIG. 19B. Implantation tool 2050 includes an inner shaft 2060 received within a tubular sleeve 2070. Inner shaft 2060 is free to rotate within sleeve 2070. Sleeve 2070 may also be slid towards the proximal end of inner shaft 2060 by pulling on grip 2074. A coil spring 2072 is connected between the sleeve 2070 and inner shaft 2060 to hold sleeve 2070 in its more distal position relative to shaft 2060. The length and diameter of implantation tool 2050 is selected so as to allow use through a cannula in a minimally invasive surgical technique thereby reducing disruption of tissues adjacent the implantation site, reducing patient recovery and improving surgical outcomes.

Referring again to FIG. 20A, shaft 2060 has at a proximal end a quick release mount 2062 to which a handle (not shown) may be attached for turning inner shaft 2060. Suitable handles for attachment to shaft 2060 include ratcheting handles, torque sensing handles and torque limiting handles. In alternative embodiments, a handle may be permanently connected to or integrated with the proximal end of shaft 2062. Inner shaft has at a distal end a head 2064. Head 2064 includes means for engaging and securing dynamic bone anchor 2000 during implantation as is described below.

As also shown in FIG. 20A, head 2064 can be received over the proximal portion of dynamic bone anchor 2000 with the ball rod 2006 received within shaft 2060 (see dashed line). In use, dynamic bone anchor 2000 is inserted into the head 2064 of shaft 2060 with the cap 2010 engaged by head 2064 and the ball rod 2006 secured within head 2064. Dynamic bone anchor 2000 is thus secured to implantation tool 2050. Dynamic bone anchor 2000 will not be released unless and until the surgeon pulls back on grip 2074. Thus, dynamic bone anchor 2000 and implantation tool can be inserted as one unit through a cannula to the implantation location in the spine facilitating the positioning and implantation of dynamic bone anchor 2000.

Figure 20B:
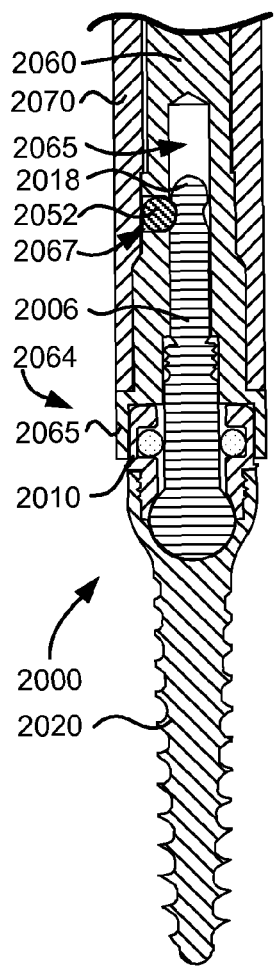
FIGS. 20B and 20C show detailed sectional views of the head of the implantation tool of FIG. 20A in relation to a dynamic bone anchor.

FIG. 20B shows a detailed sectional view of the head 2064 of the implantation tool 2050 of FIG. 20A engaged with a dynamic bone anchor 2000. As shown in FIG. 20B, head 2064 includes a socket 2065 for receiving and engaging cap 2010 of dynamic bone anchor 2000. Socket 2065 is designed to mate with cap 2010 in order to rotate the threaded shank 2020 of dynamic bone anchor 2000. Thus, the interior of socket 2065 may be hexagonal, octagonal or provided with flutes/splines etc., depending on the particular configuration of the cap 2010. Socket 2065 should be able to apply sufficient torque to cap 2010 to implant the dynamic bone anchor 2000 in a pedicle.

Referring again to FIG. 20B, head 2064 also includes a bore 2065 for receiving ball rod 2006 of dynamic bone anchor. As shown in FIG. 20B, ball rod 2006 includes a nipple 2018 at the proximal end. A ball 2052 is positioned within an aperture 2067 which passes from the exterior of shaft 2060 intersecting bore 2065 adjacent nipple 2018. Ball 2052 is held by sleeve 2070 in a position in which ball 2052 protrudes into bore 2065 so as to trap nipple 2052 within bore 2065. In a preferred embodiment, there are three such balls, however, only one is shown in this sectional view. Thus, cap 2010 is received in socket 2065 and dynamic bone anchor 2000 is locked to implantation tool 2050 by the interaction of nipple 2018 and ball(s) 2052.

Figure 20C:
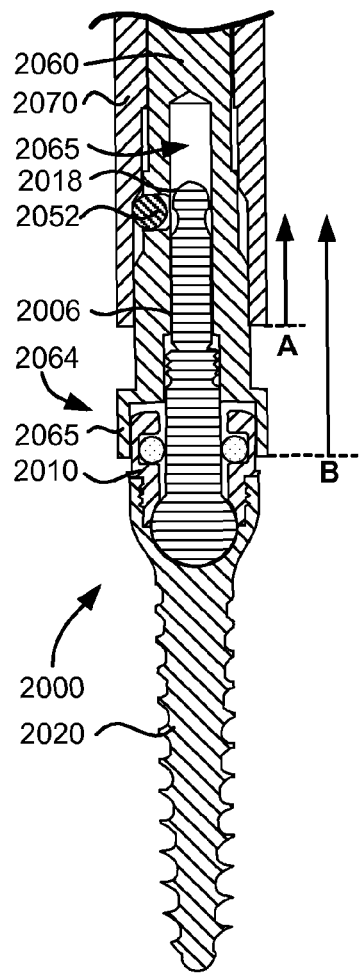

FIG. 20C shows a detailed sectional view of the head 2064 of the implantation tool 2050 of FIG. 20A configured to release a dynamic bone anchor 2000. After implantation of dynamic bone anchor 2000 it is necessary to remove implantation tool 2050. The first step is to slide sleeve 2070 proximally relative to shaft 2060 as shown by arrow A. This is achieved by pulling back on grip 2074 against the force of spring 2072 (See FIG. 20A). As sleeve 2060 is pulled proximally, ball(s) 2052 enters a portion of sleeve 2060 with a larger internal diameter. Ball(s) 2052 can move away from engagement with ball rod 2006 as they pass ramp 2065 releasing nipple 2018. At this stage both shaft 2060 and sleeve 2070 can be pulled together away from dynamic bone anchor 2000.

Figure 20D:
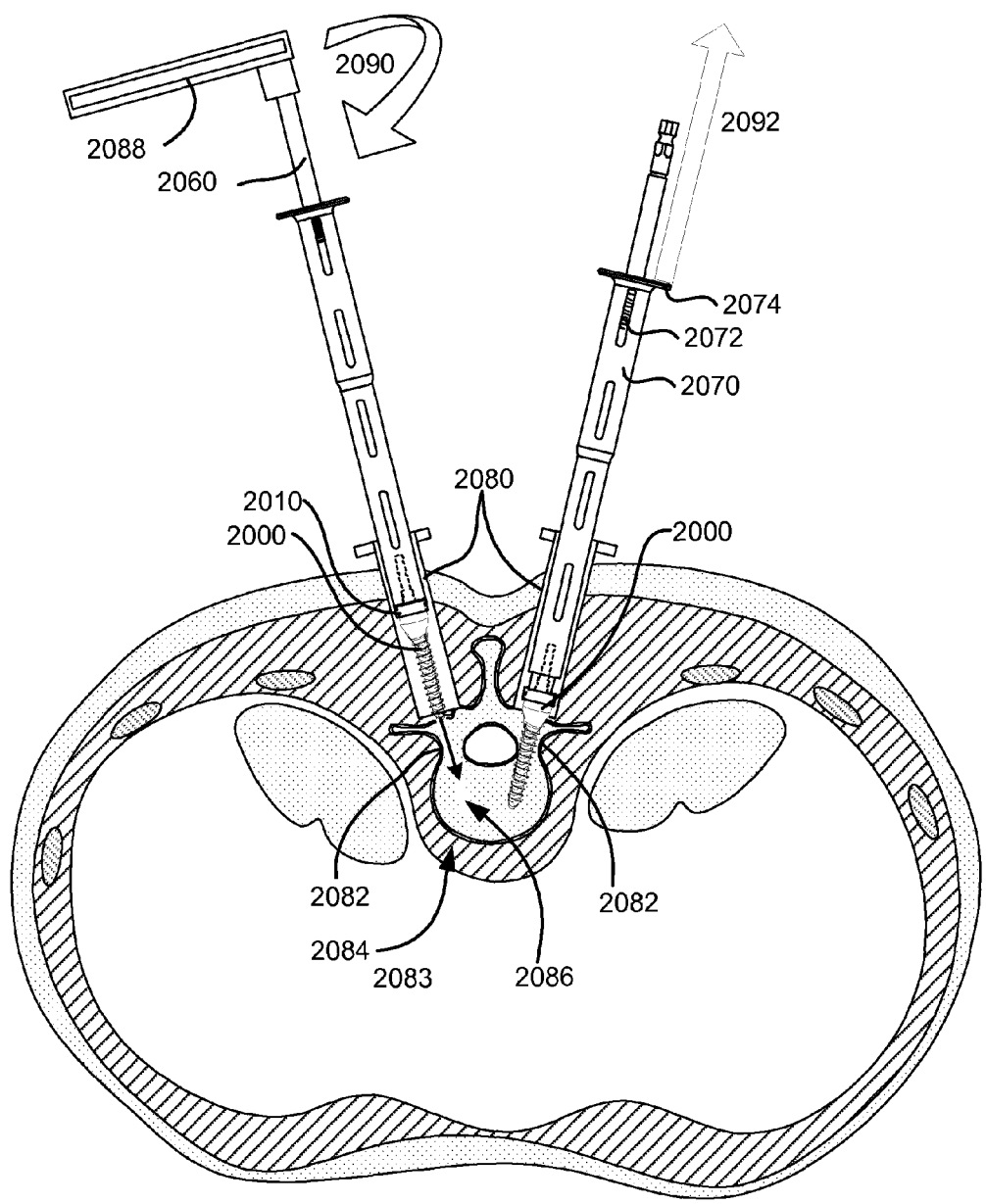
FIG. 20D is a transverse view of the lumbar spine illustrating use of the implantation tool of FIG. 20A to implant a dynamic bone anchor in the pedicles of a lumbar vertebra according to an embodiment of the invention.

FIG. 20D shows a transverse view of the lumbar spine illustrating use of the implantation tool 2050 of FIG. 20A to implant dynamic bone anchors 2000 in the pedicles 2082 of a lumbar vertebra 2084 according to an embodiment of the invention. As shown in FIG. 20D, implantation tool 2050 may be used through a cannula 2080 to implant the dynamic bone anchor in a minimally invasive procedure. The cannula 2080 is introduced to the patient to approach the pedicles posteriorly. The pedicle 2082 of the vertebra is 2084 is exposed in the conventional fashion. A hole 2086 is then drilled through the pedicle 2082 into the vertebral body 2083 of the vertebra. Next a dynamic bone anchor 2000 is selected having of suitable length, diameter and force/deflection characteristics is selected for implantation. The cap 2010 of the selected dynamic bone anchor 2000 is inserted into the head 2064 of implantation tool 2050 and secured in place.

Referring now to the left side of FIG. 20D, dynamic bone anchor 2000 and implantation tool 2050 are inserted as one assembly through cannula 2080 to the implantation site. Then dynamic bone anchor is implanted by turning a handle 2088 attached to the quick release on the proximal end of shaft 2060. The dynamic bone anchor 2000 is driven into hole 2086 until the housing is at the surface of the vertebra 2084 (see arrow 2090). The torque to drive dynamic bone anchor 2000 is provided by handle 2088 through shaft 2060 to cap 2010 of dynamic bone anchor 2000.

Referring now to the right side of FIG. 20D, when dynamic bone anchor 2000 is correctly positioned in pedicle 2082, the physician pulls back on grip 2074 against the force of spring 2072. Sleeve 2070 moves proximally relative to shaft 2060. Shaft 2060 releases the grip on dynamic bone screw 2000 and the both shaft 2060 and sleeve 2070 move away from cannula 2080 and out of the patient (see arrow 2092). Dynamic bone anchor 2000 is now correctly implanted and prepared for attachment to spinal rod and/or other spinal stabilization assembly components.

FIGS. 21A-21D show views of an attachment tool for securing a dynamic vertical rod 2100 to a dynamic bone anchor 2000 according to an embodiment of the invention. FIG. 21A shows a perspective view of an attachment tool 2150 for securing a dynamic vertical rod 2100 to a dynamic bone anchor 2000 (shown in FIG. 21C) according to an embodiment of the invention. Dynamic vertical rod 2100 may be, for example, the dynamic vertical rod 1950 of FIG. 19B. Dynamic bone anchor 2000 may be, for example, the assembly of deflection rod assembly 1900 and bone anchor 1920 as shown in FIG. 19B.

Referring first to FIG. 21A, attachment tool 2150 includes an inner shaft 2160 received within a tubular sleeve 2170. The length and diameter of attachment tool 2150 is selected so as to allow use through a cannula in a minimally invasive surgical technique thereby reducing disruption of tissues adjacent the implantation site, reducing patient recovery time and improving surgical outcomes. Inner shaft 2160 is free to rotate and slide within sleeve 2170. Inner shaft 2160 has at a proximal end an attached handle 2162. In alternative embodiments shaft 2160 may have a fitting to which a handle might be attached, for example, ratcheting handles, torque sensing handles and torque limiting handles. Inner shaft has at a distal end a head 2164 for engaging and securing the hex extension of a dynamic vertical rod 2100 (see FIG. 21B).

Referring again to FIG. 21A, sleeve 2170 includes a butterfly grip 2174 at the proximal end thereof. Sleeve 2170, has at the distal end thereof, means for engaging and securing the female hex socket of a ball of a dynamic vertical rod 2100 during connection to a dynamic bone anchor as is described below. In a preferred embodiment head 2164 includes a male hex fitting 2172 with a central aperture 2173. FIG. 21B shows an enlarged view of head 2164 from the distal end of attachment tool 2150. FIG. 21B shows male hex fitting 2172 with central aperture 2173. Through central aperture 2173 is visible female hex socket 2165 of head 2164. Protruding into female hex socket 2165 are two spring tabs 2167.

FIGS. 21C and 21D show detailed sectional views of the distal end attachment tool 2150 in relation to a dynamic vertical rod 2100 and dynamic bone anchor 2000. Referring first to FIG. 21C, which shows a detailed sectional view of the distal end of the attachment tool 2150 of FIG. 21A, engaged with a dynamic vertical rod 2100 and a dynamic bone anchor 2000. As shown in FIG. 21C, male hex fitting 2172 of head 2164 of outer sleeve 2170 fits into the female hex socket of ball 2144. At the same time a hex extension 2115 of ball rod 2006 is received within female hex socket 2165 of inner shaft 2160. When thus engaged, turning handle 2162 relative to butterfly grip 2174 (See FIG. 21A) can rotate ball rod 2006 relative to ball 2144. Attachment tool 2150 is designed to apply sufficient torque to ball rod 2006 relative to ball 2144 to secure ball rod 2006 to ball 2144 and breakaway the hex extension 2115 of ball rod 2006. In a preferred embodiment, attachment tool 2150 should be able to provide greater than 30 foot pounds of torque.

FIG. 21D shows a detailed sectional view of the distal end of the attachment tool 2150 of FIG. 21A after break away of hex extension 2115 of ball rod 2006. As shown in FIG. 21D, when ball 2144 has been tightened onto ball rod 2006, tabs 2167 on central aperture 2173 engage either side of a nipple 2118 of hex extension 2115 to secure hex extension 2115 within female hex socket 2165. Thus, when hex extension 2115 beaks away it can be removed from the patient with connection tool 2150 as shown.

FIGS. 21E-21H are lateral views of the lumbar spine illustrating steps of attaching a dynamic vertical rod 2100 to a dynamic bone anchor 2000 utilizing the attachment tool of FIG. 21A according to an embodiment of the invention. As shown in FIG. 21E, the dynamic vertical rod 2100 is implanted after the dynamic bone anchor 2000 and a polyaxial screw 2140 have already been implanted. Dynamic vertical rod 2100 is implanted in a cranially direction—preferably in a minimally invasive manner until dynamic vertical rod 2100 is positioned adjacent dynamic bone anchor 2000 and polyaxial screw 2140. The hex extension 2115 of dynamic bone anchor 2000 is then fed through ball 2144 of dynamic vertical rod 2100 as shown.

Next, as shown in FIG. 21F, connection tool 2150 is inserted through a cannula 2080 to engage ball 2144 and hex extension 2115. Ball 2144 is then turned relative to hex extension 2115 until it is fully secured to ball rod 2006. When ball 2144 is fully secured to ball rod 2006, further torque is applied until hex extension 2115 (not shown) is sheared off. In a preferred embodiment, this requires 30 foot pounds of torque and is sufficient to lock ball 2144 to ball rod 2006. Next, as shown in FIG. 21G, connection tool 2150 can be removed from cannula 2080. As previously described, hex extension 2115 (not shown) is retained inside attachment tool 2150 for easy removal from the patient. As shown in FIG. 21H a conventional tool 2184 is then inserted through cannula 2180 to operate polyaxial screw 2140 to secure the other end of dynamic vertical rod 2100.

Preserving Anatomically Correct Motion of the Spine

Figure 22A:
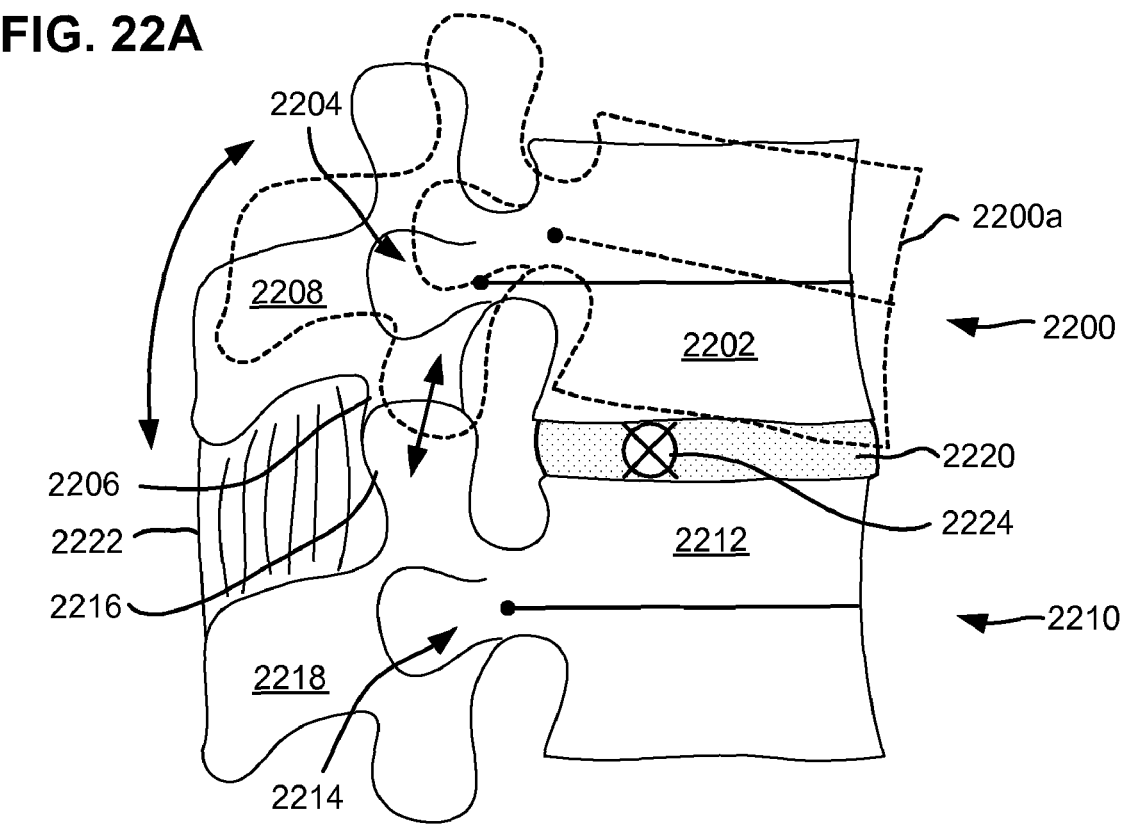
FIG. 22A is a lateral view of the lumbar spine illustrating the natural kinematics of the spine during extension and flexion.

FIG. 22A is a lateral view of the lumbar spine illustrating the natural kinematics of the spine during extension and flexion. A superior vertebra 2200 (for example L4) is shown relative to an inferior vertebra 2210 (for example L5). The primary load bearing structures are the vertebral bodies 2202 and 2102. Between the vertebral bodies lies an intervertebral disc 2220. Dorsal of the spinal bodies lie the pedicles 2204, 2214, facets 2206, 2216 and spinous processes 2208, 2218. Between the spinous process is a ligamentous band called the interspinous ligament 2222. In the healthy lumbar spines significant extension and flexion of the spine is possible in the lumbar region—approximating 35 degrees of total flexion over the entire lumbar region. As the spine flexes and extends the vertebrae move relative to one another while maintaining alignment of the vertebral bodies to support the weight of the upper body.

Between extension and flexion, the superior vertebra 2200 may move through an angle or range of about 15 degrees with respect to the inferior vertebra 2210. In the healthy spine the natural center of rotation 2224 for this rotation is located within the intervertebral disc 2220. Rotation about the natural center of rotation 2224 causes elongation of the interspinous ligament 2222 and slight separation of the facets 2206, 2216. However, this rotary motion does not occur alone. The healthy spine exhibits a phenomenon called coupling in which rotation or translation about or along one axis or plane is consistently associated with another motion about or along a second axis or plane. The dashed line 2200*a* shows the position of the superior vertebra during flexion. As can be seen, during flexion, not only does the superior vertebra 2200 rotate about the natural center of rotation 2224, but it also translates cranially and dorsally. As a consequence, normal flexion also induces up to approximately an 8 mm increase in the distance between the pedicles 2204, 2214 from a combination of elevation and forward translation. This is enabled by elongation of the interspinous band and facet separation. Similarly, lateral bending of the spine is coupled with relative axial rotation of the vertebrae.

With age, the vertebral bodies of the spine and intervertebral discs can degenerate. This spinal degeneration reduces the load-bearing ability of the spine, causes pain, reduces range of motion and can induce compensatory bone growth. The bone growth can lead to further reduction in range of motion and spinal stenosis in which the bone compresses blood vessels and nerves passing along the spine leading to inflammation and more pain. A number of spinal prosthesis have been proposed to maintain or restore the load-bearing capability of the spine, reduce discogenic instability, provide pain relief after discectomy, to top off degenerative discs above or below vertebral fusion, and/or to support degenerative discs without fusion. The basic objectives of such prostheses are load sharing and stabilization of the spine to remediate the problems identified above and reduce pain. Unfortunately, the spine is a very complex structure and it is very difficult to provide a prosthesis for load sharing and stabilization that does not also change the natural kinematics of the spine causing additional artifacts, instabilities and as a result further degeneration of the spine.

Figure 22B:
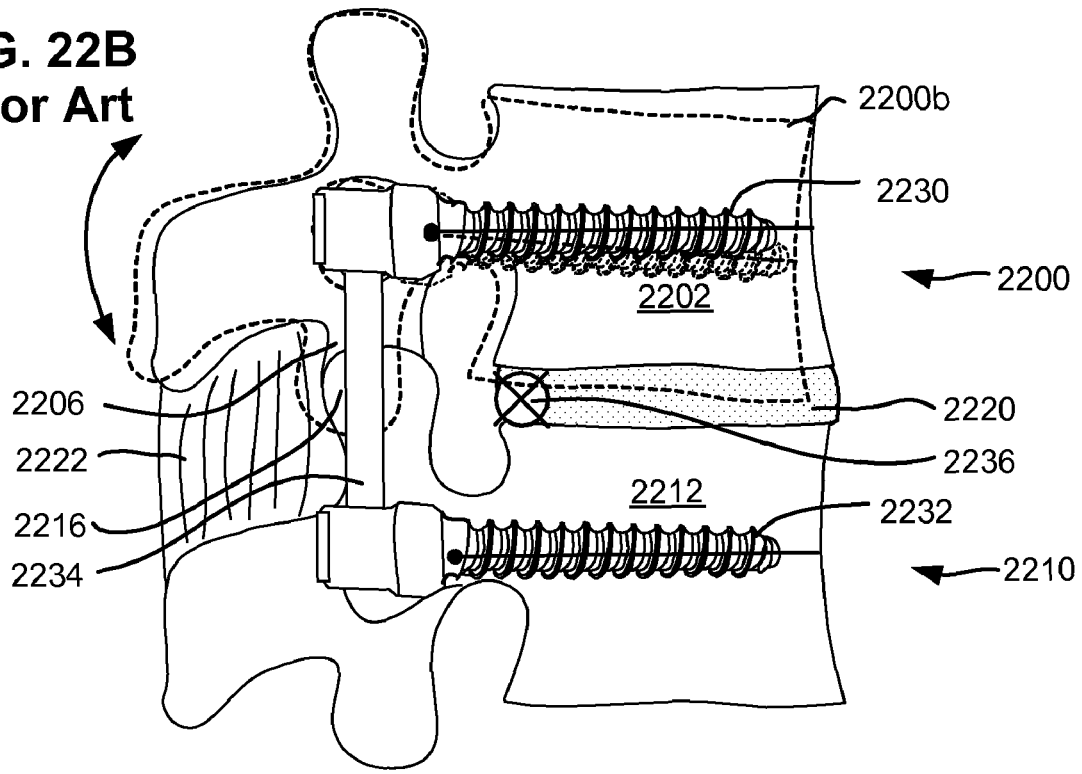
FIG. 22B is a lateral view of the lumbar spine illustrating the kinematic constraints placed on the spine by a rigid spinal rod system during extension and flexion.

FIG. 22B is a lateral view of the lumbar spine illustrating the kinematic constraints placed on the spine by a rigid spinal rod system during extension and flexion during extension and flexion. FIG. 22B shows a pedicle screw 2230 implanted in the superior vertebra 2200 and a pedicle screw 2232 implanted in the inferior vertebra 2210. The pedicle screws are connected by a rigid vertical rod 2234. The vertical rod 2234 and screws form a theoretically rigid system. The vertical rod thus transmits some of the load from the superior vertebra 2200 to the inferior vertebra 2210 thereby reducing the load on the vertebral bodies 2202, 2212 and the intervertebral disc 2220.

However, an artifact of a rigid prosthesis as shown in FIG. 22B, is that the relative rotation of the vertebra is constrained and the interpedicular distance is fixed. During flexion of the spine, some rotation is permitted by flexing of the vertical rod 2234 and the connections between the vertical rod 2234 and the pedicle screws 2230 and 2232. However, because the interpedicular distance remains essentially fixed, no elongation of the interspinous ligament 2222 is possible and the center of rotation 2236 is moved significantly dorsally of the natural center of rotation to the dorsal edge of the intervertebral disc or even further. The dashed lines 2200b show the relative movement of the superior vertebra 2200. Moreover, not only is facet separation prevented but the flexure about the new center of rotation can actually push the facets together increasing loading of the facet joints 2206, 2216. The prosthesis also interferes with the natural coupling of the spine by precluding and/or limiting the translation of the superior vertebra which is associated with rotation in natural flexion. Additionally, the flexing of the vertical rod places significant strain upon the pedicle screws and the interface between the pedicle screws 2230, 2232 and the bone which can lead either to device failure, backing out of the screws or damage to the pedicles. Furthermore, constraining motion at one segment of the spine is thought to create additional stress at adjacent segments and might therefore accelerate degeneration at those spinal segments (adjacent-level disease).

In order to overcome the problems caused by a rigid spinal prosthesis, a dynamic spine stabilization prosthesis attempts to preserve anatomical spinal motion and motion quality. An ideal prosthesis should be able to maintain intersegmental stability and permit appropriate motion at a spinal segment, e.g. ~15 degrees of flexion/extension, ~2 degrees of axial rotation, ~6 degrees lateral bending as well as relative translation of the vertebrae ~2 mm of left-right yaw, ~2 mm of elevation (separation), and/or ~2 mm of dorsal-ventral shift. The ideal prosthesis should also allow complex combinations of these motions and permit the coupling exhibited in the anatomical spine. The prosthesis should be able to preserve these motions required for normal spinal function while providing load sharing without abnormal load distribution, and spinal segment stabilization including limiting motion beyond anatomically desirable limits.

Figure 22C:
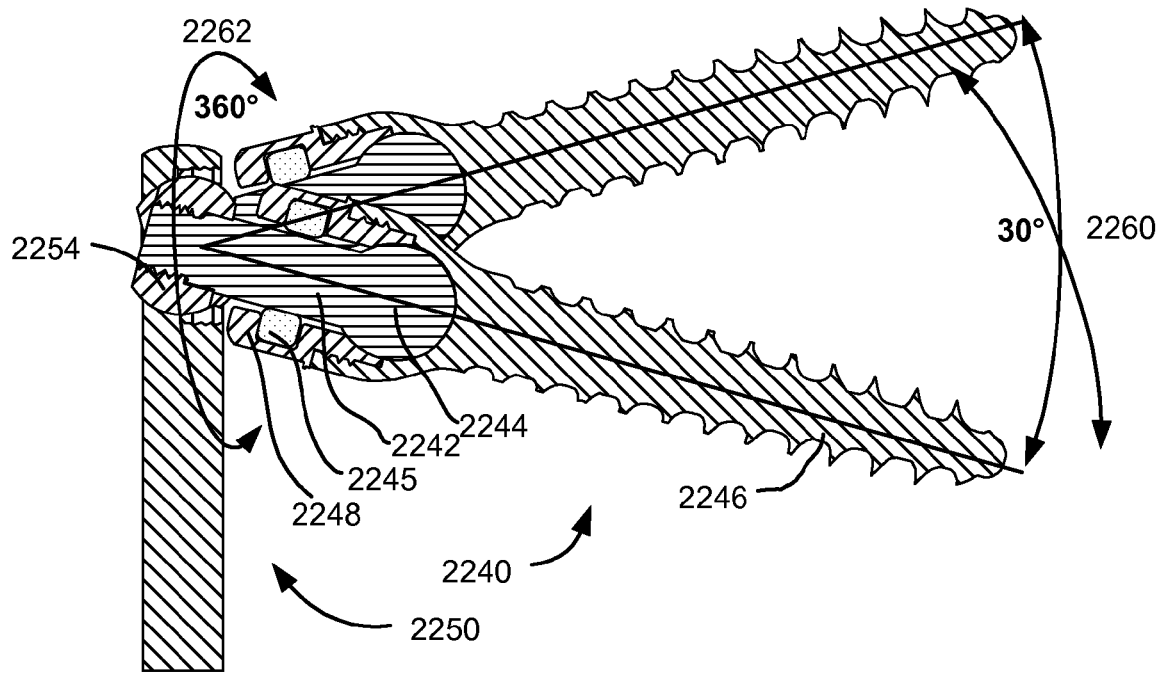
FIGS. 22C and 22D show the kinematic modes of an embodiment of the dynamic spine stabilization implant of the invention utilizing a dynamic bone anchor and dynamic vertical rod in accordance with embodiments of the invention.
Figure 22D:
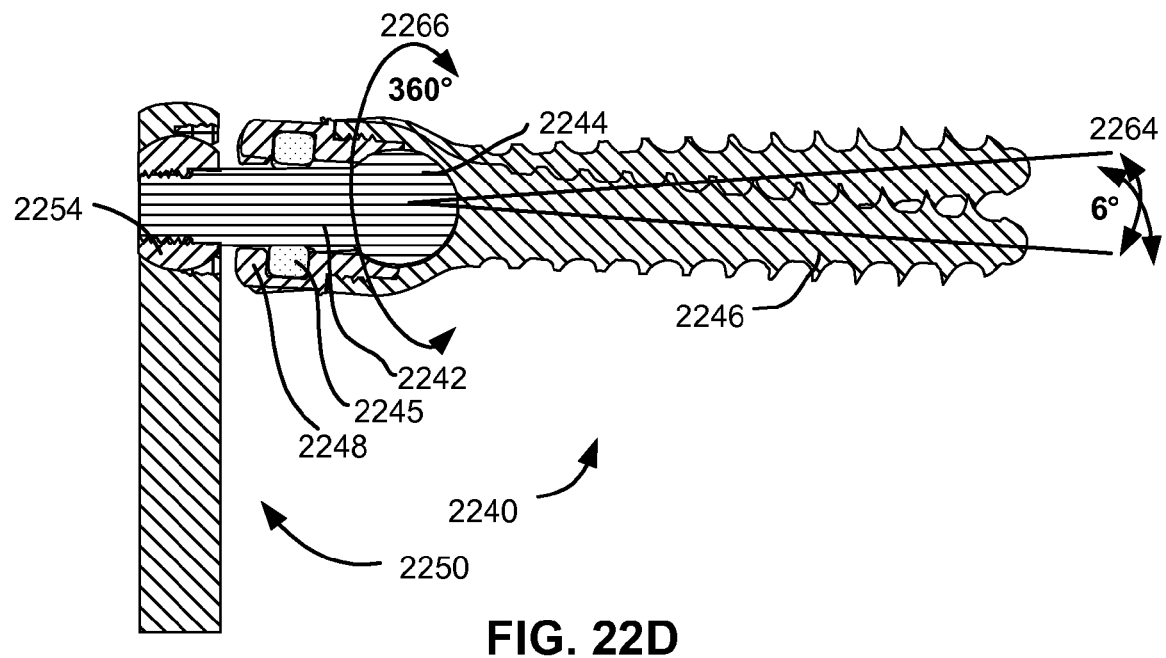

FIGS. 22C and 22D show the kinematic modes of a dynamic spine stabilization prosthesis utilizing a dynamic bone anchor and dynamic vertical rod in accordance with embodiments of the invention. FIGS. 22C and 22D show kinematic modes of a dynamic bone anchor 2240 in conjunction with a dynamic vertical rod 2250. Dynamic bone anchor 2240 includes a ball rod 2242 that pivots about ball 2244 at the distal end relative to threaded anchor 2246. Ball rod 2242 is connected at its proximal end to ball 2254 of dynamic vertical rod 2250. Deflection of ball rod 2242 relative to threaded anchor 2246 of the dynamic bone anchor 2240 is controlled by compression of compliant ring 2245 and limited by hard contact surfaces at the proximal end of the cap 2248. The three links—vertical rod 2250, ball rod 2242, and threaded anchor 2246—and two ball joints 2244, 2254 are connected in series and, thus, the movements of the linkages can be combined to provide a complex range of kinematic modes.

FIG. 22C shows the kinematic modes of ball rod 2242 relative to dynamic vertical rod 2250 assuming no motion internal to dynamic bone anchor 2240. As shown in FIG. 22C, ball rod 2242 pivots and rotates about ball 2254 of dynamic vertical rod 2250. Ball rod 2242 (and threaded anchor 2246) can pivot 15 degrees in any direction from perpendicular relative to dynamic vertical rod 2250 as shown by arrow 2260 for a total range of motion of 30 degrees. Ball rod 2242 (and threaded anchor 2246) can also rotate 360 degrees relative to dynamic vertical rod 2250 as shown by arrow 2262.

FIG. 22D shows the kinematic modes of threaded anchor 2246 relative to ball rod 2242 based solely on internal motion within dynamic bone anchor 2240. As shown in FIG. 22D, threaded anchor 2240 pivots and rotates about ball 2244 of ball rod 2242. Threaded anchor 2246 can pivot 3 degrees in any direction from perpendicular relative to ball rod 2242 as shown by arrow 2264 for a total range of motion of 6 degrees. Dynamic vertical rod can also rotate 360 degrees relative to ball rod 2242 as shown by arrow 2266.

The kinematics of the ball rod 2242 relative to dynamic vertical rod 2250 and the threaded anchor 2246 relative ball rod 2242 combine to generate more complex kinematics than would be available with either component alone. The compound kinematics more closely approximate the natural kinematics of the spine. FIGS. 22E and 22F illustrate the compound kinematics of a dynamic spinal stabilization prosthesis incorporating a dynamic bone anchor 2240 and dynamic vertical rod 2250. FIG. 22E is a simplified illustration of the kinematics of a dynamic spine stabilization prosthesis showing the movement of dynamic bone anchor 2240 relative to a fixed bone anchor 2241. FIG. 22F is a lateral view of the spine illustrating the kinematics of a spinal segment supported by the dynamic spine stabilization prosthesis of FIG. 22E.

As shown in FIGS. 22E and 22F, a dynamic spinal prosthesis incorporating both the dynamic bone anchor 2240 and dynamic vertical rod 2250 allows not only rotary motion (arrow 2270) but also coupled translation (arrow 2272) of a dynamic bone anchor 2240 relative to a bone anchor 2241. Furthermore the center of rotation 2274 is maintained at an anatomically desirable position in the intervertebral disc (See FIG. 22F). Maintenance of the natural center of rotation helps prevent uneven loading of the vertebral bodies 2202, 2212. The pivoting motion and translation are coupled and compliantly modulated by compression of the compliant member of the dynamic bone anchor (see FIG. 22D). Moreover, the prosthesis also limits the availability movement by, for example, contact between the ball rod 2242 and the cap 2248 thus providing segmental stability. The kinematics of threaded anchor 2246 of dynamic bone anchor 2240 thus closely approximate the natural kinematics of the vertebra shown in FIG. 22A. Consequently, a dynamic spinal stabilization prosthesis incorporating both dynamic vertical rod 2250 and dynamic bone anchor 2240 can stabilize the spine and provide load sharing while maintaining the center of rotation of implant vertebra within the intervertebral disc 2220 close to the natural center of rotation (see FIG. 22A) of the spine preserving natural range of motion. The kinematics of the prosthesis by allowing translation of vertebra 2200 relative to vertebra 2210 also serve to preserve facet separation during flexion seen in the natural spine. By allowing more natural kinematics, stain on the components and the bone interface is reduced leading to enhanced durability, safety and efficacy.

The rotation of the ball rod 2242 relative to the dynamic vertical rod 2250 and threaded anchor 2246 relative to the ball rod 2242 (see FIGS. 22C, 22D) also permit kinematics impossible with rigid pedicle screw systems. For example, lateral bending of the spine couples with relative rotation of the vertebrae. In the rigid spinal implant of FIG. 22B, there is no provision for such rotation which would therefore resolve as strain upon the components and component/bone interface. However, in a dynamic spinal prosthesis incorporating both dynamic vertical rod 2250 and dynamic bone anchor 2240, rotation is provided about ball 2244 and ball 2254, thus allowing both changes in the side-to-side intervertebral distance and coupled axial rotation of the vertebrae closely approximating the natural kinematics of the spine. Dynamic stabilization assemblies incorporating embodiments of the present invention can also support complex combinations of natural movements and the coupled rotations and translations of the spine, for example, lateral bending with twisting, lateral bending with flexion. Thus, anatomically correct motion of the spine is stabilized and preserved.

The close approximation of the kinematics of the dynamic spinal prosthesis and the natural kinematics of the spine results in reduced stresses at the implant/bone interface and, by using a natural center of rotation, allows even stress distribution across the vertebral bodies and intervertebral disc. The prosthesis has a decreased stiffness and increased range of motion compared to conventional rigid vertical rod systems supporting the implant segment while reducing stresses on adjacent segments. However, the dynamic spine stabilization prosthesis, with the compliant element located in-line within the dynamic bone anchor, is more robust than flexible rod systems. The degree of compliance in the dynamic bone anchor can also be tailored for the individual based upon load and anatomy. The result is anatomical load displacement curves, stabilization and preservation of anatomically correct motion and a robust surgical remediation of spinal degeneration.

Deflection Rod/Loading Rod Materials

Movement of the deflectable post relative to the bone anchor provides load sharing and dynamic stabilization properties to the dynamic stabilization assembly. As described above, deflection of the deflectable post deforms the material of the sleeve. The characteristics of the material of the sleeve in combination with the dimensions of the components of the deflection rod assembly affect the force-deflection curve of the deflection rod. The dimensions and materials may be selected to achieve the desired force-deflection characteristics.

By changing the dimensions of the deflectable post, sleeve and the shield, the deflection characteristics of the deflection rod assembly can be changed. The stiffness of components of the deflection rod assembly can be, for example, increased by increasing the diameter of the deflectable post and/or by decreasing the diameter of the inner surface of the shield. Additionally, decreasing the diameter of the deflectable post will decrease the stiffness of the deflection rod assembly while decreasing the diameter of the post and/or by increasing the diameter of the inner surface of the shield will decrease the stiffness of the deflection rod. Alternatively and/or additionally, changing the materials which comprise the components of the deflection rod assembly can also affect the stiffness and range of motion of the deflection rod. For example, making the sleeve out of stiffer and/or harder material reduces deflection of the deflectable post.

The deflectable post, bone anchor and vertical rods are preferably made of biocompatible implantable metals. The deflectable post can, for example, be made of titanium, titanium alloy, cobalt chrome, a shape memory metal, for example, Nitinol (NiTi) or stainless steel. In preferred embodiments, the deflectable post is made of cobalt chrome. In preferred embodiments, the bone anchor and vertical rods are made of titanium alloy; however, other materials, for example, stainless steel may be used instead of or in addition to the titanium components. Furthermore, the ball of the dynamic vertical rod is preferably made of cobalt chrome for good wear characteristics.

The material of the sleeve/compliant member/or-ring is a biocompatible and implantable polymer having the desired deformation characteristics. The material of the sleeve should also be able to maintain the desired deformation characteristics. Thus the material of the sleeve is preferably durable, resistant to oxidation and dimensionally stable under the conditions found in the human body. The sleeve may, for example be made from a polycarbonate urethane (PCU) such as Bionate®. If the sleeve is comprised of Bionate®, a polycarbonate urethane or other hydrophilic polymer, the sleeve can also act as a fluid-lubricated bearing for rotation of the deflectable post relative to the longitudinal axis of the deflectable post.

Suitable materials for the sleeve include polyurethanes including polycarbonate-urethanes (PCU). Suitable PCUs are available under the trade name BIONATE® from the Polymer Technology Group—DSM PTG, Inc. (Berkeley, Calif.). Bionate® PCU has good biocompatibility and has been FDA approved for long-term implantation. Bionate® PCU has good oxidative stability, biocompatibility, mechanical strength and abrasion resistance and suitable physical properties including load bearing, dimensional stability and resistance to environmental stress cracking. Bionate® PCU is also available in five hardness grades 80A, 90A, 55D, 65D and 75D—the different hardness grades imparting different deflection characteristics to components incorporating them. In a preferred embodiment, the sleeve is made of grade 80A Bionate® PCU which is 2 mm thick when uncompressed and may be compressed to about 1 mm in thickness by deflection of the post.

The sleeve can be formed by extrusion, injection, compression molding and/or machining techniques, as would be appreciated by those skilled in the art. In some embodiments, the sleeve is formed separately. For example, a sleeve may be cut or machined from a biocompatible polymer and then assembled with the deflectable post and sleeve such as by being press fit into the shield. Alternatively or additionally, a biocompatible adhesive may be used to bond the sleeve to the shield and/or post. In alternative embodiments, the sleeve may be formed in place by positioning the post and inside the shield and then filling the space between the deflectable post and the shield with liquid polymer (polymer reagents) and allowing the polymer to solidify.

A one piece PCU sleeve/compliant member/o-ring may be produced, for example by multi-shot or insert injection molding yielding density gradients which can be used to control the force/deflection response curve of the deflection rod. Voids, gaps or other structural features may also be provided to modify the compliance of the sleeve and consequently the force/deflection response curve of the deflection rod. The density gradients may be patterned in order to control the response curve of the deflection rod. The density gradients need not be symmetric. Directional variations in the density gradients may be used to create a deflection rod assembly having different force/deflection responses in different directions.

The sleeve may also include polymer regions having different properties. For example, the sleeve can include concentric rings of one or more polymers with each ring having a different hardness of stiffness or durometer. For example, each successive ring from the center outward can have a higher hardness or stiffness or durometer so that as the post is deflected outwardly from a position that is collinear with the longitudinal axis the sleeve provides increased resistance to further deflection. The sleeve may also be designed to provide different force deflection characteristics in different directions. The deflectable post could also be designed so that less resistance occurs with increased deflection of the post.

Other polymers or thermoplastics may be used to make the sleeve including, but not limited to, polyether-etherketone (PEEK), polyphenylsolfone (Radel®), or polyetherimide resin (Ultem®). Other polymers that may be suitable for use in some embodiments, for example other grades of PEEK, for example 30% glass-filled or 30% carbon filled, provided such materials are cleared for use in implantable devices by the FDA, or other regulatory body. Glass-filled PEEK is known to be ideal for improved strength, stiffness, or stability while carbon filled PEEK is known to enhance the compressive strength and stiffness of PEEK and lower its expansion rate.

Still other suitable biocompatible thermoplastic or thermoplastic polycondensate materials may be suitable, including materials that have good memory, are flexible, and/or deflectable have very low moisture absorption, and good wear and/or abrasion resistance, can be used without departing from the scope of the invention. These include polyetherketoneketone (PEKK), polyetherketone (PEK), polyetherketoneetherketoneketone (PEKEKK), and polyetheretherketoneketone (PEEKK), and generally a polyaryletheretherketone. Further, other polyketones can be used as well as other thermoplastics.

PCU materials suitable for implantation are described in U.S. Pat. No. 5,133,742 titled "Crack-Resistant Polycarbonate Urethane Polymer Prostheses" and U.S. Pat. No. 5,299,431 titled "Crack-Resistant Polycarbonate Urethane Polymer Prostheses And The Like", both of which patents are incorporated herein by reference. Other polymers that can be used in the sleeve are disclosed in the following documents, all of which are incorporated herein by reference. These documents include: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials.

The materials of the sleeve may thus be selected to create a deflection rod assembly having stiffness/deflection characteristics suitable for the needs of a patient. By selecting appropriate materials of the sleeve, the deflection characteristics of the deflection rod assembly can be configured to approach the natural dynamic motion of the spine of a particular patient, while giving dynamic support to the spine in that region. It is contemplated, for example, that the deflection rod assembly can be made in stiffness that can replicate a 70% range of motion and flexibility of the natural intact spine, a 50% range of motion and flexibility of the natural intact spine and a 30% range of motion and flexibility of the natural intact spine.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. A medical device comprising:
   a bone screw having a longitudinal axis, a proximal end and a distal end;
   the distal end of the bone screw adapted to engage a vertebra;
   a housing at the proximal end of the bone screw;
   a bore in the housing aligned with the longitudinal axis of the bone screw, the bore having an open end and the bore terminating in a spherical pocket;
   a post having a ball-shaped retainer at a first end, the post being positioned in the bore of the housing such that the ball-shaped retainer is trapped within the spherical pocket allowing the post to pivot about a pivot point at the center of the ball-shaped retainer, and a second end of the post extends through the open end of the bore;
   a compliant member positioned in the bore between the housing and post to flexibly align the post with the bore and the longitudinal axis of the bone screw; and
   a bone screw thread which extends along said bone screw and a portion of said housing, said bone screw thread extending more proximally along the housing than the pivot point at the center of the ball-shaped retainer such that, upon implantation, the bone screw and the portion of the housing are adapted to be implanted in a bone and the pivot point is adapted to be positioned within the bone.

2. The medical device of claim 1, wherein the bone screw and housing are configured such that, upon implantation, the bone screw and the portion of the housing are adapted to be implanted in a bone and the pivot point is adapted to be positioned within the bone without obstruction of pivoting of the post.

3. The medical device of claim 1, wherein the bone screw is adapted for insertion in a pedicle of a vertebra such that, upon implantation, the bone screw and the portion of the housing are adapted to be implanted in the pedicle and the pivot point is adapted to be positioned within the pedicle, without obstruction of pivoting of the post.

4. The medical device of claim 1, wherein:
   said housing comprises a limit surface positioned to contact the post upon deflection of the post away from alignment with the longitudinal axis of the bone screw.

5. The medical device of claim 1, wherein the compliant member comprises a polymer bushing.

6. The medical device of claim 1, wherein the compliant member comprises a spring.

7. The medical device of claim 1, wherein the second end of the post comprises a mount adapted to receive a spinal rod substantially perpendicular to the post.

8. The medical device of claim 1, wherein the post comprises at the second end a threaded mount to secure the post to a spinal rod substantially perpendicular to the longitudinal axis.

9. The medical device of claim 1, in combination with a spinal rod secured to the proximal end of the post substantially perpendicular to the longitudinal axis.

10. The medical device of claim 1, further comprising a ball mounted to the proximal end of the post, the ball received in a spherical pocket of a spinal rod to form a joint which permits the spinal rod to pivot relative to the post.

11. The medical device of claim 1, wherein the ball-shaped retainer and the spherical pocket form a ball joint, which ball-joint is adapted to be located adjacent to the instantaneous center of the rotation of the spine.

12. A bone screw comprising:
  an elongated shaft having a distal end and a proximal end;
  a post having a distal end and a proximal end;
  a ball joint which pivotally secures the distal end of the post to the proximal end of the elongated shaft such that the post can pivot relative to the elongated shaft;
  a tubular extension of the elongated shaft which extends over the ball joint and a distal portion of the post;
  a compliant member disposed between the post and the tubular extension of the elongated shaft which flexible aligns the post with the elongated shaft; and
  a screw thread which extends along said elongated shaft and a portion of said tubular extension, said screw thread extending more proximally than the ball joint such that, upon implantation, the elongated shaft and the portion of the tubular extension are adapted to be implanted in a bone and the ball joint is adapted to be positioned within the bone.

13. The bone screw of claim 12, wherein the ball joint is adapted to be positioned in a location adjacent or below the surface of a bone, without obstruction of pivoting of the post.

14. The bone screw of claim 12, wherein the bone screw is adapted for insertion in a pedicle of a vertebra and wherein upon implantation of the bone screw the ball joint is adapted to be positioned within the pedicle, without obstruction of pivoting of the post.

15. The bone screw of claim 12, wherein:
  said tubular extension comprises a limit surface positioned to contact the post upon deflection of the post away from alignment with the elongated shaft of the bone screw.

16. The bone screw of claim 12, wherein the compliant member comprises a polymer bushing.

17. The bone screw of claim 12, wherein the compliant member comprises a spring.

18. The bone screw of claim 12, wherein the ball joint is adapted to be implanted adjacent to the instantaneous center of the rotation of the spine.

19. A dynamic bone anchor adapted to used in a spinal stabilization system, the dynamic bone anchor comprising:
  a bone screw having a longitudinal axis, a proximal end and a distal end; the bone screw including a housing at the proximal end thereof, the housing having a bore therethrough aligned with the longitudinal axis;
  a post received in the bore of the housing such that post extends from the bore at a proximal end of the housing;
  a joint between the post and a distal end of the housing which pivotally mounts the post to the distal end of the housing such that the post can pivot about a pivot point within the joint;
  a compliant member positioned between the post and the housing which compliantly aligns the post with the longitudinal axis of the bone screw; and
  a bone screw thread which extends along said bone screw and a portion of said housing, said bone screw thread extending more proximally than the pivot point at the center of the ball-shaped retainer such that, upon implantation, the bone screw and the portion of the housing are adapted to be implanted in a bone and the pivot point is adapted to be positioned within the bone.

20. The dynamic bone anchor of claim 19, wherein the compliant member comprises a polymer bushing.

21. The dynamic bone anchor of claim 19, wherein the compliant member comprises a spring.

22. The dynamic bone anchor of claim 19, wherein the post comprises a mount adapted to receive a spinal rod substantially perpendicular to the post.

23. The dynamic bone anchor of claim 19, in combination with a spinal rod secured to a proximal end of the post substantially perpendicular to the post.

24. The dynamic bone anchor of claim 19, further comprising a ball mounted to a proximal end of the post, the ball received in a spherical pocket of a spinal rod to form a joint which permits the spinal rod to pivot relative to the post.

25. A dynamic bone anchor adapted to used in a spinal stabilization system, the dynamic bone anchor comprising:
  a bone screw having a longitudinal axis, a proximal end and a distal end; the bone screw including a housing at the proximal end thereof, the housing having a bore therethrough aligned with the longitudinal axis;
  a post received in the bore of the housing such that post extends from the bore at a proximal end of the housing;
  a joint between the post and a distal end of the housing which pivotally mounts the post to the distal end of the housing such that the post can pivot about a pivot point within the joint; and
  a bone screw thread which extends along said bone screw and a portion of said housing, said bone screw thread extending more proximally than the pivot point at the center of the ball-shaped retainer such that, upon implantation, the bone screw and the portion of the housing are adapted to be implanted in a bone and the pivot point is adapted to be positioned within the bone.

* * * * *